United States Patent
Shigeta

(10) Patent No.: US 11,576,414 B1
(45) Date of Patent: Feb. 14, 2023

(54) FOOD COMPOSITIONS CONTAINING ADDED HONEY PROTEINS

(71) Applicant: Ronald Takeo Shigeta, Berkley, CA (US)

(72) Inventor: Ronald Takeo Shigeta, Berkley, CA (US)

(*) Notice: Subject to any disclaimer, the term of this patent is extended or adjusted under 35 U.S.C. 154(b) by 0 days.

(21) Appl. No.: 17/734,986

(22) Filed: May 2, 2022

Related U.S. Application Data

(60) Provisional application No. 63/183,505, filed on May 3, 2021.

(51) Int. Cl.
| | | |
|---|---|---|
| A23L 33/17 | (2016.01) | |
| A23G 1/44 | (2006.01) | |
| A23C 19/093 | (2006.01) | |
| A23C 9/13 | (2006.01) | |
| A21D 2/26 | (2006.01) | |
| A23L 33/00 | (2016.01) | |
| A61K 38/17 | (2006.01) | |
| C07K 14/435 | (2006.01) | |
| A23L 25/10 | (2016.01) | |

(52) U.S. Cl.
CPC ............ *A23L 33/17* (2016.08); *A21D 2/26* (2013.01); *A23C 9/1315* (2013.01); *A23C 19/093* (2013.01); *A23G 1/44* (2013.01); *A23L 25/10* (2016.08); *A23L 33/40* (2016.08); *A61K 38/1767* (2013.01); *C07K 14/43572* (2013.01); *A23V 2002/00* (2013.01)

(58) Field of Classification Search
CPC .......... A23L 33/17; A23L 25/10; A23L 33/40; A21D 2/26; A23C 9/1315; A23C 19/093; A23G 1/44; A61K 38/1767; C07K 14/43572; A23V 2002/00
USPC ....... 426/661, 648, 654, 655, 658, 656, 601; 514/656
See application file for complete search history.

(56) References Cited

U.S. PATENT DOCUMENTS

| | | | |
|---|---|---|---|
| 3,806,608 | A | 4/1974 | Perret |
| 9,539,289 | B2 | 1/2017 | Gannabathula et al. |
| 9,700,067 | B2 | 7/2017 | Fraser et al. |
| 9,924,728 | B2 | 3/2018 | Pandya et al. |
| 2018/0355020 | A1 | 12/2018 | Anchel |

FOREIGN PATENT DOCUMENTS

| | | | |
|---|---|---|---|
| JP | 201220296 | * | 10/2012 |
| WO | 2019046782 | | 3/2019 |
| WO | WO 2020/22657 | * | 4/2020 |

OTHER PUBLICATIONS

Bilikova et al. "Apisimin, a new serine . . . ", Aug. 28, 2002, https://febs.onlinelibrary.wiley.com/doi/full/10.1016/S0014-5793%2802%2903272-6 . (Year: 2002).*
Gannabathula et al, "Honeybee apisimin and plant arabinogalactans in honey costimulate monocytes", Food Chemistry, vol. 168, Feb. 1, 2015, pp. 34-40.
Tian et al., "Architecture of the native major royal jelly protein 1 oligomer", Nature Communications 9, Article No. 3373, Aug. 22, 2018, pp. 39.
Banerjee et al., "Food Gels: Gelling Process and New Applications", Critical Reviews in Food Science and Nutrition, vol. 52, Issue 4, Feb. 14, 2012, pp. 334-346.
Bocian et al., "An Effective Method of Isolating Honey Proteins", Molecules, vol. 24, Issue 13, Jun. 29, 2019, pp. 1-10.
Chua et al., "Bioanalytical Characterization of the Proteins in Honey", Analytical Letters, vol. 48, Issue 4, Sep. 25, 2014, pp. 697-709.
Majtan et al., "Effect of honey and its major royal jelly protein 1 on cytokine and MMP-9 mRNA transcripts in human keratinocytes", Experimental Dermatology, vol. 19, Issue8, Jul. 21, 2010, pp. e73-e79.
K Biilikova et al., "Apisimin, a new serine-valine-rich peptide from honeybee (*Apis mellifera* L.) royal jelly: purification and molecular characterization", FEBS Letters, vol. 528, Issues 1-3, Sep. 25, 2002, pp. 125-129.
Erban et al., "The Unique Protein Composition of Honey Revealed by Comprehensive Proteomic Analysis: Allergens, Venom-like Proteins, Antibacterial Properties, Royal Jelly Proteins, Serine Proteases, and Their Inhibitors", Natural Products, vol. 82, Issues 5, Apr. 17, 2019, pp. 1217-1226.
Ferguson et al., "Evolution of the Insect Yellow Gene Family", Molecular Biology and Evolution, vol. 28, Issue 1, Jul. 23, 2010, pp. 257-272.
Linden et al., "Gelation: Principles, Models and Applications to Proteins", Modern Biopolymer Science, 2009, pp. 29-91.
Taco Nicolai, "Gelation of food protein-protein mixtures", Advances in Colloid and Interface Science 270, 2019, pp. 147-164.
Helbing et al., "Comparative analyses of the major royal jelly protein gene cluster in three Apis species with long amplicon sequencing", DNA Research, vol. 24, Issue 3, Feb. 7, 2017, pp. 279-287.
Se-Ra Won et al., "Immunological characterization of honey major protein and its application", Food Chemistry, vol. 113, Issue 4, Apr. 15, 2009, pp. 1334-1338.

(Continued)

*Primary Examiner* — Helen F Heggestad
(74) *Attorney, Agent, or Firm* — Benjamin A. Keim

(57) ABSTRACT

Food composition supplemented with one or more honey proteins provide additional protein without detracting from flavor or mouthfeel and may also possess cytostimulatory properties. The honey proteins may be royal jelly major proteins (RJMP) such as those from the western honeybee *Apis mellifera*. The honey proteins can be created by expression of recombinant DNA in a yeast or bacterium. The honey protein is selected based on physical properties of the protein and of the food composition to reduce negative mouthfeel and flavor characteristics that may be caused by added protein. Multiple different proteins may be added in a specified ratio to create a desired texture or cytostimulatory property.

20 Claims, No Drawings
Specification includes a Sequence Listing.

(56) References Cited

OTHER PUBLICATIONS

X Xue et al., "Chemical Composition of Royal Jelly", Chapter 8, Bee Products—Chemical and Biological Properties, 2017, pp. 181-190.
Novozymes, "enzymes at work", rethink tomorrow, pp. 76.

* cited by examiner

SEQUENCE LISTING

```
<160> NUMBER OF SEQ ID NOS: 88

<210> SEQ ID NO 1
<211> LENGTH: 431
<212> TYPE: PRT
<213> ORGANISM: Apis mellifera

<400> SEQUENCE: 1

Met Thr Arg Leu Phe Met Leu Val Cys Leu Gly Ile Val Cys Gln Gly
1               5                   10                  15

Thr Thr Gly Asn Ile Leu Arg Gly Glu Ser Leu Asn Lys Ser Leu Pro
            20                  25                  30

Ile Leu His Glu Trp Lys Phe Phe Asp Tyr Asp Phe Gly Ser Asp Glu
        35                  40                  45

Arg Arg Gln Asp Ala Ile Leu Ser Gly Glu Tyr Asp Tyr Lys Asn Asn
    50                  55                  60

Tyr Pro Ser Asp Ile Asp Gln Trp His Asp Lys Ile Phe Val Thr Met
65                  70                  75                  80

Leu Arg Tyr Asn Gly Val Pro Ser Ser Leu Asn Val Ile Ser Lys Lys
                85                  90                  95

Val Gly Asp Gly Gly Pro Leu Leu Gln Pro Tyr Pro Asp Trp Ser Phe
            100                 105                 110

Ala Lys Tyr Asp Asp Cys Ser Gly Ile Val Ser Ala Ser Lys Leu Ala
        115                 120                 125

Ile Asp Lys Cys Asp Arg Leu Trp Val Leu Asp Ser Gly Leu Val Asn
    130                 135                 140

Asn Thr Gln Pro Met Cys Ser Pro Lys Leu Leu Thr Phe Asp Leu Thr
145                 150                 155                 160
```

```
Thr Ser Gln Leu Leu Lys Gln Val Glu Ile Pro His Asp Val Ala Val
            165                 170                 175

Asn Ala Thr Thr Lys Gly Arg Leu Ser Ser Leu Ala Val Gln Ser Leu
        180                 185                 190

Asp Cys Asn Thr Asn Ser Asp Thr Met Val Tyr Ile Ala Asp Glu Lys
    195                 200                 205

Gly Glu Gly Leu Ile Val Tyr His Asn Ser Asp Ser Phe His Arg
    210                 215                 220

Leu Thr Ser Asn Thr Phe Asp Tyr Asp Pro Lys Phe Thr Lys Met Thr
225                 230                 235                 240

Ile Asp Gly Glu Ser Tyr Thr Ala Gln Asp Gly Ile Ser Gly Met Ala
                245                 250                 255

Leu Ser Pro Met Thr Asn Asn Leu Tyr Tyr Ser Pro Val Ala Ser Thr
            260                 265                 270

Ser Leu Tyr Tyr Val Asn Thr Glu Gln Phe Arg Thr Ser Asp Tyr Gln
        275                 280                 285

Gln Asn Asp Ile His Tyr Glu Gly Val Gln Asn Ile Leu Asp Thr Gln
    290                 295                 300

Ser Ser Ala Lys Val Val Ser Lys Ser Gly Val Leu Phe Phe Gly Leu
305                 310                 315                 320

Val Gly Asp Ser Ala Leu Gly Cys Trp Asn Glu His Arg Thr Leu Glu
                325                 330                 335

Arg His Asn Ile Arg Thr Val Ala Gln Ser Asp Glu Thr Leu Gln Met
            340                 345                 350

Ile Ala Ser Met Lys Ile Lys Glu Ala Leu Pro His Val Pro Ile Phe
        355                 360                 365

Asp Arg Tyr Ile Asn Arg Glu Tyr Ile Leu Val Leu Ser Asn Lys Met
    370                 375                 380

Gln Lys Met Val Asn Asn Asp Phe Asn Phe Asp Asp Val Asn Phe Arg
385                 390                 395                 400

Ile Met Asn Ala Asn Val Asn Glu Leu Ile Leu Asn Thr Arg Cys Glu
                405                 410                 415

Asn Pro Asp Asn Asp Arg Thr Pro Phe Lys Ile Ser Ile His Leu
            420                 425                 430

<210> SEQ ID NO 2
<211> LENGTH: 412
<212> TYPE: PRT
<213> ORGANISM: Apis mellifera

<400> SEQUENCE: 2

Asn Ile Leu Arg Gly Glu Ser Leu Asn Lys Ser Leu Pro Ile Leu His
1               5                   10                  15

Glu Trp Lys Phe Phe Asp Tyr Asp Phe Gly Ser Asp Glu Arg Arg Gln
            20                  25                  30

Asp Ala Ile Leu Ser Gly Glu Tyr Asp Tyr Lys Asn Asn Tyr Pro Ser
        35                  40                  45

Asp Ile Asp Gln Trp His Asp Lys Ile Phe Val Thr Met Leu Arg Tyr
    50                  55                  60

Asn Gly Val Pro Ser Ser Leu Asn Val Ile Ser Lys Lys Val Gly Asp
65                  70                  75                  80

Gly Gly Pro Leu Leu Gln Pro Tyr Pro Asp Trp Ser Phe Ala Lys Tyr
                85                  90                  95

Asp Asp Cys Ser Gly Ile Val Ser Ala Ser Lys Leu Ala Ile Asp Lys
            100                 105                 110
```

Cys Asp Arg Leu Trp Val Leu Asp Ser Gly Leu Val Asn Asn Thr Gln
                115                 120                 125

Pro Met Cys Ser Pro Lys Leu Leu Thr Phe Asp Leu Thr Thr Ser Gln
            130                 135                 140

Leu Leu Lys Gln Val Glu Ile Pro His Asp Val Ala Val Asn Ala Thr
145                 150                 155                 160

Thr Lys Gly Arg Leu Ser Ser Leu Ala Val Gln Ser Leu Asp Cys Asn
                165                 170                 175

Thr Asn Ser Asp Thr Met Val Tyr Ile Ala Asp Glu Lys Gly Glu Gly
            180                 185                 190

Leu Ile Val Tyr His Asn Ser Asp Asp Ser Phe His Arg Leu Thr Ser
                195                 200                 205

Asn Thr Phe Asp Tyr Asp Pro Lys Phe Thr Lys Met Thr Ile Asp Gly
            210                 215                 220

Glu Ser Tyr Thr Ala Gln Asp Gly Ile Ser Gly Met Ala Leu Ser Pro
225                 230                 235                 240

Met Thr Asn Asn Leu Tyr Tyr Ser Pro Val Ala Ser Thr Ser Leu Tyr
                245                 250                 255

Tyr Val Asn Thr Glu Gln Phe Arg Thr Ser Asp Tyr Gln Gln Asn Asp
            260                 265                 270

Ile His Tyr Glu Gly Val Gln Asn Ile Leu Asp Thr Gln Ser Ser Ala
                275                 280                 285

Lys Val Val Ser Lys Ser Gly Val Leu Phe Phe Gly Leu Val Gly Asp
290                 295                 300

Ser Ala Leu Gly Cys Trp Asn Glu His Arg Thr Leu Glu Arg His Asn
305                 310                 315                 320

Ile Arg Thr Val Ala Gln Ser Asp Glu Thr Leu Gln Met Ile Ala Ser
                325                 330                 335

Met Lys Ile Lys Glu Ala Leu Pro His Val Pro Ile Phe Asp Arg Tyr
            340                 345                 350

Ile Asn Arg Glu Tyr Ile Leu Val Leu Ser Asn Lys Met Gln Lys Met
                355                 360                 365

Val Asn Asn Asp Phe Asn Phe Asp Asp Val Asn Phe Arg Ile Met Asn
            370                 375                 380

Ala Asn Val Asn Glu Leu Ile Leu Asn Thr Arg Cys Glu Asn Pro Asp
385                 390                 395                 400

Asn Asp Arg Thr Pro Phe Lys Ile Ser Ile His Leu
                405                 410

<210> SEQ ID NO 3
<211> LENGTH: 463
<212> TYPE: PRT
<213> ORGANISM: Apis cerana

<400> SEQUENCE: 3

Met Thr Lys Trp Leu Phe Met Val Ala Cys Leu Gly Ile Ala Cys Gln
1               5                   10                  15

Gly Ala Ile Ile Arg Gln Asn Ser Ala Lys Asn Leu Glu Asn Ser Leu
                20                  25                  30

Asn Val Ile His Glu Trp Lys Tyr Ile Asp Tyr Asp Phe Gly Ser Glu
            35                  40                  45

Glu Arg Arg Gln Ala Ala Ile Gln Ser Gly Gly Tyr Asp His Thr Lys
50                  55                  60

Asn Tyr Pro Phe Asp Val Asp Gln Trp His Asp Lys Thr Phe Val Thr

```
            65                  70                  75                  80
        Ile Leu Lys Tyr Asp Gly Val Pro Ser Thr Leu Asn Met Ile Ser Asn
                            85                  90                  95

Lys Ile Gly Lys Gly Gly Arg Leu Leu Gln Pro Tyr Pro Asp Trp Ser
                        100                 105                 110

Trp Ala Glu Asn Lys Asp Cys Ser Gly Ile Val Ser Ala Phe Lys Ile
                        115                 120                 125

Ala Ile Asp Lys Phe Asp Arg Leu Trp Val Leu Asp Ser Gly Leu Ile
        130                 135                 140

Asn Arg Thr Glu Pro Ile Cys Ala Pro Lys Leu His Val Phe Asp Leu
        145                 150                 155                 160

Lys Asn Thr Lys His Leu Lys Gln Ile Glu Ile Pro His Asp Ile Ala
                        165                 170                 175

Val Asn Ala Thr Thr Gly Lys Gly Gly Leu Val Ser Leu Val Val Gln
                        180                 185                 190

Ala Met Asp Pro Met Asn Thr Leu Val Tyr Ile Ala Asp His Lys Gly
                        195                 200                 205

Asp Ala Leu Ile Val Tyr Gln Asn Ser Asp Ser Phe His Arg Met
        210                 215                 220

Thr Ser Asn Thr Phe Asp Tyr Asp Pro Arg Tyr Ala Lys Met Thr Ile
        225                 230                 235                 240

Asn Gly Glu Ser Phe Thr Leu Lys Asn Gly Ile Cys Gly Met Ala Leu
                        245                 250                 255

Ser Pro Val Thr Asn Asn Leu Tyr Tyr Ser Pro Leu Ala Ser His Gly
                        260                 265                 270

Leu Tyr Tyr Val Asn Thr Glu Pro Phe Met Lys Ser Gln Phe Gly Asp
                        275                 280                 285

Asn Asn Asn Val Gln Tyr Glu Gly Ser Gln Asp Thr Leu Asn Thr Gln
                        290                 295                 300

Ser Leu Ala Lys Ala Val Ser Lys Asp Gly Val Leu Phe Val Gly Leu
        305                 310                 315                 320

Val Gly Asn Ser Ala Leu Gly Cys Leu Asn Glu His Gln Pro Leu Gln
                        325                 330                 335

Arg Glu Asn Leu Glu Leu Val Ala Gln Asn Glu Lys Thr Leu Gln Met
                        340                 345                 350

Ile Ala Gly Met Lys Ile Lys Glu Glu Leu Pro His Phe Val Gly Ser
                        355                 360                 365

Asn Lys Pro Val Lys Asp Glu Tyr Met Leu Val Leu Ser Asn Lys Met
                        370                 375                 380

Gln Lys Ile Val Asn Asn Asp Phe Asn Phe Asn Asp Val Asn Phe Arg
        385                 390                 395                 400

Ile Leu Gly Ala Asn Val Lys Glu Leu Met Arg Asn Thr His Cys Ala
                        405                 410                 415

Asn Phe Asn Asn Lys Asn Asn Gln Lys Asn Asn Gln Lys Asn Asn
                        420                 425                 430

Asn Gln Asn Asn Asn Gln Lys Asn Asn Gln Lys Asn Asn Asn
                        435                 440                 445

Gln Lys Asn Asn Asn Gln Lys Asn Asn Asn Gln Asn Thr Asn Asn
                        450                 455                 460

<210> SEQ ID NO 4
<211> LENGTH: 446
<212> TYPE: PRT
<213> ORGANISM: Apis cerana
```

<400> SEQUENCE: 4

```
Ala Ile Ile Arg Gln Asn Ser Ala Lys Asn Leu Glu Asn Ser Leu Asn
1               5                   10                  15

Val Ile His Glu Trp Lys Tyr Ile Asp Tyr Asp Phe Gly Ser Glu Glu
            20                  25                  30

Arg Arg Gln Ala Ala Ile Gln Ser Gly Glu Tyr Asp His Thr Lys Asn
        35                  40                  45

Tyr Pro Phe Asp Val Asp Gln Trp His Asp Lys Thr Phe Val Thr Ile
    50                  55                  60

Leu Lys Tyr Asp Gly Val Pro Ser Thr Leu Asn Met Ile Ser Asn Lys
65                  70                  75                  80

Ile Gly Lys Gly Gly Arg Leu Leu Gln Pro Tyr Pro Asp Trp Ser Trp
                85                  90                  95

Ala Glu Asn Lys Asp Cys Ser Gly Ile Val Ser Ala Phe Lys Ile Ala
            100                 105                 110

Ile Asp Lys Phe Asp Arg Leu Trp Val Leu Asp Ser Gly Leu Ile Asn
        115                 120                 125

Arg Thr Glu Pro Ile Cys Ala Pro Lys Leu His Val Phe Asp Leu Lys
130                 135                 140

Asn Thr Lys His Leu Lys Gln Ile Glu Ile Pro His Asp Ile Ala Val
145                 150                 155                 160

Asn Ala Thr Thr Gly Lys Gly Leu Val Ser Leu Val Val Gln Ala
                165                 170                 175

Met Asp Pro Met Asn Thr Leu Val Tyr Ile Ala Asp His Lys Gly Asp
        180                 185                 190

Ala Leu Ile Val Tyr Gln Asn Ser Asp Asp Ser Phe His Arg Met Thr
    195                 200                 205

Ser Asn Thr Phe Asp Tyr Asp Pro Arg Tyr Ala Lys Met Thr Ile Asn
210                 215                 220

Gly Glu Ser Phe Thr Leu Lys Asn Gly Ile Cys Gly Met Ala Leu Ser
225                 230                 235                 240

Pro Val Thr Asn Asn Leu Tyr Tyr Ser Pro Leu Ala Ser His Gly Leu
                245                 250                 255

Tyr Tyr Val Asn Thr Glu Pro Phe Met Lys Ser Gln Phe Gly Asp Asn
            260                 265                 270

Asn Asn Val Gln Tyr Glu Gly Ser Gln Asp Thr Leu Asn Thr Gln Ser
        275                 280                 285

Leu Ala Lys Ala Val Ser Lys Asp Gly Val Leu Phe Val Gly Leu Val
    290                 295                 300

Gly Asn Ser Ala Leu Gly Cys Leu Asn Glu His Gln Pro Leu Gln Arg
305                 310                 315                 320

Glu Asn Leu Glu Leu Val Ala Gln Asn Glu Lys Thr Leu Gln Met Ile
                325                 330                 335

Ala Gly Met Lys Ile Lys Glu Glu Leu Pro His Phe Val Gly Ser Asn
            340                 345                 350

Lys Pro Val Lys Asp Glu Tyr Met Leu Val Leu Ser Asn Lys Met Gln
        355                 360                 365

Lys Ile Val Asn Asn Asp Phe Asn Phe Asn Asp Val Asn Phe Arg Ile
    370                 375                 380

Leu Gly Ala Asn Val Lys Glu Leu Met Arg Asn Thr His Cys Ala Asn
385                 390                 395                 400

Phe Asn Asn Lys Asn Asn Gln Lys Asn Asn Asn Gln Lys Asn Asn Asn
```

```
                    405                 410                 415
Gln Asn Asn Asn Gln Lys Asn Asn Asn Gln Lys Asn Asn Asn Gln
                420                 425                 430

Lys Asn Asn Asn Gln Lys Asn Asn Asn Gln Asn Thr Asn Asn
                435                 440                 445

<210> SEQ ID NO 5
<211> LENGTH: 433
<212> TYPE: PRT
<213> ORGANISM: Apis cerana

<400> SEQUENCE: 5

Met Thr Arg Trp Leu Phe Met Val Val Cys Leu Gly Ile Val Cys Gln
1               5                   10                  15

Gly Thr Thr Ser Ser Ile Leu Arg Gly Glu Ser Leu Asn Lys Ser Leu
                20                  25                  30

Ser Val Leu His Glu Trp Lys Phe Phe Asp Tyr Asp Phe Asp Ser Asp
            35                  40                  45

Glu Arg Arg Gln Asp Ala Ile Leu Ser Gly Glu Tyr Asp Tyr Arg Lys
        50                  55                  60

Asn Tyr Pro Ser Asp Val Asp Gln Trp His Gly Lys Ile Phe Val Thr
65                  70                  75                  80

Met Leu Arg Tyr Asn Gly Val Pro Ser Leu Asn Val Ile Ser Lys
                85                  90                  95

Lys Ile Gly Asp Gly Gly Pro Leu Leu Gln Pro Tyr Pro Asp Trp Ser
            100                 105                 110

Phe Ala Lys Tyr Asp Asp Cys Ser Gly Ile Val Ser Ala Thr Lys Leu
        115                 120                 125

Ala Ile Asp Lys Cys Asp Arg Leu Trp Val Leu Asp Ser Gly Leu Val
    130                 135                 140

Asn Asn Thr Gln Pro Met Cys Ser Pro Lys Leu Leu Thr Phe Asp Leu
145                 150                 155                 160

Thr Thr Ser Gln Leu Leu Lys Gln Val Glu Ile Pro His Asp Val Ala
                165                 170                 175

Val Asn Ala Thr Thr Gly Lys Gly Arg Leu Ser Ser Leu Ala Val Gln
            180                 185                 190

Pro Leu Asp Cys Asn Ile Asn Gly Asp Thr Met Val Tyr Ile Ala Asp
        195                 200                 205

Glu Lys Gly Glu Gly Leu Ile Val Tyr His Asp Ser Asp Asn Ser Phe
    210                 215                 220

His Arg Leu Thr Ser Lys Thr Phe Asp Tyr Asp Pro Lys Phe Thr Lys
225                 230                 235                 240

Met Thr Ile Asn Gly Glu Ser Phe Thr Thr Gln Ser Gly Ile Ser Gly
                245                 250                 255

Met Ala Leu Ser Pro Met Thr Asn Asn Leu Tyr Tyr Ser Pro Val Ala
            260                 265                 270

Ser Thr Ser Leu Tyr Tyr Val Asn Thr Glu Gln Phe Arg Thr Ser Asn
        275                 280                 285

Tyr Glu Gln Asn Ala Val His Tyr Glu Gly Val Gln Asn Ile Leu Asp
    290                 295                 300

Thr Gln Ser Ser Ala Lys Val Val Ser Lys Ser Gly Val Leu Phe Phe
305                 310                 315                 320

Gly Leu Val Gly Asp Ser Ala Leu Gly Cys Trp Asn Glu His Arg Ser
                325                 330                 335
```

```
Leu Glu Arg His Asn Ile Arg Thr Val Ala Gln Ser Asp Glu Thr Leu
                340                 345                 350

Gln Met Ile Val Gly Met Lys Ile Lys Glu Ala Leu Pro His Val Pro
            355                 360                 365

Ile Phe Asp Arg Tyr Ile Asn Arg Glu Tyr Ile Leu Val Leu Ser Asn
        370                 375                 380

Arg Met Gln Lys Met Ala Asn Asn Asp Tyr Asn Phe Asn Asp Val Asn
385                 390                 395                 400

Phe Arg Ile Met Asp Ala Asn Val Asn Asp Leu Ile Leu Asn Thr Arg
                405                 410                 415

Cys Glu Asn Pro Asn Asn Asp Asn Thr Pro Phe Lys Ile Ser Ile His
            420                 425                 430

Leu
```

<210> SEQ ID NO 6
<211> LENGTH: 192
<212> TYPE: PRT
<213> ORGANISM: Apis dorsata

<400> SEQUENCE: 6

```
Trp Lys Leu Val Asp Tyr Asp Phe Gly Ser Asn Glu Arg Arg Glu Asn
1               5                   10                  15

Ala Ile Leu Ser Gly Glu Tyr Asp Tyr Thr Lys Asn Tyr Pro Ser Asp
            20                  25                  30

Val Asp Glu Trp His Gly Lys Ile Phe Val Ser Met Leu Arg Tyr Asn
        35                  40                  45

Gly Val Pro Ser Ser Leu Asn Val Ile Ser Lys Lys Ile Gly Lys Gly
    50                  55                  60

Gly Pro Leu Leu Gln Pro Tyr Pro Asp Trp Ser Phe Ala Lys Tyr Asp
65                  70                  75                  80

Asp Cys Ser Gly Ile Val Ser Ala Ser Gln Leu Ala Ile Asp Lys Cys
                85                  90                  95

Asp Arg Leu Trp Val Leu Asp Ser Gly Leu Val Asp Asn Thr Gln Pro
            100                 105                 110

Met Cys Ser Pro Lys Leu Val Thr Phe Asp Leu Thr Thr Ser Lys Leu
        115                 120                 125

Leu Lys Gln Val Glu Ile Pro His Asn Val Ala Val Asn Thr Thr Thr
    130                 135                 140

Gly Asn Gly Arg Leu Ser Ser Leu Ala Val Gln Pro Leu Asp Cys Asn
145                 150                 155                 160

Ile Asn Gly Asp Thr Met Val Tyr Ile Ala Asp Glu Lys Gly Glu Gly
                165                 170                 175

Leu Ile Val Tyr His Asn Ser Asp Asn Ser Phe Gln Arg Leu Ser Ser
            180                 185                 190
```

<210> SEQ ID NO 7
<211> LENGTH: 452
<212> TYPE: PRT
<213> ORGANISM: Apis mellifera

<400> SEQUENCE: 7

```
Met Thr Arg Trp Leu Phe Met Val Ala Cys Leu Gly Ile Ala Cys Gln
1               5                   10                  15

Gly Ala Ile Val Arg Glu Asn Ser Pro Arg Asn Leu Glu Lys Ser Leu
            20                  25                  30

Asn Val Ile His Glu Trp Lys Tyr Phe Asp Tyr Asp Phe Gly Ser Glu
```

```
                35                  40                  45
Glu Arg Arg Gln Ala Ala Ile Gln Ser Gly Glu Tyr Asp His Thr Lys
 50                  55                  60

Asn Tyr Pro Phe Asp Val Asp Gln Trp Arg Asp Lys Thr Phe Val Thr
 65                  70                  75                  80

Ile Leu Arg Tyr Asp Gly Val Pro Ser Thr Leu Asn Val Ile Ser Gly
                 85                  90                  95

Lys Thr Gly Lys Gly Gly Arg Leu Leu Lys Pro Tyr Pro Asp Trp Ser
                100                 105                 110

Phe Ala Glu Phe Lys Asp Cys Ser Lys Ile Val Ser Ala Phe Lys Ile
            115                 120                 125

Ala Ile Asp Lys Phe Asp Arg Leu Trp Val Leu Asp Ser Gly Leu Val
        130                 135                 140

Asn Arg Thr Val Pro Val Cys Ala Pro Lys Leu His Val Phe Asp Leu
145                 150                 155                 160

Lys Thr Ser Asn His Leu Lys Gln Ile Glu Ile Pro His Asp Ile Ala
                165                 170                 175

Val Asn Ala Thr Thr Gly Lys Gly Gly Leu Val Ser Leu Ala Val Gln
                180                 185                 190

Ala Ile Asp Leu Ala Asn Thr Leu Val Tyr Met Ala Asp His Lys Gly
        195                 200                 205

Asp Ala Leu Ile Val Tyr Gln Asn Ala Asp Asp Ser Phe His Arg Leu
    210                 215                 220

Thr Ser Asn Thr Phe Asp Tyr Asp Pro Arg Tyr Ala Lys Met Thr Ile
225                 230                 235                 240

Asp Gly Glu Ser Phe Thr Leu Lys Asn Gly Ile Cys Gly Met Ala Leu
                245                 250                 255

Ser Pro Val Thr Asn Asn Leu Tyr Tyr Ser Pro Leu Ala Ser His Gly
                260                 265                 270

Leu Tyr Tyr Val Asn Thr Ala Pro Phe Met Lys Ser Gln Phe Gly Glu
            275                 280                 285

Asn Asn Val Gln Tyr Gln Gly Ser Glu Asp Ile Leu Asn Thr Gln Ser
        290                 295                 300

Leu Ala Lys Ala Val Ser Lys Asn Gly Val Leu Phe Val Gly Leu Val
305                 310                 315                 320

Gly Asn Ser Ala Val Gly Cys Trp Asn Glu His Gln Ser Leu Gln Arg
                325                 330                 335

Gln Asn Leu Glu Met Val Ala Gln Asn Asp Arg Thr Leu Gln Met Ile
            340                 345                 350

Ala Gly Met Lys Ile Lys Glu Glu Leu Pro His Phe Val Gly Ser Asn
        355                 360                 365

Lys Pro Val Lys Asp Glu Tyr Met Leu Val Leu Ser Asn Arg Met Gln
    370                 375                 380

Lys Ile Val Asn Asp Asp Phe Asn Phe Asp Asp Val Asn Phe Arg Ile
385                 390                 395                 400

Leu Gly Ala Asn Val Lys Glu Leu Ile Arg Asn Thr His Cys Val Asn
                405                 410                 415

Asn Asn Gln Asn Asp Asn Ile Gln Asn Thr Asn Gln Asn Asp Asn
                420                 425                 430

Asn Gln Lys Asn Asn Lys Lys Asn Ala Asn Asn Gln Lys Asn Asn Asn
            435                 440                 445

Gln Asn Asp Asn
    450
```

```
<210> SEQ ID NO 8
<211> LENGTH: 435
<212> TYPE: PRT
<213> ORGANISM: Apis mellifera

<400> SEQUENCE: 8

Ala Ile Val Arg Glu Asn Ser Pro Arg Asn Leu Glu Lys Ser Leu Asn
1               5                   10                  15

Val Ile His Glu Trp Lys Tyr Phe Asp Tyr Asp Phe Gly Ser Glu Glu
            20                  25                  30

Arg Arg Gln Ala Ala Ile Gln Ser Gly Glu Tyr Asp His Thr Lys Asn
        35                  40                  45

Tyr Pro Phe Asp Val Asp Gln Trp Arg Asp Lys Thr Phe Val Thr Ile
    50                  55                  60

Leu Arg Tyr Asp Gly Val Pro Ser Thr Leu Asn Val Ile Ser Gly Lys
65                  70                  75                  80

Thr Gly Lys Gly Gly Arg Leu Leu Lys Pro Tyr Pro Asp Trp Ser Phe
                85                  90                  95

Ala Glu Phe Lys Asp Cys Ser Lys Ile Val Ser Ala Phe Lys Ile Ala
            100                 105                 110

Ile Asp Lys Phe Asp Arg Leu Trp Val Leu Asp Ser Gly Leu Val Asn
        115                 120                 125

Arg Thr Val Pro Val Cys Ala Pro Lys Leu His Val Phe Asp Leu Lys
130                 135                 140

Thr Ser Asn His Leu Lys Gln Ile Glu Ile Pro His Asp Ile Ala Val
145                 150                 155                 160

Asn Ala Thr Thr Gly Lys Gly Gly Leu Val Ser Leu Ala Val Gln Ala
                165                 170                 175

Ile Asp Leu Ala Asn Thr Leu Val Tyr Met Ala Asp His Lys Gly Asp
            180                 185                 190

Ala Leu Ile Val Tyr Gln Asn Ala Asp Asp Ser Phe His Arg Leu Thr
        195                 200                 205

Ser Asn Thr Phe Asp Tyr Asp Pro Arg Tyr Ala Lys Met Thr Ile Asp
210                 215                 220

Gly Glu Ser Phe Thr Leu Lys Asn Gly Ile Cys Gly Met Ala Leu Ser
225                 230                 235                 240

Pro Val Thr Asn Asn Leu Tyr Tyr Ser Pro Leu Ala Ser His Gly Leu
                245                 250                 255

Tyr Tyr Val Asn Thr Ala Pro Phe Met Lys Ser Gln Phe Gly Glu Asn
            260                 265                 270

Asn Val Gln Tyr Gln Gly Ser Glu Asp Ile Leu Asn Thr Gln Ser Leu
        275                 280                 285

Ala Lys Ala Val Ser Lys Asn Gly Val Leu Phe Val Gly Leu Val Gly
290                 295                 300

Asn Ser Ala Val Gly Cys Trp Asn Glu His Gln Ser Leu Gln Arg Gln
305                 310                 315                 320

Asn Leu Glu Met Val Ala Gln Asn Asp Arg Thr Leu Gln Met Ile Ala
                325                 330                 335

Gly Met Lys Ile Lys Glu Glu Leu Pro His Phe Val Gly Ser Asn Lys
            340                 345                 350

Pro Val Lys Asp Glu Tyr Met Leu Val Leu Ser Asn Arg Met Gln Lys
        355                 360                 365

Ile Val Asn Asp Asp Phe Asn Phe Asp Asp Val Asn Phe Arg Ile Leu
```

```
                370             375             380
Gly Ala Asn Val Lys Glu Leu Ile Arg Asn Thr His Cys Val Asn Asn
385                 390                 395                 400

Asn Gln Asn Asp Asn Ile Gln Asn Thr Asn Asn Gln Asn Asp Asn Asn
                405                 410                 415

Gln Lys Asn Asn Lys Lys Asn Ala Asn Asn Gln Lys Asn Asn Asn Gln
            420                 425                 430

Asn Asp Asn
        435

<210> SEQ ID NO 9
<211> LENGTH: 485
<212> TYPE: PRT
<213> ORGANISM: Apis cerana

<400> SEQUENCE: 9

Met Thr Lys Trp Leu Leu Met Ala Cys Leu Gly Ile Ala Cys Gln
1               5                   10                  15

Asn Ile Arg Gly Ala Val Val Arg Glu Asn Ser Ser Arg Lys Lys Leu
                20                  25                  30

Thr Asn Thr Leu Asn Val Ile His Glu Trp Lys Tyr Val Asp Tyr Asp
            35                  40                  45

Phe Gly Ser Asp Glu Lys Arg Gln Ala Ala Ile Gln Ser Gly Glu Tyr
50                  55                  60

Asp Arg Thr Lys Asn Tyr Pro Leu Asp Val Asp Gln Trp His Asp Lys
65                  70                  75                  80

Thr Phe Val Thr Met Leu Arg Tyr Asp Gly Val Pro Ser Ser Leu Asn
                85                  90                  95

Val Val Ser Asp Lys Thr Gly Asn Gly Gly Pro Leu Leu Gln Pro Tyr
            100                 105                 110

Pro Asp Trp Ser Phe Ala Lys Tyr Glu Asp Cys Ser Gly Ile Val Ser
        115                 120                 125

Ala Asn Lys Ile Ala Ile Asp Glu Tyr Glu Arg Leu Trp Val Leu Asp
130                 135                 140

Ser Gly Leu Val Asn Asn Ile Gln Pro Met Cys Ser Pro Lys Leu Leu
145                 150                 155                 160

Ala Phe Asp Leu Thr Thr Ser Lys Leu Leu Lys Gln Val Glu Ile Pro
                165                 170                 175

His Asp Val Ala Val Asn Ala Thr Thr Gly Lys Gly Gly Leu Ala Ser
            180                 185                 190

Leu Ala Val Gln Ala Met Asp Ser Val Asn Thr Met Val Tyr Met Ala
        195                 200                 205

Asp Asn Lys Asp Asp Ala Leu Ile Val Tyr Gln Asn Ala Asp Asp Ser
210                 215                 220

Phe His Arg Leu Ser Ser His Ile Ser Asn His Asn Phe Arg Ser Asp
225                 230                 235                 240

Lys Met Ser Gln Glu Asn Leu Thr Leu Lys Glu Val Asp Asn Arg Val
                245                 250                 255

Phe Gly Met Ala Leu Ser Ser Val Thr His Asn Leu Tyr Tyr Ser Pro
            260                 265                 270

Leu Ser Ser Gln Asn Leu Tyr Tyr Val Asn Thr Thr Ser Leu Met Asn
        275                 280                 285

Ser Gln Asn Gln Gly Asn Asp Val Gln Tyr Glu Ser Val Gln Asp Val
290                 295                 300
```

```
Phe Ser Ser Gln Leu Ser Ala Lys Ala Val Ser Lys Asn Gly Val Leu
305                 310                 315                 320

Phe Phe Gly Phe Thr Asn Asn Thr Leu Gly Cys Trp Asn Glu His Gln
            325                 330                 335

Ser Leu Asp Arg Gln Asn Ile Asp Ile Val Ala Arg Asn Glu Thr Leu
        340                 345                 350

Gln Met Val Val Gly Met Lys Ile Lys Gln Asn Leu Pro Gln Ser Gly
            355                 360                 365

Lys Val Asn Asn Thr Gln Arg Asn Glu His Leu Leu Ala Leu Thr Asn
        370                 375                 380

Lys Lys Gln Asp Val Leu Asn Asn Asp Leu Asn Leu Glu His Val Asn
385                 390                 395                 400

Phe Gln Ile Leu Asp Ala Asn Val Asn Asp Leu Ile Arg Asn Ser Arg
            405                 410                 415

Cys Ala Asn Ser Asp Asn Gln Asp Asn Asn Gln His Asn Tyr Asn His
            420                 425                 430

Asn Gln Val Arg His Ser Ser Lys Ser Asp Asn Gln Asn Asn Asn Gln
        435                 440                 445

His Asn Asn Gln Ala Tyr His Ser Ser Lys Ser Asp Asn Trp Asp Asn
450                 455                 460

Asn Asn Asn Gln Ala His His Ser Ser Lys Phe Asp Asn Gln Asn Asn
465                 470                 475                 480

Asn Gln Tyr Asn Asn
            485

<210> SEQ ID NO 10
<211> LENGTH: 463
<212> TYPE: PRT
<213> ORGANISM: Apis cerana

<400> SEQUENCE: 10

Met Thr Arg Trp Leu Phe Met Val Ala Cys Leu Gly Ile Ala Cys Gln
1               5                   10                  15

Gly Ala Ile Ile Arg Gln Asn Ser Ala Lys Asn Leu Glu Asn Ser Leu
            20                  25                  30

Asn Val Ile His Glu Trp Lys Tyr Ile Asp Tyr Asp Phe Gly Ser Glu
        35                  40                  45

Glu Arg Arg Gln Ala Ala Ile Gln Ser Gly Tyr Asp His Thr Lys
    50                  55                  60

Asn Tyr Pro Phe Asp Val Asp Gln Trp His Asp Lys Thr Phe Val Thr
65              70                  75                  80

Ile Leu Lys Tyr Asp Gly Val Pro Ser Thr Leu Asn Met Ile Ser Asn
            85                  90                  95

Lys Ile Gly Lys Gly Gly Arg Leu Leu Gln Pro Tyr Pro Asp Trp Ser
        100                 105                 110

Trp Ala Glu Asn Lys Asp Cys Ser Gly Ile Val Ser Ala Phe Lys Ile
    115                 120                 125

Ala Ile Asp Lys Phe Asp Arg Leu Trp Val Leu Asp Ser Gly Leu Ile
130                 135                 140

Asn Arg Thr Glu Pro Ile Cys Ala Pro Lys Leu His Val Phe Asp Leu
145                 150                 155                 160

Lys Asn Thr Lys His Leu Lys Gln Ile Glu Ile Pro His Asp Ile Ala
            165                 170                 175

Val Asn Ala Thr Thr Gly Lys Gly Gly Leu Val Ser Leu Val Val Gln
        180                 185                 190
```

```
Ala Met Asp Pro Met Asn Thr Leu Val Tyr Ile Ala Asp His Lys Gly
        195                 200                 205

Asp Ala Leu Ile Val Tyr Gln Asn Ser Asp Ser Phe His Arg Met
    210                 215                 220

Thr Ser Asn Thr Phe Asp Tyr Asp Pro Arg Tyr Ala Lys Met Thr Ile
225                 230                 235                 240

Asn Gly Glu Ser Phe Thr Leu Lys Asn Gly Ile Cys Gly Met Ala Leu
                245                 250                 255

Ser Pro Val Thr Asn Asn Leu Tyr Tyr Ser Pro Leu Ala Ser His Gly
            260                 265                 270

Leu Tyr Tyr Val Asn Thr Glu Pro Phe Met Lys Ser Gln Phe Gly Asp
        275                 280                 285

Asn Asn Asn Val Gln Tyr Glu Gly Ser Gln Asp Thr Leu Asn Thr Gln
    290                 295                 300

Ser Leu Ala Lys Ala Val Ser Lys Asp Gly Val Leu Phe Val Gly Leu
305                 310                 315                 320

Val Gly Asn Ser Ala Leu Gly Cys Leu Asn Glu His Gln Pro Leu Gln
                325                 330                 335

Arg Glu Asn Leu Glu Leu Val Ala Gln Asn Glu Lys Thr Leu Gln Met
            340                 345                 350

Ile Ala Gly Met Lys Ile Lys Glu Glu Leu Pro His Phe Val Gly Ser
        355                 360                 365

Asn Lys Pro Val Lys Asp Glu Tyr Met Leu Val Leu Ser Asn Lys Met
    370                 375                 380

Gln Lys Ile Val Asn Asn Asp Phe Asn Phe Asn Asp Val Asn Phe Arg
385                 390                 395                 400

Ile Leu Gly Ala Asn Val Lys Glu Leu Met Arg Asn Thr His Cys Ala
                405                 410                 415

Asn Phe Asn Asn Lys Asn Asn Gln Lys Asn Asn Asn Gln Lys Asn Asn
            420                 425                 430

Asn Gln Asn Asn Asn Gln Lys Asn Asn Asn Gln Lys Asn Asn Asn
        435                 440                 445

Gln Lys Asn Asn Asn Gln Lys Asn Asn Asn Gln Asn Thr Asn Asn
    450                 455                 460

<210> SEQ ID NO 11
<211> LENGTH: 544
<212> TYPE: PRT
<213> ORGANISM: Apis mellifera

<400> SEQUENCE: 11

Met Thr Lys Trp Leu Leu Leu Val Val Cys Leu Gly Ile Ala Cys Gln
1               5                   10                  15

Asp Val Thr Ser Ala Ala Val Asn His Gln Arg Lys Ser Ala Asn Asn
            20                  25                  30

Leu Ala His Ser Met Lys Val Ile Tyr Glu Trp Lys His Ile Asp Phe
        35                  40                  45

Asp Phe Gly Ser Asp Glu Arg Arg Asp Ala Ala Ile Lys Ser Gly Glu
    50                  55                  60

Phe Asp His Thr Lys Asn Tyr Pro Phe Asp Val Asp Arg Trp Arg Asp
65                  70                  75                  80

Lys Thr Phe Val Thr Ile Glu Arg Asn Asn Gly Val Pro Ser Ser Leu
                85                  90                  95

Asn Val Val Thr Asn Lys Lys Gly Lys Gly Gly Pro Leu Leu Arg Pro
```

```
            100                 105                 110
Tyr Pro Asp Trp Ser Phe Ala Lys Tyr Glu Asp Cys Ser Gly Ile Val
        115                 120                 125
Ser Ala Phe Lys Ile Ala Val Asp Lys Phe Asp Arg Leu Trp Val Leu
        130                 135                 140
Asp Ser Gly Leu Val Asn Asn Gln Pro Met Cys Ser Pro Lys Leu
145                 150                 155                 160
Leu Thr Phe Asp Leu Lys Thr Ser Lys Leu Val Lys Gln Val Glu Ile
                165                 170                 175
Pro His Asn Ile Ala Val Asn Ala Thr Thr Gly Met Gly Glu Leu Val
                180                 185                 190
Ser Leu Ala Val Gln Ala Ile Asp Arg Thr Asn Thr Met Val Tyr Ile
                195                 200                 205
Ala Asp Glu Lys Gly Glu Gly Leu Ile Met Tyr Gln Asn Ser Asp Asp
        210                 215                 220
Ser Phe His Arg Leu Thr Ser Asn Thr Phe Asp Tyr Asp Pro Arg Tyr
225                 230                 235                 240
Thr Lys Leu Thr Val Ala Gly Glu Ser Phe Thr Val Lys Asn Gly Ile
                245                 250                 255
Tyr Gly Ile Ala Leu Ser Pro Val Thr Asn Asn Leu Tyr Tyr Ser Pro
                260                 265                 270
Leu Leu Ser His Gly Leu Tyr Tyr Val Asp Thr Glu Gln Phe Ser Asn
        275                 280                 285
Pro Gln Tyr Glu Glu Asn Asn Val Gln Tyr Glu Gly Ser Gln Asp Ile
        290                 295                 300
Leu Asn Thr Gln Ser Phe Gly Lys Val Val Ser Lys Asn Gly Val Leu
305                 310                 315                 320
Phe Leu Gly Leu Val Gly Asn Ser Gly Ile Ala Cys Val Asn Glu His
                325                 330                 335
Gln Val Leu Gln Arg Glu Ser Phe Asp Val Val Ala Gln Asn Glu Glu
            340                 345                 350
Thr Leu Gln Met Ile Val Ser Met Lys Ile Met Glu Asn Leu Pro Gln
            355                 360                 365
Ser Gly Arg Ile Asn Asp Pro Glu Gly Asn Glu Tyr Met Leu Ala Leu
        370                 375                 380
Ser Asn Arg Met Gln Lys Ile Ile Asn Asn Asp Phe Asn Phe Asn Asp
385                 390                 395                 400
Val Asn Phe Arg Ile Leu Gly Ala Asn Val Asp Asp Leu Met Arg Asn
                405                 410                 415
Thr Arg Cys Gly Arg Tyr His Asn Gln Asn Ala Gly Asn Gln Asn Ala
            420                 425                 430
Asp Asn Gln Asn Ala Asp Asn Gln Asn Ala Asn Gln Asn Ala Asp
        435                 440                 445
Asn Gln Asn Ala Asn Lys Gln Asn Gly Asn Arg Gln Asn Asp Asn Arg
450                 455                 460
Gln Asn Asp Asn Lys Gln Asn Gly Asn Arg Gln Asn Asp Asn Lys Gln
465                 470                 475                 480
Asn Gly Asn Arg Gln Asn Asp Asn Lys Gln Asn Gly Asn Arg Gln Asn
                485                 490                 495
Gly Asn Lys Gln Asn Asp Asn Lys Gln Asn Gly Asn Arg Gln Asn Asp
            500                 505                 510
Asn Lys Arg Asn Gly Asn Arg Gln Asn Asp Asn Gln Asn Asn Gln Asn
        515                 520                 525
```

Asp Asn Asn Arg Asn Asp Asn Gln Val His His Ser Lys Leu His
      530                 535                 540

<210> SEQ ID NO 12
<211> LENGTH: 523
<212> TYPE: PRT
<213> ORGANISM: Apis mellifera

<400> SEQUENCE: 12

Ala Val Asn His Gln Arg Lys Ser Ala Asn Asn Leu Ala His Ser Met
1               5                   10                  15

Lys Val Ile Tyr Glu Trp Lys His Ile Asp Phe Asp Phe Gly Ser Asp
            20                  25                  30

Glu Arg Arg Asp Ala Ala Ile Lys Ser Gly Glu Phe Asp His Thr Lys
        35                  40                  45

Asn Tyr Pro Phe Asp Val Asp Arg Trp Arg Asp Lys Thr Phe Val Thr
    50                  55                  60

Ile Glu Arg Asn Asn Gly Val Pro Ser Ser Leu Asn Val Val Thr Asn
65                  70                  75                  80

Lys Lys Gly Lys Gly Gly Pro Leu Leu Arg Pro Tyr Pro Asp Trp Ser
                85                  90                  95

Phe Ala Lys Tyr Glu Asp Cys Ser Gly Ile Val Ser Ala Phe Lys Ile
            100                 105                 110

Ala Val Asp Lys Phe Asp Arg Leu Trp Val Leu Asp Ser Gly Leu Val
        115                 120                 125

Asn Asn Asn Gln Pro Met Cys Ser Pro Lys Leu Leu Thr Phe Asp Leu
130                 135                 140

Lys Thr Ser Lys Leu Val Lys Gln Val Glu Ile Pro His Asn Ile Ala
145                 150                 155                 160

Val Asn Ala Thr Thr Gly Met Gly Glu Leu Val Ser Leu Ala Val Gln
                165                 170                 175

Ala Ile Asp Arg Thr Asn Thr Met Val Tyr Ile Ala Asp Glu Lys Gly
            180                 185                 190

Glu Gly Leu Ile Met Tyr Gln Asn Ser Asp Asp Ser Phe His Arg Leu
        195                 200                 205

Thr Ser Asn Thr Phe Asp Tyr Asp Pro Arg Tyr Thr Lys Leu Thr Val
    210                 215                 220

Ala Gly Glu Ser Phe Thr Val Lys Asn Gly Ile Tyr Gly Ile Ala Leu
225                 230                 235                 240

Ser Pro Val Thr Asn Asn Leu Tyr Tyr Ser Pro Leu Leu Ser His Gly
                245                 250                 255

Leu Tyr Tyr Val Asp Thr Glu Gln Phe Ser Asn Pro Gln Tyr Glu Glu
            260                 265                 270

Asn Asn Val Gln Tyr Glu Gly Ser Gln Asp Ile Leu Asn Thr Gln Ser
        275                 280                 285

Phe Gly Lys Val Val Ser Lys Asn Gly Val Leu Phe Leu Gly Leu Val
    290                 295                 300

Gly Asn Ser Gly Ile Ala Cys Val Asn Glu His Gln Val Leu Gln Arg
305                 310                 315                 320

Glu Ser Phe Asp Val Val Ala Gln Asn Glu Thr Leu Gln Met Ile
                325                 330                 335

Val Ser Met Lys Ile Met Glu Asn Leu Pro Gln Ser Gly Arg Ile Asn
            340                 345                 350

Asp Pro Glu Gly Asn Glu Tyr Met Leu Ala Leu Ser Asn Arg Met Gln

```
                355                 360                 365
Lys Ile Ile Asn Asn Asp Phe Asn Phe Asn Asp Val Asn Phe Arg Ile
    370                 375                 380

Leu Gly Ala Asn Val Asp Asp Leu Met Arg Asn Thr Arg Cys Gly Arg
385                 390                 395                 400

Tyr His Asn Gln Asn Ala Gly Asn Gln Asn Ala Asp Asn Gln Asn Ala
                405                 410                 415

Asp Asn Gln Asn Ala Asn Asn Gln Asn Ala Asp Asn Gln Asn Ala Asn
                420                 425                 430

Lys Gln Asn Gly Asn Arg Gln Asn Asp Asn Arg Gln Asn Asp Asn Lys
                435                 440                 445

Gln Asn Gly Asn Arg Gln Asn Asp Asn Lys Gln Asn Gly Asn Arg Gln
                450                 455                 460

Asn Asp Asn Lys Gln Asn Gly Asn Arg Gln Asn Gly Asn Lys Gln Asn
465                 470                 475                 480

Asp Asn Lys Gln Asn Gly Asn Arg Gln Asn Asp Asn Lys Arg Asn Gly
                485                 490                 495

Asn Arg Gln Asn Asp Asn Gln Asn Asn Gln Asn Asp Asn Asn Arg Asn
                500                 505                 510

Asp Asn Gln Val His His Ser Ser Lys Leu His
                515                 520

<210> SEQ ID NO 13
<211> LENGTH: 608
<212> TYPE: PRT
<213> ORGANISM: Apis cerana

<400> SEQUENCE: 13

Met Thr Lys Trp Leu Leu Leu Val Val Cys Leu Gly Ile Ala Cys Gln
1               5                   10                  15

Asp Val Thr Ser Ala Ala Val Asn His Gln Arg Lys Ser Ser Lys Asn
                20                  25                  30

Leu Ala His Ser Met Lys Val Ile Tyr Glu Trp Lys His Ile Asp Tyr
            35                  40                  45

Asp Phe Gly Ser Val Glu Arg Arg Asp Ala Ala Ile Lys Ser Gly Glu
    50                  55                  60

Phe Asp His Thr Lys Asn Tyr Pro Phe Asp Val Asp Arg Trp Arg Asp
65              70                  75                  80

Lys Thr Phe Val Thr Val Glu Arg Phe Asp Gly Val Pro Ser Ser Leu
                85                  90                  95

Asn Val Val Thr Asn Lys Lys Gly Lys Gly Gly Pro Leu Leu His Pro
                100                 105                 110

Tyr Pro Asp Trp Ser Trp Ala Lys Tyr Lys Asp Cys Ser Gly Ile Val
            115                 120                 125

Ser Ala Phe Lys Ile Ala Val Asp Lys Phe Asp Arg Leu Trp Val Leu
    130                 135                 140

Asp Ser Gly Leu Val Asn Asn Gln Pro Met Cys Ser Pro Lys Leu
145                 150                 155                 160

Val Thr Phe Asp Leu Thr Thr Ser Lys Leu Leu Lys Gln Val Glu Ile
                165                 170                 175

Pro His Asn Ile Ala Val Asn Ala Thr Thr Gly Met Gly Glu Leu Val
            180                 185                 190

Ser Leu Ala Val Gln Ala Ile Asp Pro Thr Asn Thr Met Val Tyr Ile
    195                 200                 205
```

Ala Asp Glu Arg Gly Glu Ala Leu Ile Ile Tyr Gln Asn Ser Asp Asp
210                 215                 220

Ser Phe His Arg Leu Thr Ser Asn Thr Phe Asp Tyr Asp Pro Arg Tyr
225                 230                 235                 240

Thr Lys Leu Thr Val Ala Gly Glu Ser Phe Thr Val Lys Asn Gly Ile
                245                 250                 255

Cys Gly Ile Ala Leu Ser Pro Val Thr Asn Asn Leu Tyr Tyr Ser Pro
                260                 265                 270

Leu Ala Ser His Ser Leu Tyr Tyr Val Asn Thr Glu Gln Phe Arg Asn
                275                 280                 285

Pro Gln Tyr Glu Glu Asn Asn Val Gln Tyr Glu Gly Ser Gln Asp Ile
290                 295                 300

Leu Asn Thr Gln Ser Phe Ala Lys Ala Val Ser Lys Asn Gly Val Val
305                 310                 315                 320

Phe Leu Gly Leu Val Ser Asn Ser Ala Val Gly Cys Val Asn Glu His
                325                 330                 335

Gln Val Leu Gln Lys Glu Asn Phe Asp Val Val Ala Gln Asn Glu Glu
                340                 345                 350

Thr Leu Gln Met Ile Val Ser Met Lys Ile Met Gln Asp Leu Pro Gln
                355                 360                 365

Ser Gly Arg Ile Asn Asp Pro Gly Asn Glu Tyr Met Leu Ala Leu Ser
370                 375                 380

Asn Lys Met Gln Lys Ile Ile Asn Asn Asp Phe Asn Phe Asn Asp Val
385                 390                 395                 400

Asn Phe Arg Ile Leu Gly Ala Asn Val Asn Asp Leu Thr Arg Asn Thr
                405                 410                 415

Arg Cys Ala Lys Ser Asn Asn Gln Asn Ala Asn Asn Gln Asn Ala Asn
                420                 425                 430

Asn Gln Asn Ala Asn Asn Gln Asn Ala Asn Asn Gln Asn Ala Asn Asn
                435                 440                 445

Gln Asn Asp Asn Asn Gln Asn Asp Asn Gly Asn Asn Arg Arg Asn Gly
450                 455                 460

Asn Asn Gln Asn Gly Asn Arg Gln Asn Asp Asn Lys Gln Asn Asp Asn
465                 470                 475                 480

Lys Gln Asn Ala Asn Lys Gln Asn Ala Asn Lys Gln Asn Asp Asn Lys
                485                 490                 495

Gln Asn Asp Asn Lys Gln Asn Gly Asn Arg Gln Asn Asp Asn Arg Gln
                500                 505                 510

Asn Asp Asn Lys Gln Asn Asp Asn Arg Gln Asn Asp Asn Lys Gln Asn
                515                 520                 525

Gly Asn Arg Gln Asn Asp Asn Arg Gln Asn Asp Asn Gln Arg Asn Gly
530                 535                 540

Asn Arg Gln Asn Asp Asn Arg Gln Asn Asp Asn Lys Arg Asn Gly Asn
545                 550                 555                 560

Arg Gln Asn Asp Asn Arg Gln Asn Asp Asn Lys Arg Asn Gly Asn Arg
                565                 570                 575

Gln Asn Asp Asn Lys Gln Asn Asp Asn Arg Gln Asn Asp Asn Asn Gln
                580                 585                 590

Asn Asn Asn Gln Asn Asp Asn Asn Arg Asn Asn Gln Ala His His Ser
                595                 600                 605

<210> SEQ ID NO 14
<211> LENGTH: 588
<212> TYPE: PRT

<213> ORGANISM: Apis cerana

<400> SEQUENCE: 14

```
Ala Ala Val Asn His Gln Arg Lys Ser Ser Lys Asn Leu Ala His Ser
1               5                   10                  15

Met Lys Val Ile Tyr Glu Trp Lys His Ile Asp Tyr Asp Phe Gly Ser
            20                  25                  30

Val Glu Arg Arg Asp Ala Ala Ile Lys Ser Gly Glu Phe Asp His Thr
        35                  40                  45

Lys Asn Tyr Pro Phe Asp Val Asp Arg Trp Arg Asp Lys Thr Phe Val
    50                  55                  60

Thr Val Glu Arg Phe Asp Gly Val Pro Ser Ser Leu Asn Val Val Thr
65                  70                  75                  80

Asn Lys Lys Gly Lys Gly Gly Pro Leu Leu His Pro Tyr Pro Asp Trp
                85                  90                  95

Ser Trp Ala Lys Tyr Lys Asp Cys Ser Gly Ile Val Ser Ala Phe Lys
            100                 105                 110

Ile Ala Val Asp Lys Phe Asp Arg Leu Trp Val Leu Asp Ser Gly Leu
        115                 120                 125

Val Asn Asn Gln Pro Met Cys Ser Pro Lys Leu Val Thr Phe Asp
130                 135                 140

Leu Thr Thr Ser Lys Leu Leu Lys Gln Val Glu Ile Pro His Asn Ile
145                 150                 155                 160

Ala Val Asn Ala Thr Thr Gly Met Gly Glu Leu Val Ser Leu Ala Val
                165                 170                 175

Gln Ala Ile Asp Pro Thr Asn Thr Met Val Tyr Ile Ala Asp Glu Arg
            180                 185                 190

Gly Glu Ala Leu Ile Ile Tyr Gln Asn Ser Asp Asp Ser Phe His Arg
        195                 200                 205

Leu Thr Ser Asn Thr Phe Asp Tyr Asp Pro Arg Tyr Thr Lys Leu Thr
210                 215                 220

Val Ala Gly Glu Ser Phe Thr Val Lys Asn Gly Ile Cys Gly Ile Ala
225                 230                 235                 240

Leu Ser Pro Val Thr Asn Asn Leu Tyr Tyr Ser Pro Leu Ala Ser His
                245                 250                 255

Ser Leu Tyr Tyr Val Asn Thr Glu Gln Phe Arg Asn Pro Gln Tyr Glu
            260                 265                 270

Glu Asn Asn Val Gln Tyr Glu Gly Ser Gln Asp Ile Leu Asn Thr Gln
        275                 280                 285

Ser Phe Ala Lys Ala Val Ser Lys Asn Gly Val Val Phe Leu Gly Leu
290                 295                 300

Val Ser Asn Ser Ala Val Gly Cys Val Asn Glu His Gln Val Leu Gln
305                 310                 315                 320

Lys Glu Asn Phe Asp Val Val Ala Gln Asn Glu Glu Thr Leu Gln Met
                325                 330                 335

Ile Val Ser Met Lys Ile Met Gln Asp Leu Pro Gln Ser Gly Arg Ile
            340                 345                 350

Asn Asp Pro Gly Asn Glu Tyr Met Leu Ala Leu Ser Asn Lys Met Gln
        355                 360                 365

Lys Ile Ile Asn Asn Asp Phe Asn Phe Asn Asp Val Asn Phe Arg Ile
    370                 375                 380

Leu Gly Ala Asn Val Asn Asp Leu Thr Arg Asn Thr Arg Cys Ala Lys
385                 390                 395                 400
```

```
Ser Asn Asn Gln Asn Ala Asn Asn Gln Asn Ala Asn Asn Gln Asn Ala
                405                 410                 415

Asn Asn Gln Asn Ala Asn Asn Gln Asn Ala Asn Asn Gln Asn Asp Asn
            420                 425                 430

Asn Gln Asn Asp Asn Gly Asn Asn Arg Arg Asn Gly Asn Asn Gln Asn
        435                 440                 445

Gly Asn Arg Gln Asn Asp Asn Lys Gln Asn Asp Asn Lys Gln Asn Ala
    450                 455                 460

Asn Lys Gln Asn Ala Asn Lys Gln Asn Asp Asn Lys Gln Asn Asp Asn
465                 470                 475                 480

Lys Gln Asn Gly Asn Arg Gln Asn Asp Asn Arg Gln Asn Asp Asn Lys
            485                 490                 495

Gln Asn Asp Asn Arg Gln Asn Asp Asn Lys Gln Asn Gly Asn Arg Gln
        500                 505                 510

Asn Asp Asn Arg Gln Asn Asp Asn Gln Arg Asn Gly Asn Arg Gln Asn
        515                 520                 525

Asp Asn Arg Gln Asn Asp Asn Lys Arg Asn Gly Asn Arg Gln Asn Asp
        530                 535                 540

Asn Arg Gln Asn Asp Asn Lys Arg Asn Gly Asn Arg Gln Asn Asp Asn
545                 550                 555                 560

Lys Gln Asn Asp Asn Arg Gln Asn Asp Asn Gln Asn Asn Gln
            565                 570                 575

Asn Asp Asn Asn Arg Asn Asn Gln Ala His His Ser
            580                 585

<210> SEQ ID NO 15
<211> LENGTH: 523
<212> TYPE: PRT
<213> ORGANISM: Apis florea

<400> SEQUENCE: 15

Asp Val Thr Ser Ala Ala His Gln Lys Lys Ser Ser Glu Asp Leu Ala
1               5                   10                  15

His Ser Met Lys Val Ile Tyr Glu Trp Lys His Ile Asp Tyr Asp Phe
            20                  25                  30

Gly Ser Glu Glu Lys Arg Gln Ala Ala Ile Gln Ser Gly Glu Tyr Asp
        35                  40                  45

His Thr Lys Asn Tyr Pro Phe Asp Val Asp Arg Trp His Asp Lys Thr
    50                  55                  60

Phe Val Thr Val Glu Arg Phe Asn Gly Val Pro Ser Ser Leu Asn Val
65                  70                  75                  80

Ile Thr Asn Lys Lys Gly Lys Gly Pro Leu Leu Gln Pro Tyr Pro
            85                  90                  95

Asp Trp Ser Phe Ala Lys Tyr Glu Asp Cys Ser Gly Ile Val Asn Ala
            100                 105                 110

Phe Lys Ile Ala Ile Asp Lys Val Asp Arg Leu Trp Val Leu Asp Ser
        115                 120                 125

Gly Leu Val Asn Asn Asn Leu Met Cys Ser Pro Lys Leu Leu Thr
    130                 135                 140

Phe Asp Leu Asn Thr Ser Lys Leu Leu Lys Gln Val Glu Ile Pro His
145                 150                 155                 160

Asn Ile Ala Val Asn Ala Thr Thr Gly Met Gly Glu Leu Val Ser Leu
            165                 170                 175

Ala Val Gln Val Ile Asp Pro Thr Asn Thr Met Val Tyr Ile Ala Asp
        180                 185                 190
```

Glu Arg Gly Glu Gly Leu Ile Ile Tyr Gln Asn Ser Asp Asp Ser Phe
            195                 200                 205

His Arg Leu Thr Ser Asn Thr Phe Asp Tyr Asp Pro Arg Tyr Thr Lys
210                 215                 220

Leu Thr Val Ala Gly Glu Ser Phe Thr Val Lys Asn Gly Ile Cys Gly
225                 230                 235                 240

Ile Ala Leu Ser Pro Val Thr Asn Asn Leu Tyr Tyr Ser Pro Leu Ala
                245                 250                 255

Ser His Ser Leu Tyr Tyr Val Asn Thr Glu Pro Phe Met Lys Ser Gln
                260                 265                 270

Phe Glu Glu Asn Asn Val Gln Tyr Glu Gly Ser Gln Asp Ile Leu Asn
                275                 280                 285

Thr Gln Ser Phe Ala Lys Ala Val Ser Arg Asn Gly Val Leu Phe Val
        290                 295                 300

Gly Leu Val Ser Asn Ser Gly Val Gly Cys Val Asn Glu His Gln Val
305                 310                 315                 320

Leu Gln Lys Glu Asn Phe Asp Val Val Ala Gln Asn Glu Glu Thr Leu
                325                 330                 335

Gln Met Val Val Ser Met Lys Ile Met Gln Asp Arg Gln Gln Ser Arg
        340                 345                 350

Arg Ile Asn Lys Ser Gln Arg Asn Glu Tyr Met Leu Ala Leu Ser Asn
            355                 360                 365

Arg Met Gln Lys Ile Ile Asn Asn Asn Phe Asn Phe Asp Glu Val Asn
        370                 375                 380

Phe Arg Ile Leu Gly Ala Asn Val Asn Asp Leu Ile Arg Asn Thr Arg
385                 390                 395                 400

Cys Val Asn Ser Asn Gln Asn Ala Asn Gln Asn Ala Asn Asn
                405                 410                 415

Gln Asn Ala Asn Asn Gln Asn Ala Asn Ser Gln Asn Ala Asn Asn Gln
            420                 425                 430

Asn Gly Asn Lys Gln Ser Asp Asn Lys Gln Asn Gly Asn Met Gln Asn
            435                 440                 445

Asp Asn Met Gln Asn Gly Asn Lys Gln Asn Asp Asn Lys Gln Asn Gly
        450                 455                 460

Asn Arg Gln Asn Asp Asn Arg Gln Asn Gly Asn Arg Gln Asn Gly Asn
465                 470                 475                 480

Arg Gln Asn Gly Asn Arg Gln Asn Asp Asn Lys Gln Asn Glu Asn Arg
            485                 490                 495

Gln Asn Gly Lys Arg Gln Asn Asp Arg Gln Asn Asp Asp Asn Gln
                500                 505                 510

Asn Asn Gln Asn Gly Asn Asn Gln Asn Asp Asn
            515                 520

<210> SEQ ID NO 16
<211> LENGTH: 584
<212> TYPE: PRT
<213> ORGANISM: Apis dorsata

<400> SEQUENCE: 16

Asp Val Thr Ser Ala Ala Val Asn His Gln Arg Lys Ser Leu Asn Asn
1               5                   10                  15

Leu Ala Asn Ser Met Asn Val Ile Tyr Glu Trp Lys His Ile Asp Tyr
            20                  25                  30

Asp Phe Gly Ser Glu Glu Arg Gln Gln Ala Ala Ile Gln Ser Gly Glu

```
                35                  40                  45
Phe Asp His Thr Lys Asn Tyr Pro Phe Asp Val Asp Gln Trp His Asp
 50                  55                  60
Lys Ile Phe Val Thr Ile Glu Arg Leu Asn Gly Val Pro Ser Ser Leu
 65                  70                  75                  80
Asn Val Val Thr Asn Lys Lys Gly Lys Gly Pro Leu Leu Gln Pro
                 85                  90                  95
Tyr Pro Asn Trp Ser Phe Ala Lys Tyr Glu Asp Cys Ser Gly Ile Val
                100                 105                 110
Ser Ala Phe Lys Ile Ala Ile Asp Lys Phe Asp Arg Leu Trp Val Leu
                115                 120                 125
Asp Ser Gly Leu Val Asn Asn Gln Pro Met Cys Ser Pro Lys Leu Val
                130                 135                 140
Thr Phe Asp Leu Asn Thr Ser Lys Leu Val Lys Gln Val Glu Ile Pro
145                 150                 155                 160
His Asn Ile Ala Val Asn Ala Thr Thr Gly Met Gly Glu Leu Val Ser
                165                 170                 175
Leu Ala Val Gln Ala Ile Asp Pro Thr Asn Thr Met Val Tyr Ile Ala
                180                 185                 190
Asp Glu Lys Gly Gln Gly Leu Ile Ile Tyr Gln Asn Ser Asp Asp Ser
                195                 200                 205
Phe His Arg Leu Thr Ser Asn Thr Phe Asp Tyr Asp Pro Arg Tyr Thr
                210                 215                 220
Lys Leu Thr Val Ala Gly Glu Ser Phe Thr Val Gln Asn Gly Ile Cys
225                 230                 235                 240
Gly Ile Ala Leu Ser Pro Val Thr Asn Asn Leu Tyr Tyr Ser Pro Leu
                245                 250                 255
Ala Ser His Ala Leu Tyr Tyr Val Asn Thr Glu Gln Phe Arg Lys Pro
                260                 265                 270
Gln Tyr Asp Lys Asp Asn Val Gln Tyr Glu Gly Ser Gln Asp Ile Leu
                275                 280                 285
Asp Thr Gln Ser Phe Ala Lys Val Val Ser Lys Asp Gly Val Leu Phe
                290                 295                 300
Tyr Gly Leu Val Gly Asn Ser Gly Leu Gly Cys Val Asn Glu His Gln
305                 310                 315                 320
Val Leu Gln Arg Glu Ser Phe Asp Val Val Ala Gln Asn Glu Glu Thr
                325                 330                 335
Leu Gln Met Ile Val Ser Met Lys Ile Ile Gln Asn Ile Pro Gln Phe
                340                 345                 350
Arg Ile Lys Asp Leu Arg Asn Glu Tyr Met Leu Ala Leu Ser Asn Arg
                355                 360                 365
Met Gln Lys Ile Ile Thr Asn Asp Phe Asn Phe Glu Val Asn Phe
                370                 375                 380
Arg Ile Leu Gly Ala Asn Val Asn Asp Leu Ile Arg Asn Thr Arg Cys
385                 390                 395                 400
Glu Lys Ser Thr Asn Gln Asn Asp Asn Thr Gln Asn Val Asn Asn Gln
                405                 410                 415
Asn Val Asn Asn Gln Ala Asn Asn Gln Ala Asn Asn Gln Asn
                420                 425                 430
Ala Lys Asn Gln Asn Ala Lys Asn Gln Asn Ala Asn Asn Gln Asn Ala
                435                 440                 445
Asn Asn Gln Asn Asp Asn Lys Gln Asn Gly His Gln Gln Asn Asp Asn
                450                 455                 460
```

Gln Arg Asn Asp Asn Lys Gln Asn Val Asn Lys Gln Asn Val Asn Arg
465                 470                 475                 480

Gln Asn Asp Asn Arg Lys Asn Asp Asn Arg Gln Lys Asp Ser Arg Gln
            485                 490                 495

Asn Asp Asn Arg Gln Asn Asp Asn Arg Gln Asn Asp Asn Arg Gln Asn
        500                 505                 510

Asp Asn Arg Gln Asn Asp Asn Arg Gln Asn Asp Asn Arg Gln Asn Asp
    515                 520                 525

Asn Arg Gln Asn Asp Asn Arg Gln Asn Asp Asn Arg Gln Asn Asp Asn
530                 535                 540

Arg Gln Asn Asp Asn Lys Gln Asn Gly Asn Lys Gln Asn Gly Asn Lys
545                 550                 555                 560

Gln Asn Gly Asn Arg Gln Asn Gly Asn Lys Gln Asn Glu Asn Asn Arg
            565                 570                 575

Asn Asp Asn Asn Gln Asn Asp Asn
            580

<210> SEQ ID NO 17
<211> LENGTH: 464
<212> TYPE: PRT
<213> ORGANISM: Apis mellifera

<400> SEQUENCE: 17

Met Thr Lys Trp Leu Leu Leu Met Val Cys Leu Gly Ile Ala Cys Gln
1               5                   10                  15

Asn Ile Arg Gly Gly Val Val Arg Glu Asn Ser Ser Gly Lys Asn Leu
            20                  25                  30

Thr Asn Thr Leu Asn Val Ile His Lys Trp Lys Tyr Leu Asp Tyr Asp
        35                  40                  45

Phe Asp Asn Asp Glu Arg Arg Gln Ala Ala Ile Gln Ser Gly Glu Tyr
    50                  55                  60

Asp Arg Thr Lys Asn Tyr Pro Leu Asp Val Asp Gln Trp His Asn Lys
65                  70                  75                  80

Thr Phe Leu Ala Val Ile Arg Tyr Asn Gly Val Pro Ser Ser Leu Asn
            85                  90                  95

Val Val Ser Asp Lys Thr Gly Asn Gly Gly Arg Leu Leu Gln Pro Tyr
        100                 105                 110

Pro Asp Trp Ser Phe Ala Lys Tyr Glu Asp Cys Ser Gly Ile Val Ser
    115                 120                 125

Ala His Lys Ile Ala Ile Asp Glu Tyr Glu Arg Leu Trp Val Leu Asp
    130                 135                 140

Ser Gly Leu Val Asn Asn Thr Gln Pro Met Cys Ser Pro Lys Leu Phe
145                 150                 155                 160

Ala Phe Asp Leu Asn Thr Ser Gln Leu Leu Lys Gln Val Glu Ile Pro
            165                 170                 175

His Asp Val Ala Thr Thr Gly Lys Gly Glu Leu Val Ser Leu Thr Val
        180                 185                 190

Gln Ala Met Asp Ser Thr Asn Thr Met Val Tyr Met Val Asp Asn Lys
    195                 200                 205

Asn Thr Leu Ile Ile Tyr Gln Asn Ala Asp Asp Ser Phe His Arg Leu
    210                 215                 220

Ser Ser His Thr Leu Asn His Asn Ser Asp Lys Met Ser Asp Gln Gln
225                 230                 235                 240

Glu Asn Leu Thr Leu Lys Glu Val Asp Asn Lys Val Tyr Gly Met Ala

```
                        245                 250                 255
Leu Ser Pro Val Thr His Asn Leu Tyr Tyr Asn Ser Pro Ser Ser Glu
                    260                 265                 270

Asn Leu Tyr Tyr Val Asn Thr Glu Ser Leu Met Lys Ser Glu Asn Gln
                275                 280                 285

Gly Asn Asp Val Gln Tyr Glu Arg Val Gln Asp Val Phe Asp Ser Gln
            290                 295                 300

Leu Thr Val Lys Ala Val Ser Lys Asn Gly Val Leu Leu Phe Gly Leu
305                 310                 315                 320

Ala Asn Asn Thr Leu Ser Cys Trp Asn Glu His Gln Ser Leu Asp Arg
                325                 330                 335

Gln Asn Ile Asp Val Val Ala Arg Asn Glu Asp Thr Leu Gln Met Val
                340                 345                 350

Val Ser Met Lys Ile Lys Gln Asn Val Pro Gln Ser Gly Arg Val Asn
                355                 360                 365

Asn Thr Gln Arg Asn Glu Tyr Leu Leu Ala Leu Ser Asp Arg Asn Gln
            370                 375                 380

Asn Val Leu Asn Asn Asp Leu Asn Leu Glu His Val Asn Phe Gln Ile
385                 390                 395                 400

Leu Gly Ala Asn Val Asn Asp Leu Ile Arg Asn Ser Arg Cys Ala Asn
                405                 410                 415

Phe Asp Asn Gln Asp Asn Asn His Tyr Asn His Asn His Asn Gln Ala
                420                 425                 430

Arg His Ser Ser Lys Ser Asp Asn Gln Asn Asn Asn Gln His Asn Asp
                435                 440                 445

Gln Ala His His Ser Ser Lys Ser Asn Asn Arg His Asn Asn Asn Asp
450                 455                 460

<210> SEQ ID NO 18
<211> LENGTH: 444
<212> TYPE: PRT
<213> ORGANISM: Apis mellifera

<400> SEQUENCE: 18

Gly Val Val Arg Glu Asn Ser Ser Gly Lys Asn Leu Thr Asn Thr Leu
1               5                   10                  15

Asn Val Ile His Lys Trp Lys Tyr Leu Asp Tyr Asp Phe Asp Asn Asp
                20                  25                  30

Glu Arg Arg Gln Ala Ala Ile Gln Ser Gly Glu Tyr Asp Arg Thr Lys
            35                  40                  45

Asn Tyr Pro Leu Asp Val Asp Gln Trp His Asn Lys Thr Phe Leu Ala
        50                  55                  60

Val Ile Arg Tyr Asn Gly Val Pro Ser Ser Leu Asn Val Val Ser Asp
65                  70                  75                  80

Lys Thr Gly Asn Gly Gly Arg Leu Leu Gln Pro Tyr Pro Asp Trp Ser
                85                  90                  95

Phe Ala Lys Tyr Glu Asp Cys Ser Gly Ile Val Ser Ala His Lys Ile
                100                 105                 110

Ala Ile Asp Glu Tyr Glu Arg Leu Trp Val Leu Asp Ser Gly Leu Val
            115                 120                 125

Asn Asn Thr Gln Pro Met Cys Ser Pro Lys Leu Phe Ala Phe Asp Leu
        130                 135                 140

Asn Thr Ser Gln Leu Leu Lys Gln Val Glu Ile Pro His Asp Val Ala
145                 150                 155                 160
```

Thr Thr Gly Lys Gly Glu Leu Val Ser Leu Thr Val Gln Ala Met Asp
            165                 170                 175

Ser Thr Asn Thr Met Val Tyr Met Val Asp Asn Lys Asn Thr Leu Ile
            180                 185                 190

Ile Tyr Gln Asn Ala Asp Asp Ser Phe His Arg Leu Ser Ser His Thr
            195                 200                 205

Leu Asn His Asn Ser Asp Lys Met Ser Asp Gln Gln Glu Asn Leu Thr
            210                 215                 220

Leu Lys Glu Val Asp Asn Lys Val Tyr Gly Met Ala Leu Ser Pro Val
225                 230                 235                 240

Thr His Asn Leu Tyr Tyr Asn Ser Pro Ser Ser Glu Asn Leu Tyr Tyr
            245                 250                 255

Val Asn Thr Glu Ser Leu Met Lys Ser Glu Asn Gln Gly Asn Asp Val
            260                 265                 270

Gln Tyr Glu Arg Val Gln Asp Val Phe Asp Ser Gln Leu Thr Val Lys
            275                 280                 285

Ala Val Ser Lys Asn Gly Val Leu Leu Phe Gly Leu Ala Asn Asn Thr
            290                 295                 300

Leu Ser Cys Trp Asn Glu His Gln Ser Leu Asp Arg Gln Asn Ile Asp
305                 310                 315                 320

Val Val Ala Arg Asn Glu Asp Thr Leu Gln Met Val Val Ser Met Lys
            325                 330                 335

Ile Lys Gln Asn Val Pro Gln Ser Gly Arg Val Asn Asn Thr Gln Arg
            340                 345                 350

Asn Glu Tyr Leu Leu Ala Leu Ser Asp Arg Asn Gln Asn Val Leu Asn
            355                 360                 365

Asn Asp Leu Asn Leu Glu His Val Asn Phe Gln Ile Leu Gly Ala Asn
            370                 375                 380

Val Asn Asp Leu Ile Arg Asn Ser Arg Cys Ala Asn Phe Asp Asn Gln
385                 390                 395                 400

Asp Asn Asn His Tyr Asn His Asn His Asn Gln Ala Arg His Ser Ser
            405                 410                 415

Lys Ser Asp Asn Gln Asn Asn Asn Gln His Asn Asp Gln Ala His His
            420                 425                 430

Ser Ser Lys Ser Asn Asn Arg His Asn Asn Asn Asp
            435                 440

<210> SEQ ID NO 19
<211> LENGTH: 485
<212> TYPE: PRT
<213> ORGANISM: Apis cerana

<400> SEQUENCE: 19

Met Thr Lys Trp Leu Leu Leu Met Ala Cys Leu Gly Ile Ala Cys Gln
1               5                   10                  15

Asn Ile Arg Gly Ala Val Val Arg Glu Asn Ser Ser Arg Lys Lys Leu
            20                  25                  30

Thr Asn Thr Leu Asn Val Ile His Glu Trp Lys Tyr Val Asp Tyr Asp
            35                  40                  45

Phe Gly Ser Asp Glu Lys Arg Gln Ala Ala Ile Gln Ser Gly Glu Tyr
            50                  55                  60

Asp Arg Thr Lys Asn Tyr Pro Leu Asp Val Asp Gln Trp His Asp Lys
65                  70                  75                  80

Thr Phe Val Thr Met Leu Arg Tyr Asp Gly Val Pro Ser Ser Leu Asn
            85                  90                  95

-continued

```
Val Val Ser Asp Lys Thr Gly Asn Gly Gly Pro Leu Leu Gln Pro Tyr
            100                 105                 110

Pro Asp Trp Ser Phe Ala Lys Tyr Glu Asp Cys Ser Gly Ile Val Ser
            115                 120                 125

Ala Asn Lys Ile Ala Ile Asp Glu Tyr Glu Arg Leu Trp Val Leu Asp
            130                 135                 140

Ser Gly Leu Val Asn Asn Ile Gln Pro Met Cys Ser Pro Lys Leu Leu
145                 150                 155                 160

Ala Phe Asp Leu Thr Thr Ser Lys Leu Leu Lys Gln Val Glu Ile Pro
                165                 170                 175

His Asp Val Ala Val Asn Ala Thr Thr Gly Lys Gly Leu Ala Ser
            180                 185                 190

Leu Ala Val Gln Ala Met Asp Ser Val Asn Thr Met Val Tyr Met Ala
            195                 200                 205

Asp Asn Lys Asp Asp Ala Leu Ile Val Tyr Gln Asn Ala Asp Asp Ser
            210                 215                 220

Phe His Arg Leu Ser Ser His Ile Ser Asn His Asn Phe Arg Ser Asp
225                 230                 235                 240

Lys Met Ser Gln Glu Asn Leu Thr Leu Lys Glu Val Asp Asn Arg Val
                245                 250                 255

Phe Gly Met Ala Leu Ser Ser Val Thr His Asn Leu Tyr Tyr Ser Pro
            260                 265                 270

Leu Ser Ser Gln Asn Leu Tyr Tyr Val Asn Thr Thr Ser Leu Met Asn
            275                 280                 285

Ser Gln Asn Gln Gly Asn Asp Val Gln Tyr Glu Ser Val Gln Asp Val
            290                 295                 300

Phe Ser Gln Leu Ser Ala Lys Ala Val Ser Lys Asn Gly Val Leu
305                 310                 315                 320

Phe Phe Gly Phe Thr Asn Asn Thr Leu Gly Cys Trp Asn Glu His Gln
                325                 330                 335

Ser Leu Asp Arg Gln Asn Ile Asp Ile Val Ala Arg Asn Glu Thr Leu
            340                 345                 350

Gln Met Val Val Gly Met Lys Ile Lys Gln Asn Leu Pro Gln Ser Gly
            355                 360                 365

Lys Val Asn Asn Thr Gln Arg Asn Glu His Leu Leu Ala Leu Thr Asn
370                 375                 380

Lys Lys Gln Asp Val Leu Asn Asn Asp Leu Asn Leu Glu His Val Asn
385                 390                 395                 400

Phe Gln Ile Leu Asp Ala Asn Val Asn Asp Leu Ile Arg Asn Ser Arg
                405                 410                 415

Cys Ala Asn Ser Asp Asn Gln Asp Asn Asn Gln His Asn Tyr Asn His
            420                 425                 430

Asn Gln Val Arg His Ser Ser Lys Ser Asp Asn Gln Asn Asn Asn Gln
            435                 440                 445

His Asn Asn Gln Ala Tyr His Ser Ser Lys Ser Asp Asn Trp Asp Asn
            450                 455                 460

Asn Asn Asn Gln Ala His His Ser Ser Lys Phe Asp Asn Gln Asn Asn
465                 470                 475                 480

Asn Gln Tyr Asn Asn
                485

<210> SEQ ID NO 20
<211> LENGTH: 465
```

```
<212> TYPE: PRT
<213> ORGANISM: Apis cerana

<400> SEQUENCE: 20
```

| | | | | | | | | | | | | | | |
|---|---|---|---|---|---|---|---|---|---|---|---|---|---|---|
| Ala | Val | Val | Arg | Glu | Asn | Ser | Ser | Arg | Lys | Lys | Leu | Thr | Asn | Thr | Leu |
| 1 | | | | 5 | | | | | 10 | | | | | 15 |
| Asn | Val | Ile | His | Glu | Trp | Lys | Tyr | Val | Asp | Tyr | Asp | Phe | Gly | Ser | Asp |
| | | | 20 | | | | | 25 | | | | | 30 | |
| Glu | Lys | Arg | Gln | Ala | Ala | Ile | Gln | Ser | Gly | Glu | Tyr | Asp | Arg | Thr | Lys |
| | | 35 | | | | | 40 | | | | | 45 | | |
| Asn | Tyr | Pro | Leu | Asp | Val | Asp | Gln | Trp | His | Asp | Lys | Thr | Phe | Val | Thr |
| | 50 | | | | | 55 | | | | | 60 | | | |
| Met | Leu | Arg | Tyr | Asp | Gly | Val | Pro | Ser | Ser | Leu | Asn | Val | Val | Ser | Asp |
| 65 | | | | | 70 | | | | | 75 | | | | | 80 |
| Lys | Thr | Gly | Asn | Gly | Pro | Leu | Leu | Gln | Pro | Tyr | Pro | Asp | Trp | Ser |
| | | | | 85 | | | | | 90 | | | | | 95 |
| Phe | Ala | Lys | Tyr | Glu | Asp | Cys | Ser | Gly | Ile | Val | Ser | Ala | Asn | Lys | Ile |
| | | | 100 | | | | | 105 | | | | | 110 | | |
| Ala | Ile | Asp | Glu | Tyr | Glu | Arg | Leu | Trp | Val | Leu | Asp | Ser | Gly | Leu | Val |
| | | 115 | | | | | 120 | | | | | 125 | | | |
| Asn | Asn | Ile | Gln | Pro | Met | Cys | Ser | Pro | Lys | Leu | Leu | Ala | Phe | Asp | Leu |
| 130 | | | | | 135 | | | | | 140 | | | | | |
| Thr | Thr | Ser | Lys | Leu | Leu | Lys | Gln | Val | Glu | Ile | Pro | His | Asp | Val | Ala |
| 145 | | | | 150 | | | | | 155 | | | | | 160 |
| Val | Asn | Ala | Thr | Thr | Gly | Lys | Gly | Leu | Ala | Ser | Leu | Ala | Val | Gln |
| | | | | 165 | | | | | 170 | | | | | 175 |
| Ala | Met | Asp | Ser | Val | Asn | Thr | Met | Val | Tyr | Met | Ala | Asp | Asn | Lys | Asp |
| | | | 180 | | | | | 185 | | | | | 190 | | |
| Asp | Ala | Leu | Ile | Val | Tyr | Gln | Asn | Ala | Asp | Asp | Ser | Phe | His | Arg | Leu |
| | | | 195 | | | | | 200 | | | | | 205 | | |
| Ser | Ser | His | Ile | Ser | Asn | His | Asn | Phe | Arg | Ser | Asp | Lys | Met | Ser | Gln |
| | 210 | | | | | 215 | | | | | 220 | | | | |
| Glu | Asn | Leu | Thr | Leu | Lys | Glu | Val | Asp | Asn | Arg | Val | Phe | Gly | Met | Ala |
| 225 | | | | 230 | | | | | 235 | | | | | 240 |
| Leu | Ser | Ser | Val | Thr | His | Asn | Leu | Tyr | Tyr | Ser | Pro | Leu | Ser | Ser | Gln |
| | | | | 245 | | | | | 250 | | | | | 255 | |
| Asn | Leu | Tyr | Tyr | Val | Asn | Thr | Thr | Ser | Leu | Met | Asn | Ser | Gln | Asn | Gln |
| | 260 | | | | | 265 | | | | | 270 | | | | |
| Gly | Asn | Asp | Val | Gln | Tyr | Glu | Ser | Val | Gln | Asp | Val | Phe | Ser | Ser | Gln |
| | | 275 | | | | | 280 | | | | | 285 | | | |
| Leu | Ser | Ala | Lys | Ala | Val | Ser | Lys | Asn | Gly | Val | Leu | Phe | Phe | Gly | Phe |
| | 290 | | | | | 295 | | | | | 300 | | | | |
| Thr | Asn | Asn | Thr | Leu | Gly | Cys | Trp | Asn | Glu | His | Gln | Ser | Leu | Asp | Arg |
| 305 | | | | | 310 | | | | | 315 | | | | | 320 |
| Gln | Asn | Ile | Asp | Ile | Val | Ala | Arg | Asn | Glu | Thr | Leu | Gln | Met | Val | Val |
| | | | 325 | | | | | 330 | | | | | 335 | | |
| Gly | Met | Lys | Ile | Lys | Gln | Asn | Leu | Pro | Gln | Ser | Gly | Lys | Val | Asn | Asn |
| | | | 340 | | | | | 345 | | | | | 350 | | |
| Thr | Gln | Arg | Asn | Glu | His | Leu | Leu | Ala | Leu | Thr | Asn | Lys | Lys | Gln | Asp |
| | | 355 | | | | | 360 | | | | | 365 | | | |
| Val | Leu | Asn | Asn | Asp | Leu | Asn | Leu | Glu | His | Val | Asn | Phe | Gln | Ile | Leu |
| | 370 | | | | | 375 | | | | | 380 | | | | |
| Asp | Ala | Asn | Val | Asn | Asp | Leu | Ile | Arg | Asn | Ser | Arg | Cys | Ala | Asn | Ser |
| 385 | | | | | 390 | | | | | 395 | | | | | 400 |

```
Asp Asn Gln Asp Asn Asn Gln His Asn Tyr Asn His Asn Gln Val Arg
            405                 410                 415

His Ser Ser Lys Ser Asp Asn Gln Asn Asn Gln His Asn Asn Gln
            420                 425                 430

Ala Tyr His Ser Ser Lys Ser Asp Asn Trp Asp Asn Asn Asn Gln
            435                 440                 445

Ala His His Ser Ser Lys Phe Asp Asn Gln Asn Asn Asn Gln Tyr Asn
450                 455                 460

Asn
465

<210> SEQ ID NO 21
<211> LENGTH: 485
<212> TYPE: PRT
<213> ORGANISM: Apis cerana

<400> SEQUENCE: 21

Met Thr Lys Trp Leu Leu Leu Met Ala Cys Leu Gly Ile Ala Cys Gln
1               5                   10                  15

Asn Ile Arg Gly Ala Val Val Arg Glu Asn Ser Ser Arg Lys Lys Leu
            20                  25                  30

Thr Asn Thr Leu Asn Val Ile His Glu Trp Lys Tyr Val Asp Tyr Asp
        35                  40                  45

Phe Gly Ser Asp Glu Lys Arg Gln Ala Ala Ile Gln Ser Gly Glu Tyr
    50                  55                  60

Asp Arg Thr Lys Asn Tyr Pro Leu Asp Val Asp Gln Trp Gln Asp Lys
65                  70                  75                  80

Thr Phe Val Thr Met Leu Arg Tyr Asp Gly Val Pro Ser Ser Leu Asn
                85                  90                  95

Val Val Ser Asn Lys Thr Gly Asn Gly Gly Pro Leu Leu Gln Pro Tyr
            100                 105                 110

Pro Asp Trp Ser Phe Ala Lys Tyr Glu Asp Cys Ser Gly Ile Val Ser
            115                 120                 125

Ala Asn Lys Ile Ala Ile Asp Glu Tyr Glu Arg Leu Trp Val Leu Asp
130                 135                 140

Ser Gly Leu Val Asn Asn Ile Gln Pro Met Cys Ser Pro Lys Leu Leu
145                 150                 155                 160

Ala Phe Asp Leu Thr Thr Ser Lys Leu Leu Lys Gln Val Glu Ile Pro
                165                 170                 175

His Asp Val Ala Val Asn Ala Thr Thr Gly Lys Gly Gly Leu Ala Ser
            180                 185                 190

Leu Ala Val Gln Ala Met Asp Ser Val Asn Thr Met Val Tyr Met Ala
        195                 200                 205

Asp Asn Lys Asp Asp Ala Leu Ile Val Tyr Gln Asn Ala Asp Asp Ser
    210                 215                 220

Phe His Arg Leu Ser Ser His Ile Ser Asn His Asn Phe Arg Ser Asp
225                 230                 235                 240

Lys Met Ser Gln Glu Asn Leu Thr Leu Lys Glu Val Asp Asn Arg Val
                245                 250                 255

Phe Gly Met Ala Leu Ser Ser Val Thr His Asn Leu Tyr Tyr Ser Pro
            260                 265                 270

Leu Ser Ser Gln Asn Leu Tyr Tyr Val Asn Thr Thr Ser Leu Met Asn
        275                 280                 285

Ser Gln Asn Gln Gly Asn Asp Val Gln Tyr Glu Ser Val Gln Asp Val
```

```
            290                 295                 300
Phe Ser Ser Gln Leu Ser Ala Lys Ala Val Ser Lys Asn Gly Val Leu
305                 310                 315                 320

Phe Phe Gly Phe Thr Asn Asn Thr Leu Gly Cys Trp Asn Glu His Gln
                325                 330                 335

Ser Leu Asp Arg Gln Asn Ile Asp Ile Val Ala Arg Asn Glu Thr Leu
            340                 345                 350

Gln Met Val Val Gly Met Lys Ile Lys Gln Asn Leu Pro Gln Ser Gly
                355                 360                 365

Lys Val Asn Asn Thr Gln Arg Asn Glu His Leu Leu Ala Leu Thr Asn
            370                 375                 380

Lys Lys Gln Asp Val Leu Asn Asn Asp Leu Asn Leu Glu Arg Val Asn
385                 390                 395                 400

Phe Gln Ile Leu Asp Ala Asn Val Asn Asp Leu Ile Arg Asn Ser Arg
                405                 410                 415

Cys Ala Asn Ser Asp Asn Gln Asp Asn Asn Gln His Asn Tyr Asn His
            420                 425                 430

Asn Gln Ala Arg His Ser Ser Lys Ser Asp Asn Gln Asn Asn Asn Gln
                435                 440                 445

His Asn Asn Gln Ala Tyr His Ser Ser Lys Ser Asp Asn Trp Asp Asn
450                 455                 460

Asn Asn Asn Gln Ala His His Ser Ser Lys Phe Asp Asn Gln Asn Asn
465                 470                 475                 480

Asn Gln Tyr Asn Asn
                485

<210> SEQ ID NO 22
<211> LENGTH: 465
<212> TYPE: PRT
<213> ORGANISM: Apis cerana

<400> SEQUENCE: 22

Ala Val Val Arg Glu Asn Ser Ser Arg Lys Lys Leu Thr Asn Thr Leu
1               5                   10                  15

Asn Val Ile His Glu Trp Lys Tyr Val Asp Tyr Asp Phe Gly Ser Asp
                20                  25                  30

Glu Lys Arg Gln Ala Ala Ile Gln Ser Gly Glu Tyr Asp Arg Thr Lys
            35                  40                  45

Asn Tyr Pro Leu Asp Val Asp Gln Trp Gln Asp Lys Thr Phe Val Thr
50                  55                  60

Met Leu Arg Tyr Asp Gly Val Pro Ser Ser Leu Asn Val Val Ser Asn
65                  70                  75                  80

Lys Thr Gly Asn Gly Gly Pro Leu Leu Gln Pro Tyr Pro Asp Trp Ser
                85                  90                  95

Phe Ala Lys Tyr Glu Asp Cys Ser Gly Ile Val Ser Ala Asn Lys Ile
                100                 105                 110

Ala Ile Asp Glu Tyr Glu Arg Leu Trp Val Leu Asp Ser Gly Leu Val
            115                 120                 125

Asn Asn Ile Gln Pro Met Cys Ser Pro Lys Leu Leu Ala Phe Asp Leu
130                 135                 140

Thr Thr Ser Lys Leu Leu Lys Gln Val Glu Ile Pro His Asp Val Ala
145                 150                 155                 160

Val Asn Ala Thr Thr Gly Lys Gly Gly Leu Ala Ser Leu Ala Val Gln
                165                 170                 175
```

Ala Met Asp Ser Val Asn Thr Met Val Tyr Met Ala Asp Asn Lys Asp
            180                 185                 190

Asp Ala Leu Ile Val Tyr Gln Asn Ala Asp Asp Ser Phe His Arg Leu
        195                 200                 205

Ser Ser His Ile Ser Asn His Asn Phe Arg Ser Asp Lys Met Ser Gln
    210                 215                 220

Glu Asn Leu Thr Leu Lys Glu Val Asp Asn Arg Val Phe Gly Met Ala
225                 230                 235                 240

Leu Ser Ser Val Thr His Asn Leu Tyr Tyr Ser Pro Leu Ser Ser Gln
                245                 250                 255

Asn Leu Tyr Tyr Val Asn Thr Thr Ser Leu Met Asn Ser Gln Asn Gln
            260                 265                 270

Gly Asn Asp Val Gln Tyr Glu Ser Val Gln Asp Val Phe Ser Ser Gln
        275                 280                 285

Leu Ser Ala Lys Ala Val Ser Lys Asn Gly Val Leu Phe Phe Gly Phe
    290                 295                 300

Thr Asn Asn Thr Leu Gly Cys Trp Asn Glu His Gln Ser Leu Asp Arg
305                 310                 315                 320

Gln Asn Ile Asp Ile Val Ala Arg Asn Glu Thr Leu Gln Met Val Val
                325                 330                 335

Gly Met Lys Ile Lys Gln Asn Leu Pro Gln Ser Gly Lys Val Asn Asn
            340                 345                 350

Thr Gln Arg Asn Glu His Leu Leu Ala Leu Thr Asn Lys Lys Gln Asp
        355                 360                 365

Val Leu Asn Asn Asp Leu Asn Leu Glu Arg Val Asn Phe Gln Ile Leu
    370                 375                 380

Asp Ala Asn Val Asn Asp Leu Ile Arg Asn Ser Arg Cys Ala Asn Ser
385                 390                 395                 400

Asp Asn Gln Asp Asn Asn Gln His Asn Tyr Asn His Asn Gln Ala Arg
                405                 410                 415

His Ser Ser Lys Ser Asp Asn Gln Asn Asn Asn Gln His Asn Asn Gln
            420                 425                 430

Ala Tyr His Ser Ser Lys Ser Asp Asn Trp Asp Asn Asn Asn Asn Gln
        435                 440                 445

Ala His His Ser Ser Lys Phe Asp Asn Gln Asn Asn Asn Gln Tyr Asn
    450                 455                 460

Asn
465

<210> SEQ ID NO 23
<211> LENGTH: 598
<212> TYPE: PRT
<213> ORGANISM: Apis mellifera

<400> SEQUENCE: 23

Met Thr Thr Trp Leu Leu Leu Val Val Cys Leu Gly Ile Ala Cys Gln
1               5                   10                  15

Gly Ile Thr Ser Val Thr Val Arg Glu Asn Ser Pro Arg Lys Leu Ala
            20                  25                  30

Asn Ser Met Asn Val Ile His Glu Trp Lys Tyr Leu Asp Tyr Asp Phe
        35                  40                  45

Gly Ser Asp Glu Arg Arg Gln Ala Ala Met Gln Ser Gly Glu Tyr Asp
    50                  55                  60

His Thr Lys Asn Tyr Pro Phe Asp Val Asp Gln Trp Arg Gly Met Thr
65                  70                  75                  80

```
Phe Val Thr Val Pro Arg Tyr Lys Gly Val Pro Ser Ser Leu Asn Val
                85                  90                  95
Ile Ser Glu Lys Ile Gly Asn Gly Gly Arg Leu Leu Gln Pro Tyr Pro
            100                 105                 110
Asp Trp Ser Trp Ala Asn Tyr Lys Asp Cys Ser Gly Ile Val Ser Ala
        115                 120                 125
Tyr Lys Ile Ala Ile Asp Lys Phe Asp Arg Leu Trp Ile Leu Asp Ser
    130                 135                 140
Gly Ile Ile Asn Asn Thr Gln Pro Met Cys Ser Pro Lys Leu His Val
145                 150                 155                 160
Phe Asp Leu Asn Thr Ser His Gln Leu Lys Gln Val Val Met Pro His
                165                 170                 175
Asp Ile Ala Val Asn Ala Ser Thr Gly Asn Gly Gly Leu Val Ser Leu
            180                 185                 190
Val Val Gln Ala Met Asp Pro Val Asn Thr Ile Val Tyr Met Ala Asp
        195                 200                 205
Asp Lys Gly Asp Ala Leu Ile Val Tyr Gln Asn Ser Asp Glu Ser Phe
    210                 215                 220
His Arg Leu Thr Ser Asn Thr Phe Asp Tyr Asp Pro Lys Tyr Ile Lys
225                 230                 235                 240
Met Met Asp Ala Gly Glu Ser Phe Thr Ala Gln Asp Gly Ile Phe Gly
                245                 250                 255
Met Ala Leu Ser Pro Met Thr Asn Asn Leu Tyr Tyr Ser Pro Leu Ser
            260                 265                 270
Ser Arg Ser Leu Tyr Tyr Val Asn Thr Lys Pro Phe Met Lys Ser Glu
        275                 280                 285
Tyr Gly Ala Asn Asn Val Gln Tyr Gln Gly Val Gln Asp Ile Phe Asn
    290                 295                 300
Thr Glu Ser Ile Ala Lys Ile Met Ser Lys Asn Gly Val Leu Phe Phe
305                 310                 315                 320
Gly Leu Met Asn Asn Ser Ala Ile Gly Cys Trp Asn Glu His Gln Pro
                325                 330                 335
Leu Gln Arg Glu Asn Met Asp Met Val Ala Gln Asn Glu Glu Thr Leu
            340                 345                 350
Gln Thr Val Val Ala Met Lys Met Met His Leu Pro Gln Ser Asn Lys
        355                 360                 365
Met Asn Arg Met His Arg Met Asn Arg Val Asn Arg Val Asn Arg Met
    370                 375                 380
Asp Arg Met Asp Arg Ile Asp Arg Met Asp Arg Met Asp Arg Met Asp
385                 390                 395                 400
Thr Met Asp Thr Met Asp Arg Ile Asp Arg Met Asp Arg Met Asp Arg
                405                 410                 415
Ile Asp Arg Ile Asp Arg Met His Thr Met Thr Met Asp Thr Met
            420                 425                 430
Asp Arg Thr Asp Lys Met Ser Ser Met Asp Arg Met Asp Arg Met Asp
    435                 440                 445
Arg Val Asp Arg Met Asp Thr Met Asp Arg Thr Asp Lys Met Ser Ser
450                 455                 460
Met Asp Arg Met Asp Arg Met Asp Arg Val Asp Thr Met Asp Thr Met
                465                 470                 475                 480
Asp Thr Met Asp Arg Met Asp Arg Met Asp Arg Met Asp Arg Met Asp
                485                 490                 495
```

```
Arg Met Asp Arg Met Asp Thr Met Asp Arg Thr Asp Lys Met Ser Arg
            500                 505                 510

Ile Asp Arg Met Asp Lys Ile Asp Arg Met Asp Arg Met Asp Arg Thr
            515                 520                 525

Asn Arg Met Asp Arg Met Asn Arg Met Asn Arg Gln Met Asn Glu Tyr
        530                 535                 540

Met Met Ala Leu Ser Met Lys Leu Gln Lys Phe Ile Asn Asn Asp Tyr
545                 550                 555                 560

Asn Phe Asn Glu Val Asn Phe Arg Ile Leu Gly Ala Asn Val Asn Asp
                565                 570                 575

Leu Ile Met Asn Thr Arg Cys Ala Asn Ser Asp Asn Gln Asn Asn Asn
            580                 585                 590

Gln Asn Lys His Asn Asn
        595

<210> SEQ ID NO 24
<211> LENGTH: 581
<212> TYPE: PRT
<213> ORGANISM: Apis mellifera

<400> SEQUENCE: 24

Ile Thr Ser Val Thr Val Arg Glu Asn Ser Pro Arg Lys Leu Ala Asn
1               5                   10                  15

Ser Met Asn Val Ile His Glu Trp Lys Tyr Leu Asp Tyr Asp Phe Gly
            20                  25                  30

Ser Asp Glu Arg Arg Gln Ala Ala Met Gln Ser Gly Glu Tyr Asp His
        35                  40                  45

Thr Lys Asn Tyr Pro Phe Asp Val Asp Gln Trp Arg Gly Met Thr Phe
    50                  55                  60

Val Thr Val Pro Arg Tyr Lys Gly Val Pro Ser Ser Leu Asn Val Ile
65                  70                  75                  80

Ser Glu Lys Ile Gly Asn Gly Gly Arg Leu Leu Gln Pro Tyr Pro Asp
                85                  90                  95

Trp Ser Trp Ala Asn Tyr Lys Asp Cys Ser Gly Ile Val Ser Ala Tyr
            100                 105                 110

Lys Ile Ala Ile Asp Lys Phe Asp Arg Leu Trp Ile Leu Asp Ser Gly
        115                 120                 125

Ile Ile Asn Asn Thr Gln Pro Met Cys Ser Pro Lys Leu His Val Phe
    130                 135                 140

Asp Leu Asn Thr Ser His Gln Leu Lys Gln Val Val Met Pro His Asp
145                 150                 155                 160

Ile Ala Val Asn Ala Ser Thr Gly Asn Gly Gly Leu Val Ser Leu Val
                165                 170                 175

Val Gln Ala Met Asp Pro Val Asn Thr Ile Val Tyr Met Ala Asp Asp
            180                 185                 190

Lys Gly Asp Ala Leu Ile Val Tyr Gln Asn Ser Asp Glu Ser Phe His
        195                 200                 205

Arg Leu Thr Ser Asn Thr Phe Asp Tyr Asp Pro Lys Tyr Ile Lys Met
    210                 215                 220

Met Asp Ala Gly Glu Ser Phe Thr Ala Gln Asp Gly Ile Phe Gly Met
225                 230                 235                 240

Ala Leu Ser Pro Met Thr Asn Asn Leu Tyr Tyr Ser Pro Leu Ser Ser
                245                 250                 255

Arg Ser Leu Tyr Tyr Val Asn Thr Lys Pro Phe Met Lys Ser Glu Tyr
            260                 265                 270
```

```
Gly Ala Asn Asn Val Gln Tyr Gln Gly Val Gln Asp Ile Phe Asn Thr
            275                 280                 285

Glu Ser Ile Ala Lys Ile Met Ser Lys Asn Gly Val Leu Phe Phe Gly
290                 295                 300

Leu Met Asn Asn Ser Ala Ile Gly Cys Trp Asn Glu His Gln Pro Leu
305                 310                 315                 320

Gln Arg Glu Asn Met Asp Met Val Ala Gln Asn Glu Glu Thr Leu Gln
            325                 330                 335

Thr Val Val Ala Met Lys Met Met His Leu Pro Gln Ser Asn Lys Met
            340                 345                 350

Asn Arg Met His Arg Met Asn Arg Val Asn Arg Val Asn Arg Met Asp
            355                 360                 365

Arg Met Asp Arg Ile Asp Arg Met Asp Arg Met Asp Arg Met Asp Thr
            370                 375                 380

Met Asp Thr Met Asp Arg Ile Asp Arg Met Asp Arg Met Asp Arg Ile
385                 390                 395                 400

Asp Arg Ile Asp Arg Met His Thr Met Asp Thr Met Asp Thr Met Asp
            405                 410                 415

Arg Thr Asp Lys Met Ser Ser Met Asp Arg Met Asp Arg Met Asp Arg
            420                 425                 430

Val Asp Arg Met Asp Thr Met Asp Arg Thr Asp Lys Met Ser Ser Met
            435                 440                 445

Asp Arg Met Asp Arg Met Asp Arg Val Asp Thr Met Asp Thr Met Asp
            450                 455                 460

Thr Met Asp Arg Met Asp Arg Met Asp Arg Met Asp Arg Met Asp Arg
465                 470                 475                 480

Met Asp Arg Met Asp Thr Met Asp Arg Thr Asp Lys Met Ser Arg Ile
            485                 490                 495

Asp Arg Met Asp Lys Ile Asp Arg Met Asp Arg Met Asp Arg Thr Asn
            500                 505                 510

Arg Met Asp Arg Met Asn Arg Met Asn Arg Gln Met Asn Glu Tyr Met
            515                 520                 525

Met Ala Leu Ser Met Lys Leu Gln Lys Phe Ile Asn Asn Asp Tyr Asn
            530                 535                 540

Phe Asn Glu Val Asn Phe Arg Ile Leu Gly Ala Asn Val Asn Asp Leu
545                 550                 555                 560

Ile Met Asn Thr Arg Cys Ala Asn Ser Asp Asn Gln Asn Asn Asn Gln
            565                 570                 575

Asn Lys His Asn Asn
            580

<210> SEQ ID NO 25
<211> LENGTH: 579
<212> TYPE: PRT
<213> ORGANISM: Apis cerana

<400> SEQUENCE: 25

Met Thr Ser Trp Leu Leu Val Val Cys Leu Gly Ile Ala Cys Gln
1               5                   10                  15

Gly Ile Thr Gly Ala Thr Val Arg Glu Asn Ser Ser Arg Asn Leu Ala
            20                  25                  30

Asn Ser Met Asn Val Ile His Glu Trp Lys Tyr Leu Asp Tyr Asp Phe
            35                  40                  45

Gly Ser Asp Glu Lys Arg Gln Ala Ala Ile Gln Ser Gly Glu Tyr Asp
```

```
                50                  55                  60
His Thr Lys Asn Tyr Pro Phe Asp Val Asp Arg Trp His Asp Met Thr
 65                  70                  75                  80

Phe Val Thr Val Leu Arg Tyr Lys Gly Val Pro Ser Ser Leu Asn Val
                     85                  90                  95

Ile Ser Lys Lys Ile Gly Asn Gly Gly Pro Leu Leu Gln Pro Tyr Pro
                100                 105                 110

Asp Trp Ser Trp Ala Asn Tyr Lys Asp Cys Ser Gly Ile Val Ser Ala
                115                 120                 125

Tyr Lys Ile Ala Ile Asp Lys Phe Asp Arg Leu Trp Val Leu Asp Ser
                130                 135                 140

Gly Ile Ile Asn Asn Thr Gln Pro Met Cys Ser Pro Lys Leu His Val
145                 150                 155                 160

Phe Asp Leu Asn Thr Ser Gln Gln Ile Lys Gln Val Met Met Pro His
                165                 170                 175

Asp Ile Ala Ile Asn Ala Thr Thr Gly Lys Gly Gly Leu Glu Asn Leu
                180                 185                 190

Val Val Gln Ala Met Asp Pro Met Asn Thr Leu Val Tyr Met Ala Asp
                195                 200                 205

Asn Lys Gly Asp Ala Leu Ile Val Tyr Gln Asn Ser Asp Asp Ser Phe
                210                 215                 220

His Arg Leu Thr Ser Asn Thr Phe Asp Tyr Asp Pro Lys Tyr Ile Lys
225                 230                 235                 240

Met Met Ala Ala Gly Glu Ser Phe Thr Leu Gln Asp Gly Ile Phe Gly
                245                 250                 255

Met Ala Leu Ser Pro Met Thr Asn Asn Leu Tyr Tyr Ser Pro Leu Ala
                260                 265                 270

Ser Arg Ser Leu Tyr Tyr Val Asn Thr Lys Pro Phe Met Lys Ser Gln
                275                 280                 285

Tyr Gly Thr Asn Val Gln His Glu Gly Val Gln Asp Ile Phe Asn
                290                 295                 300

Thr Gln Ser Ile Ala Lys Ile Met Ser Lys Asn Gly Val Leu Phe Phe
305                 310                 315                 320

Gly Leu Met Asn Asn Ser Ala Ile Gly Cys Trp Asn Glu His Gln Pro
                325                 330                 335

Leu Gln Arg Gln Asn Met Asp Met Val Ala Gln Asn Glu Glu Thr Leu
                340                 345                 350

Gln Thr Val Val Ala Met Lys Met Met His Leu Pro Gln Ser Asn Arg
                355                 360                 365

Met Asn Arg Met His Arg Met Asn Ser Met Asn Arg Met Asp Arg Met
370                 375                 380

Asp Arg Met Asp Arg Met Asp Arg Met Asp Arg Met Asp Arg Met Asp
385                 390                 395                 400

Arg Met Asp Arg Met Asp Arg Met Asp Arg Met Asp Arg Met Asp Arg
                405                 410                 415

Met Asp Arg Met Asp Arg Met Asp Ile Met Asp Arg Thr Asn Lys Met
                420                 425                 430

Asp Arg Met Asp Arg Met Asp Ile Met Asp Lys Met Asn Lys Met Asp
                435                 440                 445

Arg Met Asp Ser Met Ile Arg Ile Asp Lys Met Asp Arg Met Asp Arg
                450                 455                 460

Met His Arg Ile Asp Ile Met Asn Arg Met Asp Arg Met Asp Arg Met
465                 470                 475                 480
```

```
Asp Thr Arg Ile Asp Thr Arg Met Asp Arg Met Asp Lys
            485                 490                 495

Met Asp Lys Ile Asn Lys Met His Arg Met Gly Arg Met Asp Arg Met
            500                 505                 510

Asp Arg Met Asn Arg Met Asn Arg Gln Met Asn Glu Tyr Met Met Ala
            515                 520                 525

Leu Ser Met Lys Leu Gln Lys Phe Ile Asn Asn Asp Tyr Asn Phe Asn
            530                 535                 540

Glu Val Asn Phe Arg Ile Leu Ala Ala Asn Val Asn Asp Leu Ile Met
545                 550                 555                 560

Asn Thr Arg Cys Ala Asn Ser Asn Asn Gln Asn Asp Asn Gln Asn Lys
            565                 570                 575

His Asn Asn

<210> SEQ ID NO 26
<211> LENGTH: 559
<212> TYPE: PRT
<213> ORGANISM: Apis cerana

<400> SEQUENCE: 26

Ala Thr Val Arg Glu Asn Ser Ser Arg Asn Leu Ala Asn Ser Met Asn
1               5                   10                  15

Val Ile His Glu Trp Lys Tyr Leu Asp Tyr Asp Phe Gly Ser Asp Glu
            20                  25                  30

Lys Arg Gln Ala Ala Ile Gln Ser Gly Glu Tyr Asp His Thr Lys Asn
            35                  40                  45

Tyr Pro Phe Asp Val Asp Arg Trp His Asp Met Thr Phe Val Thr Val
    50                  55                  60

Leu Arg Tyr Lys Gly Val Pro Ser Ser Leu Asn Val Ile Ser Lys Lys
65                  70                  75                  80

Ile Gly Asn Gly Gly Pro Leu Leu Gln Pro Tyr Pro Asp Trp Ser Trp
                85                  90                  95

Ala Asn Tyr Lys Asp Cys Ser Gly Ile Val Ser Ala Tyr Lys Ile Ala
            100                 105                 110

Ile Asp Lys Phe Asp Arg Leu Trp Val Leu Asp Ser Gly Ile Ile Asn
            115                 120                 125

Asn Thr Gln Pro Met Cys Ser Pro Lys Leu His Val Phe Asp Leu Asn
            130                 135                 140

Thr Ser Gln Gln Ile Lys Gln Val Met Met Pro His Asp Ile Ala Ile
145                 150                 155                 160

Asn Ala Thr Thr Gly Lys Gly Gly Leu Glu Asn Leu Val Val Gln Ala
            165                 170                 175

Met Asp Pro Met Asn Thr Leu Val Tyr Met Ala Asp Asn Lys Gly Asp
            180                 185                 190

Ala Leu Ile Val Tyr Gln Asn Ser Asp Asp Ser Phe His Arg Leu Thr
            195                 200                 205

Ser Asn Thr Phe Asp Tyr Asp Pro Lys Tyr Ile Lys Met Met Ala Ala
    210                 215                 220

Gly Glu Ser Phe Thr Leu Gln Asp Gly Ile Phe Gly Met Ala Leu Ser
225                 230                 235                 240

Pro Met Thr Asn Asn Leu Tyr Tyr Ser Pro Leu Ala Ser Arg Ser Leu
            245                 250                 255

Tyr Tyr Val Asn Thr Lys Pro Phe Met Lys Ser Gln Tyr Gly Thr Asn
            260                 265                 270
```

```
Asn Val Gln His Glu Gly Val Gln Asp Ile Phe Asn Thr Gln Ser Ile
            275                 280                 285

Ala Lys Ile Met Ser Lys Asn Gly Val Leu Phe Phe Gly Leu Met Asn
        290                 295                 300

Asn Ser Ala Ile Gly Cys Trp Asn Glu His Gln Pro Leu Gln Arg Gln
305                 310                 315                 320

Asn Met Asp Met Val Ala Gln Asn Glu Glu Thr Leu Gln Thr Val Val
                325                 330                 335

Ala Met Lys Met Met His Leu Pro Gln Ser Asn Arg Met Asn Arg Met
        340                 345                 350

His Arg Met Asn Ser Met Asn Arg Met Asp Arg Met Asp Arg Met Asp
                355                 360                 365

Arg Met Asp Arg Met Asp Arg Met Asp Arg Met Asp Arg Met Asp Arg
        370                 375                 380

Met Asp Arg Met Asp Arg Met Asp Arg Met Asp Arg Met Asp Arg Met
385                 390                 395                 400

Asp Arg Met Asp Ile Met Asp Arg Thr Asn Lys Met Asp Arg Met Asp
                405                 410                 415

Arg Met Asp Ile Met Asp Lys Met Asn Lys Met Asp Arg Met Asp Ser
        420                 425                 430

Met Ile Arg Ile Asp Lys Met Asp Arg Met Asp Arg Met His Arg Ile
                435                 440                 445

Asp Ile Met Asn Arg Met Asp Arg Met Asp Arg Met Asp Thr Arg Ile
        450                 455                 460

Asp Thr Arg Met Asp Arg Met Asp Arg Met Asp Lys Met Asp Lys Ile
465                 470                 475                 480

Asn Lys Met His Arg Met Gly Arg Met Asp Arg Met Asp Arg Met Asn
                485                 490                 495

Arg Met Asn Arg Gln Met Asn Glu Tyr Met Met Ala Leu Ser Met Lys
        500                 505                 510

Leu Gln Lys Phe Ile Asn Asn Asp Tyr Asn Phe Asn Glu Val Asn Phe
        515                 520                 525

Arg Ile Leu Ala Ala Asn Val Asn Asp Leu Ile Met Asn Thr Arg Cys
        530                 535                 540

Ala Asn Ser Asn Asn Gln Asn Asp Asn Gln Asn Lys His Asn Asn
545                 550                 555

<210> SEQ ID NO 27
<211> LENGTH: 184
<212> TYPE: PRT
<213> ORGANISM: Apis florea

<400> SEQUENCE: 27

Tyr Asp Phe Gly Ser Asp Glu Lys Arg Gln Ala Ala Ile Gln Ser Gly
1               5                   10                  15

Glu Tyr Asp His Thr Lys Asn Tyr Pro Phe Asp Val Asp His Trp His
            20                  25                  30

Asp Met Thr Phe Val Thr Val Leu Arg Tyr Lys Gly Val Pro Ser Ser
        35                  40                  45

Leu Asn Val Ile Ser Glu Lys Thr Gly Asn Gly Gln Leu Leu Gln
        50                  55                  60

Pro Tyr Pro Asp Trp Ser Trp Ala Asp Tyr Lys Asp Cys Ser Gly Ile
65                  70                  75                  80

Val Ser Ala Tyr Lys Ile Ala Ile Asp Lys Phe Asp Arg Leu Trp Val
```

-continued

```
                85                  90                  95
Met Asp Ser Gly Ile Ile Asn Asn Thr Gln Pro Met Cys Ser Pro Lys
            100                 105                 110

Leu His Ile Phe Asp Leu Asn Thr Ser Gln His Leu Lys Gln Val Thr
        115                 120                 125

Ile Pro His Asp Ile Ala Val Asn Ala Thr Thr Gly Lys Gly Gly Leu
    130                 135                 140

Glu Tyr Leu Val Val Gln Ala Met Asp Pro Ile Asn Thr Met Val Tyr
145                 150                 155                 160

Met Ala Asp Asn Lys Gly Asp Ala Leu Ile Ile Tyr Gln Asn Ser Asp
                165                 170                 175

Asn Ser Phe Gln Arg Met Ser Ser
            180

<210> SEQ ID NO 28
<211> LENGTH: 189
<212> TYPE: PRT
<213> ORGANISM: Apis dorsata

<400> SEQUENCE: 28

Trp Lys Leu Val Asp Tyr Asp Phe Gly Ser Asp Glu Arg Arg Gln Ala
1               5                   10                  15

Ala Ile Gln Ser Gly Glu Tyr Asp His Thr Lys Asn Tyr Pro Phe Asp
            20                  25                  30

Val Asp Gln Trp His Asp Met Thr Phe Val Thr Val Leu Arg Tyr Lys
        35                  40                  45

Gly Val Pro Ser Ser Leu Asn Ile Ile Ser Glu Lys Thr Gly Asn Gly
    50                  55                  60

Gly Pro Leu Leu Gln Pro Tyr Pro Asp Trp Ser Ser Ala Asn Tyr Glu
65                  70                  75                  80

Asp Cys Ser Gly Ile Val Ser Ala Tyr Lys Ile Ala Ile Asp Lys Phe
                85                  90                  95

Asp Arg Leu Trp Val Leu Asp Ser Gly Ile Ile Asn Asn Thr Gln Pro
            100                 105                 110

Met Cys Ser Pro Lys Leu His Val Phe Asp Leu Asn Thr Ser Gln Gln
        115                 120                 125

Val Lys Gln Val Thr Met Pro His Asp Ile Ala Val Asn Ala Thr Thr
    130                 135                 140

Gly Lys Gly Gly Leu Glu Tyr Leu Val Val Gln Ala Ile Asp Pro Met
145                 150                 155                 160

Asn Thr Met Val Tyr Met Ala Asp Asn Lys Gly Asp Ala Leu Ile Ile
                165                 170                 175

Tyr Gln Asn Ser Asp Asp Ser Phe His Arg Met Ser Ser
            180                 185

<210> SEQ ID NO 29
<211> LENGTH: 191
<212> TYPE: PRT
<213> ORGANISM: Apis florea

<400> SEQUENCE: 29

Tyr Glu Trp Lys Leu Val Asp Tyr Asp Phe Gly Ser Asp Glu Arg Arg
1               5                   10                  15

Gln Ala Ala Ile Gln Ser Gly Glu Tyr Asp Arg Met Lys Asn Tyr Pro
            20                  25                  30

Ser Asp Val Asp Gln Trp His Asp Lys Thr Phe Val Thr Met Leu Arg
```

```
                35                  40                  45
Tyr Asp Gly Val Pro Ser Ser Leu Asn Val Ser Glu Lys Thr Gly
 50                  55                  60

Asn Gly Gly Pro Leu Leu Gln Pro Tyr Pro Asp Trp Ser Phe Ala Lys
 65                  70                  75                  80

Tyr Glu Asp Cys Ser Gly Ile Val Ser His Lys Ile Ala Ile Asp
                 85                  90                  95

Lys Phe Asp Arg Leu Trp Val Leu Asp Ser Gly Leu Ile Asn Asn Ile
                100                 105                 110

Gln Leu Ile Cys Ser Pro Lys Leu Leu Ala Phe Asp Leu Asn Thr Ser
                115                 120                 125

Gln Leu Leu Lys Gln Val Glu Ile Pro His Asp Ile Ala Val Asn Ala
130                 135                 140

Ser Thr Gly Ile Gly Gly Leu Val Ser Leu Val Val Gln Asp Met Asp
145                 150                 155                 160

Leu Ile Asn Thr Met Val Tyr Ile Ala Asp Asp Arg Gly Asn Ala Leu
                165                 170                 175

Ile Val Tyr Gln Asn Ser Asp Asp Ser Phe Gln Arg Leu Ser Ser
                180                 185                 190

<210> SEQ ID NO 30
<211> LENGTH: 185
<212> TYPE: PRT
<213> ORGANISM: Apis florea

<400> SEQUENCE: 30

Trp Lys Tyr Phe Asp Tyr Asn Phe Gly Ser Asn Glu Arg Arg Gln Ala
 1               5                  10                  15

Ala Ile Gln Ser Gly Glu Tyr Asn Tyr Lys Asn Asn Phe Pro Ile Asp
                 20                  25                  30

Val Asp Arg Trp His Asp Lys Thr Phe Val Thr Ile Ile Arg Asp Ser
                 35                  40                  45

Gly Val Pro Ser Ser Leu Asn Val Ile Ser Asn Lys Ile Gly Asp Gly
 50                  55                  60

Gly Pro Leu Leu Glu Pro Tyr Pro Asn Trp Ser Trp Ala Lys Asn Gln
 65                  70                  75                  80

Asn Cys Ser Gly Ile Thr Ser Val Tyr Arg Val Ala Ile Asp Val Trp
                 85                  90                  95

Asp Arg Leu Trp Val Leu Asp Asn Gly Ile Ser Gly Gln Thr Ser Val
                100                 105                 110

Cys Ser Ser Gln Ile Val Val Phe Asp Leu Lys Thr Ser Gln Leu Leu
                115                 120                 125

Lys Gln Val Lys Ile Pro His Asn Ile Ala Ile Asn Ser Thr Thr Gly
                130                 135                 140

Ser Arg Asn Leu Val Thr Pro Ile Val Gln Ser Phe Asp Tyr Asn Asn
145                 150                 155                 160

Thr Leu Val Tyr Ile Ala Asp Val Glu Gly Tyr Ala Leu Ile Ile Tyr
                165                 170                 175

Asn Asn Ala Asp Asp Ser Phe Gln Arg
                180                 185

<210> SEQ ID NO 31
<211> LENGTH: 432
<212> TYPE: PRT
<213> ORGANISM: Apis florea
```

<400> SEQUENCE: 31

```
Met Thr Ser Trp Leu Leu Leu Val Val Leu Ser Val Asp Ile Ala Cys
1               5                   10                  15

His Gly Ile Thr Gly Ala Asn Ile Ile Pro Glu Asn Ser Ser Arg Asn
            20                  25                  30

Leu Val Asn Ser Leu Asn Val Ile His Glu Trp Lys Tyr Ile Asp Tyr
        35                  40                  45

Asp Phe Gly Ser Asp Glu Arg Arg Gln Asn Ala Ile Gln Ser Gly Glu
    50                  55                  60

Tyr Asp His Thr Lys Asn Tyr Pro Phe Asp Ile Asp Gln Trp His Asp
65                  70                  75                  80

Lys Ile Phe Ile Thr Val Ile Arg Tyr Asp Gly Val Pro Ser Ser Leu
                85                  90                  95

Asn Ile Ile Ser Asp Lys Ile Gly Asn Gly Arg Leu Leu Gln Pro
            100                 105                 110

Tyr Pro Asp Trp Ser Trp Thr Asn Tyr Lys Asp Cys Ser Gly Ile Val
            115                 120                 125

Ser Val Tyr Arg Ile Ala Ile Asp Lys Phe Asp Arg Leu Trp Val Leu
    130                 135                 140

Asp Ser Gly Leu Val Asn Asn Thr Gln His Met Cys Ser Pro Lys Leu
145                 150                 155                 160

Leu Ala Phe Asp Leu Asn Thr Ser His Leu Leu Lys Gln Ile His Val
                165                 170                 175

Pro His Asp Ile Ala Val Asn Ala Thr Thr Gly Lys Gly Gly Leu Val
            180                 185                 190

Phe Leu Ala Val Gln Ala Val Asp Pro Ile Asn Thr Met Val Tyr Met
    195                 200                 205

Ser Asp Asn Arg Gly Asn Ala Leu Ile Ile Tyr Gln Asn Ser Asp Asp
210                 215                 220

Ser Phe His Arg Leu Thr Ser Asn Thr Phe Asp Tyr Asp Pro Arg Tyr
225                 230                 235                 240

Ile Lys Met Thr Ile Glu Gly Glu Ser Leu Thr Leu Glu Asp Gly Ile
                245                 250                 255

Phe Gly Ile Ala Val Ser Pro Val Thr Asn Asn Leu Tyr Tyr Ser Pro
            260                 265                 270

Leu Ser Ser His Gly Leu Tyr Tyr Val Asn Thr Glu Pro Phe Met Lys
        275                 280                 285

Ser Gln Tyr Gly Gly Asn Asp Val Gln Tyr Asn Gly Val Glu Asp Ile
    290                 295                 300

Tyr Asn Thr Gln Leu Ser Ala Lys Ala Val Ser Lys Asn Gly Val Leu
305                 310                 315                 320

Phe Phe Gly Leu Val His Asn Ser Ala Val Gly Cys Leu Asn Glu His
                325                 330                 335

Gln Gln Ile Gln Arg Gln Asn Ile Asn Met Val Ala Gln Asn Lys Glu
            340                 345                 350

Thr Leu Gln Met Ile Ile Ala Met Lys Ile Leu Glu Asp Leu Gln Gln
        355                 360                 365

Phe Gly Lys Ile Asn Arg Thr Gln Arg Asn Glu Tyr Met Leu Val Leu
    370                 375                 380

Ser Asn Arg Ile Gln Lys Ile Val Asn Asp Phe Asn Phe Asp Glu
385                 390                 395                 400

Ile Asn Phe Arg Ile Leu Lys Ala Asn Val Asn Asp Leu Ile Arg Asn
                405                 410                 415
```

Thr Arg Cys Ala Asn Asn Asp Ile Gln Asn Asn Lys Asn Asn Asn
        420                 425                 430

<210> SEQ ID NO 32
<211> LENGTH: 410
<212> TYPE: PRT
<213> ORGANISM: Apis florea

<400> SEQUENCE: 32

Asn Ile Ile Pro Glu Asn Ser Ser Arg Asn Leu Val Asn Ser Leu Asn
1               5                   10                  15

Val Ile His Glu Trp Lys Tyr Ile Asp Tyr Asp Phe Gly Ser Asp Glu
            20                  25                  30

Arg Arg Gln Asn Ala Ile Gln Ser Gly Glu Tyr Asp His Thr Lys Asn
        35                  40                  45

Tyr Pro Phe Asp Ile Asp Gln Trp His Asp Lys Ile Phe Ile Thr Val
    50                  55                  60

Ile Arg Tyr Asp Gly Val Pro Ser Ser Leu Asn Ile Ile Ser Asp Lys
65                  70                  75                  80

Ile Gly Asn Gly Gly Arg Leu Leu Gln Pro Tyr Pro Asp Trp Ser Trp
                85                  90                  95

Thr Asn Tyr Lys Asp Cys Ser Gly Ile Val Ser Val Tyr Arg Ile Ala
            100                 105                 110

Ile Asp Lys Phe Asp Arg Leu Trp Val Leu Asp Ser Gly Leu Val Asn
        115                 120                 125

Asn Thr Gln His Met Cys Ser Pro Lys Leu Leu Ala Phe Asp Leu Asn
    130                 135                 140

Thr Ser His Leu Leu Lys Gln Ile His Val Pro His Asp Ile Ala Val
145                 150                 155                 160

Asn Ala Thr Thr Gly Lys Gly Gly Leu Val Phe Leu Ala Val Gln Ala
                165                 170                 175

Val Asp Pro Ile Asn Thr Met Val Tyr Met Ser Asp Asn Arg Gly Asn
            180                 185                 190

Ala Leu Ile Ile Tyr Gln Asn Ser Asp Asp Ser Phe His Arg Leu Thr
        195                 200                 205

Ser Asn Thr Phe Asp Tyr Asp Pro Arg Tyr Ile Lys Met Thr Ile Glu
    210                 215                 220

Gly Glu Ser Leu Thr Leu Glu Asp Gly Ile Phe Gly Ile Ala Val Ser
225                 230                 235                 240

Pro Val Thr Asn Asn Leu Tyr Tyr Ser Pro Leu Ser Ser His Gly Leu
                245                 250                 255

Tyr Tyr Val Asn Thr Glu Pro Phe Met Lys Ser Gln Tyr Gly Gly Asn
            260                 265                 270

Asp Val Gln Tyr Asn Gly Val Glu Asp Ile Tyr Asn Thr Gln Leu Ser
        275                 280                 285

Ala Lys Ala Val Ser Lys Asn Gly Val Leu Phe Phe Gly Leu Val His
    290                 295                 300

Asn Ser Ala Val Gly Cys Leu Asn Glu His Gln Gln Ile Gln Arg Gln
305                 310                 315                 320

Asn Ile Asn Met Val Ala Gln Asn Lys Glu Thr Leu Gln Met Ile Ile
                325                 330                 335

Ala Met Lys Ile Leu Glu Asp Leu Gln Gln Phe Gly Lys Ile Asn Arg
            340                 345                 350

Thr Gln Arg Asn Glu Tyr Met Leu Val Leu Ser Asn Arg Ile Gln Lys

```
                 355                 360                 365

Ile Val Asn Asn Asp Phe Asn Phe Asp Glu Ile Asn Phe Arg Ile Leu
        370                 375                 380

Lys Ala Asn Val Asn Asp Leu Ile Arg Asn Thr Arg Cys Ala Asn Asn
385                 390                 395                 400

Asp Ile Gln Asn Asn Asn Lys Asn Asn Asn
                405                 410

<210> SEQ ID NO 33
<211> LENGTH: 430
<212> TYPE: PRT
<213> ORGANISM: Apis dorsata

<400> SEQUENCE: 33

Met Thr Arg Trp Leu Leu Leu Val Cys Leu Gly Val Ala Ser His Gly
1               5                   10                  15

Ile Thr Gly Thr Ile Thr Pro Glu Asn Ser Ser Arg Asn Leu Ala Asn
                20                  25                  30

Ser Leu Asn Val Ile His Glu Trp Lys Tyr Leu Asp Tyr Asp Phe Gly
            35                  40                  45

Ser Glu Glu Lys Arg Gln Ala Ala Ile Gln Ser Gly Glu Tyr Asp Phe
        50                  55                  60

Thr Lys Asn Tyr Leu Phe Asp Val Asp Gln Trp His Asp Lys Thr Phe
65                  70                  75                  80

Ala Thr Val Ile Arg Tyr Asp Gly Val Pro Ser Ser Leu Asn Val Ile
                85                  90                  95

Ser Asp Lys Ile Gly Asn Gly Gly Arg Leu Leu Gln Pro Tyr Pro Asp
            100                 105                 110

Trp Ser Trp Ala Lys Tyr Lys Asp Cys Ser Gly Ile Val Ser Val Tyr
        115                 120                 125

Lys Ile Ser Ile Asp Lys Phe Asp Arg Leu Trp Val Leu Asp Ser Gly
130                 135                 140

Leu Ile Asn Asn Thr Lys Leu Ile Cys Ser Pro Lys Leu Leu Ala Phe
145                 150                 155                 160

Asp Leu Asn Thr Ser Gln Leu Leu Lys Gln Val His Ile Pro His Asp
                165                 170                 175

Ile Ala Val Asn Ala Thr Thr Gly Lys Gly Gly Leu Val Phe Leu Ala
            180                 185                 190

Val Gln Ala Val Asp Pro Ile Asn Thr Met Ala Tyr Met Ala Asp Asn
        195                 200                 205

Arg Gly Asn Ala Leu Ser Val Tyr Gln Asn Ser Asp Asn Ser Leu His
210                 215                 220

Arg Leu Thr Ser Asn Thr Phe Asp Tyr Asp Pro Arg Tyr Thr Glu Phe
225                 230                 235                 240

Thr Ile Ala Gly Glu Ser Phe Ile Leu Gln Asp Gly Ile Phe Gly Ile
                245                 250                 255

Ala Val Ser Pro Val Thr Asn Asn Leu Tyr Tyr Ser Pro Leu Ser Ser
            260                 265                 270

Arg Ser Leu Tyr Tyr Val Asn Thr Glu Pro Phe Met Lys Ser Glu Tyr
        275                 280                 285

Glu Gly Asn Asn Val Gln Tyr Lys Gly Val Glu Asp Ile Tyr Asn Thr
        290                 295                 300

Gln Leu Ser Ala Lys Ala Val Ser Lys Asn Gly Val Val Phe Phe Gly
305                 310                 315                 320
```

```
Leu Val Asn Asn Ser Ala Leu Gly Cys Leu Asn Glu His Gln Pro Ile
                    325                 330                 335

Gln Arg Gln Asn Ile Asp Met Val Ala Gln Asn Glu Glu Thr Leu Gln
            340                 345                 350

Met Ile Phe Ser Ile Lys Ile Lys Gln Asp Phe Pro Gln Ser Asn Arg
            355                 360                 365

Ile Asn Lys Thr Glu Arg Asn Glu Tyr Met Leu Ala Leu Ser Asn Arg
        370                 375                 380

Leu Gln Lys Phe Met Asn His Asn Tyr Asn Phe Asn Glu Val Asn Phe
385                 390                 395                 400

Arg Val Leu Ser Ala Asn Val Asn Asp Leu Ile Lys Asn Thr Arg Cys
                405                 410                 415

Ala Asn Phe Asn Asn Gln Ala His His Ser Ser Lys Ser His
                420                 425                 430

<210> SEQ ID NO 34
<211> LENGTH: 411
<212> TYPE: PRT
<213> ORGANISM: Apis dorsata

<400> SEQUENCE: 34

Thr Ile Thr Pro Glu Asn Ser Ser Arg Asn Leu Ala Asn Ser Leu Asn
1               5                   10                  15

Val Ile His Glu Trp Lys Tyr Leu Asp Tyr Asp Phe Gly Ser Glu Glu
            20                  25                  30

Lys Arg Gln Ala Ala Ile Gln Ser Gly Glu Tyr Asp Phe Thr Lys Asn
        35                  40                  45

Tyr Leu Phe Asp Val Asp Gln Trp His Asp Lys Thr Phe Ala Thr Val
    50                  55                  60

Ile Arg Tyr Asp Gly Val Pro Ser Ser Leu Asn Val Ile Ser Asp Lys
65                  70                  75                  80

Ile Gly Asn Gly Gly Arg Leu Leu Gln Pro Tyr Pro Asp Trp Ser Trp
                85                  90                  95

Ala Lys Tyr Lys Asp Cys Ser Gly Ile Val Ser Val Tyr Lys Ile Ser
            100                 105                 110

Ile Asp Lys Phe Asp Arg Leu Trp Val Leu Asp Ser Gly Leu Ile Asn
        115                 120                 125

Asn Thr Lys Leu Ile Cys Ser Pro Lys Leu Leu Ala Phe Asp Leu Asn
    130                 135                 140

Thr Ser Gln Leu Leu Lys Gln Val His Ile Pro His Asp Ile Ala Val
145                 150                 155                 160

Asn Ala Thr Thr Gly Lys Gly Gly Leu Val Phe Leu Ala Val Gln Ala
                165                 170                 175

Val Asp Pro Ile Asn Thr Met Ala Tyr Met Ala Asp Asn Arg Gly Asn
            180                 185                 190

Ala Leu Ser Val Tyr Gln Asn Ser Asp Asn Ser Leu His Arg Leu Thr
        195                 200                 205

Ser Asn Thr Phe Asp Tyr Asp Pro Arg Tyr Thr Glu Phe Thr Ile Ala
    210                 215                 220

Gly Glu Ser Phe Ile Leu Gln Asp Gly Ile Phe Gly Ile Ala Val Ser
225                 230                 235                 240

Pro Val Thr Asn Asn Leu Tyr Tyr Ser Pro Leu Ser Ser Arg Ser Leu
                245                 250                 255

Tyr Tyr Val Asn Thr Glu Pro Phe Met Lys Ser Glu Tyr Glu Gly Asn
            260                 265                 270
```

```
Asn Val Gln Tyr Lys Gly Val Glu Asp Ile Tyr Asn Thr Gln Leu Ser
            275                 280                 285

Ala Lys Ala Val Ser Lys Asn Gly Val Phe Phe Gly Leu Val Asn
290                 295                 300

Asn Ser Ala Leu Gly Cys Leu Asn Glu His Gln Pro Ile Gln Arg Gln
305                 310                 315                 320

Asn Ile Asp Met Val Ala Gln Asn Glu Glu Thr Leu Gln Met Ile Phe
            325                 330                 335

Ser Ile Lys Ile Lys Gln Asp Phe Pro Gln Ser Asn Arg Ile Asn Lys
            340                 345                 350

Thr Glu Arg Asn Glu Tyr Met Leu Ala Leu Ser Asn Arg Leu Gln Lys
            355                 360                 365

Phe Met Asn His Asn Tyr Asn Phe Asn Glu Val Asn Phe Arg Val Leu
        370                 375                 380

Ser Ala Asn Val Asn Asp Leu Ile Lys Asn Thr Arg Cys Ala Asn Phe
385                 390                 395                 400

Asn Asn Gln Ala His His Ser Ser Lys Ser His
            405                 410

<210> SEQ ID NO 35
<211> LENGTH: 9
<212> TYPE: PRT
<213> ORGANISM: Apis mellifera

<400> SEQUENCE: 35

Glu Pro Phe Lys Ile Ser Ile His Leu
1               5

<210> SEQ ID NO 36
<211> LENGTH: 95
<212> TYPE: PRT
<213> ORGANISM: Apis mellifera

<400> SEQUENCE: 36

Met Lys Ile Tyr Phe Ile Val Gly Leu Leu Phe Met Ala Met Val Ala
1               5                   10                  15

Ile Met Ala Ala Pro Val Glu Asp Glu Phe Glu Pro Leu Glu His Phe
            20                  25                  30

Glu Asn Glu Glu Arg Ala Asp Arg His Arg Arg Val Thr Cys Asp Leu
        35                  40                  45

Leu Ser Phe Lys Gly Gln Val Asn Asp Ser Ala Cys Ala Ala Asn Cys
    50                  55                  60

Leu Ser Leu Gly Lys Ala Gly Gly His Cys Glu Lys Gly Val Cys Ile
65                  70                  75                  80

Cys Arg Lys Thr Ser Phe Lys Asp Leu Trp Asp Lys Arg Phe Gly
            85                  90                  95

<210> SEQ ID NO 37
<211> LENGTH: 76
<212> TYPE: PRT
<213> ORGANISM: Apis mellifera

<400> SEQUENCE: 37

Ala Pro Val Glu Asp Glu Phe Glu Pro Leu Glu His Phe Glu Asn Glu
1               5                   10                  15

Glu Arg Ala Asp Arg His Arg Arg Val Thr Cys Asp Leu Leu Ser Phe
            20                  25                  30
```

Lys Gly Gln Val Asn Asp Ser Ala Cys Ala Ala Asn Cys Leu Ser Leu
            35                  40                  45

Gly Lys Ala Gly Gly His Cys Glu Lys Gly Val Cys Ile Cys Arg Lys
    50                  55                  60

Thr Ser Phe Lys Asp Leu Trp Asp Lys Arg Phe Gly
65                  70                  75

<210> SEQ ID NO 38
<211> LENGTH: 78
<212> TYPE: PRT
<213> ORGANISM: Apis mellifera

<400> SEQUENCE: 38

Met Ser Lys Ile Val Ala Val Val Leu Ala Ala Phe Cys Val Ala
1               5                   10                  15

Met Leu Val Ser Asp Val Ser Ala Lys Thr Ser Ile Ser Val Lys Gly
                20                  25                  30

Glu Ser Asn Val Asp Val Ser Gln Ile Asn Ser Leu Val Ser Ser
            35                  40                  45

Ile Val Ser Gly Ala Asn Val Ser Ala Val Leu Leu Ala Gln Thr Leu
    50                  55                  60

Val Asn Ile Leu Gln Ile Leu Ile Asp Ala Asn Val Phe Ala
65                  70                  75

<210> SEQ ID NO 39
<211> LENGTH: 54
<212> TYPE: PRT
<213> ORGANISM: Apis mellifera

<400> SEQUENCE: 39

Lys Thr Ser Ile Ser Val Lys Gly Glu Ser Asn Val Asp Val Ser
1               5                   10                  15

Gln Ile Asn Ser Leu Val Ser Ser Ile Val Ser Gly Ala Asn Val Ser
                20                  25                  30

Ala Val Leu Leu Ala Gln Thr Leu Val Asn Ile Leu Gln Ile Leu Ile
            35                  40                  45

Asp Ala Asn Val Phe Ala
    50

<210> SEQ ID NO 40
<211> LENGTH: 78
<212> TYPE: PRT
<213> ORGANISM: Apis cerana

<400> SEQUENCE: 40

Met Ser Lys Ile Ile Ala Val Val Leu Ala Ala Phe Cys Val Ala
1               5                   10                  15

Met Leu Val Ser Asp Val Ser Ala Lys Thr Ser Ile Ser Ala Lys Ala
                20                  25                  30

Glu Ser Asn Val Asp Val Ser Gln Ile Asn Ser Leu Val Ser Ser
            35                  40                  45

Ile Val Ser Gly Ala Asn Val Ser Ala Val Leu Leu Ala Gln Thr Leu
    50                  55                  60

Val Asn Ile Leu Gln Ile Leu Ile Asp Ala Asn Val Phe Ala
65                  70                  75

<210> SEQ ID NO 41
<211> LENGTH: 54
<212> TYPE: PRT

<213> ORGANISM: Apis cerana

<400> SEQUENCE: 41

Lys Thr Ser Ile Ser Ala Lys Ala Glu Ser Asn Val Asp Val Val Ser
1               5                   10                  15

Gln Ile Asn Ser Leu Val Ser Ser Ile Val Ser Gly Ala Asn Val Ser
            20                  25                  30

Ala Val Leu Leu Ala Gln Thr Leu Val Asn Ile Leu Gln Ile Leu Ile
        35                  40                  45

Asp Ala Asn Val Phe Ala
    50

<210> SEQ ID NO 42
<211> LENGTH: 1293
<212> TYPE: DNA
<213> ORGANISM: Apis mellifera
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature

```
<222> LOCATION: (72)..(72)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
```

-continued

```
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
```

-continued

```
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (456)..(456)
```

```
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
```

```
<222> LOCATION: (552)..(552)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
```

-continued

```
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
```

-continued

```
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (921)..(921)
```

-continued

```
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (960)..(960)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
<222> LOCATION: (999)..(999)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1005)..(1005)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
```

-continued

```
<222> LOCATION: (1023)..(1023)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1065)..(1065)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1086)..(1086)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1122)..(1122)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1137)..(1137)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
```

```
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1200)..(1200)
<223> OTHER INFORMATION: n is a, c, g, or t
<220> FEATURE:
<221> NAME/KEY: misc_feature
<222> LOCATION: (1212)..(1212)
<223> OTHER INFORMATION: n is a, c, g, or t
<220> FEATURE:
<221> NAME/KEY: misc_feature
<222> LOCATION: (1218)..(1218)
<223> OTHER INFORMATION: n is a, c, g, or t
<220> FEATURE:
<221> NAME/KEY: misc_feature
<222> LOCATION: (1227)..(1227)
<223> OTHER INFORMATION: n is a, c, g, or t
<220> FEATURE:
<221> NAME/KEY: misc_feature
<222> LOCATION: (1233)..(1233)
<223> OTHER INFORMATION: n is a, c, g, or t
<220> FEATURE:
<221> NAME/KEY: misc_feature
<222> LOCATION: (1239)..(1239)
<223> OTHER INFORMATION: n is a, c, g, or t
<220> FEATURE:
<221> NAME/KEY: misc_feature
<222> LOCATION: (1242)..(1242)
<223> OTHER INFORMATION: n is a, c, g, or t
<220> FEATURE:
<221> NAME/KEY: misc_feature
<222> LOCATION: (1254)..(1254)
<223> OTHER INFORMATION: n is a, c, g, or t
<220> FEATURE:
<221> NAME/KEY: misc_feature
<222> LOCATION: (1266)..(1266)
<223> OTHER INFORMATION: n is a, c, g, or t
<220> FEATURE:
<221> NAME/KEY: misc_feature
<222> LOCATION: (1269)..(1269)
<223> OTHER INFORMATION: n is a, c, g, or t
<220> FEATURE:
<221> NAME/KEY: misc_feature
<222> LOCATION: (1272)..(1272)
<223> OTHER INFORMATION: n is a, c, g, or t
<220> FEATURE:
<221> NAME/KEY: misc_feature
<222> LOCATION: (1284)..(1284)
<223> OTHER INFORMATION: n is a, c, g, or t
<220> FEATURE:
<221> NAME/KEY: misc_feature
<222> LOCATION: (1293)..(1293)
<223> OTHER INFORMATION: n is a, c, g, or t

<400> SEQUENCE: 42
atgacnmgny tnttyatgyt ngtntgyytn ggnathgtnt gycarggnac nacnggnaay      60
athytnmgng gngarwsnyt naayaarwsn ytnccnathy tncaygartg gaarttytty    120
gaytaygayt tyggnwsnga ygarmgnmgn cargaygcna thytnwsngg ngartaygay    180
tayaaraaya aytayccnws ngayathgay cartggcayg ayaarathtt ygtnacnatg    240
ytnmgntaya ayggngtncc nwsnwsnytn aaygtnathw snaaraargt nggngayggn    300
ggnccnytny tncarccnta yccngaytgg wsnttygcna artaygayga ytgywsnggn    360
athgtnwsng cnwsnaaryt ngcnathgay aartgygaym gnytntgggt nytngaywsn    420
ggnytngtna ayaaytacnca rccnatgtgy wsnccnaary tntnacntt ygayytnacn    480 acnwsncary tnytnaarca rgtngarath ccncaygayg tngcngtnaa ygcnacnacn    540
```

```
aarggnmgny tnwsnwsnyt ngcngtncar wsnytngayt g

```
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
```

```
<222> LOCATION: (231)..(231)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
```

-continued

```
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
```

-continued

```
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (555)..(555)
```

```
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
```

```
<222> LOCATION: (669)..(669)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
```

```
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (885)..(885)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
```

-continued

```
<220> FEATURE:
<221> NAME/KEY: misc_feature
<222> LOCATION: (912)..(912)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (960)..(960)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (999)..(999)
<223> OTHER INFORMATION: n is a, c, g, or t
<220> FEATURE:
<221> NAME/KEY: misc_feature
<222> LOCATION: (1002)..(1002)
```

```
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1086)..(1086)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1137)..(1137)
<223> OTHER INFORMATION: n is a, c, g, or t
<220> FEATURE:
<221> NAME/KEY: misc_feature
```

<222> LOCATION: (1140)..(1140)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1161)..(1161)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1197)..(1197)
<223> OTHER INFORMATION: n is a, c, g, or t
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1209)..(1209)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1224)..(1224)
<223> OTHER INFORMATION: n is a, c, g, or t
<220> FEATURE:
<221> NAME/KEY: misc_feature
<222> LOCATION: (1230)..(1230)
<223> OTHER INFORMATION: n is a, c, g, or t
<220> FEATURE:
<221> NAME/KEY: misc_feature
<222> LOCATION: (1236)..(1236)
<223> OTHER INFORMATION: n is a, c, g, or t
<220> FEATURE:
<221> NAME/KEY: misc_feature
<222> LOCATION: (1245)..(1245)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1323)..(1323)
<223> OTHER INFORMATION: n is a, c, g, or t

<400> SEQUENCE: 43
atgacnmgnt ggytnttyat ggtngcntgy ytnggnathg cntgycargg ngcnathgtn 60
mgngaraayw snccnmgnaa yytngaraar wsnytnaayg tnathcayga rtggaartay 120
ttygaytayg ayttyggnws ngargarmgn mgncargcng cnathcarws nggngartay 180
gaycayacna araaytaycc nttygaygtn gaycartggm gngayaarac nttygtnacn 240
athytnmgnt aygayggngt nccnwsnacn ytnaaygtna thwsnggnaa racnggnaar 300
ggnggnmgny tnytnaarcc ntayccngay tggwsnttyg cngarttyaa rgaytgywsn 360
aarathgtnw sngcnttyaa rathgcnath gayaarttyg aymgnytntg ggtnytngay 420
wsnggnytng tnaaymgnac ngtnccngtn tgygcnccna arytncaygt nttygayytn 480
aaracnwsna aycayytnaa rcarathgar athccncayg ayathgcngt naaygcnacn 540

```
acnggnaarg gnggnytngt nwsnytngcn gtncargcna thgayytngc naayacnytn    600
gtntayatgg cngaycayaa rggngaygcn ytnathgtnt aycaraaygc ngaygaywsn    660
ttycaymgny tnacnwsnaa yacnttygay taygayccnm gntaygcnaa ratgacnath    720
gayggngarw snttyacnyt naaraayggn athtgyggna tggcnytnws nccngtnacn    780
aayaayytnt aytaywsncc nytngcnwsn cayggnytnt aytaygtnaa yacngcnccn    840
ttyatgaarw sncarttygg ngaraayaay gtncartayc arggnwsnga rgayathytn    900
aayacncarw snytngcnaa rgcngtnwsn aaraayggng tnytnttygt nggnytngtn    960
ggnaaywsng cngtnggntg ytggaaygar caycarwsny tncarmgnca raayytngar   1020
atggtngcnc araaygaymg nacnytncar atgathgcng gnatgaarat haargargar   1080
ytnccncayt tygtnggnws naayaarccn gtnaargayg artayatgyt ngtnytnwsn   1140
aaymgnatgc araarathgt naaygaygay ttyaayttyg aygaygtnaa yttymgnath   1200
ytnggngcna aygtnaarga rytnathmgn aayacncayt gygtnaayaa yaaycaraay   1260
gayaayathc araayacnaa yaaycaraay gayaayaayc araaraayaa yaaraaraay   1320
gcnaayaayc araaraayaa yaaycaraay gayaay                             1356
```

```
<210> SEQ ID NO 44
<211> LENGTH: 1632
<212> TYPE: DNA
<213> ORGANISM: Apis cerana
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
```

-continued

```
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
```

-continued

```
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
```

-continued

```
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (438)..(438)
```

-continued

```
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
```

```
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
```

-continued

```
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
```

-continued

```
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (903)..(903)
```

```
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (960)..(960)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (984)..(984)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (993)..(993)
<223> OTHER INFORMATION: n is a, c, g, or t
<220> FEATURE:
<221> NAME/KEY: misc_feature
<222> LOCATION: (999)..(999)
<223> OTHER INFORMATION: n is a, c, g, or t
<220> FEATURE:
<221> NAME/KEY: misc_feature
```

-continued

```
<222> LOCATION: (1014)..(1014)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1107)..(1107)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1125)..(1125)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1149)..(1149)
<223> OTHER INFORMATION: n is a, c, g, or t
<220> FEATURE:
```

-continued

```
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1161)..(1161)
<223> OTHER INFORMATION: n is a, c, g, or t
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: misc_feature
<222> LOCATION: (1212)..(1212)
<223> OTHER INFORMATION: n is a, c, g, or t
<220> FEATURE:
<221> NAME/KEY: misc_feature
<222> LOCATION: (1218)..(1218)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1224)..(1224)
<223> OTHER INFORMATION: n is a, c, g, or t
<220> FEATURE:
<221> NAME/KEY: misc_feature
<222> LOCATION: (1230)..(1230)
<223> OTHER INFORMATION: n is a, c, g, or t
<220> FEATURE:
<221> NAME/KEY: misc_feature
<222> LOCATION: (1239)..(1239)
<223> OTHER INFORMATION: n is a, c, g, or t
<220> FEATURE:
<221> NAME/KEY: misc_feature
<222> LOCATION: (1245)..(1245)
<223> OTHER INFORMATION: n is a, c, g, or t
<220> FEATURE:
<221> NAME/KEY: misc_feature
<222> LOCATION: (1251)..(1251)
<223> OTHER INFORMATION: n is a, c, g, or t
<220> FEATURE:
<221> NAME/KEY: misc_feature
<222> LOCATION: (1254)..(1254)
<223> OTHER INFORMATION: n is a, c, g, or t
<220> FEATURE:
<221> NAME/KEY: misc_feature
<222> LOCATION: (1260)..(1260)
<223> OTHER INFORMATION: n is a, c, g, or t
<220> FEATURE:
<221> NAME/KEY: misc_feature
<222> LOCATION: (1263)..(1263)
<223> OTHER INFORMATION: n is a, c, g, or t
<220> FEATURE:
<221> NAME/KEY: misc_feature
<222> LOCATION: (1281)..(1281)
<223> OTHER INFORMATION: n is a, c, g, or t
<220> FEATURE:
<221> NAME/KEY: misc_feature
<222> LOCATION: (1284)..(1284)
<223> OTHER INFORMATION: n is a, c, g, or t
<220> FEATURE:
<221> NAME/KEY: misc_feature
<222> LOCATION: (1296)..(1296)
<223> OTHER INFORMATION: n is a, c, g, or t
<220> FEATURE:
<221> NAME/KEY: misc_feature
<222> LOCATION: (1311)..(1311)
<223> OTHER INFORMATION: n is a, c, g, or t
<220> FEATURE:
<221> NAME/KEY: misc_feature
<222> LOCATION: (1326)..(1326)
<223> OTHER INFORMATION: n is a, c, g, or t
```

-continued

```
<220> FEATURE:
<221> NAME/KEY: misc_feature
<222> LOCATION: (1341)..(1341)
<223> OTHER INFORMATION: n is a, c, g, or t
<220> FEATURE:
<221> NAME/KEY: misc_feature
<222> LOCATION: (1356)..(1356)
<223> OTHER INFORMATION: n is a, c, g, or t
<220> FEATURE:
<221> NAME/KEY: misc_feature
<222> LOCATION: (1371)..(1371)
<223> OTHER INFORMATION: n is a, c, g, or t
<220> FEATURE:
<221> NAME/KEY: misc_feature
<222> LOCATION: (1377)..(1377)
<223> OTHER INFORMATION: n is a, c, g, or t
<220> FEATURE:
<221> NAME/KEY: misc_feature
<222> LOCATION: (1392)..(1392)
<223> OTHER INFORMATION: n is a, c, g, or t
<220> FEATURE:
<221> NAME/KEY: misc_feature
<222> LOCATION: (1416)..(1416)
<223> OTHER INFORMATION: n is a, c, g, or t
<220> FEATURE:
<221> NAME/KEY: misc_feature
<222> LOCATION: (1422)..(1422)
<223> OTHER INFORMATION: n is a, c, g, or t
<220> FEATURE:
<221> NAME/KEY: misc_feature
<222> LOCATION: (1446)..(1446)
<223> OTHER INFORMATION: n is a, c, g, or t
<220> FEATURE:
<221> NAME/KEY: misc_feature
<222> LOCATION: (1452)..(1452)
<223> OTHER INFORMATION: n is a, c, g, or t
<220> FEATURE:
<221> NAME/KEY: misc_feature
<222> LOCATION: (1476)..(1476)
<223> OTHER INFORMATION: n is a, c, g, or t
<220> FEATURE:
<221> NAME/KEY: misc_feature
<222> LOCATION: (1482)..(1482)
<223> OTHER INFORMATION: n is a, c, g, or t
<220> FEATURE:
<221> NAME/KEY: misc_feature
<222> LOCATION: (1491)..(1491)
<223> OTHER INFORMATION: n is a, c, g, or t
<220> FEATURE:
<221> NAME/KEY: misc_feature
<222> LOCATION: (1521)..(1521)
<223> OTHER INFORMATION: n is a, c, g, or t
<220> FEATURE:
<221> NAME/KEY: misc_feature
<222> LOCATION: (1527)..(1527)
<223> OTHER INFORMATION: n is a, c, g, or t
<220> FEATURE:
<221> NAME/KEY: misc_feature
<222> LOCATION: (1545)..(1545)
<223> OTHER INFORMATION: n is a, c, g, or t
<220> FEATURE:
<221> NAME/KEY: misc_feature
<222> LOCATION: (1551)..(1551)
<223> OTHER INFORMATION: n is a, c, g, or t
<220> FEATURE:
<221> NAME/KEY: misc_feature
<222> LOCATION: (1557)..(1557)
<223> OTHER INFORMATION: n is a, c, g, or t
<220> FEATURE:
<221> NAME/KEY: misc_feature
<222> LOCATION: (1596)..(1596)
<223> OTHER INFORMATION: n is a, c, g, or t
<220> FEATURE:
<221> NAME/KEY: misc_feature
<222> LOCATION: (1611)..(1611)
<223> OTHER INFORMATION: n is a, c, g, or t
<220> FEATURE:
<221> NAME/KEY: misc_feature
<222> LOCATION: (1620)..(1620)
```

<223> OTHER INFORMATION: n is a, c, g, or t
<220> FEATURE:
<221> NAME/KEY: misc_feature
<222> LOCATION: (1623)..(1623)
<223> OTHER INFORMATION: n is a, c, g, or t
<220> FEATURE:
<221> NAME/KEY: misc_feature
<222> LOCATION: (1629)..(1629)
<223> OTHER INFORMATION: n is a, c, g, or t

<400> SEQUENCE: 44

```
atgacnaart ggytnytnyt ngtngtntgy ytnggnathg cntgycarga ygtnacnwsn     60
gcngcngtna aycaycarmg naarwsngcn aayaayytng cncaywsnat gaargtnath    120
taygartgga arcayathga yttygaytty ggnwsngayg armgnmgnga ygcngcnath    180
aarwsnggng arttygayca yacnaaraay tayccnttyg aygtngaymg ntggmgngay    240
aaracnttyg tnacnathga rmgnaayaay ggngtnccnw snwsnytnaa ygtngtnacn    300
aayaaraarg gnaarggngg nccnytnytn mgnccntayc cngaytggws nttygcnaar    360
taygargayt gywsnggnat hgtnwsngcn ttyaarathg cngtngayaa rttygaymgn    420
ytntgggtny tngaywsngg nytngtnaay aayaaycarc cnatgtgyws nccnaarytn    480
ytnacnttyg ayytnaarac nwsnaarytn gtnaarcarg tngarathcc ncayaayath    540
gcngtnaayg cnacnacngg natgggngar ytngtnwsny tngcngtnca rgcnathgay    600
mgnacnaaya cnatggtnta yathgcngay garaarggng arggnytnat hatgtaycar    660
aaywsngayg aywsnttyca ymgnytnacn wsnaayacnt tygaytayga yccnmgntay    720
acnaarytna cngtngcngg ngarwsntty acngtnaara ayggnathta yggnathgcn    780
ytnwsnccng tnacnaayaa yytntaytay wsnccnytny tnwsncaygg nytntaytay    840
gtngayacng arcarttyws naayccncar taygargara ayaaygtnca rtaygarggn    900
wsncargaya thytnaayac ncarwsntty ggnaargtng tnwsnaaraa yggngtnytn    960
ttyytnggny tngtnggnaa ywsnggnath gcntgygtna aygarcayca rgtnytncar   1020
mgngarwsnt tygaygtngt ngcncaraay gargaracny tncaratgat hgtnwsnatg   1080
aarathatgg araayytncc ncarwsnggn mgnathaayg ayccngargg naaygartay   1140
atgytngcny tnwsnaaymg natgcaraar athathaaya aygayttyaa yttyaaygay   1200
gtnaayttym gnathytngg ngcnaaygtn gaygayytna tgmgnaayac nmgntgyggn   1260
mgntaycaya aycaraaygc nggnaaycar aaygcngaya aycaraaygc ngayaaycar   1320
aaygcnaaya aycaraaygc ngayaaycar aaygcnaaya arcaraaygg naaymgncar   1380
aaygayaaym gncaraayga yaayaarcar aayggnaaym gncaraayga yaayaarcar   1440
aayggnaaym gncaraayga yaayaarcar aayggnaaym gncaraaygg naayaarcar   1500
aaygayaaya arcaraaygg naaymgncar aaygayaaya armgnaaygg naaymgncar   1560
aaygayaayc araayaayca raaygayaay aaymgnaayg ayaaycargt ncaycaywsn   1620
wsnaarytnc ay                                                         1632
```

<210> SEQ ID NO 45
<211> LENGTH: 1392
<212> TYPE: DNA
<213> ORGANISM: Apis florea
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature

```
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
```

```
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
```

```
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (375)..(375)
```

```
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
```

```
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
```

```
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
```

-continued

```
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (867)..(867)
```

```
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (960)..(960)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
```

```
<222> LOCATION: (975)..(975)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (999)..(999)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: misc_feature
<222> LOCATION: (1056)..(1056)
<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1086)..(1086)
<223> OTHER INFORMATION: n is a, c, g, or t
<220> FEATURE:
<221> NAME/KEY: misc_feature
<222> LOCATION: (1092)..(1092)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
```

```
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1116)..(1116)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1137)..(1137)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t
<220> FEATURE:
<221> NAME/KEY: misc_feature
<222> LOCATION: (1161)..(1161)
<223> OTHER INFORMATION: n is a, c, g, or t
<220> FEATURE:
<221> NAME/KEY: misc_feature
<222> LOCATION: (1173)..(1173)
<223> OTHER INFORMATION: n is a, c, g, or t
<220> FEATURE:
<221> NAME/KEY: misc_feature
<222> LOCATION: (1179)..(1179)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1209)..(1209)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1224)..(1224)
<223> OTHER INFORMATION: n is a, c, g, or t
<220> FEATURE:
<221> NAME/KEY: misc_feature
<222> LOCATION: (1230)..(1230)
<223> OTHER INFORMATION: n is a, c, g, or t
<220> FEATURE:
<221> NAME/KEY: misc_feature
<222> LOCATION: (1236)..(1236)
<223> OTHER INFORMATION: n is a, c, g, or t
```

```
<220> FEATURE:
<221> NAME/KEY: misc_feature
<222> LOCATION: (1239)..(1239)
<223> OTHER INFORMATION: n is a, c, g, or t
<220> FEATURE:
<221> NAME/KEY: misc_feature
<222> LOCATION: (1245)..(1245)
<223> OTHER INFORMATION: n is a, c, g, or t
<220> FEATURE:
<221> NAME/KEY: misc_feature
<222> LOCATION: (1296)..(1296)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1305)..(1305)
<223> OTHER INFORMATION: n is a, c, g, or t
<220> FEATURE:
<221> NAME/KEY: misc_feature
<222> LOCATION: (1308)..(1308)
<223> OTHER INFORMATION: n is a, c, g, or t
<220> FEATURE:
<221> NAME/KEY: misc_feature
<222> LOCATION: (1314)..(1314)
<223> OTHER INFORMATION: n is a, c, g, or t
<220> FEATURE:
<221> NAME/KEY: misc_feature
<222> LOCATION: (1350)..(1350)
<223> OTHER INFORMATION: n is a, c, g, or t
<220> FEATURE:
<221> NAME/KEY: misc_feature
<222> LOCATION: (1359)..(1359)
<223> OTHER INFORMATION: n is a, c, g, or t
<220> FEATURE:
<221> NAME/KEY: misc_feature
<222> LOCATION: (1362)..(1362)
<223> OTHER INFORMATION: n is a, c, g, or t
<220> FEATURE:
<221> NAME/KEY: misc_feature
<222> LOCATION: (1368)..(1368)
<223> OTHER INFORMATION: n is a, c, g, or t
<220> FEATURE:
<221> NAME/KEY: misc_feature
<222> LOCATION: (1377)..(1377)
<223> OTHER INFORMATION: n is a, c, g, or t

<400> SEQUENCE: 45
atgacnaart ggytnytnyt natggtntgy ytnggnathg cntgycaraa yathmgnggn      60
ggngtngtnm ngaraayws nwsnggnaar aayytnacna ayacnytnaa ygtnathcay     120
aartggaart ayytngayta ygayttygay aaygaygarm gnmgncargc ngcnathcar     180
wsnggngart aygaymgnac naaraaytay ccnytngayg tngaycartg gcayaayaar     240
acnttyytng cngtnathmg ntayaayggn gtnccnwsnw snytnaaygt ngtnwsngay     300
aaracnggna ayggnggnmg nytnytncar ccntayccng aytggwsntt ygcnaartay     360
gargaytgyw snggnathgt nwsngcncay aarathgcna thgaygarta ygarmgnytn     420
tgggtnytng aywsnggnyt ngtnaayaay acncarccna tgtgywsncc naarytntty     480
gcnttygayy tnaayacnws ncarytnytn aarcargtng arathccnca ygaygtngcn     540
acnacnggna arggngaryt ngtnwsnytn acngtncarg cnatggayws nacnaayacn     600
atggtntaya tggtngayaa yaaraayacn ytnathatht aycaraaygc ngaygaywsn     660
ttycaymgny tnwsnwsnca yacnytnaay cayaaywsng ayaaratgws ngaycarcar     720
garaayytna cnytnaarga rgtngayaay aargtntayg gnatggcnyt nwsnccngtn     780
acncayaayy tntaytayaa ywsnccnwsn wsngaraayy tntaytaygt naayacngar     840
```
wsnytnatga arwsngaraa ycarggnaay gaygtncart aygarmgngt ncargaygtn 900
ttygaywsnc arytnacngt naargcngtn wsnaaraayg gngtnytnyt nttyggnytn 960
gcnaayaaya cnytnwsntg ytggaaygar caycarwsny tngaymgnca raayathgay 1020
gtngtngcnm gnaaygarga yacnytncar atggtngtnw snatgaarat haarcaraay 1080
gtnccncarw snggnmgngt naayaayacn carmgnaayg artayytnyt ngcnytnwsn 1140
gaymgnaayc araaygtnyt naayaaygay ytnaayytng arcaygtnaa yttycarath 1200
ytnggngcna aygtnaayga yytnathmgn aaywsnmgnt gygcnaaytt ygayaaycar 1260
gayaayaayc aytayaayca yaaycayaay cargcnmgnc aywsnwsnaa rwsngayaay 1320
caraayaaya aycarcayaa ygaycargcn caycaywsnw snaarwsnaa yaaymgncay 1380
aayaayaayg ay 1392

<210> SEQ ID NO 46
<211> LENGTH: 1794
<212> TYPE: DNA
<213> ORGANISM: Apis cerana
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature

```
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
```

-continued

```
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
```

-continued

```
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (435)..(435)
```

```
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
```

```
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
```

-continued

```
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
```

-continued

```
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (939)..(939)
```

```
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<221> NAME/KEY: misc_feature
<222> LOCATION: (1035)..(1035)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1053)..(1053)
<223> OTHER INFORMATION: n is a, c, g, or t
<220> FEATURE:
<221> NAME/KEY: misc_feature
<222> LOCATION: (1056)..(1056)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1065)..(1065)
<223> OTHER INFORMATION: n is a, c, g, or t
<220> FEATURE:
<221> NAME/KEY: misc_feature
<222> LOCATION: (1068)..(1068)
<223> OTHER INFORMATION: n is a, c, g, or t
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
```

```
<222> LOCATION: (1089)..(1089)
<223> OTHER INFORMATION: n is a, c, g, or t
<220> FEATURE:
<221> NAME/KEY: misc_feature
<222> LOCATION: (1092)..(1092)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1122)..(1122)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1149)..(1149)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1176)..(1176)
<223> OTHER INFORMATION: n is a, c, g, or t
<220> FEATURE:
<221> NAME/KEY: misc_feature
<222> LOCATION: (1185)..(1185)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: misc_feature
<222> LOCATION: (1212)..(1212)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1230)..(1230)
<223> OTHER INFORMATION: n is a, c, g, or t
<220> FEATURE:
<221> NAME/KEY: misc_feature
<222> LOCATION: (1239)..(1239)
<223> OTHER INFORMATION: n is a, c, g, or t
<220> FEATURE:
```

-continued

```
<221> NAME/KEY: misc_feature
<222> LOCATION: (1248)..(1248)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
<222> LOCATION: (1266)..(1266)
<223> OTHER INFORMATION: n is a, c, g, or t
<220> FEATURE:
<221> NAME/KEY: misc_feature
<222> LOCATION: (1275)..(1275)
<223> OTHER INFORMATION: n is a, c, g, or t
<220> FEATURE:
<221> NAME/KEY: misc_feature
<222> LOCATION: (1284)..(1284)
<223> OTHER INFORMATION: n is a, c, g, or t
<220> FEATURE:
<221> NAME/KEY: misc_feature
<222> LOCATION: (1293)..(1293)
<223> OTHER INFORMATION: n is a, c, g, or t
<220> FEATURE:
<221> NAME/KEY: misc_feature
<222> LOCATION: (1302)..(1302)
<223> OTHER INFORMATION: n is a, c, g, or t
<220> FEATURE:
<221> NAME/KEY: misc_feature
<222> LOCATION: (1305)..(1305)
<223> OTHER INFORMATION: n is a, c, g, or t
<220> FEATURE:
<221> NAME/KEY: misc_feature
<222> LOCATION: (1317)..(1317)
<223> OTHER INFORMATION: n is a, c, g, or t
<220> FEATURE:
<221> NAME/KEY: misc_feature
<222> LOCATION: (1320)..(1320)
<223> OTHER INFORMATION: n is a, c, g, or t
<220> FEATURE:
<221> NAME/KEY: misc_feature
<222> LOCATION: (1329)..(1329)
<223> OTHER INFORMATION: n is a, c, g, or t
<220> FEATURE:
<221> NAME/KEY: misc_feature
<222> LOCATION: (1338)..(1338)
<223> OTHER INFORMATION: n is a, c, g, or t
<220> FEATURE:
<221> NAME/KEY: misc_feature
<222> LOCATION: (1347)..(1347)
<223> OTHER INFORMATION: n is a, c, g, or t
<220> FEATURE:
<221> NAME/KEY: misc_feature
<222> LOCATION: (1350)..(1350)
<223> OTHER INFORMATION: n is a, c, g, or t
<220> FEATURE:
<221> NAME/KEY: misc_feature
<222> LOCATION: (1356)..(1356)
<223> OTHER INFORMATION: n is a, c, g, or t
<220> FEATURE:
<221> NAME/KEY: misc_feature
<222> LOCATION: (1365)..(1365)
<223> OTHER INFORMATION: n is a, c, g, or t
<220> FEATURE:
<221> NAME/KEY: misc_feature
<222> LOCATION: (1374)..(1374)
<223> OTHER INFORMATION: n is a, c, g, or t
<220> FEATURE:
<221> NAME/KEY: misc_feature
<222> LOCATION: (1377)..(1377)
<223> OTHER INFORMATION: n is a, c, g, or t
<220> FEATURE:
<221> NAME/KEY: misc_feature
<222> LOCATION: (1389)..(1389)
<223> OTHER INFORMATION: n is a, c, g, or t
<220> FEATURE:
<221> NAME/KEY: misc_feature
<222> LOCATION: (1392)..(1392)
<223> OTHER INFORMATION: n is a, c, g, or t
```

```
<220> FEATURE:
<221> NAME/KEY: misc_feature
<222> LOCATION: (1401)..(1401)
<223> OTHER INFORMATION: n is a, c, g, or t
<220> FEATURE:
<221> NAME/KEY: misc_feature
<222> LOCATION: (1410)..(1410)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1422)..(1422)
<223> OTHER INFORMATION: n is a, c, g, or t
<220> FEATURE:
<221> NAME/KEY: misc_feature
<222> LOCATION: (1428)..(1428)
<223> OTHER INFORMATION: n is a, c, g, or t
<220> FEATURE:
<221> NAME/KEY: misc_feature
<222> LOCATION: (1437)..(1437)
<223> OTHER INFORMATION: n is a, c, g, or t
<220> FEATURE:
<221> NAME/KEY: misc_feature
<222> LOCATION: (1446)..(1446)
<223> OTHER INFORMATION: n is a, c, g, or t
<220> FEATURE:
<221> NAME/KEY: misc_feature
<222> LOCATION: (1455)..(1455)
<223> OTHER INFORMATION: n is a, c, g, or t
<220> FEATURE:
<221> NAME/KEY: misc_feature
<222> LOCATION: (1464)..(1464)
<223> OTHER INFORMATION: n is a, c, g, or t
<220> FEATURE:
<221> NAME/KEY: misc_feature
<222> LOCATION: (1473)..(1473)
<223> OTHER INFORMATION: n is a, c, g, or t
<220> FEATURE:
<221> NAME/KEY: misc_feature
<222> LOCATION: (1482)..(1482)
<223> OTHER INFORMATION: n is a, c, g, or t
<220> FEATURE:
<221> NAME/KEY: misc_feature
<222> LOCATION: (1491)..(1491)
<223> OTHER INFORMATION: n is a, c, g, or t
<220> FEATURE:
<221> NAME/KEY: misc_feature
<222> LOCATION: (1500)..(1500)
<223> OTHER INFORMATION: n is a, c, g, or t
<220> FEATURE:
<221> NAME/KEY: misc_feature
<222> LOCATION: (1509)..(1509)
<223> OTHER INFORMATION: n is a, c, g, or t
<220> FEATURE:
<221> NAME/KEY: misc_feature
<222> LOCATION: (1518)..(1518)
<223> OTHER INFORMATION: n is a, c, g, or t
<220> FEATURE:
<221> NAME/KEY: misc_feature
<222> LOCATION: (1521)..(1521)
<223> OTHER INFORMATION: n is a, c, g, or t
<220> FEATURE:
<221> NAME/KEY: misc_feature
<222> LOCATION: (1533)..(1533)
<223> OTHER INFORMATION: n is a, c, g, or t
<220> FEATURE:
<221> NAME/KEY: misc_feature
<222> LOCATION: (1536)..(1536)
<223> OTHER INFORMATION: n is a, c, g, or t
<220> FEATURE:
<221> NAME/KEY: misc_feature
<222> LOCATION: (1545)..(1545)
<223> OTHER INFORMATION: n is a, c, g, or t
<220> FEATURE:
<221> NAME/KEY: misc_feature
<222> LOCATION: (1563)..(1563)
```

```
<223> OTHER INFORMATION: n is a, c, g, or t
<220> FEATURE:
<221> NAME/KEY: misc_feature
<222> LOCATION: (1572)..(1572)
<223> OTHER INFORMATION: n is a, c, g, or t
<220> FEATURE:
<221> NAME/KEY: misc_feature
<222> LOCATION: (1581)..(1581)
<223> OTHER INFORMATION: n is a, c, g, or t
<220> FEATURE:
<221> NAME/KEY: misc_feature
<222> LOCATION: (1584)..(1584)
<223> OTHER INFORMATION: n is a, c, g, or t
<220> FEATURE:
<221> NAME/KEY: misc_feature
<222> LOCATION: (1590)..(1590)
<223> OTHER INFORMATION: n is a, c, g, or t
<220> FEATURE:
<221> NAME/KEY: misc_feature
<222> LOCATION: (1599)..(1599)
<223> OTHER INFORMATION: n is a, c, g, or t
<220> FEATURE:
<221> NAME/KEY: misc_feature
<222> LOCATION: (1608)..(1608)
<223> OTHER INFORMATION: n is a, c, g, or t
<220> FEATURE:
<221> NAME/KEY: misc_feature
<222> LOCATION: (1617)..(1617)
<223> OTHER INFORMATION: n is a, c, g, or t
<220> FEATURE:
<221> NAME/KEY: misc_feature
<222> LOCATION: (1641)..(1641)
<223> OTHER INFORMATION: n is a, c, g, or t
<220> FEATURE:
<221> NAME/KEY: misc_feature
<222> LOCATION: (1644)..(1644)
<223> OTHER INFORMATION: n is a, c, g, or t
<220> FEATURE:
<221> NAME/KEY: misc_feature
<222> LOCATION: (1647)..(1647)
<223> OTHER INFORMATION: n is a, c, g, or t
<220> FEATURE:
<221> NAME/KEY: misc_feature
<222> LOCATION: (1656)..(1656)
<223> OTHER INFORMATION: n is a, c, g, or t
<220> FEATURE:
<221> NAME/KEY: misc_feature
<222> LOCATION: (1695)..(1695)
<223> OTHER INFORMATION: n is a, c, g, or t
<220> FEATURE:
<221> NAME/KEY: misc_feature
<222> LOCATION: (1704)..(1704)
<223> OTHER INFORMATION: n is a, c, g, or t
<220> FEATURE:
<221> NAME/KEY: misc_feature
<222> LOCATION: (1710)..(1710)
<223> OTHER INFORMATION: n is a, c, g, or t
<220> FEATURE:
<221> NAME/KEY: misc_feature
<222> LOCATION: (1713)..(1713)
<223> OTHER INFORMATION: n is a, c, g, or t
<220> FEATURE:
<221> NAME/KEY: misc_feature
<222> LOCATION: (1716)..(1716)
<223> OTHER INFORMATION: n is a, c, g, or t
<220> FEATURE:
<221> NAME/KEY: misc_feature
<222> LOCATION: (1722)..(1722)
<223> OTHER INFORMATION: n is a, c, g, or t
<220> FEATURE:
<221> NAME/KEY: misc_feature
<222> LOCATION: (1731)..(1731)
<223> OTHER INFORMATION: n is a, c, g, or t
<220> FEATURE:
<221> NAME/KEY: misc_feature
<222> LOCATION: (1743)..(1743)
<223> OTHER INFORMATION: n is a, c, g, or t
<220> FEATURE:
<221> NAME/KEY: misc_feature
```

<222> LOCATION: (1746)..(1746)
<223> OTHER INFORMATION: n is a, c, g, or t
<220> FEATURE:
<221> NAME/KEY: misc_feature
<222> LOCATION: (1752)..(1752)
<223> OTHER INFORMATION: n is a, c, g, or t
<220> FEATURE:
<221> NAME/KEY: misc_feature
<222> LOCATION: (1758)..(1758)
<223> OTHER INFORMATION: n is a, c, g, or t

<400> SEQUENCE: 46

```
atgacnacnt ggytnytnyt ngtngtntgy ytnggnathg cntgycargg nathacnwsn      60
gtnacngtnm gngaraayws nccnmgnaar ytngcnaayw snatgaaygt nathcaygar     120
tggaartayy tngaytayga yttyggnwsn gaygarmgnm gncargcngc natgcarwsn     180
ggngartayg aycayacnaa raaytayccn ttygaygtng aycartggmg nggnatgacn     240
ttygtnacng tnccnmgnta yaarggngtn ccnwsnwsny tnaaygtnat hwsngaraar     300
athggnaayg gnggnmgnyt nytncarccn tayccngayt ggwsntgggc naaytayaar     360
gaytgywsng gnathgtnws ngcntayaar athgcnathg ayaarttyga ymgnytntgg     420
athytngayw snggnathat haayaayacn carccnatgt gywsnccnaa rytncaygtn     480
ttygayytna ayacnwsnca ycarytnaar cargtngtna tgccncayga yathgcngtn     540
aaygcnwsna cnggnaaygg nggnytngtn wsnytngtng tncargcnat ggayccngtn     600
aayacnathg tntayatggc ngaygayaar ggngaygcny tnathgtnta ycaraaywsn     660
gaygarwsnt tycaymgnyt nacnwsnaay acnttygayt aygayccnaa rtayathaar     720
atgatggayg cnggngarws nttyacngcn cargayggna thttyggnat ggcnytnwsn     780
ccnatgacna ayaayytnta ytaywsnccn ytnwsnwsnm gnwsnytnta ytaygtnaay     840
acnaarccnt tyatgaarws ngartayggn gcnaayaayg tncartayca rggngtncar     900
gayathttya ayacngarws nathgcnaar athatgwsna araayggngt nytnttytty     960
ggnytnatga ayaaywsngc nathggntgy tggaaygarc aycarccnyt ncarmgngar    1020
aayatggaya tggtngcnca raaygargar acnytncara cngtngtngc natgaaratg    1080
atgcayytnc cncarwsnaa yaaratgaay mgnatgcaym gnatgaaymg ngtnaaymgn    1140
gtnaaymgna tggaymgnat ggaymgnath gaymgnatgg aymgnatgga ymgnatggay    1200
acnatggaya cnatggaymg nathgaymgn atggaymgna tggaymgnat hgaymgnath    1260
gaymgnatgc ayacnatgga yacnatggay acnatggaym gnacngayaa ratgwsnwsn    1320
atggaymgna tggaymgnat ggaymgngtn gaymgnatgg ayacnatgga ymgnacngay    1380
aaratgwsnw snatggaymg natggaymgn atggaymgng tngayacnat ggayacnatg    1440
gayacnatgg aymgnatgga ymgnatggay mgnatggaym gnatggaymg natggaymgn    1500
atggayacna tggaymgnac ngayaaratg wsnmgnathg aymgnatgga yaarathgay    1560
mgnatggaym gnatggaymg nacnaaymgn atggaymgna tgaaymgnat gaaymgncar    1620
atgaaygart ayatgatggc nytnwsnatg aarytncara arttyathaa yaaygaytay    1680
aayttyaayg argtnaaytt ymgnathytn ggngcnaayg tnaaygayyt nathatgaay    1740
acnmgntgyg cnaaywsnga yaaycaraay aayaaycara ayaarcayaa yaay          1794
```

<210> SEQ ID NO 47
<211> LENGTH: 27
<212> TYPE: DNA
<213> ORGANISM: Apis mellifera
<220> FEATURE:

<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 47
garccnttya arathwsnat hcayytn     27

<210> SEQ ID NO 48
<211> LENGTH: 285
<212> TYPE: DNA
<213> ORGANISM: Apis mellifera
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature

```
<222> LOCATION: (114)..(114)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
```

<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t

<400> SEQUENCE: 48

```
atgaaratht ayttyathgt nggnytnytn ttyatggcna tggtngcnat hatggcngcn      60
ccngtngarg aygarttyga rccnytngar cayttygara aygargarmg ngcngaymgn     120
caymgnmgng tnacntgyga yytnytnwsn ttyaarggnc argtnaayga ywsngcntgy     180
gcngcnaayt gyytnwsnyt nggnaargcn ggnggncayt gygaaargg ngtntgyath     240 tgymgnaara cnwsnttyaa rgayytntgg gayaarmgnt tyggn                    285
```

<210> SEQ ID NO 49
<211> LENGTH: 234
<212> TYPE: DNA
<213> ORGANISM: Apis cerana
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature

```
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
```

```
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
```

```
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<400> SEQUENCE: 49
atgwsnaara thgtngcngt ngtngtnytn gcngcnttyt gygtngcnat gytngtnwsn 60
gaygtnwsng cnaaracnws nathwsngtn aarggngarw snaaygtnga ygtngtnwsn 120
carathaayw snytngtnws nwsnathgtn wsnggngcna aygtnwsngc ngtnytnytn 180
gcncaracny tngtnaayat hytncarath ytnathgayg cnaaygtntt ygcn 234

<210> SEQ ID NO 50
<211> LENGTH: 778
<212> TYPE: PRT
<213> ORGANISM: Apis cerana

<400> SEQUENCE: 50

Met Leu Ile Cys Ser Ile Asn Val Gly Val Val Asn His Thr Arg Glu
1 5 10 15

Ser Pro Thr Leu Ile Pro Tyr Pro Ser Phe Glu Ala His Gln Tyr Glu
20 25 30

Ala Gly Ser Val Pro Glu Ile Ile Ser Pro Phe Arg Ile Arg Val Asp
35 40 45

Arg Cys Glu Arg Leu Trp Val Leu Asp Thr Gly Phe Thr Asp Ile Leu
50 55 60

Gln Asn Pro Glu Gln Glu Ala Pro Pro Ala Leu Leu Val Tyr Asp Leu
65 70 75 80

Lys Asn Asp Arg Leu Leu Arg Lys Phe Val Ile Pro Glu Asp Gln Lys
85 90 95

Thr His Asp Ser Leu Phe Ala Asn Ile Ala Leu Glu Asp Tyr Ser Cys
100 105 110

Glu Asp Thr Phe Ala Tyr Leu Gly Asp Leu Gly Gly Pro Gly Leu Val
115 120 125

Val Tyr Ser Trp Lys Ser Arg Lys Ser Trp Leu Val Lys His Arg Phe
130 135 140

Phe Gln Pro Asp Pro Gln Ser Glu Glu Phe Asn Val Ser Gly Ile Ser
145 150 155 160

Phe His Trp Thr Asp Gly Leu Phe Gly Met Ser Ile Ala Pro Ser Asn
165 170 175

Asp Gly Tyr Ser Val Met Tyr Phe His Pro Leu Ser Ser Thr Met Glu
180 185 190

```
Tyr Ser Val Ser Thr Lys Ile Leu Arg Asp Pro Glu Arg Ala Asn Ser
            195                 200                 205
Pro Asp Asn Phe Lys Glu Phe Arg Ala Leu Gly Ser Arg Gly His Asn
    210                 215                 220
Gly Gln Ser Ser Val Ser Phe Leu Asp Pro Asn Thr Gly Val Leu Phe
225                 230                 235                 240
Tyr Ala Leu Thr Asn Leu Asn Ala Ile Ala Cys Trp Lys Pro Arg Asn
                245                 250                 255
Thr Phe Thr Leu His Gln Gln Gly Phe Ile Tyr Gln Asn Ser Ile Thr
            260                 265                 270
Met Val Phe Pro Asn Asp Leu Lys Ile Asp Gln Asn Gly Asn Ile Trp
    275                 280                 285
Val Leu Ser Asp Arg Leu Pro Thr Phe Met Tyr Ala Arg Leu Asp Pro
290                 295                 300
Glu Asp Tyr Asn Phe Arg Ile Leu Met Gly Ser Ala Lys Glu Ala Ile
305                 310                 315                 320
Arg Asp Thr Lys Gly Glu Lys Asn Asp Thr Met Gly Lys Ser Glu Ser
                325                 330                 335
Ser Ile Pro Gly Phe Glu Asn Phe Pro Gly Arg Glu Ala Lys Val Lys
            340                 345                 350
Thr Gly Tyr Ala Tyr Leu Glu Gly Arg Arg Gln Val Asp Gly Ala Glu
    355                 360                 365
Asp Leu Trp Arg Ile Gly Asn Ser Leu Tyr Asp Leu Glu Gly Phe Ala
    370                 375                 380
Lys Phe His Pro Gly Gly Ala Glu Trp Ile Arg Leu Thr Lys Gly Thr
385                 390                 395                 400
Asp Ile Thr Glu Leu Phe Gln Thr His His Leu Thr Asp Lys Ala Thr
                405                 410                 415
Lys Leu Leu Pro Lys Tyr Phe Ile Arg Glu Ala Val Val Pro Arg Lys
            420                 425                 430
Leu Pro Leu Thr Phe Glu Pro Asn Gly Phe Phe Ser Thr Phe Lys Arg
    435                 440                 445
Arg Ala Leu Glu Ala Leu Lys Asp Val Asn Phe His Gln Pro Ser Thr
450                 455                 460
Lys Thr Asn Leu Ile Ala Asp Phe Leu Phe Thr Ser Ser Leu Ile Phe
465                 470                 475                 480
Ser Ile Leu Thr Ala Tyr Thr Gln Ser Tyr Leu Met Ile Val Phe Thr
                485                 490                 495
Gly Ile Leu Leu Ala Trp Thr Ala Ile Ser Gly His Asn Tyr Leu His
            500                 505                 510
Met Lys Asp Asn Phe Arg Met Tyr Tyr Phe Asp Leu Ser Thr Met Ser
    515                 520                 525
Ser Lys Asp Trp Arg Ile Thr His Ala Met Ser His Met Tyr Pro
530                 535                 540
Asn Thr Leu Trp Asp Tyr Glu Ile Tyr Ala Phe Glu Pro Phe Ile His
545                 550                 555                 560
Trp Leu Pro Asp Pro Lys Lys Ser Leu Val Met Thr Phe Val Ser Gln
                565                 570                 575
Leu Met Ser Pro Ile Ile Trp Ala Leu Val Phe Tyr Glu Gln Ala Ile
            580                 585                 590
Lys Arg Tyr Tyr Ser Val Phe Phe Glu Tyr Lys Thr Phe Glu Ile Arg
    595                 600                 605
Asp Ala Ile Pro Phe Phe Leu Pro Val Leu Met Ser Phe Phe Thr Pro
```

-continued

```
          610                 615                 620
Asn Phe Phe Thr Ala Val Lys Leu Trp Leu Leu Ile Ile Met Ala Thr
625                 630                 635                 640

Ser Phe Ile Phe Ser Ile Ile Gly Phe Asn Ala Ala His His His Pro
                645                 650                 655

Asp Ile Phe His Asp Gly Asp Ile Tyr Arg Asp Asp Tyr Asp Trp Gly
                660                 665                 670

Val Leu Glu Leu Asp Ala Val Arg Glu Arg Lys Val Ile Asp Asp Ser
                675                 680                 685

Asp Phe Leu Val Leu Thr Asn Phe Gly Leu His Gly Leu His His Leu
            690                 695                 700

Leu Pro Thr Val Asp His Ser Tyr Leu Pro Leu Cys Val Asn Ala Phe
705                 710                 715                 720

Glu Gln Thr Cys Lys Glu Phe Gly Ile Gly Ile Glu Lys Phe Thr Gln
                725                 730                 735

Trp Glu Leu Ile Lys Gly Gln Phe Lys Gln Leu Ala His Arg Asp Phe
                740                 745                 750

Tyr Ser Ser Pro Ser Gly Cys Arg Ser Lys Arg Gly Gly Asn Ala Glu
            755                 760                 765

Pro Ser Asn Trp Gly Leu Asn Ala Gly Arg
770                 775
```

<210> SEQ ID NO 51
<211> LENGTH: 481
<212> TYPE: PRT
<213> ORGANISM: Apis cerana

<400> SEQUENCE: 51

```
Met Lys Lys Val Leu Pro Glu Glu Met Asn Phe Asn Ile Asn Thr Tyr
1                   5                   10                  15

Ile His Lys Asp Ile Val Gln Val Tyr Lys Leu Ser Val Lys Thr Arg
                20                  25                  30

Pro Leu Leu Asn Ile Glu Met Phe Arg Lys Thr Phe Val Leu Leu Val
            35                  40                  45

Ser Leu Ala Tyr Leu Gly Ser Val Tyr Gly Ile Gln Arg Trp Gly Thr
        50                  55                  60

Gln Phe Gly Gln Ala Pro Leu Leu Glu Arg Phe Phe Trp Arg Thr Leu
65                  70                  75                  80

Asp Phe Ala Tyr Pro Asp Glu Ala Ser Lys Thr Met Ala Met Met Lys
                85                  90                  95

Gly Glu Tyr Ile Pro Glu Asn Ala Leu Pro Val Gly Ile Glu Ile Trp
                100                 105                 110

Arg Asn Lys Leu Phe Val Thr Val Pro Arg Trp Arg Asn Gly Ile Pro
            115                 120                 125

Ala Thr Leu Thr Tyr Ile Ser Leu Asp Thr Asn Arg Gly Gly Thr Pro
        130                 135                 140

Lys Leu Thr Pro Tyr Pro Asn Trp Thr Gln Asn Lys Ala Gly Ala Cys
145                 150                 155                 160

Gly Ser Ala Ile Thr Thr Ala Tyr Arg Ile His Ala Asp Ser Cys Asp
                165                 170                 175

Arg Leu Trp Val Leu Asp Thr Gly Thr Ile Gly Ile Gly Asn Thr Thr
            180                 185                 190

Ile Gln Ala Cys Pro Tyr Thr Leu Asn Ile Phe Asp Leu Thr Ser Asp
        195                 200                 205
```

```
Lys Leu Leu Arg Gln Tyr Arg Leu Arg Ala Glu Asp Ile Asn Met Ala
    210                 215                 220

Leu Ile Arg Ile Arg Val Lys Lys Asn Thr Phe Ile Ala Asn Ile Ala
225                 230                 235                 240

Val Asp Leu Gly Lys Gly Gly Cys Asn Asp Ala Phe Ala Tyr Met Ser
                245                 250                 255

Asp Glu Leu Gly Tyr Gly Leu Ile Val Tyr Ser Trp Glu Gln Asn Arg
            260                 265                 270

Ser Trp Arg Ile Thr His Ser Tyr Phe Met Pro Asp Pro Leu Ala Gly
        275                 280                 285

Asp Tyr Asn Ile Gly Gly Leu Asn Phe Gln Trp Gly Glu Gly Ile
    290                 295                 300

Phe Gly Met Ser Leu Ser Pro Ile Ser Val Asn Gly Tyr Arg Thr Leu
305                 310                 315                 320

Phe Phe His Pro Leu Ser Ser Arg Arg Glu Phe Ala Val Ser Thr Arg
                325                 330                 335

Ile Leu Arg Asp Glu Asn Leu Ser Gln Asn Ser Tyr His Glu Phe Gln
            340                 345                 350

Ile Leu Pro Glu Arg Gly Glu Leu Gly His Cys Thr Ala Ser Val Met
        355                 360                 365

Asp Glu Asn Gly Leu Gln Phe Phe Asn Leu Ile Asp Gln Asn Ala Val
    370                 375                 380

Gly Cys Trp Asn Ser Leu Leu Pro Tyr Ser Pro Glu Asn Gln Ala Val
385                 390                 395                 400

Val Ala Arg His Asp Glu Ala Met Ile Phe Pro Ser Asp Val Lys Ile
                405                 410                 415

Asn Arg Gly Leu Leu Trp Ile Ile Ser Asp Arg Met Pro Val Phe Leu
            420                 425                 430

Leu Ser Thr Leu Asn Tyr Thr Asp Val Asn Phe Arg Ile Leu Thr Met
        435                 440                 445

Pro Val Arg Asp Ala Ile Ala Gly Thr Ile Cys Glu Asn Ser Ala Trp
    450                 455                 460

Gly Phe Val Gly Asn Ser Leu Cys Phe Ile Asn Thr Cys Gly Ile Gln
465                 470                 475                 480

Phe
```

<210> SEQ ID NO 52
<211> LENGTH: 524
<212> TYPE: PRT
<213> ORGANISM: Apis cerana

<400> SEQUENCE: 52

```
Met Thr Lys Trp Leu Leu Val Val Cys Leu Gly Ile Ala Cys Gln
1               5                   10                  15

Asp Val Thr Ser Ala Ala Val Asn His Gln Arg Lys Ser Ser Lys Asn
            20                  25                  30

Leu Ala His Ser Met Lys Val Ile Tyr Glu Trp Lys His Ile Asp Tyr
        35                  40                  45

Asp Phe Gly Ser Val Glu Arg Arg Asp Ala Ala Ile Lys Ser Gly Glu
    50                  55                  60

Phe Asp His Thr Lys Asn Tyr Pro Phe Asp Val Asp Arg Trp Arg Asp
65                  70                  75                  80

Lys Thr Phe Val Thr Val Glu Arg Phe Asp Gly Val Pro Ser Ser Leu
                85                  90                  95
```

```
Asn Val Val Thr Asn Lys Lys Gly Lys Gly Pro Leu Leu His Pro
                100             105             110
Tyr Pro Asp Trp Ser Trp Ala Asn Tyr Lys Asp Cys Ser Gly Ile Val
    115             120             125
Ser Ala Phe Lys Ile Ala Val Asp Lys Phe Asp Arg Leu Trp Val Leu
130             135             140
Asp Ser Gly Leu Val Asn Asn Gln Pro Met Cys Ser Pro Lys Leu
145             150             155             160
Val Thr Phe Asp Leu Thr Thr Ser Lys Leu Leu Lys Gln Val Glu Ile
                165             170             175
Pro His Asn Ile Ala Val Asn Ala Thr Thr Gly Met Gly Glu Leu Val
                180             185             190
Ser Leu Ala Val Gln Ala Ile Asp Pro Thr Asn Thr Met Val Tyr Ile
            195             200             205
Ala Asp Glu Arg Gly Glu Ala Leu Ile Ile Tyr Gln Asn Ser Asp Asp
            210             215             220
Ser Phe His Arg Leu Thr Ser Asn Thr Phe Asp Tyr Asp Pro Arg Tyr
225             230             235             240
Thr Lys Leu Thr Val Ala Gly Glu Ser Phe Thr Val Lys Asn Gly Ile
                245             250             255
Cys Gly Ile Ala Leu Ser Pro Val Thr Asn Asn Leu Tyr Tyr Ser Pro
            260             265             270
Leu Ala Ser His Ser Leu Tyr Tyr Val Asn Thr Glu Gln Phe Arg Asn
            275             280             285
Pro Gln Tyr Glu Glu Ser Asn Val Gln Tyr Glu Gly Ser Gln Asp Ile
        290             295             300
Leu Asn Thr Gln Ser Phe Ala Lys Ala Val Ser Lys Asn Gly Val Val
305             310             315             320
Phe Leu Gly Leu Val Ser Asn Ser Ala Val Gly Cys Val Asn Glu His
                325             330             335
Gln Val Leu Gln Lys Glu Asn Phe Asp Val Val Ala Gln Asn Glu Glu
            340             345             350
Thr Leu Gln Met Ile Val Ser Met Lys Ile Met Gln Asp Leu Pro Gln
            355             360             365
Ser Gly Arg Ile Asn Asp Pro Gly Asn Glu Tyr Met Leu Ala Leu Ser
370             375             380
Asn Lys Met Gln Lys Ile Ile Asn Asn Asp Phe Asn Phe Asn Asp Val
385             390             395             400
Asn Phe Arg Ile Leu Gly Ala Asn Val Asn His Leu Thr Arg Asn Thr
                405             410             415
Arg Cys Ala Lys Ser Asn Asn Gln Asn Ala Asn Asn Gln Asn Ala Asn
            420             425             430
Asn Gln Asn Ala Asn Asn Gln Asn Ala Asn Asn Gln Asn Ala Asn Asn
            435             440             445
Gln Asn Asp Asn Asn Gln Asn Asp Asn Gly Asn Asn Arg Arg Asn Gly
            450             455             460
Asn Asn Gln Asn Gly Asn Arg Gln Asn Asp Asn Lys Gln Asn Asp Asn
465             470             475             480
Lys Gln Asn Ala Asn Lys Gln Asn Asp Asn Lys Gln Asn Val Thr Arg
                485             490             495
Gln Asn Asp Asn Arg Gln Asn Asp Asn Lys Gln Asn Asp Asn Arg Gln
            500             505             510
Asn Asp Asn Arg Gln Asn Asp Asn Gln Ala Glu Trp
```

```
              515                 520

<210> SEQ ID NO 53
<211> LENGTH: 539
<212> TYPE: PRT
<213> ORGANISM: Apis cerana

<400> SEQUENCE: 53

Met Thr Lys Trp Leu Leu Val Val Cys Leu Gly Ile Ala Cys Gln
1               5                   10                  15

Asp Val Thr Ser Ala Ala Val Asn His Gln Arg Lys Ser Ser Lys Asn
            20                  25                  30

Leu Ala His Ser Met Lys Val Ile Tyr Glu Trp Lys His Ile Asp Tyr
        35                  40                  45

Asp Phe Gly Ser Val Glu Arg Arg Asp Ala Ala Ile Lys Ser Gly Glu
    50                  55                  60

Phe Asp His Thr Lys Asn Tyr Pro Phe Asp Val Asp Arg Trp Arg Asp
65              70                  75                  80

Lys Thr Phe Val Thr Val Glu Arg Phe Asp Gly Val Pro Ser Ser Leu
                85                  90                  95

Asn Val Val Thr Asn Lys Lys Gly Lys Gly Pro Leu Leu His Pro
            100                 105                 110

Tyr Pro Asp Trp Ser Trp Ala Asn Tyr Lys Asp Cys Ser Gly Ile Val
        115                 120                 125

Ser Ala Phe Lys Ile Ala Val Asp Lys Phe Asp Arg Leu Trp Val Leu
    130                 135                 140

Asp Ser Gly Leu Val Asn Asn Gln Pro Met Cys Ser Pro Lys Leu
145                 150                 155                 160

Val Thr Phe Asp Leu Thr Thr Ser Lys Leu Leu Lys Gln Val Glu Ile
                165                 170                 175

Pro His Asn Ile Ala Val Asn Ala Thr Thr Gly Met Gly Glu Leu Val
            180                 185                 190

Ser Leu Ala Val Gln Ala Ile Asp Pro Thr Asn Thr Met Val Tyr Ile
        195                 200                 205

Ala Asp Glu Arg Gly Glu Ala Leu Ile Ile Tyr Gln Asn Ser Asp Asp
    210                 215                 220

Ser Phe His Arg Leu Thr Ser Asn Thr Phe Asp Tyr Asp Pro Arg Tyr
225                 230                 235                 240

Thr Lys Leu Thr Val Ala Gly Glu Ser Phe Thr Val Lys Asn Gly Ile
                245                 250                 255

Cys Gly Ile Ala Leu Ser Pro Val Thr Asn Asn Leu Tyr Tyr Ser Pro
            260                 265                 270

Leu Ala Ser His Ser Leu Tyr Tyr Val Asn Thr Glu Gln Phe Arg Asn
        275                 280                 285

Pro Gln Tyr Glu Glu Ser Asn Val Gln Tyr Glu Gly Ser Gln Asp Ile
    290                 295                 300

Leu Asn Thr Gln Ser Phe Ala Lys Ala Val Ser Lys Asn Gly Val Val
305                 310                 315                 320

Phe Leu Gly Leu Val Ser Asn Ser Ala Val Gly Cys Val Asn Glu His
                325                 330                 335

Gln Val Leu Gln Lys Glu Asn Phe Asp Val Val Ala Gln Asn Glu Glu
            340                 345                 350

Thr Leu Gln Met Ile Val Ser Met Lys Ile Met Gln Asp Leu Pro Gln
        355                 360                 365
```

-continued

```
Ser Gly Arg Ile Asn Asp Pro Gly Asn Glu Tyr Met Leu Ala Leu Ser
    370                 375                 380

Asn Lys Met Gln Lys Ile Ile Asn Asn Asp Phe Asn Phe Asn Asp Val
385                 390                 395                 400

Asn Phe Arg Ile Leu Gly Ala Asn Val Asn His Leu Thr Arg Asn Thr
                405                 410                 415

Arg Cys Ala Lys Ser Asn Asn Gln Asn Ala Asn Asn Gln Asn Ala Asn
                420                 425                 430

Asn Gln Asn Ala Asn Asn Gln Asn Ala Asn Asn Gln Asn Ala Asn Asn
            435                 440                 445

Gln Asn Asp Asn Asn Gln Asn Asp Asn Gly Asn Asn Arg Arg Asn Gly
        450                 455                 460

Asn Asn Gln Asn Gly Asn Arg Gln Asn Asp Asn Lys Gln Asn Asp Asn
465                 470                 475                 480

Lys Gln Asn Ala Asn Lys Gln Asn Ala Asn Lys Gln Asn Asp Asn Lys
                485                 490                 495

Gln Asn Asp Asn Arg Gln Asn Asp Asn Arg Gln Asn Asp Asn Lys Lys
                500                 505                 510

Asn Asp Asn Arg Gln Asn Asp Asn Lys Gln Asn Asp Asn Arg Gln Asn
            515                 520                 525

Asp Asn Arg Gln Asn Asp Asn Gln Ala Glu Trp
        530                 535

<210> SEQ ID NO 54
<211> LENGTH: 925
<212> TYPE: PRT
<213> ORGANISM: Apis cerana

<400> SEQUENCE: 54

Met Lys Asn Thr Gln Thr Asn Ile Tyr Val Glu Val Asn Gly Lys Gln
1               5                   10                  15

Ile Ser Asn Gly Lys Glu Glu Ile Val Glu Asn Glu Asn Asp Glu Val
            20                  25                  30

Asp Ala Val Gln Gln Ala Ile Gly Asn Leu Gly Arg Trp Gln Ile Tyr
        35                  40                  45

Val Cys Leu Ala Ile Ser Leu Val Lys Phe Pro Ile Ala Trp His Gln
50                  55                  60

Leu Ala Ile Val Phe Met Ala Pro His Gln Asp Tyr Asn Cys Thr Ser
65                  70                  75                  80

Pro Thr Arg Thr Glu Thr Ala Asp Gln Cys Val Thr Asn Val Asn Gly
                85                  90                  95

Thr Leu Leu Glu Cys Thr Glu Trp Glu Tyr Asp Arg Arg Thr Phe Thr
            100                 105                 110

Glu Thr Ile Ile Ser Gln Trp Asn Leu Val Cys Ser Arg Thr His Tyr
        115                 120                 125

Ala Asn Ile Gln Gln Ser Ile Leu Met Phe Gly Val Leu Leu Gly Asn
    130                 135                 140

Ile Ile Phe Gly Asn Leu Ala Asp Arg Tyr Gly Arg Lys Met Pro Leu
145                 150                 155                 160

Met Ile Ser Val Val Leu Gln Leu Ala Ser Gly Ile Gly Cys Ala Val
                165                 170                 175

Val Pro Trp Phe Pro Ala Leu Leu Met Lys Leu Leu Ser Ala Leu
            180                 185                 190

Ala Thr Gly Gly Thr Met Val Thr Ser Tyr Val Ile Cys Met Glu Ile
        195                 200                 205
```

```
Val Gly Thr Lys Trp Arg Ala Ala Ile Thr Val Leu Tyr Gln Ile Pro
    210                 215                 220

Phe Ser Leu Gly His Met Ser Leu Ala Gly Leu Ala Tyr Tyr Phe Arg
225                 230                 235                 240

His Trp Gln His Leu Gln Ile Ala Ile Thr Leu Pro Ser Val Ile Leu
                245                 250                 255

Leu Ser Tyr Trp Trp Ile Val Pro Glu Ser Pro Arg Trp Leu Leu Ala
                260                 265                 270

Phe Gly Lys Gln Arg Ala Ala Cys Lys Ile Leu Gln Lys Ala Ala Asn
            275                 280                 285

Ile Asn Asn Ile Lys Asn Lys Asp Ile Pro Asp Met Val Lys Gln His
    290                 295                 300

Cys Leu His Gln Asn Ser Lys Arg Ser Asp Phe Asp His Lys Ala Ser
305                 310                 315                 320

Phe Leu Asp Leu Phe Arg Thr Pro Asn Met Arg Ile Lys Ser Leu Ser
                325                 330                 335

Ile Phe Phe Asn Trp Val Val Cys Gly Met Gly Leu Phe Gly Met Ser
                340                 345                 350

Gln Tyr Ile Gly Gln Val Gly Gly Asn Ile Phe Val Asn Phe Thr Val
            355                 360                 365

Ser Gly Ala Ile Gln Ile Pro Gly Asn Phe Val Ala Trp Trp Ala Met
370                 375                 380

Asn Lys Leu Gly Arg Arg Ile Thr Leu Ile Cys Ser Asn Ser Ile Ala
385                 390                 395                 400

Gly Ile Ser Ala Leu Leu Leu Val Ile Val Ser Asn Asp Ile Glu Trp
                405                 410                 415

Leu Arg Leu Ile Leu Val Cys Leu Gly Ile Val Gly Met Ser Val Ser
                420                 425                 430

Phe Thr Thr Val Tyr Leu Phe Ser Gly Glu Leu Phe Pro Thr Val Val
            435                 440                 445

Arg Asn Ile Gly Val Gly Thr Ser Ser Met Cys Ala Arg Ile Gly Ser
                450                 455                 460

Ile Thr Ala Pro Phe Val Val Ser Leu Asp His Ile Gln Thr Trp Leu
465                 470                 475                 480

Pro Pro Ala Cys Phe Gly Ile Leu Pro Leu Leu Gly Ala Ala Leu Cys
                485                 490                 495

Phe Leu Leu Pro Glu Thr Val Gly Cys Thr Leu Pro Glu Thr Leu Gln
                500                 505                 510

Asp Asp Met Trp His Phe Leu Trp Ile Val Phe Leu Val Leu Ala Asn
            515                 520                 525

Gly Glu Glu Ile Lys Thr Ile Tyr Ser Trp Asn Val Ile Glu Tyr Asn
530                 535                 540

Phe Pro Asn Asp Asn Ile Arg Asn Thr Leu Ile Ser Asn Gly Asp Tyr
545                 550                 555                 560

Ile Glu Glu Asn Asn Met Pro Asn Gly Ile Gln Ile Trp Asn Asp Lys
                565                 570                 575

Val Phe Ile Thr Ile Pro Arg Trp Lys Asn Gly Val Pro Ser Asn Leu
            580                 585                 590

Asn Phe Phe Leu Lys Asn Asp Gly Ser Glu Ser Pro Lys Leu Asn Pro
            595                 600                 605

Tyr Pro Asn Trp Glu Met Asn Asn Ile Asn Lys Val Asp Ser Ile Ile
    610                 615                 620
```

-continued

```
Asn Ile Arg Val Arg Val Asp Ala Cys Asp Arg Leu Trp Gly Val
625                 630                 635                 640

Asp Thr Gly Val Asp Asp Ile Leu Gly Asn Asn Thr Val Ile His Gln
            645                 650                 655

Pro Arg Ile Ile Ile Asp Leu Lys Thr Asp Lys Ile Leu Arg Ile
            660                 665                 670

Tyr Pro Leu Lys Ser Ser Asp Gln Thr Ser Asp Ser Phe Phe Val Asp
            675                 680                 685

Leu Val Ile Asp Val Asp Pro Asn Asn Cys Asp Asn Thr Tyr Ala Tyr
            690                 695                 700

Ile Ser Asp Leu Gly Gly Tyr Ala Leu Val Val Tyr Ser Trp Ala Lys
705                 710                 715                 720

Asn Asp Ser Trp Arg Ile Thr His Asn Phe Phe Tyr Phe Asp Pro Arg
                725                 730                 735

Tyr Gly Asn Tyr Asn Ile Asn Gly Phe Asn Phe Gln Trp Lys Asp Gly
            740                 745                 750

Leu Phe Gly Leu Ser Leu Ser Ala Leu Gln Thr Asp Gly Tyr Lys Ile
            755                 760                 765

Leu Tyr Phe His Ala Met Ser Ser Ile Ala Glu Phe Ser Val Ser Thr
770                 775                 780

Glu Val Leu Gln Asp His Thr Leu Glu Lys Ser Ser Asp Tyr Tyr Ala
785                 790                 795                 800

Phe His Phe Glu Gly Glu Lys Gly Pro Asn Ser Gln Gly Pro Ser Ser
                805                 810                 815

Val Ile Asp Thr Asn Thr Gly Val Asp Tyr Phe Thr Gln Ile Asn Arg
            820                 825                 830

Asn Gly Ile Ala Cys Trp Asp Thr Thr Thr Glu Leu Asn Pro Asn Thr
            835                 840                 845

Phe Ile Leu Val Ala Glu Asp Asn Thr Thr Met Val Phe Cys Asn Asp
850                 855                 860

Leu Ser Ile Asp Arg Ser Ser Asn Thr Met Tyr Val Leu Ser Asp Asn
865                 870                 875                 880

Phe Gln Gln Leu Leu Phe Ser Lys Tyr Asp Val Lys Lys His Asn Phe
                885                 890                 895

Phe Ile Thr Val Phe Asp Leu Asp Phe Leu Thr Asn Ala Cys Lys Lys
            900                 905                 910

Lys Asp Asp Lys Pro Lys Arg Leu Pro His Ile Leu
            915                 920                 925

<210> SEQ ID NO 55
<211> LENGTH: 485
<212> TYPE: PRT
<213> ORGANISM: Apis cerana

<400> SEQUENCE: 55

Met Thr Lys Trp Leu Leu Leu Met Ala Cys Leu Gly Ile Ala Cys Gln
1               5                   10                  15

Asn Ile Arg Gly Ala Val Val Arg Glu Asn Ser Ser Arg Lys Lys Leu
            20                  25                  30

Thr Asn Thr Leu Asn Val Ile His Glu Trp Lys Tyr Val Asp Tyr Asp
        35                  40                  45

Phe Gly Ser Asp Glu Lys Arg Gln Ala Ala Ile Gln Ser Gly Glu Tyr
    50                  55                  60

Asp Arg Thr Lys Asn Tyr Pro Leu Asp Val Asp Gln Trp His Asp Lys
65                  70                  75                  80
```

```
Thr Phe Val Thr Met Leu Arg Tyr Asp Gly Val Pro Ser Ser Leu Asn
                85                  90                  95

Val Val Ser Asp Lys Thr Gly Asn Gly Gly Pro Leu Leu Gln Pro Tyr
               100                 105                 110

Pro Asp Trp Ser Phe Ala Lys Tyr Glu Asp Cys Ser Gly Ile Val Ser
               115                 120                 125

Ala Asn Lys Ile Ala Ile Asp Glu Tyr Glu Arg Leu Trp Val Leu Asp
    130                 135                 140

Ser Gly Leu Val Asn Asn Ile Gln Pro Met Cys Ser Pro Lys Leu Leu
145                 150                 155                 160

Ala Phe Asp Leu Thr Thr Ser Lys Leu Leu Lys Gln Val Glu Ile Pro
                165                 170                 175

His Asp Val Ala Val Asn Ala Thr Thr Gly Lys Gly Gly Leu Ala Ser
                180                 185                 190

Leu Ala Val Gln Ala Met Asp Ser Val Asn Thr Met Val Tyr Met Ala
                195                 200                 205

Asp Asn Lys Asp Asp Ala Leu Ile Val Tyr Gln Asn Ala Asp Asp Ser
    210                 215                 220

Phe His Arg Leu Ser Ser His Ile Ser Asn His Asn Phe Arg Ser Asp
225                 230                 235                 240

Lys Met Ser Gln Glu Asn Leu Thr Leu Lys Glu Val Asp Asn Arg Val
                245                 250                 255

Phe Gly Met Ala Leu Ser Ser Val Thr His Asn Leu Tyr Tyr Ser Pro
                260                 265                 270

Leu Ser Ser Gln Asn Leu Tyr Tyr Val Asn Thr Thr Ser Leu Met Asn
                275                 280                 285

Ser Gln Asn Gln Gly Asn Asp Val Gln Tyr Glu Ser Val Gln Asp Val
                290                 295                 300

Phe Ser Ser Gln Leu Ser Ala Lys Ala Val Ser Lys Asn Gly Val Leu
305                 310                 315                 320

Phe Phe Gly Phe Thr Asn Asn Thr Leu Gly Cys Trp Asn Glu His Gln
                325                 330                 335

Ser Leu Asp Arg Gln Asn Ile Asp Ile Val Ala Arg Asn Glu Thr Leu
                340                 345                 350

Gln Met Val Val Gly Met Lys Ile Lys Gln Asn Leu Pro Gln Ser Gly
                355                 360                 365

Lys Val Asn Asn Thr Gln Arg Asn Glu His Leu Leu Ala Leu Thr Asn
    370                 375                 380

Lys Lys Gln Asp Val Leu Asn Asn Asp Leu Asn Leu Glu His Val Asn
385                 390                 395                 400

Phe Gln Ile Leu Asp Ala Asn Val Asn Asp Leu Ile Arg Asn Ser Arg
                405                 410                 415

Cys Ala Asn Ser Asp Asn Gln Asp Asn Asn Gln His Asn Tyr Asn His
                420                 425                 430

Asn Gln Val Arg His Ser Ser Lys Ser Asp Asn Gln Asn Asn Asn Gln
                435                 440                 445

His Asn Asn Gln Ala Tyr His Ser Ser Lys Ser Asp Asn Trp Asp Asn
    450                 455                 460

Asn Asn Asn Gln Ala His His Ser Ser Lys Phe Asp Asn Gln Asn Asn
465                 470                 475                 480

Asn Gln Tyr Asn Asn
                485
```

<210> SEQ ID NO 56
<211> LENGTH: 468
<212> TYPE: PRT
<213> ORGANISM: Apis cerana

<400> SEQUENCE: 56

Met Thr Lys Trp Leu Phe Met Val Ala Cys Leu Gly Ile Ala Cys Gln
1               5                   10                  15

Gly Ala Ile Ile Arg Gln Asn Ser Ala Lys Asn Leu Glu Asn Ser Leu
            20                  25                  30

Asn Val Ile His Glu Trp Lys Tyr Ile Asp Tyr Asp Phe Gly Ser Glu
        35                  40                  45

Glu Arg Arg Gln Ala Ala Ile Gln Ser Gly Glu Tyr Asp His Thr Lys
    50                  55                  60

Asn Tyr Pro Phe Asp Val Asp Gln Trp His Asp Lys Thr Phe Val Thr
65                  70                  75                  80

Ile Leu Lys Tyr Asp Gly Val Pro Ser Thr Leu Asn Met Ile Ser Asn
                85                  90                  95

Lys Ile Gly Lys Gly Arg Leu Leu Gln Pro Tyr Pro Asp Trp Ser
            100                 105                 110

Trp Ala Glu Asn Lys Asp Cys Ser Gly Ile Val Ser Ala Phe Lys Ile
        115                 120                 125

Ala Ile Asp Lys Phe Asp Arg Leu Trp Val Leu Asp Ser Gly Leu Ile
    130                 135                 140

Asn Arg Thr Glu Pro Ile Cys Ala Pro Lys Leu His Val Phe Asp Leu
145                 150                 155                 160

Lys Asn Thr Lys His Leu Lys Gln Ile Glu Ile Pro His Asp Ile Ala
                165                 170                 175

Val Asn Ala Thr Thr Gly Lys Gly Gly Leu Val Ser Leu Val Val Gln
            180                 185                 190

Ala Met Asp Pro Met Asn Thr Leu Val Tyr Ile Ala Asp His Lys Gly
        195                 200                 205

Asp Ala Leu Ile Val Tyr Gln Asn Ser Asp Asp Ser Phe His Arg Met
    210                 215                 220

Thr Ser Asn Thr Phe Asp Tyr Asp Pro Arg Tyr Ala Lys Met Thr Ile
225                 230                 235                 240

Asn Gly Glu Ser Phe Thr Leu Lys Asn Gly Ile Cys Gly Met Ala Leu
                245                 250                 255

Ser Pro Val Thr Asn Asn Leu Tyr Tyr Ser Pro Leu Ala Ser His Gly
            260                 265                 270

Leu Tyr Tyr Val Asn Thr Glu Pro Phe Met Lys Ser Gln Phe Gly Asp
        275                 280                 285

Asn Asn Asn Val Gln Tyr Glu Gly Ser Gln Asp Thr Leu Asn Thr Gln
    290                 295                 300

Ser Leu Ala Lys Ala Val Ser Lys Asp Gly Val Leu Phe Val Gly Leu
305                 310                 315                 320

Val Gly Asn Ser Ala Leu Gly Cys Leu Asn Glu His Gln Pro Leu Gln
                325                 330                 335

Arg Glu Asn Leu Glu Leu Val Ala Gln Asn Glu Lys Thr Leu Gln Met
            340                 345                 350

Ile Ala Gly Met Lys Ile Lys Glu Glu Leu Pro His Phe Val Gly Ser
        355                 360                 365

Asn Lys Pro Val Lys Asp Glu Tyr Met Leu Val Leu Ser Asn Lys Met
    370                 375                 380

```
Gln Lys Ile Val Asn Asn Asp Phe Asn Phe Asn Asp Val Asn Phe Arg
385                 390                 395                 400

Ile Leu Gly Ala Asn Val Lys Glu Leu Met Arg Asn Thr His Cys Ala
                405                 410                 415

Asn Phe Asn Asn Lys Asn Asn Gln Lys Asn Asn Gln Lys Asn Asn
            420                 425                 430

Asn Gln Asn Asn Asn Gln Lys Asn Asn Gln Lys Asn Asn
        435                 440                 445

Gln Lys Asn Asn Asn Gln Lys Asn Asn Gln Lys Asn Asn Gln
    450                 455                 460

Asn Thr Asn Asn
465

<210> SEQ ID NO 57
<211> LENGTH: 220
<212> TYPE: PRT
<213> ORGANISM: Apis cerana

<400> SEQUENCE: 57

Cys Leu Gly Ile Ala Cys Gln Gly Ala Ile Val Arg Lys Lys Ser Ala
1               5                   10                  15

Arg Asn Leu Glu Asn Ser Leu Asn Val Leu His Glu Trp Lys Tyr Ile
            20                  25                  30

Asp Tyr Asp Phe Gly Ser Glu Arg Arg Gln Ala Ala Ile Gln Ser
        35                  40                  45

Gly Glu Tyr Asp His Thr Lys Asn Tyr Pro Phe Asp Val Asp Gln Trp
50                  55                  60

Arg Asp Lys Thr Phe Val Thr Val Leu Arg Tyr Asp Gly Val Pro Ser
65                  70                  75                  80

Ser Leu Asn Val Ile Ser Asp Lys Thr Gly Asn Gly Gly Arg Leu Leu
                85                  90                  95

Gln Pro Tyr Pro Asp Trp Leu Trp Thr Lys Tyr Lys Asp Cys Ser Gly
            100                 105                 110

Ile Val Asn Ala Tyr Asn Ile Ala Val Asp Lys Tyr Asp Arg Leu Trp
        115                 120                 125

Val Leu Asp Ser Gly Leu Ile Asn Asn Ile Gln Pro Met Cys Ser Pro
130                 135                 140

Lys Leu Leu Val Phe Asp Leu Asn Ser Ser Gln Leu Leu Lys Gln Val
145                 150                 155                 160

Asp Ile Pro His Asp Ile Ala Val Asn Thr Thr Thr Glu Asn Gly Arg
                165                 170                 175

Leu Ala Ser Leu Val Val Gln Ala Met Asn Pro Met Asn Thr Leu Val
            180                 185                 190

Tyr Leu Ser Asp Asn Lys Gly Asp Ala Leu Ile Val Tyr Gln Asn Ser
        195                 200                 205

Asp Asp Ser Phe His Arg Leu Ser Ser Asn Thr Leu
210                 215                 220

<210> SEQ ID NO 58
<211> LENGTH: 222
<212> TYPE: PRT
<213> ORGANISM: Apis cerana

<400> SEQUENCE: 58

Cys Leu Gly Ile Ala Cys Gln Gly Thr Thr Ser Ser Ile Leu Arg Gly
1               5                   10                  15
```

-continued

```
Glu Ser Leu Asn Lys Ser Leu Ser Val Leu His Glu Trp Lys Phe Phe
             20                  25                  30

Asp Tyr Asp Phe Asp Ser Asp Glu Arg Arg Gln Asp Ala Ile Leu Ser
         35                  40                  45

Gly Glu Tyr Asp Tyr Arg Lys Asn Tyr Pro Ser Asp Val Asp Gln Trp
 50                  55                  60

His Gly Lys Ile Phe Val Thr Met Leu Arg Tyr Asn Gly Val Pro Ser
 65                  70                  75                  80

Ser Leu Asn Val Ile Ser Lys Lys Ile Gly Asp Gly Pro Leu Leu
             85                  90                  95

Gln Pro Tyr Pro Asp Trp Ser Phe Ala Lys Tyr Asp Cys Ser Gly
                100                 105                 110

Ile Val Ser Ala Thr Lys Leu Ala Ile Asp Lys Cys Asp Arg Leu Trp
             115                 120                 125

Val Leu Asp Ser Gly Leu Val Asn Asn Thr Gln Pro Met Cys Ser Pro
130                 135                 140

Lys Leu Leu Thr Phe Asp Leu Thr Thr Ser Gln Leu Leu Lys Gln Val
145                 150                 155                 160

Glu Ile Pro His Asp Val Ala Val Asn Ala Thr Thr Gly Lys Gly Arg
                165                 170                 175

Leu Ser Ser Leu Ala Val Gln Pro Leu Asp Cys Asn Ile Asn Gly Asp
             180                 185                 190

Thr Met Val Tyr Ile Ala Asp Glu Lys Gly Glu Gly Leu Ile Val Tyr
             195                 200                 205

His Asp Ser Asp Asn Ser Phe His Arg Leu Ser Ser Asn Thr
210                 215                 220

<210> SEQ ID NO 59
<211> LENGTH: 222
<212> TYPE: PRT
<213> ORGANISM: Apis cerana

<400> SEQUENCE: 59

Cys Leu Gly Ile Ala Cys Gln Gly Ile Thr Gly Ala Thr Val Arg Glu
1               5                   10                  15

Asn Ser Ser Arg Asn Leu Ala Asn Ser Met Asn Val Ile His Glu Trp
             20                  25                  30

Lys Tyr Leu Asp Tyr Asp Phe Gly Ser Asp Glu Lys Arg Gln Ala Ala
         35                  40                  45

Ile Gln Ser Gly Glu Tyr Asp His Thr Lys Asn Tyr Pro Phe Asp Val
 50                  55                  60

Asp Arg Trp His Asp Met Thr Phe Val Thr Val Leu Arg Tyr Lys Gly
 65                  70                  75                  80

Val Pro Ser Ser Leu Asn Val Ile Ser Lys Lys Ile Gly Asn Gly Gly
             85                  90                  95

Pro Leu Leu Gln Pro Tyr Pro Asp Trp Ser Trp Ala Asn Tyr Lys Asp
                100                 105                 110

Cys Ser Gly Ile Val Ser Ala Tyr Lys Ile Ala Ile Asp Lys Phe Asp
             115                 120                 125

Arg Leu Trp Val Leu Asp Ser Gly Ile Ile Asn Asn Thr Gln Pro Met
             130                 135                 140

Cys Ser Pro Lys Leu His Val Phe Asp Leu Asn Thr Ser Gln Gln Ile
145                 150                 155                 160

Lys Gln Val Met Met Pro His Asp Ile Ala Ile Asn Ala Thr Thr Gly
```

```
            165                 170                 175
Lys Gly Gly Leu Glu Asn Leu Val Val Gln Ala Met Asp Pro Met Asn
            180                 185                 190

Thr Leu Val Tyr Met Ala Asp Ser Lys Gly Asp Ala Leu Ile Val Tyr
            195                 200                 205

Gln Asn Ser Asp Asp Ser Phe His Arg Leu Thr Ser Asn Thr
    210                 215                 220
```

<210> SEQ ID NO 60
<211> LENGTH: 94
<212> TYPE: PRT
<213> ORGANISM: Apis cerana

<400> SEQUENCE: 60

```
Gly Val Leu Phe Leu Gly Leu Val Asn Ser Ala Ile Gly Cys Trp
1               5                   10                  15

Asn Glu His Gln Pro Leu Gln Lys Gln Asn Met Asp Met Val Ala Gln
            20                  25                  30

Asn Glu Glu Thr Leu Gln Ile Ile Thr Ser Val Lys Ile Ile Gln Asn
            35                  40                  45

Leu Ser Tyr Ser Gly Arg Met Asn Arg Ile His Lys Asn Glu Tyr Met
    50                  55                  60

Leu Ala Leu Ser Asn Arg Met Gln Lys Ile Val Asn Asn Asp Phe Asn
65                  70                  75                  80

Phe Asn Asp Ile Asn Phe Arg Ile Leu Gly Ala Asn Glu Gly
                85                  90
```

<210> SEQ ID NO 61
<211> LENGTH: 172
<212> TYPE: PRT
<213> ORGANISM: Apis cerana

<400> SEQUENCE: 61

```
Trp Lys Tyr Phe Asp Tyr Asn Phe Gly Ser Asn Glu Arg Arg Gln Ala
1               5                   10                  15

Ala Ile Gln Ser Gly Lys Tyr Asn Tyr Lys Asn Asn Phe Pro Ile Asp
            20                  25                  30

Val Asp Arg Trp His Asp Lys Thr Phe Val Thr Ile Leu Arg Asn Asn
            35                  40                  45

Gly Val Pro Ser Ser Leu Asn Val Ile Ser Asn Lys Ile Gly Asn Gly
    50                  55                  60

Gly Pro Leu Leu Glu Pro Tyr Pro Asn Trp Ser Trp Ala Glu Asn Gln
65                  70                  75                  80

Asn Cys Ser Gly Ile Thr Ser Val Tyr Arg Val Ala Ile Asp Val Trp
                85                  90                  95

Gly Arg Leu Trp Val Leu Asp Asn Gly Ile Ser Gly Gln Thr Ser Val
            100                 105                 110

Cys Ser Ser Gln Ile Val Val Phe Asp Leu Lys Thr Ser Lys Leu Leu
            115                 120                 125

Lys Gln Val Lys Ile Pro His Asn Ile Ala Val Asn Ser Thr Thr Gly
    130                 135                 140

Asn Ile Asn Val Val Thr Pro Ile Val Gln Ser Phe Asp Tyr Asn Asn
145                 150                 155                 160

Thr Leu Val Tyr Ile Ala Asp Val Glu Gly Tyr Ala
            165                 170
```

```
<210> SEQ ID NO 62
<211> LENGTH: 466
<212> TYPE: PRT
<213> ORGANISM: Apis cerana

<400> SEQUENCE: 62

Met Thr Lys Trp Leu Leu Leu Val Val Cys Leu Gly Ile Ala Cys Gln
1               5                   10                  15

Asp Val Thr Ser Ala Ala Val Asn His Gln Arg Lys Ser Ser Lys Asn
            20                  25                  30

Leu Ala His Ser Met Lys Val Ile Tyr Glu Trp Lys His Ile Asp Tyr
        35                  40                  45

Asp Phe Gly Ser Val Glu Arg Arg Asp Ala Ala Ile Lys Ser Gly Glu
    50                  55                  60

Phe Asp His Thr Lys Asn Tyr Pro Phe Asp Val Asp Arg Trp Arg Asp
65                  70                  75                  80

Lys Thr Phe Val Thr Val Glu Arg Phe Asp Gly Val Pro Ser Ser Leu
                85                  90                  95

Asn Val Val Thr Asn Lys Lys Gly Lys Gly Gly Pro Leu Leu His Pro
            100                 105                 110

Tyr Pro Asp Trp Ser Trp Ala Asn Tyr Lys Asp Cys Ser Gly Ile Val
        115                 120                 125

Ser Ala Phe Lys Ile Ala Val Asp Lys Phe Asp Arg Leu Trp Val Leu
    130                 135                 140

Asp Ser Gly Leu Val Asn Asn Asn Gln Pro Met Cys Ser Pro Lys Leu
145                 150                 155                 160

Val Thr Phe Asp Leu Thr Thr Ser Lys Leu Leu Lys Gln Val Glu Ile
                165                 170                 175

Pro His Asn Ile Ala Val Asn Ala Thr Thr Gly Met Gly Glu Leu Val
            180                 185                 190

Ser Leu Ala Val Gln Ala Ile Asp Pro Thr Asn Thr Met Val Tyr Ile
        195                 200                 205

Ala Asp Glu Arg Gly Glu Ala Leu Ile Ile Tyr Gln Asn Ser Asp Asp
    210                 215                 220

Ser Phe His Arg Leu Thr Ser Asn Thr Phe Asp Tyr Asp Pro Arg Tyr
225                 230                 235                 240

Thr Lys Leu Thr Val Ala Gly Glu Ser Phe Thr Val Lys Asn Gly Ile
                245                 250                 255

Cys Gly Ile Ala Leu Ser Pro Val Thr Asn Asn Leu Tyr Tyr Ser Pro
            260                 265                 270

Leu Ala Ser His Ser Leu Tyr Tyr Val Asn Thr Glu Gln Phe Arg Asn
        275                 280                 285

Pro Gln Tyr Glu Glu Ser Asn Val Gln Tyr Gly Ser Gln Asp Ile
    290                 295                 300

Leu Asn Thr Gln Ser Phe Ala Lys Ala Val Ser Lys Asn Gly Val Val
305                 310                 315                 320

Phe Leu Gly Leu Val Ser Asn Ser Ala Val Gly Cys Val Asn Glu His
                325                 330                 335

Gln Val Leu Gln Lys Glu Asn Phe Asp Val Val Ala Gln Asn Glu Glu
            340                 345                 350

Thr Leu Gln Met Ile Val Ser Met Lys Ile Met Gln Asp Leu Pro Gln
        355                 360                 365

Ser Gly Arg Ile Asn Asp Pro Gly Asn Glu Tyr Met Leu Ala Leu Ser
    370                 375                 380
```

-continued

```
Asn Lys Met Gln Lys Ile Ile Asn Asn Asp Phe Asn Phe Asn Asp Val
385                 390                 395                 400

Asn Phe Arg Ile Leu Gly Ala Asn Val Lys Glu Leu Met Arg Asn Thr
            405                 410                 415

His Cys Ala Asn Phe Asn Asn Lys Asn Gln Lys Asn Asn Asn Gln
        420                 425                 430

Lys Asn Asn Asn Gln Asn Asn Asn Gln Lys Asn Asn Gln Lys
        435                 440                 445

Asn Asn Asn Gln Lys Asn Asn Gln Lys Asn Asn Gln Asn Thr
450                 455                 460

Asn Asn
465

<210> SEQ ID NO 63
<211> LENGTH: 468
<212> TYPE: PRT
<213> ORGANISM: Apis cerana

<400> SEQUENCE: 63

Met Thr Arg Trp Leu Phe Met Val Ala Cys Leu Gly Ile Ala Cys Gln
1               5                   10                  15

Gly Ala Ile Ile Arg Gln Asn Ser Ala Lys Asn Leu Glu Asn Ser Leu
            20                  25                  30

Asn Val Ile His Glu Trp Lys Tyr Ile Asp Tyr Asp Phe Gly Ser Glu
        35                  40                  45

Glu Arg Arg Gln Ala Ala Ile Gln Ser Gly Glu Tyr Asp His Thr Lys
    50                  55                  60

Asn Tyr Pro Phe Asp Val Asp Gln Trp His Asp Lys Thr Phe Val Thr
65                  70                  75                  80

Ile Leu Lys Tyr Asp Gly Val Pro Ser Thr Leu Asn Met Ile Ser Asn
                85                  90                  95

Lys Ile Gly Lys Gly Gly Arg Leu Leu Gln Pro Tyr Pro Asp Trp Ser
            100                 105                 110

Trp Ala Glu Asn Lys Asp Cys Ser Gly Ile Val Ser Ala Phe Lys Ile
        115                 120                 125

Ala Ile Asp Lys Phe Asp Arg Leu Trp Val Leu Asp Ser Gly Leu Ile
    130                 135                 140

Asn Arg Thr Glu Pro Ile Cys Ala Pro Lys Leu His Val Phe Asp Leu
145                 150                 155                 160

Lys Asn Thr Lys His Leu Lys Gln Ile Glu Ile Pro His Asp Ile Ala
                165                 170                 175

Val Asn Ala Thr Thr Gly Lys Gly Leu Val Ser Leu Val Val Gln
            180                 185                 190

Ala Met Asp Pro Met Asn Thr Leu Val Tyr Ile Ala Asp His Lys Gly
        195                 200                 205

Asp Ala Leu Ile Val Tyr Gln Asn Ser Asp Asp Ser Phe His Arg Met
    210                 215                 220

Thr Ser Asn Thr Phe Asp Tyr Asp Pro Arg Tyr Ala Lys Met Thr Ile
225                 230                 235                 240

Asn Gly Glu Ser Phe Thr Leu Lys Asn Gly Ile Cys Gly Met Ala Leu
                245                 250                 255

Ser Pro Val Thr Asn Asn Leu Tyr Tyr Ser Pro Leu Ala Ser His Gly
            260                 265                 270

Leu Tyr Tyr Val Asn Thr Glu Pro Phe Met Lys Ser Gln Phe Gly Asp
        275                 280                 285
```

Asn Asn Asn Val Gln Tyr Glu Gly Ser Gln Asp Thr Leu Asn Thr Gln
    290                 295                 300

Ser Leu Ala Lys Ala Val Ser Lys Asp Gly Val Leu Phe Val Gly Leu
305                 310                 315                 320

Val Gly Asn Ser Ala Leu Gly Cys Leu Asn Glu His Gln Pro Leu Gln
                325                 330                 335

Arg Glu Asn Leu Glu Leu Val Ala Gln Asn Glu Lys Thr Leu Gln Met
            340                 345                 350

Ile Ala Gly Met Lys Ile Lys Glu Glu Leu Pro His Phe Val Gly Ser
        355                 360                 365

Asn Lys Pro Val Lys Asp Glu Tyr Met Leu Val Leu Ser Asn Lys Met
    370                 375                 380

Gln Lys Ile Val Asn Asn Asp Phe Asn Phe Asn Asp Val Asn Phe Arg
385                 390                 395                 400

Ile Leu Gly Ala Asn Val Lys Glu Leu Met Arg Asn Thr His Cys Ala
                405                 410                 415

Asn Phe Asn Asn Lys Asn Asn Gln Lys Asn Asn Gln Lys Asn Asn
            420                 425                 430

Asn Gln Asn Asn Asn Gln Lys Asn Asn Gln Lys Asn Asn
        435                 440                 445

Gln Lys Asn Asn Asn Gln Lys Asn Asn Gln Lys Asn Asn Gln
    450                 455                 460

Asn Thr Asn Asn
465

<210> SEQ ID NO 64
<211> LENGTH: 304
<212> TYPE: PRT
<213> ORGANISM: Apis cerana

<400> SEQUENCE: 64

Met Thr Lys Trp Leu Leu Leu Val Val Cys Leu Gly Ile Ala Cys Gln
1               5                   10                  15

Asp Val Thr Ser Ala Ala Val Asn His Gln Arg Lys Ser Ser Lys Asn
            20                  25                  30

Leu Ala His Ser Met Lys Val Ile Tyr Glu Trp Lys His Ile Asp Tyr
        35                  40                  45

Asp Phe Gly Ser Val Glu Arg Arg Asp Ala Ala Ile Lys Ser Gly Glu
    50                  55                  60

Phe Asp His Thr Lys Asn Tyr Pro Phe Asp Val Asp Arg Trp Arg Asp
65                  70                  75                  80

Lys Thr Phe Val Thr Val Glu Arg Phe Asp Gly Val Pro Ser Ser Leu
                85                  90                  95

Asn Val Val Thr Asn Lys Lys Gly Lys Gly Pro Leu Leu His Pro
            100                 105                 110

Tyr Pro Asp Trp Ser Trp Ala Asn Tyr Lys Asp Cys Ser Gly Ile Val
        115                 120                 125

Ser Ala Phe Lys Ile Ala Val Asp Lys Phe Asp Arg Leu Trp Val Leu
    130                 135                 140

Asp Ser Gly Leu Val Asn Asn Gln Pro Met Cys Ser Pro Lys Leu
145                 150                 155                 160

Val Thr Phe Asp Leu Asn Thr Ser Lys Leu Leu Lys Gln Val Glu Ile
                165                 170                 175

Pro His Asn Ile Ala Val Asn Ala Thr Thr Gly Met Gly Glu Leu Val

```
            180                 185                 190
Ser Leu Ala Val Gln Ala Val Asp Pro Thr Asn Thr Met Val Tyr Ile
            195                 200                 205

Ala Asp Glu Arg Gly Glu Ala Leu Ile Ile Tyr Gln Asn Ser Asp Asp
            210                 215                 220

Ser Phe His Arg Leu Thr Ser Asn Thr Phe Asp Tyr Asp Pro Arg Tyr
225                 230                 235                 240

Thr Lys Leu Thr Val Ala Gly Glu Ser Phe Thr Val Lys Asn Gly Ile
            245                 250                 255

Cys Gly Ile Ala Leu Ser Pro Val Thr Asn Asn Leu Tyr Tyr Ser Pro
            260                 265                 270

Leu Leu Leu Thr Val Cys Ile Met Leu Thr Gln Asn Asn Ser Gly Ile
            275                 280                 285

His Asn Met Lys Lys Val Thr Ser Asn Met Lys Asp Pro Lys Ile Phe
            290                 295                 300

<210> SEQ ID NO 65
<211> LENGTH: 437
<212> TYPE: PRT
<213> ORGANISM: Apis cerana

<400> SEQUENCE: 65

Met Ser Phe Asn Ile Trp Trp Leu Ile Leu Tyr Phe Gly Ile Val Cys
1               5                   10                  15

Gln Thr Ile Thr Lys Ala His Tyr Tyr Ser Arg His Phe Lys Ala Asn
            20                  25                  30

Ala Leu Lys Val Val Tyr Gln Trp Lys Tyr Phe Asp Tyr Asn Phe Gly
            35                  40                  45

Ser Asn Glu Arg Arg Gln Ala Ala Ile Gln Ser Gly Lys Tyr Asn Tyr
        50                  55                  60

Lys Asn Asn Phe Pro Ile Asp Val Asp Arg Trp His Gly Lys Val Tyr
65                  70                  75                  80

Lys Val Leu Ile Ile Ile Glu Tyr Leu Cys Arg Ile Asn Ser Thr Asn
                85                  90                  95

Gln Asn Lys Thr Phe Val Thr Ile Leu Arg Asn Asn Gly Val Pro Ser
            100                 105                 110

Ser Leu Asn Val Ile Ser Asn Lys Ile Gly Asn Gly Gly Pro Leu Leu
            115                 120                 125

Glu Pro Tyr Pro Asn Trp Ser Trp Ala Glu Asn Gln Asn Cys Ser Gly
        130                 135                 140

Ile Thr Ser Val Tyr Arg Val Ala Ile Asp Val Trp Asp Arg Leu Trp
145                 150                 155                 160

Val Leu Asp Asn Gly Ile Ser Gly Gln Thr Ser Val Cys Ser Ser Gln
                165                 170                 175

Ile Val Val Phe Asp Leu Lys Thr Ser Lys Leu Leu Lys Gln Val Lys
            180                 185                 190

Ile Pro His Asn Ile Ala Val Asn Ser Thr Thr Gly Asn Arg Asn Val
            195                 200                 205

Val Thr Pro Ile Val Gln Ser Phe Asp Tyr Asn Asn Thr Leu Val Tyr
            210                 215                 220

Ile Ala Asp Val Glu Gly Tyr Ala Leu Ile Ile Tyr Asn Asn Ala Asp
225                 230                 235                 240

Asp Ser Phe Gln Arg Leu Thr Ser Thr Phe Val Tyr Asp Pro Arg
                245                 250                 255
```

-continued

```
Tyr Thr Asn Tyr Thr Ile Asn Glu Glu Ser Phe Thr Leu Gln Asp Gly
            260                 265                 270

Ile Leu Gly Met Ala Leu Ser Arg Lys Thr Gln Asn Leu Tyr Tyr Ser
            275                 280                 285

Ala Met Ser Ser His Asn Leu Asn Tyr Val Asn Thr Lys Gln Phe Thr
290                 295                 300

Gln Gly Lys Tyr Gln Ala Asn Asn Ile Gln Tyr Gln Gly Ala Ser Asp
305                 310                 315                 320

Ile Leu Trp Thr Gln Ala Thr Ala Lys Ala Ile Ser Lys Thr Gly Ala
                325                 330                 335

Leu Phe Phe Gly Leu Val Thr Asp Thr Ala Leu Gly Cys Trp Asn Glu
            340                 345                 350

Asn Arg Pro Leu Lys Arg Gly Asn Ile Glu Ile Val Ala Lys Asn Asn
            355                 360                 365

Asp Thr Leu Gln Phe Ile Ser Gly Leu Lys Ile Ser Lys Glu Ile Ser
        370                 375                 380

Ser His Ile Phe Gly Tyr Gln Asn Asn Glu Tyr Ile Trp Ala Leu Ser
385                 390                 395                 400

Asn Lys Tyr Gln Lys Ile Ala Asn Gly Asp Leu Asn Phe Asn Glu Val
                405                 410                 415

Asn Phe Arg Ile Leu Thr Ala Pro Phe Leu Leu Val Arg Asp Phe Ile
            420                 425                 430

Thr Tyr Ala Gln Thr
            435
```

<210> SEQ ID NO 66
<211> LENGTH: 155
<212> TYPE: PRT
<213> ORGANISM: Apis cerana

<400> SEQUENCE: 66

```
Met Thr Ser Trp Leu Leu Val Val Cys Leu Gly Ile Ala Cys Gln
1               5                   10                  15

Gly Ile Thr Gly Ala Thr Val Arg Glu Asn Ser Ser Arg Asn Leu Ala
            20                  25                  30

Asn Ser Met Asn Val Ile His Glu Trp Lys Tyr Leu Asp Tyr Asp Phe
        35                  40                  45

Gly Ser Asp Glu Lys Arg Gln Ala Ala Ile Gln Ser Gly Glu Tyr Asp
    50                  55                  60

His Thr Lys Asn Tyr Pro Phe Asp Val Asp Arg Trp His Gly Lys Ile
65                  70                  75                  80

Ser Ile Asp Lys Phe Asp Arg Leu Trp Val Leu Asp Ser Gly Ile Ile
                85                  90                  95

Asn Asn Thr Gln Pro Met Cys Ser Pro Lys Leu His Val Phe Asp Leu
            100                 105                 110

Asn Thr Ser Gln Gln Ile Lys Gln Val Met Met Pro His Asp Ile Ala
        115                 120                 125

Ile Asn Ala Thr Thr Gly Lys Gly Gly Leu Glu Asn Leu Val Val Gln
    130                 135                 140

Ala Met Asp Pro Met Asn Thr Leu Leu Ser Leu
145                 150                 155
```

<210> SEQ ID NO 67
<211> LENGTH: 808
<212> TYPE: PRT
<213> ORGANISM: Apis cerana

<400> SEQUENCE: 67

| | | | | | | | | | | | | | | |
|---|---|---|---|---|---|---|---|---|---|---|---|---|---|---|
|Met|Leu|His|Leu|Phe|Leu|Leu|Ala|Gly|Leu|Phe|Cys|Thr|Leu|Thr|Glu|
|1| | | |5| | | | |10| | | | |15| |

Cys Thr Glu Ile Leu Glu Thr Ile Val Gln Trp Pro Leu Leu Asp Phe
                    20                  25                  30

Ala Leu Pro Tyr Asp Arg Glu Phe Leu Asn Gln Tyr Arg Pro Glu Asn
                35                  40                  45

Val Val Pro Thr Gly Ile Glu Val Gly Trp Asp Lys Ile Phe Ile Ser
 50                  55                  60

Val Pro Arg Leu Arg Val Gly Ile Pro Ala Thr Leu Asn Tyr Ile Ser
 65                  70                  75                  80

Lys Asn Leu Pro Leu Glu Ser Ser Pro Gln Leu Asn Ala Tyr Pro Ser
                85                  90                  95

Trp Asp Trp His Ser Ala Gly Lys Gly Asp Leu Asn Cys Ser Leu Leu
                100                 105                 110

Ile Ser Val Tyr Arg Thr Lys Leu Asp Arg Cys Asn Arg Leu Trp Val
            115                 120                 125

Ile Asp Ser Gly Val Met Thr Ser Ile Asp Asp Phe Arg Pro Val Cys
            130                 135                 140

Gln Pro Lys Ile Met Val Phe Asp Val Lys Thr Asp Gln Leu Val Arg
145                 150                 155                 160

Gln Tyr Thr Phe Pro Arg Glu Ser Leu Arg Pro Asn Thr Leu Leu Thr
                165                 170                 175

Asn Leu Ile Leu Asp Asp Thr Ser Ala Thr Thr Cys Asp Asp Met Phe
                180                 185                 190

Leu Tyr Ile Ser Asp Thr Thr Gly Pro Gly Ile Ile Val Phe Asp Gly
            195                 200                 205

Ala Thr Asp Arg Ser Trp Arg Ile Leu His Ala Ser Met Tyr Pro His
            210                 215                 220

Pro Asp Phe Ser Thr Tyr Arg Ile Gly Ser Asp Met Phe Glu Leu Phe
225                 230                 235                 240

Asp Gly Val Ile Gly Leu Ala Phe Ser Ala Arg Leu Gly Thr Leu Tyr
                245                 250                 255

Tyr Gln Pro Leu Ala Thr Asp Arg Leu Phe Ser Val Pro Thr Thr Ala
                260                 265                 270

Leu Gln Ala Gly Pro Pro Ala Phe Gly Glu Gln Leu Pro Val Thr Leu
            275                 280                 285

Val Gly Lys Lys Ser Ser Gln Gly Leu Ala Leu Ala Val Asp Pro Arg
            290                 295                 300

Glu Asp Thr Ile Leu Phe Ala Pro Phe Thr Glu Met Ala Ile Ala Ser
305                 310                 315                 320

Trp Gln Pro Gln Thr Asn Gln Gln Arg Ile Leu Ala Tyr Thr Pro Glu
                325                 330                 335

Lys Leu Gln Phe Val Ala Glu Ile Arg Trp Ala Glu Arg Asp Asn Gly
                340                 345                 350

Asn Ile Trp Val Met Ser Thr Lys Phe Gln Lys Phe Lys Gln Glu
            355                 360                 365

Glu Met Arg Gln Phe Tyr Phe Ser Val Ile Leu Phe Leu Leu Ala Ile
            370                 375                 380

Ala Asp Ser Gln Thr Gln Glu Lys Leu Lys Asn Ile Tyr Ser Trp Lys
385                 390                 395                 400

Ala Leu Glu Phe Ala Phe Pro Asn Glu Phe Ala Lys Leu Ala Ala Ile

```
                405                 410                 415
Lys Ser Gly Ser Tyr Ile Pro Gly Val Ser Leu Pro Ile Asp Val Asp
            420                 425                 430

Val Tyr Asn Thr Asp Leu His Phe Phe Tyr Asn Thr Lys Leu Asn Ser
            435                 440                 445

Leu Phe Gln Glu Arg Gln Ser Thr Val Phe Val Ala Ile Pro Arg Ile
    450                 455                 460

Gln Asp Gly Val Pro Leu Thr Leu Gly Tyr Val Thr Lys Glu Val Ser
465                 470                 475                 480

Val Asp Gly Asn Pro Leu Ile Ala Pro Tyr Pro Ser Trp Ser Tyr Asn
                485                 490                 495

Asp Val Lys Tyr Cys Asp Gly Leu Thr Ser Val Tyr Arg Met Gln Val
            500                 505                 510

Asp Lys Cys Gly Arg Leu Trp Val Leu Asp Thr Gly Ile Leu Gly Glu
        515                 520                 525

Lys Gln Thr Cys Arg Pro Lys Ile His Val Phe Ser Leu His Asp Asn
530                 535                 540

Lys Leu Ile Thr Met Tyr Arg Phe Pro Gln Asn Gln Phe Lys Asp Ser
545                 550                 555                 560

Ser Leu Phe Val Thr Ile Ala Val Asp Val Arg Asp Thr Glu Asp Lys
                565                 570                 575

Cys Lys Asp Thr Phe Ala Tyr Ile Ala Asp Val Thr Gly Phe Ala Leu
            580                 585                 590

Leu Val Tyr Asp Phe Arg Asn Ser Arg Ser Trp Lys Ile Thr Asn Asn
        595                 600                 605

Leu Phe Tyr Pro Tyr Pro Tyr Gly Thr Phe Asn Ile Lys Gly Asp
    610                 615                 620

Thr Phe Asp Leu Met Asp Gly Ile Leu Gly Leu Ala Leu Gly Pro Ile
625                 630                 635                 640

Arg Asn Asn Asp Arg Ile Leu Tyr Phe His Ser Leu Ala Ser Arg Ile
                645                 650                 655

Glu Ser Trp Val His Thr Ser Val Ile Arg Asn Tyr Thr Leu Phe Asn
            660                 665                 670

Glu Asn Ser Glu Ala Ala Ala Arg Ser Phe Val Pro Phe Ser Ile Glu
        675                 680                 685

Arg Ser Ser Gln Ser Val Ala Glu Val Met Asp Arg Asn Gly Val Leu
    690                 695                 700

Phe Phe Gly Leu Leu Ser Asp Leu Ala Ile Gly Cys Trp Asn Ser Glu
705                 710                 715                 720

His Phe Phe Glu Tyr Gly Gly Asn Asn Ile Glu Ile Val Lys Asp
                725                 730                 735

Pro Glu Thr Leu Gln Phe Pro Ser Gly Met Lys Ile Ile Ser Ser Lys
            740                 745                 750

Lys Gly Ile Gln Glu Leu Trp Val Phe Thr Ile Ser Phe Gln Lys Tyr
        755                 760                 765

Met Thr Gly Thr Leu Asn Ser Asn Glu Thr Asn Phe Arg Ile Gln Ala
    770                 775                 780

Gly Leu Val Asp Glu Leu Val Arg Gly Thr Lys Cys Asp Val Ser Leu
785                 790                 795                 800

Leu Gly Arg Phe Ile Pro Ser Gln
                805

<210> SEQ ID NO 68
```

```
<211> LENGTH: 552
<212> TYPE: PRT
<213> ORGANISM: Apis cerana

<400> SEQUENCE: 68
```

| | | | | | | | | | | | | | | | |
|---|---|---|---|---|---|---|---|---|---|---|---|---|---|---|---|
| Met | Ala | Asn | Val | Val | Pro | Trp | Leu | Leu | Ser | Ile | Cys | Leu | Phe | Gly | Leu |
| 1 | | | | 5 | | | | | 10 | | | | | 15 | |
| Gln | Glu | Ile | Ala | Ile | Gln | Pro | Gly | Ser | Asn | Ala | Leu | Ser | Arg | Asn | Leu |
| | | | 20 | | | | | 25 | | | | | 30 | | |
| Glu | Thr | Ser | Gly | Gln | Arg | Ser | Val | Ser | Ser | Gly | Phe | Arg | Ser | Ser | Leu |
| | | 35 | | | | | 40 | | | | | 45 | | | |
| Arg | Asn | Tyr | Lys | Thr | Leu | Ile | Ser | Ser | His | Asp | Glu | Leu | Pro | Gly | His |
| | 50 | | | | | 55 | | | | | 60 | | | | |
| Ile | Asn | Cys | Asp | Ser | Ser | Lys | Phe | Asp | Glu | Asp | Leu | Met | Asn | Lys | Leu |
| 65 | | | | | 70 | | | | | 75 | | | | | 80 |
| Pro | Thr | Thr | Pro | Glu | Tyr | Asn | Asn | His | Leu | Tyr | Gly | Ser | Thr | Pro | Asp |
| | | | | 85 | | | | | 90 | | | | | 95 | |
| Ser | Arg | Asp | Tyr | Phe | Ser | Arg | Pro | Phe | Glu | Lys | Arg | Leu | His | Ser | Arg |
| | | | 100 | | | | | 105 | | | | | 110 | | |
| Leu | Pro | Gly | Arg | Asn | Phe | Asn | Leu | Leu | Arg | Thr | Asp | Ala | Asn | Ser | Val |
| | | 115 | | | | | 120 | | | | | 125 | | | |
| Asn | Glu | Leu | Glu | Ser | His | Gly | Phe | Asn | Tyr | Asp | Pro | Gly | Arg | Gly | His |
| | 130 | | | | | 135 | | | | | 140 | | | | |
| Ile | Glu | Asp | Asp | Tyr | Val | Gly | Pro | Ala | Met | Glu | Leu | Val | Tyr | Ala | Trp |
| 145 | | | | | 150 | | | | | 155 | | | | | 160 |
| Ser | Thr | Ile | Asp | Tyr | Thr | Tyr | Asp | Ser | Ile | Glu | Ala | Arg | Asp | Ser | Ala |
| | | | | 165 | | | | | 170 | | | | | 175 | |
| Ile | Phe | Asp | Gly | Asp | Phe | Ile | Ala | Glu | Asn | Asn | Leu | Pro | Leu | Gly | Leu |
| | | | 180 | | | | | 185 | | | | | 190 | | |
| Glu | Val | Trp | Arg | Asp | Lys | Val | Phe | Ile | Thr | Leu | Pro | Lys | Trp | Lys | Asp |
| | | 195 | | | | | 200 | | | | | 205 | | | |
| Gly | Ile | Pro | Val | Thr | Leu | Ser | Thr | Val | Pro | Lys | His | Ser | Lys | Thr | Lys |
| | 210 | | | | | 215 | | | | | 220 | | | | |
| Ser | Pro | Lys | Leu | Arg | Pro | Tyr | Pro | Asn | Trp | Glu | Trp | His | Thr | Val | Gly |
| 225 | | | | | 230 | | | | | 235 | | | | | 240 |
| Asn | Cys | Asp | Gly | Leu | Thr | Ser | Val | Phe | Arg | Ile | Gln | Val | Asp | Glu | Cys |
| | | | | 245 | | | | | 250 | | | | | 255 | |
| Asp | Arg | Leu | Trp | Val | Leu | Asp | Ser | Gly | Lys | Val | Asp | Ile | Ala | Lys | Gly |
| | | | 260 | | | | | 265 | | | | | 270 | | |
| Gly | Asn | Leu | Ala | Cys | Pro | Pro | Ala | Ile | Phe | Ile | Phe | Asp | Leu | Thr | Thr |
| | | 275 | | | | | 280 | | | | | 285 | | | |
| Asp | Thr | Leu | Ile | Arg | Lys | Tyr | Ile | Ile | Pro | Asn | Glu | Gln | Val | Lys | Glu |
| | 290 | | | | | 295 | | | | | 300 | | | | |
| Asp | Ser | Leu | Tyr | Thr | Asn | Ile | Val | Asp | Ile | Arg | Asn | Glu | Asp | Cys |
| 305 | | | | | 310 | | | | | 315 | | | | | 320 |
| Gly | Ser | Ala | Ile | Ala | Tyr | Ile | Ser | Asp | Val | Phe | Arg | Tyr | Gly | Leu | Leu |
| | | | | 325 | | | | | 330 | | | | | 335 | |
| Val | Tyr | Asp | Phe | Phe | Lys | Asp | Ser | Ser | Phe | Arg | Ile | Gln | His | His | Phe |
| | | | 340 | | | | | 345 | | | | | 350 | | |
| Phe | Tyr | Pro | Asp | Pro | Leu | Ala | Ser | Lys | Tyr | Glu | Ile | His | Gly | Leu | Lys |
| | | 355 | | | | | 360 | | | | | 365 | | | |
| Phe | Gln | Trp | Thr | Asp | Gly | Ile | Phe | Gly | Met | Ala | Leu | Ser | Pro | Val | Asp |
| | 370 | | | | | 375 | | | | | 380 | | | | |
| Ile | His | Asp | Asp | Arg | Thr | Leu | Phe | Phe | His | Pro | Met | Ser | Ser | Phe | Arg |

```
385                 390                 395                 400
Glu Phe Ala Val Ser Thr Ser Ile Leu Gly Asp Lys Thr Ala Glu
                405                 410                 415

Glu Asn Thr Asp Tyr Phe Met Pro Ile Gly Arg Pro Arg Ala Lys Asp
                420                 425                 430

Tyr Gly His Ser Ser Gly Ser Val Ile Asp Arg Asn Gly Val Met Phe
            435                 440                 445

Phe Asn Met Val Thr Arg Asp Ser Val Trp Cys Trp Asp Thr Arg Lys
        450                 455                 460

Glu Tyr Ile Pro Gln Asn Leu Gly Val Ile Gly Thr Ser Asn Leu Ser
465                 470                 475                 480

Leu Val Phe Pro Asn Asp Ile Lys Val Asp His Glu Tyr Asp Gln Asn
                485                 490                 495

Val Trp Val Leu Ser Asn Lys Leu Ala Met Tyr Leu Tyr Gly Ser Ile
                500                 505                 510

Asp Ser Ser Lys Ile Asn Tyr Arg Ile Phe Lys Ala Asn Val Lys Glu
            515                 520                 525

Ala Val Lys Asp Thr Val Cys Asp Pro Asn Tyr Val Val Pro Gly Ser
        530                 535                 540

Glu His Gly Tyr Asp Glu Ile Cys
545                 550

<210> SEQ ID NO 69
<211> LENGTH: 582
<212> TYPE: PRT
<213> ORGANISM: Apis cerana

<400> SEQUENCE: 69

Met Thr Ser Trp Leu Leu Val Val Cys Leu Gly Ile Ala Cys Gln
1               5                   10                  15

Gly Ile Thr Gly Ala Thr Val Arg Glu Asn Ser Ser Arg Asn Leu Ala
            20                  25                  30

Asn Ser Met Asn Val Ile His Glu Trp Lys Tyr Leu Asp Tyr Asp Phe
        35                  40                  45

Gly Ser Asp Glu Lys Arg Gln Ala Ala Ile Gln Ser Gly Glu Tyr Asp
    50                  55                  60

His Thr Lys Asn Tyr Pro Phe Asp Val Asp Arg Trp His Asp Met Thr
65                  70                  75                  80

Phe Val Thr Val Leu Arg Tyr Lys Gly Val Pro Ser Ser Leu Asn Val
                85                  90                  95

Ile Ser Lys Lys Ile Gly Asn Gly Gly Pro Leu Leu Gln Pro Tyr Pro
            100                 105                 110

Asp Trp Ser Trp Ala Asn Tyr Lys Asp Cys Ser Gly Ile Val Ser Ala
        115                 120                 125

Tyr Lys Ile Ala Ile Asp Lys Phe Asp Arg Leu Trp Val Leu Asp Ser
    130                 135                 140

Gly Ile Ile Asn Asn Thr Gln Pro Met Cys Ser Pro Lys Leu His Val
145                 150                 155                 160

Phe Asp Leu Asn Thr Ser Gln Gln Ile Lys Gln Val Met Met Pro His
                165                 170                 175

Asp Ile Ala Ile Asn Ala Thr Thr Gly Lys Gly Gly Leu Glu Asn Leu
            180                 185                 190

Val Val Gln Ala Met Asp Pro Met Asn Thr Leu Val Tyr Met Ala Asp
        195                 200                 205
```

Asn Lys Gly Asp Ala Leu Ile Val Tyr Gln Asn Ser Asp Asp Ser Phe
210                 215                 220

His Arg Leu Thr Ser Asn Thr Phe Asp Tyr Asp Pro Lys Tyr Ile Lys
225                 230                 235                 240

Met Met Ala Ala Gly Glu Ser Phe Thr Leu Gln Asp Gly Ile Phe Gly
            245                 250                 255

Met Ala Leu Ser Pro Met Thr Asn Asn Leu Tyr Tyr Ser Pro Leu Ala
            260                 265                 270

Ser Arg Ser Leu Tyr Tyr Ile Asn Thr Lys Pro Phe Met Lys Ser Gln
        275                 280                 285

Tyr Gly Thr Asn Val Gln His Glu Gly Val Gln Asp Ile Phe Asn
290                 295                 300

Thr Gln Ser Ile Ala Lys Ile Met Ser Lys Asn Gly Val Leu Phe Phe
305                 310                 315                 320

Gly Leu Met Asn Asn Ser Ala Ile Gly Cys Trp Asn Glu His Gln Pro
                325                 330                 335

Leu Gln Arg Gln Asn Met Asp Met Val Ala Gln Asn Glu Glu Thr Leu
            340                 345                 350

Gln Thr Val Val Ala Met Lys Met Met His Leu Pro Gln Ser Asn Arg
        355                 360                 365

Met Asn Arg Met His Arg Met Asn Ser Met Asn Arg Met Asp Arg Met
370                 375                 380

Asp Arg Met Asp Arg Met Asp Arg Met Asp Lys Met Asp Arg Met Asp
385                 390                 395                 400

Arg Met Asp Arg Met Asp Arg Met Asp Arg Met Asp Arg Met Asp Arg
            405                 410                 415

Met Asp Arg Met Asp Arg Met Asp Arg Met Asp Ile Met Asp Arg Thr
            420                 425                 430

Asn Lys Met Asp Arg Met Asp Arg Met Asp Ile Met Asp Lys Thr Asn
        435                 440                 445

Lys Met Asp Arg Met Asp Ser Met Ile Arg Ile Asp Lys Met Asp Arg
    450                 455                 460

Met Asp Arg Met His Arg Ile Asp Ile Met Asn Arg Met Asp Arg Met
465                 470                 475                 480

Asp Arg Met Asp Thr Arg Ile Asp Thr Arg Met Asp Arg Met Asp Arg
                485                 490                 495

Met Asp Lys Met Asp Lys Ile Asn Lys Met His Arg Met Gly Arg Met
            500                 505                 510

Asp Arg Met Asp Arg Met Asn Arg Met Asn Arg Gln Met Asn Glu Tyr
        515                 520                 525

Met Met Ala Leu Ser Met Lys Leu Gln Lys Phe Ile Asn Asn Asp Tyr
530                 535                 540

Asn Phe Asn Glu Val Asn Phe Arg Ile Leu Ala Ala Asn Val Asn Asp
545                 550                 555                 560

Leu Ile Met Asn Thr Arg Cys Ala Asn Ser Asn Gln Asn Asp Asn
                565                 570                 575

Gln Asn Lys His Asn Asn
            580

<210> SEQ ID NO 70
<211> LENGTH: 283
<212> TYPE: PRT
<213> ORGANISM: Apis cerana

<400> SEQUENCE: 70

Met Cys Ser Pro Lys Leu Leu Ala Phe Asp Leu Thr Thr Ser Lys Leu
1               5                   10                  15

Leu Lys Gln Val Glu Ile Pro Tyr Asp Ile Ala Val Asn Ala Ser Thr
                20                  25                  30

Gly Met Gly Gly Leu Val Ser Leu Val Val Gln Ala Met Asp Pro Met
            35                  40                  45

Asn Thr Met Val Tyr Ile Ala Asp Asp Arg Gly Asp Ala Leu Ile Ile
        50                  55                  60

Tyr Gln Asn Ser Asp Asp Ser Phe His Arg Leu Ser Ser Asn Thr Phe
65                  70                  75                  80

Asp Asn Asp Pro Arg Tyr Ser Glu Leu Thr Val Ala Gly Glu Ser Phe
                85                  90                  95

Thr Val His Asp Gly Ile Phe Gly Met Ala Leu Ser Pro Val Thr Asn
            100                 105                 110

Asn Leu Tyr Tyr Ser Pro Leu Thr Ser His Ser Leu Tyr Tyr Val Asn
            115                 120                 125

Thr Glu Pro Phe Met Lys Ser Gln Tyr Gly Glu Asn Asn Ile Gln Tyr
        130                 135                 140

Glu Gly Ile Gln Asp Ile Phe Asn Thr Gln Ser Ser Ala Lys Val Met
145                 150                 155                 160

Ser Lys Asn Gly Val Leu Phe Phe Gly Leu Val Asn Asn Ser Ala Ile
                165                 170                 175

Gly Cys Trp Asn Glu His Gln Pro Leu Gln Lys Gln Asn Met Asp Met
            180                 185                 190

Val Ala Gln Asn Glu Glu Thr Leu Gln Thr Ile Thr Ser Val Lys Ile
            195                 200                 205

Ile Gln Asn Leu Gln Tyr Ser Gly Arg Met Asn Arg Ile His Lys Asn
        210                 215                 220

Glu Tyr Met Leu Ala Leu Ser Asn Arg Met Gln Lys Ile Val Asn Asn
225                 230                 235                 240

Asp Phe Asn Phe Asn Asp Ile Asn Phe Arg Ile Leu Gly Ala Asn Val
                245                 250                 255

Lys Asn Leu Ile Lys Asn Thr Arg Cys Ala Asn Ser Lys Asn Gln Asn
            260                 265                 270

Asn Asn Gln Lys Lys His Lys Asn Gln Ala His
            275                 280

<210> SEQ ID NO 71
<211> LENGTH: 96
<212> TYPE: PRT
<213> ORGANISM: Apis cerana

<400> SEQUENCE: 71

Met Asn Ala Val Ser Arg Thr Val Ala Gln Ser Asp Glu Thr Leu Gln
1               5                   10                  15

Met Ile Val Gly Met Lys Ile Lys Glu Ala Leu Pro His Val Pro Ile
                20                  25                  30

Phe Asp Arg Tyr Ile Asn Arg Glu Tyr Ile Leu Val Leu Ser Asn Arg
            35                  40                  45

Met Gln Lys Met Ala Asn Asp Tyr Asn Phe Asn Asp Val Asn Phe
        50                  55                  60

Arg Ile Met Asp Ala Asn Val Asn Asp Leu Ile Leu Asn Thr Arg Cys
65                  70                  75                  80

Glu Asn Pro Asn Asn Asp Asn Thr Pro Phe Lys Ile Ser Ile His Leu

<210> SEQ ID NO 72
<211> LENGTH: 416
<212> TYPE: PRT
<213> ORGANISM: Apis cerana

<400> SEQUENCE: 72

```
Met Arg Lys Met Phe Lys Asn Tyr Pro His Ser His Asp Ile Thr Ile
1               5                   10                  15
Ile Asp Asn Asn Glu Ser Leu Ile Lys Leu Leu Pro Gly Asn Leu Phe
                20                  25                  30
Ser Arg Arg Ser Asp Arg Met Lys Arg Leu Leu Cys Val Ile Leu Ser
            35                  40                  45
Leu Thr Ser Leu Thr Lys Ile Phe Gln Leu Ser Asp Gly Thr Pro Val
        50                  55                  60
Leu Pro Gln Pro Leu Ile Phe Ser Gly Leu Ser Leu Asp Trp Pro Cys
65                  70                  75                  80
Gln Ser Thr Lys Asn Ile Tyr Glu Thr Ser Gly Arg Tyr Ile Ala Arg
                85                  90                  95
Asn Val Ile Ala Thr Arg Ala Gln Ile Phe Glu Asp Lys Ala Ile Leu
            100                 105                 110
Ala Leu Pro Arg Tyr Lys Pro Gly Val Pro Phe Thr Leu Gly Ile Leu
        115                 120                 125
Asp Leu Lys Ser Gln Asn Asn Cys Glu Pro Lys Val Ala Pro Phe Pro
    130                 135                 140
Cys Trp Ala Ile Gln Glu Gly Asn Cys Gln Ala Leu Gln Ser Ala
145                 150                 155                 160
Val Asp Ile Val Leu Asp Val Gln Asp Ile Leu Trp Val Leu Asp Val
                165                 170                 175
Gly Ile Val Asn Thr Leu Glu Gln Pro Val Arg Arg Cys Pro Pro Lys
            180                 185                 190
Val Val Gly Val Asn Ala Lys Thr Gly Lys Val Asn Phe Val Val Lys
        195                 200                 205
Val Ile Asp Leu Ser Ser Leu Ala Asp Ile Asn Ser Arg Leu Gln Tyr
    210                 215                 220
Met Ala Val Asp Tyr Ala Glu Asp Gly Gln Val Tyr Val Tyr Ile Ser
225                 230                 235                 240
Asp Ala Gly Ser Gly Ala Ile Ile Val Tyr Asn Val Thr Thr Asp Thr
                245                 250                 255
Gly Tyr Arg Val Val Leu Pro Ala Ala Val Ala Gly Cys Thr Asp Lys
            260                 265                 270
Pro Asp Ala Leu Tyr Ile Ala Leu Val Arg Arg Glu Ser Cys Gly Pro
        275                 280                 285
Val Leu Tyr Phe Thr Phe Leu Gly Ser Asn Arg Met Phe Ala Ile Lys
    290                 295                 300
Ala Val Asn Leu Arg Ser Gly Asn Ala Asn Gly Ser Ile Val Asp Ile
305                 310                 315                 320
Gly Gly Lys Lys Asn Lys Ile Val Leu Leu Gly Thr Asp Asn Ala Ala
                325                 330                 335
Thr Ile Phe Phe Arg Ile Lys Gly Asp Ser Ser Ile Tyr Met Trp Asn
            340                 345                 350
Thr Asp Thr Ser Phe Val Gln Asp Asn Phe Leu Leu Val Gln Lys Ala
        355                 360                 365
```

```
Gly Asp Cys Arg Leu Pro Thr Glu Val Ile Pro Gly Tyr Asn Asp Leu
    370                 375                 380

Met Trp Val Ile Glu Ser Asn Phe Gln Asp Tyr Ile Asp Asn Asn Val
385                 390                 395                 400

Ser Cys Ser Gly Thr Ser Val Ala Val His Pro Leu Met Asn Ser Ser
                405                 410                 415

<210> SEQ ID NO 73
<211> LENGTH: 396
<212> TYPE: PRT
<213> ORGANISM: Apis cerana

<400> SEQUENCE: 73

Met Lys Ala Gly Gly Leu Glu Val Ala Phe Gln Trp Lys Tyr Leu Asp
1               5                   10                  15

Trp Leu Trp Pro Thr Val His Leu Thr Gly Lys Asn Gln Thr Leu Gly
                20                  25                  30

Asn Ala Phe Thr Gln Asp Val Asp Ile Asp Lys Tyr Gly Arg Val Phe
                35                  40                  45

Val Thr Ser Pro Gln Trp Leu Glu Gly Val Pro Ile Ser Leu Ser Leu
50                  55                  60

Val Thr Lys Val Ser Gly Ile Gly Gly Pro Leu Leu Val Pro Tyr Pro
65                  70                  75                  80

Asp Trp Thr Trp His Thr Ser Tyr Asn Cys Asp Gly Ile Ile Ser Val
                85                  90                  95

Tyr Arg Leu Ala Ile Asp Glu Cys Asn Arg Leu Trp Val Val Asp Thr
                100                 105                 110

Gly Arg Val Gln Gly Asn Ala Val Cys Pro Thr Lys Ile Leu Ile Phe
                115                 120                 125

Asp Leu Ala Thr Asp His Leu Leu His Lys Tyr Val Val Pro Asp Asp
                130                 135                 140

Gln Val Leu Phe Gly Lys Ala Ala Leu Val Thr Pro Ile Val Asp Val
145                 150                 155                 160

Gly Lys Thr Cys Leu Asp Thr Tyr Leu Tyr Val Ala Asp Val Asp Gln
                165                 170                 175

Asn Gly Leu Leu Ile Tyr Asp Leu Tyr His Asp Tyr Ser Trp Arg Val
                180                 185                 190

Asn Asn Thr Arg Gly Asn Ala Phe Gly Pro Asp Asp Ala Thr Asn
                195                 200                 205

Ile Thr Ile Ala Gly Glu Ser Phe Asp Leu Thr Asp Gly Thr Leu Gly
210                 215                 220

Met Ser Leu Ser Pro Tyr Gly Tyr Phe Asn Glu Arg Tyr Leu Tyr Phe
225                 230                 235                 240

Asn Ser Leu Ala Ser Tyr Arg Gln Lys Phe Thr Asp Thr Tyr Ser Leu
                245                 250                 255

Lys Gln Ser Lys Tyr Lys Glu Pro Ile Val Leu Glu Ser Asn Tyr Lys
                260                 265                 270

Arg Ala Ser Gln Ala Gly Val Gln Ala Thr Ser Arg Arg Gly Val Ile
                275                 280                 285

Phe Phe Gln Leu Val Gln Leu Thr Ala Val Ala Cys Trp Asn Ile Glu
                290                 295                 300

Lys Pro Phe Ile Pro Glu Asn Val Val Ile Ala Gln Asp Glu Lys
305                 310                 315                 320

Thr Leu Gln Tyr Val Ser Gly Ile Lys Val Ile Thr Asn Asn Gln Gly
                325                 330                 335
```

```
Glu Glu Glu Leu Trp Phe Asn Thr Asn Arg Leu Gln Lys Thr Ile Asn
            340                 345                 350

Met Thr Leu Lys Pro Thr Glu Thr Asn Phe Arg Ile Ile Arg Gly Lys
            355                 360                 365

Val Asp Asp Ile Val Arg Gly Thr Asn Cys Glu Pro Ser Gly Ala Lys
            370                 375                 380

His Gly Phe Pro Asp Thr Asn Phe Trp His Arg Ile
385                 390                 395

<210> SEQ ID NO 74
<211> LENGTH: 431
<212> TYPE: PRT
<213> ORGANISM: Apis cerana

<400> SEQUENCE: 74

Met Lys Ile Val Val Leu Leu Val Thr Leu Val Ala Val Ala Lys Cys
1               5                   10                  15

His Glu Pro Phe Arg Val Val Phe Gln Trp Asn Thr Ile Asp Val Met
            20                  25                  30

Trp Pro Ser Glu Glu Asn Lys Glu Tyr Ala Ile Ser His Asn Asp Tyr
        35                  40                  45

Val Pro Ala Asn Asn Phe Ile Ala Gly Ile Lys Phe Trp Lys Gly Lys
    50                  55                  60

Met Tyr Leu Thr Ile Pro Arg Trp Lys Asp Gly Val Pro Val Thr Leu
65                  70                  75                  80

Gly Val Thr Ser Ala Lys Pro Val Asn Tyr Ile Thr Ala Pro Lys Leu
                85                  90                  95

Glu Ala Phe Pro Ser Trp Glu Met Gln Lys Ile Gly Asp Cys Ser Ala
            100                 105                 110

Phe Gln Met Val Gln Ser Met Glu Ile Asp Pro Ile Gly Arg Met Trp
        115                 120                 125

Val Leu Asp Ser Gly Lys Met Ser Pro Leu Ser Leu Glu Val Lys Thr
    130                 135                 140

Thr Cys Pro Pro Arg Leu Val Ile Leu Asp Leu Glu Lys Asn Gly Glu
145                 150                 155                 160

Val Leu Arg Ile Tyr Glu Phe Pro Thr Asn Val Ala His His Gly Thr
                165                 170                 175

Thr His Leu Asn Asp Ile Val Leu Asp His Glu Asp Gly Gly Met Ala
            180                 185                 190

Tyr Ile Thr Asp Ser Asp Arg Asn Asp Pro Gly Ile Ile Val Tyr Ser
        195                 200                 205

Leu Arg Asn Asn Thr Ser Trp Lys Val Arg His Asp Ser Met Lys Ala
    210                 215                 220

Lys Gln Glu Ala Val Lys Phe Met Ile Ser Lys Thr Pro Ile Asn Ile
225                 230                 235                 240

Pro Val Pro Val Asp Gly Ile Ala Leu Ser Pro Ala Ser Ser Asn Asp
                245                 250                 255

Arg Gln Ile Tyr Tyr Ser Pro Leu Ser Ser Phe His Leu Tyr Ser Ile
            260                 265                 270

Pro Thr Ser Val Leu Lys Asn Asn Ala Ser Asn Val Asp Ser Tyr Val
        275                 280                 285

Lys Glu Leu Gly Arg Lys Asn Ser Gln Thr Asp Gly Met Met Met Ser
    290                 295                 300

Ala Lys Gly Val Leu Tyr Phe Gly Leu Leu Ala Asp Asp Ala Val Ala
```

|     |     |     |     |     |     |     |     |     |     |     |     |     |     |     |     |
| --- | --- | --- | --- | --- | --- | --- | --- | --- | --- | --- | --- | --- | --- | --- | --- |
| 305 | | | | | 310 | | | | | 315 | | | | | 320 |

Met Trp Asp Thr Lys Gln Ser Ile Ser Phe Thr Thr Gly Gln Arg Val
                          325                            330                           335

Ile Ser Arg Asp His Glu Arg Met Gln Trp Pro Asp Thr Phe Ala Phe
              340                            345                           350

Asp Glu Asp Gly Asn Phe Tyr Cys Val Thr Asn Ser Leu Gln Asn Ile
              355                            360                        365

Leu Glu Asn Arg Val Asn Val Ser Ile Pro Asn Tyr Arg Val Val Arg
370                           375                           380

Ser Gln Thr Gly Val Lys Ser Tyr Gln Tyr Leu Glu Asp Gly Thr Ala
385                           390                         395                     400

Pro Glu Gln Pro Glu Ile Pro Thr Ser Ala Ala Asn Arg Ile Ser Leu
              405                            410                           415

Ala Val Thr Thr Gly Leu Thr Ile Leu Leu Ala Phe Val Val Gln
              420                            425                        430

<210> SEQ ID NO 75
<211> LENGTH: 380
<212> TYPE: PRT
<213> ORGANISM: Apis cerana

<400> SEQUENCE: 75

Met Thr Lys Trp Leu Phe Met Val Ala Cys Leu Gly Ile Ala Cys Gln
1                     5                         10                       15

Gly Ala Ile Ile Arg Gln Asn Ser Ala Lys Asn Leu Glu Asn Ser Leu
               20                         25                        30

Asn Val Ile His Glu Trp Lys Tyr Ile Asp Tyr Asp Phe Gly Ser Glu
               35                         40                        45

Glu Arg Arg Gln Ala Ala Ile Gln Ser Gly Tyr Asp His Thr Lys
       50                        55                        60

Asn Tyr Pro Phe Asp Val Asp Gln Trp His Asp Lys Thr Phe Val Thr
65                    70                        75                       80

Ile Leu Lys Tyr Asp Gly Val Pro Ser Thr Leu Asn Met Ile Ser Asn
               85                         90                        95

Lys Ile Gly Lys Gly Gly Arg Leu Leu Gln Pro Tyr Pro Asp Trp Ser
             100                       105                     110

Trp Ala Glu Asn Lys Asp Cys Ser Gly Ile Val Ser Ala Phe Lys Ile
             115                       120                     125

Ala Ile Asp Lys Phe Asp Arg Leu Trp Val Leu Asp Ser Gly Leu Ile
             130                       135                    140

Asn Arg Thr Glu Pro Ile Cys Ala Pro Lys Leu His Val Phe Asp Leu
145                   150                       155                    160

Lys Asn Thr Lys His Leu Lys Gln Ile Glu Ile Pro His Asp Ile Ala
             165                       170                     175

Val Asn Ala Thr Thr Gly Lys Gly Gly Leu Val Ser Leu Val Val Gln
             180                       185                    190

Ala Met Asp Pro Met Asn Thr Leu Val Tyr Ile Ala Asp His Lys Gly
             195                       200                    205

Asp Ala Leu Ile Val Tyr Gln Asn Ser Asp Asp Ser Phe His Arg Met
             210                       215                    220

Thr Ser Asn Thr Phe Asp Tyr Asp Pro Arg Tyr Ala Lys Met Thr Ile
225                   230                       235                    240

Asn Gly Glu Ser Phe Thr Leu Lys Asn Gly Ile Cys Gly Met Ala Leu
             245                       250                    255

```
Ser Pro Val Thr Asn Asn Leu Tyr Tyr Ser Pro Leu Ala Ser His Gly
            260                 265                 270

Leu Tyr Tyr Val Asn Thr Glu Pro Phe Met Lys Ser Gln Phe Gly Asp
        275                 280                 285

Asn Asn Asn Val Gln Tyr Glu Gly Ser Gln Asp Thr Leu Asn Thr Gln
        290                 295                 300

Ser Leu Ala Lys Ala Val Ser Lys Asp Gly Val Leu Phe Val Gly Leu
305                 310                 315                 320

Val Gly Asn Ser Ala Leu Gly Cys Leu Asn Glu His Gln Pro Leu Gln
                325                 330                 335

Arg Glu Asn Leu Glu Leu Val Ala Gln Asn Glu Lys Thr Leu Gln Met
            340                 345                 350

Ile Ala Gly Met Lys Ile Lys Glu Glu Leu Pro His Phe Val Gly Ser
        355                 360                 365

Asn Lys Pro Val Lys Glu Met Asn Ile Cys Trp Leu
        370                 375                 380

<210> SEQ ID NO 76
<211> LENGTH: 598
<212> TYPE: PRT
<213> ORGANISM: Apis cerana

<400> SEQUENCE: 76

Met Thr Ser Trp Leu Leu Val Val Cys Leu Gly Ile Ala Cys Gln
1               5                   10                  15

Gly Ile Thr Gly Ala Thr Val Arg Glu Asn Ser Ser Arg Asn Leu Ala
            20                  25                  30

Asn Ser Met Asn Val Ile His Glu Trp Lys Tyr Leu Asp Tyr Asp Phe
        35                  40                  45

Gly Ser Asp Glu Lys Arg Gln Ala Ala Ile Gln Ser Gly Glu Tyr Asp
    50                  55                  60

His Thr Lys Asn Tyr Pro Phe Asp Val Asp Arg Trp His Asp Met Thr
65                  70                  75                  80

Phe Val Thr Val Leu Arg Tyr Lys Gly Val Pro Ser Ser Leu Asn Val
                85                  90                  95

Ile Ser Lys Lys Ile Gly Asn Gly Gly Pro Leu Leu Gln Pro Tyr Pro
            100                 105                 110

Asp Trp Ser Trp Ala Asn Tyr Lys Asp Cys Ser Gly Ile Val Ser Ala
        115                 120                 125

Tyr Lys Ile Ala Ile Asp Lys Phe Asp Arg Leu Trp Val Leu Asp Ser
130                 135                 140

Gly Ile Ile Asn Asn Thr Gln Pro Met Cys Ser Pro Lys Leu His Val
145                 150                 155                 160

Phe Asp Leu Asn Thr Ser Gln Gln Ile Lys Gln Val Met Met Pro His
                165                 170                 175

Asp Ile Ala Ile Asn Ala Thr Thr Gly Lys Gly Gly Leu Glu Asn Leu
            180                 185                 190

Val Val Gln Ala Met Asp Pro Met Asn Thr Leu Val Tyr Met Ala Asp
        195                 200                 205

Asn Lys Gly Asp Ala Leu Ile Val Tyr Gln Asn Ser Asp Asp Ser Phe
    210                 215                 220

His Arg Leu Thr Ser Asn Thr Phe Asp Tyr Asp Pro Lys Tyr Ile Lys
225                 230                 235                 240

Met Met Ala Ala Gly Glu Ser Phe Thr Leu Gln Asp Gly Ile Phe Gly
                245                 250                 255
```

```
Met Ala Leu Ser Pro Met Thr Asn Asn Leu Tyr Tyr Ser Pro Leu Ala
            260                 265                 270

Ser Arg Ser Leu Tyr Tyr Ile Asn Thr Lys Pro Phe Met Lys Ser Gln
        275                 280                 285

Tyr Gly Thr Asn Val Gln His Glu Gly Val Gln Asp Ile Phe Asn
    290                 295                 300

Thr Gln Ser Ile Ala Lys Ile Met Ser Lys Asn Gly Val Leu Phe Phe
305                 310                 315                 320

Gly Leu Met Asn Asn Ser Ala Ile Gly Cys Trp Asn Glu His Gln Pro
                325                 330                 335

Leu Gln Arg Gln Asn Met Asp Met Val Ala Gln Asn Glu Glu Thr Leu
            340                 345                 350

Gln Thr Val Val Ala Met Lys Met Met His Leu Pro Gln Ser Asn Arg
        355                 360                 365

Met Asn Arg Met His Lys Met Asn Arg Val Asn Ser Met Asn Arg Met
    370                 375                 380

Asp Arg Met Asp Arg Met Asp Lys Met Asp Arg Met Asp Arg Met Asp
385                 390                 395                 400

Arg Met Asp Arg Ile Asp Gly Met Asp Arg Met Asp Arg Met Asp Arg
                405                 410                 415

Met Asp Arg Met His Thr Met Asp Thr Met Tyr Arg Met Asp Arg Ile
            420                 425                 430

Asp Arg Met Asp Arg Met Asp Ile Met Asp Arg Thr Asn Lys Met Asp
        435                 440                 445

Arg Met Asp Arg Met Asp Ile Met Asp Lys Met Asn Lys Met Asp Arg
    450                 455                 460

Met Asp Ser Met Ile Arg Ile Asp Lys Met Asp Arg Met Asp Arg Met
465                 470                 475                 480

Asp Arg Ile Asp Ile Met Asn Arg Met Asp Arg Met Asp Arg Met Asp
                485                 490                 495

Thr Met Asp Arg Ile Asp Thr Met Asp Arg Met Asp Arg Met Asp Arg
            500                 505                 510

Met Asp Lys Met Asp Lys Ile Asn Lys Met His Arg Met Gly Arg Met
        515                 520                 525

Asp Arg Met Asp Arg Met Asn Arg Met Asn Arg Gln Met Asn Glu Tyr
    530                 535                 540

Met Met Ala Leu Ser Met Lys Leu Gln Lys Phe Ile Asn Asp Tyr
545                 550                 555                 560

Asn Phe Asn Glu Val Asn Phe Arg Ile Leu Ala Ala Asn Val Asn Asp
                565                 570                 575

Leu Ile Met Asn Thr Arg Cys Ala Asn Ser Asn Asn Gln Asn Asp Asn
            580                 585                 590

Gln Asn Lys His Asn Asn
        595

<210> SEQ ID NO 77
<211> LENGTH: 431
<212> TYPE: PRT
<213> ORGANISM: Apis cerana

<400> SEQUENCE: 77

Met Lys Ile Val Val Leu Leu Val Thr Leu Val Ala Val Ala Lys Cys
1               5                   10                  15

His Glu Pro Phe Arg Val Val Phe Gln Trp Asn Thr Ile Asp Val Met
```

-continued

```
             20                  25                  30
Trp Pro Ser Glu Glu Asn Lys Glu Tyr Ala Ile Ser His Asn Asp Tyr
         35                  40                  45
Val Pro Ala Asn Asn Phe Ile Ala Gly Ile Lys Phe Trp Lys Gly Lys
 50                  55                  60
Met Tyr Leu Thr Ile Pro Arg Trp Lys Asp Gly Val Pro Val Thr Leu
 65                  70                  75                  80
Gly Val Thr Ser Ala Lys Pro Val Asn Tyr Ile Thr Ala Pro Lys Leu
                 85                  90                  95
Glu Ala Phe Pro Ser Trp Glu Met Gln Lys Ile Gly Asp Cys Ser Ala
                100                 105                 110
Phe Gln Met Val Gln Ser Met Glu Ile Asp Pro Ile Gly Arg Met Trp
                115                 120                 125
Val Leu Asp Ser Gly Lys Met Ser Pro Leu Ser Leu Glu Val Lys Thr
                130                 135                 140
Thr Cys Pro Pro Arg Leu Val Ile Leu Asp Leu Glu Lys Asn Gly Glu
145                 150                 155                 160
Val Leu Arg Ile Tyr Glu Phe Pro Thr Asn Val Ala His His Gly Thr
                165                 170                 175
Thr His Leu Asn Asp Ile Val Leu Asp His Glu Asp Gly Gly Met Ala
                180                 185                 190
Tyr Ile Thr Asp Ser Asp Arg Asn Asp Pro Gly Ile Ile Val Tyr Ser
                195                 200                 205
Leu Arg Asn Asn Thr Ser Trp Lys Val Arg His Asp Ser Met Lys Ala
                210                 215                 220
Lys Gln Glu Ala Val Lys Phe Met Ile Ser Lys Thr Pro Ile Asn Ile
225                 230                 235                 240
Pro Val Pro Val Asp Gly Ile Ala Leu Ser Pro Ala Ser Ser Asn Asp
                245                 250                 255
Arg Gln Ile Tyr Tyr Ser Pro Leu Ser Ser Phe His Leu Tyr Ser Ile
                260                 265                 270
Pro Thr Ser Val Leu Lys Asn Asn Ala Ser Asn Val Asp Ser Tyr Val
                275                 280                 285
Lys Glu Leu Gly Arg Lys Asn Ser Gln Thr Asp Gly Met Met Met Ser
                290                 295                 300
Ala Lys Gly Val Leu Tyr Phe Gly Leu Leu Ala Asp Asp Ala Val Ala
305                 310                 315                 320
Met Trp Asp Thr Lys Gln Ser Ile Ser Phe Thr Thr Gly Gln Arg Val
                325                 330                 335
Ile Ser Arg Asp His Glu Arg Met Gln Trp Pro Asp Thr Phe Ala Phe
                340                 345                 350
Asp Glu Asp Gly Asn Phe Tyr Cys Val Thr Asn Ser Leu Gln Asn Ile
                355                 360                 365
Leu Glu Asn Arg Val Asn Val Ser Ile Pro Asn Tyr Arg Val Val Arg
                370                 375                 380
Ser Gln Thr Gly Val Lys Ser Tyr Gln Tyr Leu Glu Asp Gly Thr Ala
385                 390                 395                 400
Pro Glu Gln Pro Glu Ile Pro Thr Ser Ala Ala Asn Arg Ile Ser Leu
                405                 410                 415
Ala Val Thr Thr Gly Leu Thr Ile Leu Leu Ala Phe Val Val Gln
                420                 425                 430

<210> SEQ ID NO 78
```

```
<211> LENGTH: 599
<212> TYPE: PRT
<213> ORGANISM: Apis cerana

<400> SEQUENCE: 78

Met Met Ala Ala Gly Glu Ser Phe Thr Leu Gln Asp Gly Ile Phe Gly
1               5                   10                  15

Met Ala Leu Ser Pro Met Thr Asn Asn Leu Tyr Tyr Ser Pro Leu Ala
            20                  25                  30

Ser Arg Ser Leu Tyr Tyr Ile Asn Thr Lys Pro Phe Met Lys Ser Gln
        35                  40                  45

Tyr Gly Thr Asn Val Gln His Glu Gly Val Gln Asp Ile Phe Asn
    50                  55                  60

Thr Gln Ser Ile Ala Lys Ile Met Ser Lys Asn Gly Val Leu Phe Phe
65                  70                  75                  80

Gly Leu Met Asn Asn Ser Ala Ile Gly Cys Trp Asn Glu His Gln Pro
                85                  90                  95

Leu Gln Arg Gln Asn Met Asp Met Val Ala Gln Asn Glu Glu Thr Leu
            100                 105                 110

Gln Thr Val Val Ala Met Lys Met Met His Leu Pro Gln Ser Asn Arg
        115                 120                 125

Met Asn Arg Met His Arg Met Asn Ser Met Asn Arg Met Asp Arg Met
130                 135                 140

Asp Arg Met Asp Arg Met Asp Arg Met Asp Arg Met Asp Ile Met Asp
145                 150                 155                 160

Arg Thr Asn Lys Met Asp Arg Met Asp Arg Met Asp Ile Met Asp Lys
                165                 170                 175

Thr Asn Lys Met Asp Arg Met Asp Ser Met Ile Arg Ile Asp Lys Met
            180                 185                 190

Asp Arg Met Asn Arg Met His Arg Ile Asp Ile Met Asn Arg Met Asp
        195                 200                 205

Arg Met Asp Arg Met Asp Thr Arg Ile Asp Thr Arg Met Asp Arg Met
    210                 215                 220

Asp Arg Met Asp Lys Met Asp Lys Ile Asn Lys Met His Arg Met Gly
225                 230                 235                 240

Arg Met Asp Arg Met Asp Arg Met Asn Arg Met Asn Arg Gln Met Asn
                245                 250                 255

Glu Tyr Met Met Ala Leu Ser Met Lys Leu Gln Lys Phe Ile Asn Asn
            260                 265                 270

Asp Tyr Asn Phe Asn Glu Ile Asp Lys Phe Asp Arg Leu Trp Val Leu
        275                 280                 285

Asp Ser Gly Leu Ile Asn Asn Thr Lys Leu Ile Cys Ser Pro Lys Leu
    290                 295                 300

Leu Ala Phe Asp Leu Asn Ile Ser Gln Leu Leu Lys Gln Val His Ile
305                 310                 315                 320

Pro His Asp Ile Ala Val Asn Ala Ile Thr Gly Lys Gly Gly Leu Val
                325                 330                 335

Phe Leu Ala Val His Ala Val Asp Pro Ile Asn Asn Met Ala Tyr Met
            340                 345                 350

Ala Asp Asn Arg Gly Asn Ala Leu Ser Val Tyr Gln Asn Ser Asp Asp
        355                 360                 365

Ser Leu His Arg Leu Thr Ser Asn Thr Phe Asp Tyr Asp Ser Arg Tyr
    370                 375                 380

Thr Glu Leu Thr Ile Ala Gly Glu Ser Phe Thr Leu Gln Asp Gly Ile
```

```
                385                 390                 395                 400
Phe Arg Ile Ala Val Ser Pro Val Thr Asn Asn Leu Tyr Tyr Ser Pro
                405                 410                 415

Leu Ser Ser Arg Ser Leu Val Glu Asp Ile Tyr Asn Thr Gln Leu Ser
                420                 425             430

Ala Lys Ala Val Ser Lys Asn Gly Val Val Phe Phe Gly Leu Val Asn
            435                 440                 445

Asn Ser Val Leu Gly Cys Leu Asn Glu Tyr Gln Pro Ile Gln Arg Gln
450                 455                 460

Asn Ile Val Asn Lys Thr Phe Val Thr Ile Leu Lys Tyr Asp Gly Val
465                 470                 475                 480

Pro Ser Thr Leu Asn Met Ile Ser Asn Lys Ile Gly Lys Gly Gly Arg
                485                 490                 495

Leu Leu Gln Pro Tyr Pro Asp Trp Ser Trp Ala Glu Asn Lys Asp Cys
                500                 505                 510

Ser Gly Ile Val Ser Ala Phe Lys Ile Ala Ile Asp Lys Phe Asp Arg
            515                 520                 525

Leu Trp Val Leu Asp Ser Gly Leu Ile Asn Arg Thr Glu Pro Ile Cys
        530                 535                 540

Ala Pro Lys Leu His Val Phe Asp Leu Lys Asn Thr Lys His Leu Lys
545                 550                 555                 560

Gln Ile Glu Ile Pro His Asp Ile Ala Val Asn Ala Thr Thr Gly Lys
                565                 570                 575

Gly Gly Leu Val Ser Leu Val Val Gln Ala Met Asp Pro Met Asn Thr
            580                 585                 590

Leu Val Ser Leu Asn Tyr Asn
        595

<210> SEQ ID NO 79
<211> LENGTH: 576
<212> TYPE: PRT
<213> ORGANISM: Apis cerana

<400> SEQUENCE: 79

Met Thr Ser Trp Leu Leu Val Val Cys Leu Gly Ile Ala Cys Gln
1               5                   10                  15

Gly Ile Thr Gly Ala Thr Val Arg Glu Asn Ser Ser Arg Asn Leu Ala
            20                  25                  30

Asn Ser Met Asn Val Ile His Glu Trp Lys Tyr Leu Asp Tyr Asp Phe
        35                  40                  45

Gly Ser Asp Glu Lys Arg Gln Ala Ala Ile Gln Ser Gly Glu Tyr Asp
    50                  55                  60

His Thr Lys Asn Tyr Pro Phe Asp Val Asp Arg Trp His Asp Met Thr
65                  70                  75                  80

Phe Val Thr Val Leu Arg Tyr Lys Gly Val Pro Ser Ser Leu Asn Val
                85                  90                  95

Ile Ser Lys Lys Ile Gly Asn Gly Gly Pro Leu Leu Gln Pro Tyr Pro
            100                 105                 110

Asp Trp Ser Trp Ala Asn Tyr Lys Asp Cys Ser Gly Ile Val Ser Ala
        115                 120                 125

Tyr Lys Ile Ala Ile Asp Lys Phe Asp Arg Leu Trp Val Leu Asp Ser
    130                 135                 140

Gly Ile Ile Asn Asn Thr Gln Pro Met Cys Ser Pro Lys Leu His Val
145                 150                 155                 160
```

```
Phe Asp Leu Asn Thr Ser Gln Gln Ile Lys Gln Val Met Met Pro His
                165                 170                 175
Asp Ile Ala Ile Asn Ala Thr Thr Gly Lys Gly Gly Leu Glu Asn Leu
                180                 185                 190
Val Val Gln Ala Met Asp Pro Met Asn Thr Leu Val Tyr Met Ala Asp
                195                 200                 205
Asn Lys Gly Asp Ala Leu Ile Val Tyr Gln Asn Ser Asp Ser Phe
    210                 215                 220
His Arg Leu Thr Ser Asn Thr Phe Asp Tyr Asp Pro Lys Tyr Ile Lys
225                 230                 235                 240
Met Met Ala Ala Gly Glu Ser Phe Thr Leu Gln Asp Gly Ile Phe Gly
                245                 250                 255
Met Ala Leu Ser Pro Met Thr Asn Asn Leu Tyr Tyr Ser Pro Leu Ala
                260                 265                 270
Ser Arg Ser Leu Tyr Tyr Ile Asn Thr Lys Pro Phe Met Lys Ser Gln
                275                 280                 285
Tyr Gly Thr Asn Asn Val Gln His Glu Gly Val Gln Asp Ile Phe Asn
                290                 295                 300
Thr Gln Ser Ile Ala Lys Ile Met Ser Lys Asn Gly Val Leu Phe Phe
305                 310                 315                 320
Gly Leu Met Asn Asn Ser Ala Ile Gly Cys Trp Asn Glu His Gln Pro
                325                 330                 335
Leu Gln Arg Gln Asn Met Asp Met Val Ala Gln Asn Glu Glu Thr Leu
                340                 345                 350
Gln Thr Val Val Ala Met Lys Met Met His Leu Pro Gln Ser Asn Arg
                355                 360                 365
Met Asn Arg Met His Arg Met Asn Ser Met Asn Arg Met Asp Arg Met
370                 375                 380
Asp Arg Met Asp Arg Met Asp Arg Met Asp Arg Met Asp Arg Met Asp
385                 390                 395                 400
Arg Met Asp Arg Met Asp Arg Met Asp Arg Met Asp Arg Met Asp Arg
                405                 410                 415
Met Asp Arg Met Asp Ile Met Asp Arg Thr Asn Lys Met Asp Arg Met
                420                 425                 430
Asp Arg Met Asp Ile Met Asp Lys Thr Asn Lys Met Asp Arg Met Asp
                435                 440                 445
Ser Met Ile Arg Ile Asp Lys Met Asp Arg Met Asp Arg Met His Arg
    450                 455                 460
Ile Asp Ile Met Asn Arg Met Asp Arg Met Asp Arg Met Asp Thr Arg
465                 470                 475                 480
Ile Asp Thr Arg Met Asp Arg Met Asp Arg Met Asp Lys Met Asp Lys
                485                 490                 495
Ile Asn Lys Met His Arg Met Gly Arg Met Asp Arg Met Asp Arg Met
                500                 505                 510
Asn Arg Met Asn Arg Gln Met Asn Glu Tyr Met Met Ala Leu Ser Met
                515                 520                 525
Lys Leu Gln Lys Phe Ile Asn Asn Asp Tyr Asn Phe Asn Glu Val Asn
    530                 535                 540
Phe Arg Ile Leu Ala Ala Asn Val Asn Asp Leu Ile Met Asn Thr Arg
545                 550                 555                 560
Cys Ala Asn Ser Asn Asn Gln Asn Asp Asn Gln Asn Lys His Asn Asn
                565                 570                 575
```

<210> SEQ ID NO 80
<211> LENGTH: 1173
<212> TYPE: PRT
<213> ORGANISM: Apis cerana

<400> SEQUENCE: 80

```
Met Lys Ser Gln Phe Gly Asp Asn Asn Val Gln Tyr Glu Gly Ser
1               5                  10                  15

Gln Asp Thr Leu Asn Thr Gln Ser Leu Ala Lys Ala Val Ser Lys Asp
            20                  25                  30

Gly Val Leu Phe Val Gly Leu Val Gly Asn Ser Ala Leu Gly Cys Leu
        35                  40                  45

Asn Glu His Gln Pro Leu Gln Arg Glu Asn Leu Glu Leu Val Ala Gln
    50                  55                  60

Asn Glu Lys Thr Leu Gln Met Ile Ala Gly Met Lys Ile Lys Glu Glu
65                  70                  75                  80

Leu Pro His Phe Val Gly Ser Asn Lys Pro Val Lys Asp Glu Tyr Met
                85                  90                  95

Leu Val Leu Asn Lys Thr Phe Val Thr Val Leu Arg Tyr Asp Gly Val
            100                 105                 110

Pro Ser Ser Leu Asn Val Ile Ser Asp Lys Thr Gly Asn Gly Gly Arg
        115                 120                 125

Leu Leu Gln Pro Tyr Pro Asp Trp Ser Trp Thr Lys Tyr Lys Asp Cys
    130                 135                 140

Ser Gly Ile Val Asn Ala Tyr Asn Ile Ala Val Asp Lys Tyr Asp Arg
145                 150                 155                 160

Leu Trp Val Leu Asp Ser Gly Leu Ile Asn Asn Ile Gln Pro Met Cys
                165                 170                 175

Ser Pro Lys Leu Leu Val Phe Asp Leu Asn Ser Ser Gln Leu Leu Lys
            180                 185                 190

Gln Val Asp Ile Pro His Asp Ile Ala Val Asn Thr Thr Thr Glu Asn
        195                 200                 205

Gly Arg Leu Ala Ser Leu Val Val Gln Ala Met Asn Pro Met Asn Thr
    210                 215                 220

Leu Ser Leu Thr Asn Asn Leu Tyr Tyr Ser Pro Leu Ala Ser Arg Asp
225                 230                 235                 240

Leu Tyr Tyr Val Asn Thr Lys Pro Phe Met Lys Ser Glu Tyr Gly Glu
                245                 250                 255

Asn Asn Val Gln Tyr Lys Gly Val Gln Asn Ile Phe Asn Thr Gln Ser
            260                 265                 270

Thr Ala Lys Ala Val Ser Lys Asn Gly Val Leu Phe Gly Leu Val
        275                 280                 285

Asn Asn Thr Ala Val Gly Cys Trp Asn Glu His Gln Thr Leu Gln Arg
    290                 295                 300

Glu Asn Thr Asp Met Val Ala Gln Asn Glu Glu Thr Leu Gln Met Ile
305                 310                 315                 320

Val Gly Met Lys Ile Lys Glu Leu Leu Pro His Ile Val Ile Ile Asp
                325                 330                 335

Ile Asn Asn Ile Ile Asn Asn Glu Tyr Met Leu Val Leu Ser Asn Arg
            340                 345                 350

Met Gln Lys Ile Leu Asn Asn Asp Leu Asn Phe Asn Asp Ile Asn Phe
        355                 360                 365

Arg Ile Leu Ile Gly Glu Lys Ile Phe Phe Arg Lys Met Ile Arg Trp
    370                 375                 380
```

```
Leu Leu Leu Met Tyr Leu Gly Ile Ala Cys Gln Gly Val Thr Asp Ile
385                 390                 395                 400

His Ser Lys Asn Leu Thr Asn Ser Leu Lys Val Ile Tyr Glu Trp Lys
                405                 410                 415

Tyr Ile Asp Tyr Asp Phe Gly Ser Asp Glu Lys Arg Gln Ala Ala Ile
            420                 425                 430

Gln Ser Gly Asp Tyr Asn Tyr Thr Met Asn Tyr Leu Phe Asp Thr Asp
        435                 440                 445

Gln Trp Gly Asp Lys Thr Phe Val Ile Ile Met Lys Phe Asn Gly Val
450                 455                 460

Pro Ser Ser Leu Asn Val Ile Thr Asn Lys Thr Gly Asn Gly Gly Pro
465                 470                 475                 480

Leu Leu Ala Pro Tyr Pro Asp Trp Thr Trp Ala Lys Asn Glu Asn Cys
                485                 490                 495

Ser Gly Ile Met Ser Val Tyr Lys Ile Glu Ile Asp Ile Cys Asp Arg
            500                 505                 510

Leu Trp Val Leu Asp Ser Gly Leu Ile Asn Asn Val Gln Ser Val Cys
        515                 520                 525

Pro Pro Gln Leu Leu Val Phe Asp Leu Asn Thr Ser Gln Leu Leu Lys
530                 535                 540

Gln Val Lys Ile Pro His Asp Ile Ala Val Asn Thr Thr Thr Gly Asn
545                 550                 555                 560

Gly Ala Leu Val Thr Leu Ser Val Gln Pro Leu Ser Cys Glu Val Asn
                565                 570                 575

Gly Ser Thr Leu Val Tyr Ile Gly Asp Asn Glu Gly Phe Ala Leu Ile
            580                 585                 590

Ile Tyr Asn Asn Ser Asp Asn Ser Phe Gln Arg Leu Thr Ser Ser Thr
        595                 600                 605

Phe Ala Ser Asp Pro Arg Tyr Thr Thr Phe Thr Ile Asn Gly Glu Ser
610                 615                 620

Phe Thr Leu Gln Ser Gly Ile Phe Gly Met Ala Leu Ser Pro Val Thr
625                 630                 635                 640

Gln Asn Leu Tyr Tyr Ser Ala Leu Ser Ser His Asn Leu Asn Tyr Val
                645                 650                 655

Asn Thr Glu Gln Phe Leu Lys Ser Gln Tyr Gln Ala Asn Asn Val His
            660                 665                 670

Tyr Gln Gly Lys Glu Asn Ile Leu Trp Thr Gln Ala Ser Ala Lys Gly
        675                 680                 685

Ile Ser Asp Asn Gly Val Leu Phe Phe Gly Leu Val Gly Asp Thr Ser
690                 695                 700

Leu Ala Cys Trp Asn Glu Asn Arg Leu Leu Asp Arg Lys Asn Ile Glu
705                 710                 715                 720

Val Val Ala Lys Asn Lys Glu Thr Leu Gln Ala Ile Thr Gly Leu Lys
                725                 730                 735

Val Lys Arg Lys Ile Leu Leu Phe Val Val His Gly Phe Pro Val Glu
            740                 745                 750

Tyr Glu Tyr Val Leu Ala Ala Asn Ala Leu Lys Val Val Tyr Gln Trp
        755                 760                 765

Lys Tyr Phe Asp Tyr Asn Phe Gly Ser Asn Glu Arg Arg Gln Ala Ala
770                 775                 780

Ile Gln Ser Gly Lys Tyr Asn Tyr Lys Asn Asn Phe Pro Ile Asp Val
785                 790                 795                 800

Asp Arg Trp His Gly Lys Val Tyr Lys Val Leu Ile Ile Ile Glu Tyr
```

805                 810                 815
Leu Cys Arg Ile Asn Ser Thr Asn Gln Asn Lys Thr Phe Val Thr Ile
            820                 825                 830
Leu Arg Asn Asn Gly Val Pro Ser Ser Leu Asn Val Ile Ser Asn Lys
        835                 840                 845
Ile Gly Asn Gly Gly Pro Leu Leu Glu Pro Tyr Pro Asn Trp Ser Trp
    850                 855                 860
Ala Glu Asn Gln Asn Cys Ser Gly Ile Thr Ser Val Tyr Arg Val Ala
865                 870                 875                 880
Ile Asp Val Trp Asp Arg Leu Trp Val Leu Asp Asn Gly Ile Ser Gly
                885                 890                 895
Gln Thr Ser Val Cys Ser Ser Gln Ile Val Val Phe Asp Leu Lys Thr
            900                 905                 910
Ser Lys Leu Leu Lys Gln Val Lys Ile Pro His Asn Ile Ala Val Asn
        915                 920                 925
Ser Thr Thr Gly Asn Arg Asn Val Val Thr Pro Ile Val Gln Ser Phe
    930                 935                 940
Asp Tyr Asn Asn Thr Leu Val Tyr Ile Ala Asp Val Glu Gly Tyr Ala
945                 950                 955                 960
Leu Ile Ile Tyr Asn Asn Ala Asp Asp Ser Phe Gln Arg Leu Thr Ser
                965                 970                 975
Ser Thr Phe Val Tyr Asp Pro Arg Tyr Thr Asn Tyr Thr Ile Asn Glu
            980                 985                 990
Glu Ser Phe Thr Leu Gln Asp Gly Ile Leu Gly Met Ala Leu Ser Arg
        995                 1000                1005
Lys Thr Gln Asn Leu Tyr Tyr Ser Ala Met Ser Ser His Asn Leu
    1010                1015                1020
Asn Tyr Val Asn Thr Lys Gln Phe Thr Gln Gly Lys Tyr Gln Ala
    1025                1030                1035
Asn Asn Ile Gln Tyr Gln Gly Ala Ser Asp Ile Leu Trp Thr Gln
    1040                1045                1050
Ala Thr Ala Lys Ala Ile Ser Lys Thr Gly Ala Leu Phe Phe Gly
    1055                1060                1065
Leu Val Thr Asp Thr Ala Leu Gly Cys Trp Asn Glu Asn Arg Pro
    1070                1075                1080
Leu Lys Arg Gly Asn Ile Glu Ile Val Ala Lys Asn Asn Asp Thr
    1085                1090                1095
Leu Gln Phe Ile Ser Gly Leu Lys Ile Ser Lys Glu Ile Ser Ser
    1100                1105                1110
His Ile Phe Gly Tyr Gln Asn Asn Glu Tyr Ile Trp Ala Leu Ser
    1115                1120                1125
Asn Lys Tyr Gln Lys Ile Ala Asn Gly Asp Leu Asn Phe Asn Glu
    1130                1135                1140
Val Asn Phe Arg Ile Leu Thr Ala Pro Val Asn Gln Leu Ile Ser
    1145                1150                1155
His Thr Arg Cys Glu Asn Pro Asn Thr Asn Phe Phe Ser Ile His
    1160                1165                1170

<210> SEQ ID NO 81
<211> LENGTH: 435
<212> TYPE: PRT
<213> ORGANISM: Apis cerana

<400> SEQUENCE: 81

-continued

```
Met Thr Asn Trp Leu Leu Ile Val Cys Leu Ser Ile Ala Cys Gln
1               5                   10                  15

Asp Val Thr Ser Ala Ile His Arg Arg Lys Ser Ser Lys Asn Leu Glu
                20                  25                  30

His Ser Met Asn Val Ile His Glu Trp Lys Tyr Leu Asp Tyr Asp Phe
            35                  40                  45

Asp Ser Asn Glu Lys Lys Gln Ala Ala Ile Gln Phe Gly Glu Tyr Asp
        50                  55                  60

Tyr Thr Lys Asn Tyr Pro Phe Asp Val Asp Gln Trp His Asp Lys Thr
65                  70                  75                  80

Phe Val Ala Val Ile Arg Tyr Asp Gly Val Pro Ser Ser Leu Asn Val
                85                  90                  95

Ile Ser Asp Lys Thr Gly Asn Gly Arg Leu Leu Gln Pro Tyr Pro
                100                 105                 110

Asp Trp Ser Trp Ala Asn Tyr Lys Asp Cys Ser Gly Ile Val Ser Val
            115                 120                 125

Tyr Lys Ile Ala Ile Asp Lys Phe Asp Arg Leu Trp Val Leu Asp Ser
        130                 135                 140

Gly Leu Ile Asn Asn Ile Gln Leu Met Cys Ser Pro Lys Leu Leu Ala
145                 150                 155                 160

Phe Asp Leu Thr Thr Ser Lys Leu Leu Lys Gln Val Glu Ile Pro Tyr
                165                 170                 175

Asp Ile Ala Val Asn Ala Ser Thr Arg Met Gly Gly Leu Val Ser Leu
                180                 185                 190

Val Val Gln Ala Met Asp Pro Met Asn Thr Met Val Tyr Ile Ala Asp
            195                 200                 205

Asp Arg Gly Asp Ala Leu Ile Val Tyr Gln Asn Ser Asp Asp Ser Phe
        210                 215                 220

His Arg Leu Asn Ser Asn Thr Phe Asp Asn Asp Pro Arg Tyr Ser Glu
225                 230                 235                 240

Leu Thr Val Ala Gly Glu Ser Phe Thr Val His Asp Gly Ile Phe Gly
                245                 250                 255

Met Ala Leu Ser Pro Val Thr Asn Asn Leu Tyr Tyr Ser Pro Leu Thr
            260                 265                 270

Ser His Ser Leu Tyr Tyr Val Asn Thr Glu Pro Phe Met Lys Ser Gln
        275                 280                 285

Tyr Gly Glu Asn Asn Ile Gln Tyr Glu Gly Ile Gln Asp Ile Phe Asn
        290                 295                 300

Thr Gln Ser Ser Ala Lys Val Met Ser Lys Asn Gly Val Leu Phe Phe
305                 310                 315                 320

Gly Leu Val Asn Ser Ala Ile Gly Cys Trp Asn Glu His Gln Pro
                325                 330                 335

Leu Gln Lys Gln Asn Met Asp Met Val Ala Gln Asn Glu Glu Thr Leu
            340                 345                 350

Gln Ile Ile Thr Ser Val Lys Ile Ile Gln Asn Leu Ser Tyr Ser Gly
        355                 360                 365

Arg Met Asn Arg Ile His Lys Asn Glu Tyr Met Leu Ala Leu Ser Asn
        370                 375                 380

Arg Met Gln Lys Ile Val Asn Asn Asp Phe Asn Phe Asn Asp Ile Asn
385                 390                 395                 400

Phe Arg Ile Leu Gly Ala Asn Val Lys Asn Leu Ile Lys Asn Thr Arg
                405                 410                 415

Cys Ala Asn Ser Lys Asn Gln Asn Asn Gln Lys Lys His Lys Asn
```

```
                        420             425             430

Gln Ala His
        435

<210> SEQ ID NO 82
<211> LENGTH: 375
<212> TYPE: PRT
<213> ORGANISM: Apis cerana

<400> SEQUENCE: 82

Met Tyr Ile Lys Gly His Phe Ala Pro Ala Phe Thr Leu Thr Ala Ile
1               5                   10                  15

Leu Ala Val Val Leu Glu Leu Ile Ser Cys Gly Asn Ala Thr Leu Pro
            20                  25                  30

Glu Thr Ile Lys Trp Thr Gly Gly Asn Phe Glu Trp Pro Ser Ser Thr
        35                  40                  45

Thr Lys Asn Met Tyr Lys Ser Asn Gly Lys Tyr Ile Pro Lys Asn Val
    50                  55                  60

Ile Ala Thr Arg Val Ala Met His Asn Asn Glu Ala Ile Val Ala Leu
65                  70                  75                  80

Pro Arg Phe Lys Ala Gly Ile Pro Ala Thr Leu Ala Lys Leu Ser Lys
                85                  90                  95

Glu Ala Gln Asn Cys Glu Ala Thr Leu Ile Pro Tyr Pro Cys Trp Ser
            100                 105                 110

Leu Gln Glu Glu Gly Thr Cys Thr Ala Leu Gln Asn Val Val Asp Leu
        115                 120                 125

Tyr Leu Asp Pro Gln Asn Ile Leu Trp Ile Leu Asp Thr Gly Val Val
    130                 135                 140

Asp Thr Leu Asp Glu Pro Val Arg Lys Cys Pro Ala Lys Val Leu Ala
145                 150                 155                 160

Ile Asp Val Thr Ser Glu Lys Leu Ile Lys Thr Val Glu Leu Thr Gly
                165                 170                 175

Leu Thr Ser Pro Thr Ser Arg Leu Gln Tyr Val Val Ser Asp Tyr Thr
            180                 185                 190

Gln Asp Gly Arg Val Phe Ile Tyr Val Ser Asp Ala Ala Ser Arg Ala
        195                 200                 205

Ile Leu Val Tyr Asp Val Thr Ser Gly Arg Gly Tyr Arg Val Val Leu
    210                 215                 220

Pro Gln Ala Val Ser Met Gly Cys Thr Arg Arg Asp Val Leu Tyr Leu
225                 230                 235                 240

Ala Leu Leu Arg Arg Ser Asp Gly Ser Thr Cys Leu Ile Phe Thr Tyr
                245                 250                 255

Leu Ser Ser Ser Arg Met Phe Ser Ile Arg Thr Glu His Leu Arg Asn
            260                 265                 270

Gly Ser Thr Arg Gly Arg Ile His Asp Leu Gly Met Lys Pro Arg Lys
        275                 280                 285

Met Val Val Leu Gly Thr Asp Asn Gly Ser Ala Leu Phe Phe Arg Tyr
    290                 295                 300

Glu Gly Glu Ala Asp Val Tyr Arg Trp Asp Ala Ala Ser Asn Pro Phe
305                 310                 315                 320

Asp Pro Arg Cys Phe Lys Lys Val Tyr Thr Ser Ala Glu Cys Asn Leu
                325                 330                 335

Val Thr His Ile Val Ala Asp Tyr Ala Arg Gly Ser Met Arg Val Leu
            340                 345                 350
```

```
Glu Ser Asn Phe Pro Asp Tyr Met Gln Gly Thr Val Gly Cys Gly Ala
            355                 360                 365

Thr Gln Val Leu Asn Val Met
    370                 375

<210> SEQ ID NO 83
<211> LENGTH: 433
<212> TYPE: PRT
<213> ORGANISM: Apis cerana

<400> SEQUENCE: 83

Met Thr Arg Trp Leu Phe Met Val Val Cys Leu Gly Ile Val Cys Gln
1               5                   10                  15

Gly Thr Thr Ser Ser Ile Leu Arg Gly Glu Ser Leu Asn Lys Ser Leu
            20                  25                  30

Ser Val Leu His Glu Trp Lys Phe Phe Asp Tyr Asp Phe Asp Ser Asp
        35                  40                  45

Glu Arg Arg Gln Asp Ala Ile Leu Ser Gly Tyr Asp Tyr Arg Lys
    50                  55                  60

Asn Tyr Pro Ser Asp Val Asp Gln Trp His Gly Lys Ile Phe Val Thr
65                  70                  75                  80

Met Leu Arg Tyr Asn Gly Val Pro Ser Ser Leu Asn Val Ile Ser Lys
                85                  90                  95

Lys Ile Gly Asp Gly Gly Pro Leu Leu Gln Pro Tyr Pro Asp Trp Ser
            100                 105                 110

Phe Ala Lys Tyr Asp Asp Cys Ser Gly Ile Val Ser Ala Thr Lys Leu
        115                 120                 125

Ala Ile Asp Lys Cys Asp Arg Leu Trp Val Leu Asp Ser Gly Leu Val
    130                 135                 140

Asn Asn Thr Gln Pro Met Cys Ser Pro Lys Leu Leu Thr Phe Asp Leu
145                 150                 155                 160

Thr Thr Ser Gln Leu Leu Lys Gln Val Glu Ile Pro His Asp Val Ala
                165                 170                 175

Val Asn Ala Thr Thr Gly Lys Gly Arg Leu Ser Ser Leu Ala Val Gln
            180                 185                 190

Pro Leu Asp Cys Asn Ile Asn Gly Asp Thr Met Val Tyr Ile Ala Asp
        195                 200                 205

Glu Lys Gly Glu Gly Leu Ile Val Tyr His Asp Ser Asp Tyr Ser Phe
    210                 215                 220

His Arg Leu Thr Ser Lys Thr Phe Asp Tyr Asp Pro Lys Phe Thr Lys
225                 230                 235                 240

Met Thr Ile Asn Gly Glu Ser Phe Thr Thr Gln Asn Gly Ile Ser Gly
                245                 250                 255

Met Ala Leu Ser Pro Met Thr Asn Asn Leu Tyr Tyr Ser Pro Val Ala
            260                 265                 270

Ser Thr Ser Leu Tyr Tyr Val Asn Thr Glu Gln Phe Arg Thr Ser Asn
        275                 280                 285

Tyr Glu Gln Asn Ala Val His Tyr Glu Gly Val Gln Asn Ile Leu Asp
    290                 295                 300

Thr Gln Ser Ser Ala Lys Val Val Ser Lys Ser Gly Val Leu Phe Phe
305                 310                 315                 320

Gly Leu Val Gly Asp Ser Ala Leu Gly Cys Trp Asn Glu His Arg Ser
                325                 330                 335

Leu Glu Arg His Asn Ile Arg Thr Val Ala Gln Ser Asp Glu Thr Leu
            340                 345                 350
```

-continued

```
Gln Met Ile Val Gly Met Lys Ile Lys Glu Ala Leu Pro His Val Pro
        355                 360                 365

Ile Phe Asp Arg Tyr Ile Asn Arg Glu Tyr Ile Leu Val Leu Ser Asn
        370                 375                 380

Arg Met Gln Lys Met Ala Asn Asn Asp Tyr Asn Phe Asn Asp Val Asn
385                 390                 395                 400

Phe Arg Ile Met Asp Ala Asn Val Asn Asp Leu Ile Leu Asn Thr Arg
                405                 410                 415

Cys Glu Asn Pro Asn Asn Asp Asn Thr Pro Phe Lys Ile Ser Ile His
                420                 425                 430

Leu

<210> SEQ ID NO 84
<211> LENGTH: 424
<212> TYPE: PRT
<213> ORGANISM: Apis cerana

<400> SEQUENCE: 84

Met Ser Phe Asn Ile Trp Trp Leu Ile Leu Tyr Phe Gly Ile Val Cys
1               5                   10                  15

Gln Thr Ile Thr Lys Ala His Tyr Tyr Ser Arg His Phe Lys Ala Asn
            20                  25                  30

Ala Leu Lys Val Val Tyr Gln Trp Lys Tyr Phe Asp Tyr Asn Phe Gly
        35                  40                  45

Ser Asn Glu Arg Arg Gln Ala Ala Ile Gln Ser Gly Lys Tyr Asn Tyr
    50                  55                  60

Lys Asn Asn Phe Pro Ile Asp Val Asp Arg Trp His Asp Lys Thr Phe
65                  70                  75                  80

Val Thr Ile Leu Arg Asn Asn Gly Val Pro Ser Ser Leu Asn Val Ile
                85                  90                  95

Ser Asn Lys Ile Gly Asn Gly Gly Pro Leu Leu Glu Pro Tyr Pro Asn
            100                 105                 110

Trp Ser Trp Ala Glu Asn Gln Asn Cys Ser Gly Ile Thr Ser Val Tyr
        115                 120                 125

Arg Val Ala Ile Asp Val Trp Asp Arg Leu Trp Val Leu Asp Asn Gly
    130                 135                 140

Ile Ser Gly Gln Thr Ser Val Cys Ser Ser Gln Ile Val Val Phe Asp
145                 150                 155                 160

Leu Lys Thr Ser Lys Leu Leu Lys Gln Val Lys Ile Pro His Asn Ile
                165                 170                 175

Ala Val Asn Ser Thr Gly Asn Arg Asn Val Val Thr Pro Ile Val
            180                 185                 190

Gln Ser Phe Asp Tyr Asn Asn Thr Leu Val Tyr Ile Ala Asp Val Glu
        195                 200                 205

Gly Tyr Ala Leu Ile Ile Tyr Asn Asn Ala Asp Asp Ser Phe Gln Arg
    210                 215                 220

Leu Thr Ser Ser Thr Phe Val Tyr Asp Pro Arg Tyr Thr Asn Tyr Thr
225                 230                 235                 240

Ile Asn Glu Glu Ser Phe Thr Leu Gln Asp Gly Ile Leu Gly Met Ala
                245                 250                 255

Leu Ser Arg Lys Thr Gln Asn Leu Tyr Tyr Ser Ala Met Ser Ser His
            260                 265                 270

Asn Leu Asn Tyr Val Asn Thr Lys Gln Phe Thr Gln Gly Lys Tyr Gln
        275                 280                 285
```

```
Ala Asn Asn Ile Gln Tyr Gln Gly Ala Ser Asp Ile Leu Trp Thr Gln
        290                 295                 300

Ala Thr Ala Lys Ala Ile Ser Lys Thr Gly Ala Leu Phe Phe Gly Leu
305                 310                 315                 320

Val Thr Asp Thr Ala Leu Gly Cys Trp Asn Glu Asn Arg Pro Leu Lys
            325                 330                 335

Arg Gly Asn Ile Glu Ile Val Ala Lys Asn Asn Asp Thr Leu Gln Phe
            340                 345                 350

Ile Ser Gly Leu Lys Ile Ser Lys Glu Ile Ser Ser His Ile Phe Gly
        355                 360                 365

Tyr Gln Asn Asn Glu Tyr Ile Trp Ala Leu Ser Asn Lys Tyr Gln Lys
        370                 375                 380

Ile Ala Asn Gly Asp Leu Asn Phe Asn Glu Val Asn Phe Arg Ile Leu
385                 390                 395                 400

Thr Ala Pro Val Asn Gln Leu Ile Ser His Thr Arg Cys Glu Asn Pro
            405                 410                 415

Asn Thr Asn Phe Phe Ser Ile His
            420

<210> SEQ ID NO 85
<211> LENGTH: 411
<212> TYPE: PRT
<213> ORGANISM: Apis cerana

<400> SEQUENCE: 85

Met Trp His Phe Leu Trp Ile Val Phe Leu Val Leu Ala Asn Gly Glu
1               5                   10                  15

Glu Ile Lys Thr Ile Tyr Ser Trp Asn Val Ile Glu Tyr Asn Phe Pro
            20                  25                  30

Asn Asp Asn Ile Arg Asn Thr Leu Ile Ser Asn Gly Asp Tyr Ile Glu
        35                  40                  45

Glu Asn Asn Met Pro Asn Gly Met Gln Ile Trp Asn Asp Lys Val Phe
    50                  55                  60

Ile Thr Ile Pro Arg Trp Lys Asn Gly Val Pro Ser Asn Leu Asn Phe
65                  70                  75                  80

Phe Leu Lys Asn Asp Gly Ser Glu Ser Pro Lys Leu Asn Pro Tyr Pro
                85                  90                  95

Asn Trp Glu Met Asn Asn Ile Asn Lys Val Asp Ser Ile Ile Asn Ile
            100                 105                 110

Ile Arg Val Arg Val Asp Ala Cys Asp Arg Leu Trp Gly Val Asp Thr
        115                 120                 125

Gly Val Asp Asp Ile Leu Gly Asn Asn Thr Val Ile His Gln Pro Arg
    130                 135                 140

Ile Ile Ile Ile Asp Leu Lys Thr Asp Lys Ile Leu Arg Ile Tyr Pro
145                 150                 155                 160

Leu Lys Ser Ser Asp Gln Thr Ser Asp Ser Phe Phe Val Asp Leu Val
                165                 170                 175

Ile Asp Val Asp Pro Asn Asn Cys Asp Asn Thr Tyr Ala Tyr Ile Ser
            180                 185                 190

Asp Leu Gly Gly Tyr Ala Leu Val Val Tyr Ser Trp Ala Lys Asn Asp
        195                 200                 205

Ser Trp Arg Ile Thr His Asn Phe Phe Tyr Asp Pro Arg Tyr Gly
    210                 215                 220

Asn Tyr Asn Ile Asn Gly Phe Asn Phe Gln Trp Lys Asp Gly Leu Phe
```

```
                    225                 230                 235                 240
        Gly Leu Ser Leu Ser Ala Leu Gln Thr Asp Gly Tyr Lys Ile Leu Tyr
                        245                 250                 255
        Phe His Ala Met Ser Ser Ile Ala Glu Phe Ser Val Ser Thr Glu Val
                        260                 265                 270
        Leu Gln Asp His Thr Leu Glu Lys Ser Ser Asp Tyr Tyr Ala Phe His
                        275                 280                 285
        Phe Glu Gly Glu Lys Gly Pro Asn Ser Gln Gly Pro Ser Ser Val Ile
                    290                 295                 300
        Asp Thr Asn Thr Gly Val Asp Tyr Phe Thr Gln Ile Asn Arg Asn Gly
        305                 310                 315                 320
        Ile Ala Cys Trp Asp Thr Thr Glu Leu Asn Pro Asn Thr Phe Ile
                        325                 330                 335
        Leu Val Ala Glu Asp Asn Thr Thr Met Val Phe Cys Asn Asp Leu Ser
                        340                 345                 350
        Ile Asp Arg Ser Ser Asn Thr Met Tyr Val Leu Ser Asp Asn Phe Gln
                        355                 360                 365
        Gln Leu Leu Phe Ser Lys Tyr Asp Val Lys Lys His Asn Phe Phe Ile
                        370                 375                 380
        Thr Val Phe Asp Leu Asp Phe Leu Thr Asn Ala Cys Lys Lys Lys Asp
        385                 390                 395                 400
        Asp Lys Pro Lys Arg Arg Leu Pro His Ile Leu
                        405                 410

<210> SEQ ID NO 86
<211> LENGTH: 202
<212> TYPE: PRT
<213> ORGANISM: Apis cerana

<400> SEQUENCE: 86

Met Thr Ile Glu Gly Glu Ser Phe Thr Gln Asn Gly Ile Ser Gly
        1               5                   10                  15

Met Ala Leu Ser Pro Leu Thr Asn Asn Leu Tyr Tyr Ser Pro Leu Ala
                        20                  25                  30

Ser Arg Asp Leu Tyr Tyr Val Asn Thr Lys Pro Phe Met Lys Ser Glu
                        35                  40                  45

Tyr Gly Glu Asn Asn Val Gln Tyr Lys Gly Val Gln Asn Ile Phe Asn
            50                  55                  60

Thr Gln Ser Thr Ala Lys Ala Val Ser Lys Asn Gly Val Leu Phe Phe
        65                  70                  75                  80

Gly Leu Val Asn Asn Thr Ala Val Gly Cys Trp Asn Glu His Gln Thr
                        85                  90                  95

Leu Gln Arg Glu Asn Thr Asp Met Val Ala Gln Asn Glu Glu Thr Leu
                        100                 105                 110

Gln Met Ile Val Gly Met Lys Ile Lys Glu Leu Leu Pro His Ile Val
                        115                 120                 125

Ile Ile Asp Ile Asn Asn Ile Ile Asn Asn Glu Tyr Met Leu Val Leu
                    130                 135                 140

Ser Asn Arg Met Gln Lys Ile Leu Asn Asn Asp Leu Asn Phe Asn Asp
        145                 150                 155                 160

Ile Asn Phe Arg Ile Leu Ile Gly Gly Val Thr Asp Leu Leu Glu Asn
                        165                 170                 175

Thr Arg Cys Ala Asn Ser Asn Ile Gln Asn Asn Asn Asn Gln Ile Thr
                        180                 185                 190
```

-continued

```
Ile Leu Thr Val Lys Ile Thr Ile Thr Ile
            195                 200

<210> SEQ ID NO 87
<211> LENGTH: 78
<212> TYPE: PRT
<213> ORGANISM: Apis dorsata

<400> SEQUENCE: 87

Val Asn Asn Ser Ala Leu Gly Cys Trp Asn Glu His Gln Ser Leu Gln
1               5                   10                  15

Arg Gln Asn Met Asp Met Val Ala Gln Asn Glu Glu Thr Leu Gln Met
            20                  25                  30

Ile Ile Ser Val Lys Ile Met Gln Asn Leu Pro Tyr Ser Gly Arg Met
            35                  40                  45

Asn Arg Ile His Lys Asn Glu Tyr Ile Leu Ala Leu Ser Asn Arg Met
        50                  55                  60

Gln Lys Ile Val Asn Asn Asp Phe Asn Phe Asn Lys Ile Asn
65                  70                  75

<210> SEQ ID NO 88
<211> LENGTH: 82
<212> TYPE: PRT
<213> ORGANISM: Apis dorsata

<400> SEQUENCE: 88

Met Lys Met Met His Leu Ser Gln Ser Asn Asn Met Asn Arg Met His
1               5                   10                  15

Asn Met Asn Arg Met Asp Lys Met Asn Gly Met Asp Arg Ile Asn Arg
            20                  25                  30

Met Asp Ser Met Asp Arg Met Asp Ser Met Asp Arg Val Asp Arg Met
            35                  40                  45

Asp Ser Met Asp Arg Met Asp Arg Met Asp Arg Ile Asp Arg Met Asp
        50                  55                  60

Arg Met Asn Lys Met Asp Asn Met Asp Arg Met Asp Arg Gln Lys Asn
65                  70                  75                  80

Glu Tyr
```

FOOD COMPOSITIONS CONTAINING ADDED HONEY PROTEINS

PRIORITY APPLICATION

This application claims the benefit of U.S. Provisional Application Ser. No. 63/183,505 filed on May 3, 2021, the contents of which are hereby incorporated by reference in their entirety.

SEQUENCE LISTING

The Sequence Listing associated with this application is provided in text format in lieu of a paper copy and is hereby incorporated by reference into the specification. The name of the text file containing the Sequence Listing is AM1-0001US_Sequence_Listing_ST25.txt. The text file is 378 kb, was created on May 2, 2022, and is being submitted electronically concurrent with the filing of the specification.

TECHNICAL FIELD

This present disclosure relates generally to food compositions supplemented with heterologically produced proteins. Specifically, this disclosure describes food compositions to which honey proteins are added.

BACKGROUND

Foods supplemented with added protein are highly desirable foods. Protein may be added to many types of foods such as energy bars and shakes. High-protein foods may be used for weight loss, sports nutrition, and meal replacement. Protein rich foods can aid in recovery from physical activity and create feelings of satiety to aid in weight loss. Protein is a popular ingredient in athletic performance as it does not interfere with fat loss and helps with recovery from physical exercise or exertion (Lemon, 1991). Fats and carbohydrates may be viewed by consumers as less desirable. Many diets emphasize low carbohydrate and higher protein intake. Low carbohydrate Atkins and keto diets are popular and clinically effective for weight loss and even used in clinical therapy (Kossoff, 2008). Paleo diets are popularly associated with diets which are more in line with human's ancestral diets and are popularly considered healthy (Lindeberg S, 2007). The market for foods supplemented with additional protein is increasing especially in consumer-packaged goods foods. (Formanski, 2019). Accordingly, there is broad demand for higher levels of proteins in foods.

The protein added to foods can come from animal or non-animal sources. Animal sources include eggs and milk that provide casein or whey protein. Non-animal sources include soybeans, peas, rice, potatoes, and hemp. The proteins used to supplement foods are generally isolated from natural products and selected due to price and availability. Protein derived from plants are the most popular protein supplements with markets growing rapidly year on year (The plant-based protein market is changing what it takes to succeed, 2020). Despite their ubiquity as supplements, plant protein ingredients may taste astringent and have a chalky or dry mouthfeel. Protein supplements generally have a bland or unsavory taste. Thus, while added plant proteins are tolerated in performance/athletic products, consumers do not accept unpalatable taste and mouthfeel in food products consumed for taste and eating experience.

Honey is a natural, non-plant source of proteins. However, the amount of protein in honey is very low. Typically honey contains about 82% sugars (primarily fructose and glucose), 17% water, 0.3% proteins, with the remainder vitamins and minerals. Honey is a highly valued food product and has been touted as a natural remedy for wounds, respiratory infections, and other ailments. Most honey consumed by humans is produced by honeybees of the genus *Apis*. The specific composition of honey depends on the species of insect and flowers pollen.

Although honey has been used by humans for thousands of years, surprisingly little is known about the proteins in honey. Many of the proteins found in honey are also present in Royal Jelly. The most abundant class of proteins found in honey are the major royal jelly proteins (RJMP) such as RJMP-1, RJMP-2, RJMP-5, and RJMP-7. (Chua, Lee, & Chan, 2015).

Isolation of proteins from honey is laborious and expensive. Currently, the most popular method of protein isolation from honey is dialysis against distilled water and lyophilization of the dialysate. There are also chemical methods used such as sodium tungstate, ammonium sulfate, and acetone precipitation. A more recently developed technique uses extraction with saturated phenol. (Bocian, Buczkowicz, Jaromin, Hus, & Legáth, 2019).

It would be desirable to develop food compositions with added protein that have a neutral or beneficial effect on flavor and mouthfeel. Moreover, it would be also desirable if added protein was a functional food component that provides benefits to consumer health. It would able be desirable to create food compositions with these properties in a cost-effective manner at scale. The following disclosure is made with respect to these and other considerations.

SUMMARY

This disclosure describes food compositions supplemented by addition of honey proteins created through man-made methods. Supplementing food compositions with one or more of the proteins identified in this disclosure increase protein content and also provide additional benefits or advantages. The added proteins may have at least one characteristic that improves a food formulation such as imparting a more desirable texture. The added proteins may contribute functional benefits such as cytostimulation of cells lining the gut.

Presently, it is difficult to manipulate the texture of food. However, regulating the amount of gel in a food composition is one technique to manipulate texture. The extent of gel formation may be controlled by adjusting the ratio of specific honey proteins added to a food composition.

The inventors have identified that food compositions supplemented with added protein will have improved flavor and mouthfeel if the protein is selected based on characteristics of the food composition. Many proteins commonly added to food compositions are isolated from plants. However, adding plant proteins to a food composition can produce a dry or chalky mouthfeel that is frequently associated with protein bars or protein shakes.

Specifically, food compositions with low water content will have no perceivable change in mouthfeel if the added protein is hydrophobic. Food compositions with low water content include hydrophobic food compositions, high-fat food compositions and high-sugar food compositions. The added proteins may be selected based on characteristics of the food composition so that addition of the proteins does not negatively affect the flavor or mouthfeel. The food composition may have smooth and/or uniform mouthfeel. The food composition may be formulated without use of any animal products.

Honey is one source of edible proteins that are not derived from plants. Honey proteins are found in nature in honey which has a low water content and high sugar content. Honey proteins have not previously been used to supplement food compositions because of the difficult and cost associated with isolating the proteins from honey.

However, modern techniques for industrial production of proteins allows for the economical, large-scale creation of any natural or artificial protein. With this technology proteins may be manufactured using microorganisms more easily and economically than isolation from natural sources. Recombinant technology is used presently to create proteins that are found in dairy processing, cheese making, detergents and soaps, toothpaste (novozymes). Honey proteins can be recombinantly produced using known polypeptide expression techniques (e.g., heterologous expression techniques using bacterial cells, insect cells, fungal cells such as yeast, plant cells such as tobacco, soybean, or *Arabidopsis*, or mammalian cells) more efficiently and at lower cost than isolation from a natural source. Proteins that are to be used in food compositions may be manufactured in microorganisms that have Generally Recognized as Safe (GRAS) status with a regulatory agency such as the Food and Drug Administration. Additional details of recombinant protein expression are provided below.

Addition of honey proteins to food compositions can introduce cytostimulatory properties in addition to increasing the protein content. Honey is known to have anti-inflammatory, wound healing, and antibiotic properties. Thus, food compositions supplemented with additional recombinant honey proteins may be functional foods that provide a cytostimulatory benefit in addition to higher protein content.

The food composition contains at least about 1 percent of the honey protein by weight. In an implementation, at least about 20 percent of the total protein in the food composition is the honey protein.

The honey proteins may come from any number of insects such as honeybees in the genus *Apis* including *Apis mellifera* and *Apis cerana*. The sequences of the honey proteins may also be the sequence of similar proteins in other insect genera include those that do not typically produce honey. The honey protein added to the food composition may be one of the royal jelly major proteins (RJMP). The RJMP may be any of RJMP-1, RJMP-2, RJMP-3, RJMP-4, RJMP-5, RJMP-6, RJMP-9, or RJMP-10. The honey protein may be apisimin. The honey protein may have a sequence with 60%, 65%, 70%, 75%, 80%, 85%, 90%, 91%, 92%, 93%, 94%, 95%, 96%, 97%, 98%, 99% or 100% sequence identity with the protein sequence as provided in any of SEQ ID NOs: 1-41 and 50-88.

In implementation, more than one honey protein is added to the food composition. For example, an RJMP and apisimin may both be added to the food composition. In one implementation, RJMP-1 and apisimin are both added to the food composition.

A food composition may be supplemented with two, or more, recombinant honey proteins. For example, a food composition may be supplemented with recombinant RJMP1 and apisimin proteins. In one implementation, two, or more, recombinant honey proteins may be coexpressed in an appropriate expression system such as a vector introduced into a host cell. Expression products containing both proteins are purified and added to the food composition. In one implementation, both recombinant honey proteins are produced and purified separately. Each of the purified recombinant proteins is added individually to the food composition.

If two or more, proteins are added to the food composition, each may be added at a predetermined molar ratio to the other. The predetermined molar ratio may be selected to achieve a specific cytostimulatory property. In an implementation involving two proteins, the molar ratio may be any ratio between about 1:100 to about 100:1. For example, the molar ratio may be about 1:1.

In one aspect, the food composition after addition of one or more common honey proteins may have a cytostimulatory property that the food composition did not possess prior to addition of the honey proteins. Cytostimulation refers to the emission of cytokines from cells which are in contact with the protein at a detectably higher level than in the absence of the protein. The cytostimulatory property may be cellular production of cytokines such as Tumor Necrosis Factor-alpha, IL1-beta, Transforming Growth Factor-beta, (Majtan J, 2010) stimulation of inflammatory response, wound healing, cellular regrowth. Direct antimicrobial effects on some pathogenic microbes also result from RJMP1. (Brudzynski, 2015) (Vezeteu, 2017) This cytostimulatory activity has been proven to be effective with RJMP1 in cell culture. Because other RJMP proteins are highly similar, they are also expected to have cytostimulatory activity. All RJMP proteins are capable of forming gel aggregates which help to create the characteristic texture of honey which has a higher surface tension and greater viscosity than liquid sugar alone.

Also provided are methods for producing the honey proteins using recombinant expression techniques. This method comprises inserting a gene encoding a honey protein into a plasmid, introducing the plasmid into an appropriate recombinant host cell, culturing the host cell for a suitable time and under suitable conditions such that the protein of interest is expressed, and then purifying the protein. The host similar be, for example, a bacterial cell such as *E. coli* or a yeast cell such as *Saccharomyces*. In some methods the plasmid may express the protein directly. In other methods, the gene encoding the protein may be incorporated into a chromosome of the host cell. The strains may be designed to secrete the desired product protein outside the cell or accumulate the protein product inside the cell. The strains are often modified in other ways by genetic manipulation to enhance the productivity of the cells.

Production of protein by cells are then produced in liquid media. Vessels which monitor and control the environment, oxygen, pH, carbon source, nitrogen source, mineral concentrations. Sizes of the vessels start at milliliter volumes for evaluation purposes and extend to 100,000s of liters for full scale production.

The protein may be removed in batches over time, continuously, or all at the end of the fermentation production run. Once removed the protein is harvested and concentrated, usually purified in one or more industrial manufacturing processes collectively called 'downstream processing'. Examples of such steps include centrifugation, tangential flow filtration, presses, chromatography and ultra and micro filtration. The protein product may be prepared as a concentrated solution in a mixture of water and alcohol or dried to a powder using vacuum and or heating.

It is to be understood that one, some, or all of the properties of the various implementations described herein may be combined to form other implementations consistent with the present disclosure. These and other aspects of the present disclosure will become apparent upon reference to the following detailed description and attached drawings. All references disclosed herein are hereby incorporated by reference in their entirety as if each were incorporated individually.

DETAILED DESCRIPTION

This disclosure describes food compositions supplemented with recombinantly produced honey proteins. The food compositions may be functional foods that provide a benefit beyond calories and typical nutritional components of food. It is now possible to synthesize large quantities of proteins using microorganisms such as yeast or bacteria through industrial biotechnology. A recombinant protein is a protein encoded by a gene—recombinant DNA—that has been cloned in a system that supports expression of the gene and translation of messenger RNA. Proteins that cannot be efficiently extracted from natural sources may now be manufactured efficiently and at scale using recombinant techniques.

The protein added to a food product may be selected based on characteristics of the food product and the protein. Without being bound by theory, it is believed that similar hydrophobicity/hydrophilicity between the protein and food product improves mouthfeel. Hydrophobic foods may be supplemented with proteins that mix well with oils. These include lipophilic and amphipathic proteins. Hydrophobic foods include foods with high lipid content or high sugar content. Examples include chocolate, jelly, and baked goods. Hydrophilic food products such as beverages may be mixed with hydrophilic proteins that are water soluble. Examples include water and fruit juice.

A. Definitions

The following terms have the following meanings unless otherwise indicated. Any undefined terms have their art-recognized meanings. Art recognized meanings may be determined by reference to any of the documents described in this disclosure as well as to other publications.

As used herein and in the appended claims, the singular forms "a," "an" and "the" include plural reference unless the context clearly dictates otherwise.

It is understood that aspects and implementations of the disclosure described herein include "comprising," "consisting," and "consisting essentially of" aspects and implementations.

The term "about," "approximately," or "similar to" means within an acceptable error range for the particular value as determined by one of ordinary skill in the art, which can depend in part on how the value is measured or determined, or on the limitations of the measurement system. It should be understood that all ranges and quantities described below are approximations and are not intended to limit the invention. Where ranges and numbers are used these can be approximate to include statistical ranges or measurement errors or variation. In some embodiments, for instance, measurements could be plus or minus 10%.

The use of the alternative (e.g., "or") should be understood to mean either one, both, or any combination thereof of the alternatives.

The terms "in part," "at least in part," "a portion," or similar referents are to be construed as meaning at least a portion or part of the whole including up to the entire noun referenced.

As used herein, the terms "include," "have" and "comprise" are used synonymously, which terms and variants thereof are intended to be construed as non-limiting.

Unless indicated otherwise, percentage (%) of ingredients or components refer to total % by weight.

The term "gel" as used herein means a homogenous solution that is continuous, insoluble, soft elastic, solid-like, without sharp angles that resists deformation when one applies a tractive force to it.

The term "amphipathic" is a descriptive word for a substance or a chemical compound that possesses both hydrophobic and hydrophilic portions in its structure. Amphipathic proteins are comprised of polar and nonpolar sequences of amino acids. For instance, a protein may be made up of hydrophilic portions of polar (charged) amino acids (e.g., Asp-Ser, Tyr-Glu) and hydrophobic portions of nonpolar amino acids (e.g., Gly-Pro, Ile-Pro-Met).

The term "hydrophobicity" as applied to a protein indicates how soluble the protein is in water. Protein hydrophobicity may be measured by any known technique such as probe spectrofluorometry using ANS, CPA, DPH, Prodan, SDS binding, hydrophobic interaction chromatography, contact angle, and hydrophobic partition.

The term "honey protein" refers to any protein naturally found in the honey produced by insects such as, but not limited to, the honeybee $Apis$ $mellifera$ or other $Apis$ species known to produce honey. Honey proteins include major royal jelly proteins, jelllein, and apisimin. Any of the honey proteins described herein that can be used for producing food compositions can have at least 60% (e.g., at least 60%, 70%, 75%, 80%, 85%, 90%, 95%, 97%, 98%, 99%, or 100%) sequence identity to the amino acid sequence of the corresponding wild-type protein or fragment thereof. For example, a honey protein can have at least 70% sequence identity to any of the amino acid sequences set forth in this disclosure.

The terms "cytostimulatory" and "cytostimulation," refer to the stimulation of immune cells to produce cytokines such as interleukins (e.g., interleukin-1) and tumor necrosis factor alpha (TNF-$\alpha$) when exposed to a stimulatory agent.

The term "subject" references to a mammal. The subject may be a human.

B. Food Compositions

A food composition includes any type of solid or liquid material that is either eaten or drunk by any animal, including humans, for nutrition or pleasure. Any type of food composition may be supplemented with recombinant proteins including any of the recombinant proteins provided in this disclosure. For example, the food composition may be any of a protein bar, an energy bar, chocolate, fats, gels, emulsions, dairy or imitation dairy such as cheese, cream cheese, soft cheese, cheese sauce, hard cheese, or yogurt. The food composition may have any structure or composition and may be a solid, a gel, or an emulsion.

The food composition following addition of recombinant protein may be a high-protein food composition. A high-protein food composition typically contains 5-30 g of total protein per serving. The food compositions of this disclosure may include at least about 5, 6, 7, 8, 9, 10, 11, 12, 13, 14, 15, 16, 17, 18, 19, 20, 21, 22, 23, 24, 25, 26, 27, 28, 29, or 30 g of protein per serving. In an implementation, the food compositions include at least about 0.5%, 0.6%, 0.7%, 0.8%, 0.9%, 1%, 2%, 3%, 4%, 5%, 10%, 15%, 20%, or 25% protein based on the total weight of the food composition. For example, beverages including water may be supplemented with honey proteins to the amount of about 0.8-5% by weight. Solid foods such as chocolate or cheese may be supplemented with honey proteins to the amount of about 10-20% by weight.

In an implementation, the food composition is hydrophobic. Examples of hydrophobic food compositions include unbaked dough and baked goods such as bread, cookies, crackers, and cakes. Additional examples of hydrophobic food compositions include nut butters, oils and fats such as cream or whipped cream In an implementation, the food composition is hydrophilic. Examples of hydrophilic food compositions include water-based beverages.

In an implementation, the food composition is a high-fat food composition. A high-fat food composition is a food composition that has a fat content of more than 20 percent fat by weight for solid foods and 10 percent for liquid foods. A high-fat food composition is a food composition that contains at least 21 g, of protein per serving. Examples of high-fat food compositions include butter, lard, and chocolate. (Arambepola, 2009)

In an implementation, the food composition is a high-sugar food composition. A high-sugar food composition is a food composition containing more than 20 percent sugar by weight. A high-sugar food composition is a food composition that contains at least 10 g of sugar per serving. Examples of high-sugar food compositions include honey, jelly, and jam.

The food compositions of the present disclosure may be created by mixing one or more recombinant proteins with other components of the food composition during manufacture. Methods for manufacturing a particular food composition will vary with the specific type of food and are known to those of ordinary skill in the art. Generally, the recombinant proteins will be isolated and purified prior to mixing with other components of the food composition. The recombinant proteins may or may not be dried prior to mixing.

In an implementation, recombinant proteins are mixed with a food composition in liquid or dry powder form. For example, recombinant protein may be mixed with melted chocolate, chocolate syrup, and/or coca butter prior to hardening and shaping of the chocolate into a bar or other form. The food composition may be heated to decrease viscosity and improve mixing of the recombinant proteins. In an implementation, the recombinant proteins are dried and mixed with other components of the food composition.

Also provided herein are methods of making high-protein chocolate by addition of one or more recombinant proteins to a food composition primarily comprising chocolate. The methods include mixing purified recombinant proteins with liquid chocolate. Methods for making chocolate are well known to those of ordinary skill in the art. See e.g. Stephen Beckett, *The Science of Chocolate*, Royal Society of Chemistry (2019).

Gelation

Gelation is a general way to convert a fluid to a solid and has been used since antiquity to produce a variety of foods with distinctive textures. Gelation of proteins is one of the principal means to give desirable texture to food products. Most food proteins can be classified as globular proteins, but casein and gelatin are also important food proteins. A common feature to all protein gelation reactions is that they require some initial structural transition that can be considered transformation from an unreactive to a reactive structure that increases the probability of intermolecular interactions. Gel networks trap large quantities of water into a solid mass that behaves elastically on a timescale such that it is perceived as a solid. The solid, elastic structure of gels provides them with textures that are desirable to consumers. Gels may be identified as coherent, two-component systems formed by a solid substance, finely dispersed or dissolved in a liquid phase (referred to as solvent) that exhibit solid-type of behavior as mechanical forces are exerted on them and are continuous in both the dispersed and the solvent phase.

Gel formation is a principal dimension to food texture. (Bhattacharya, 2012) Gels thicken and stabilize a food. The effect of gels range from creating syrupy viscosity (e.g. in a thick soup) to a tough something that requires tearing (e.g. a fruit roll or gummy bear). Gels can create a matrix that will set to solidity when exposed to extremes of pH or when baked (e.g., doughs for breads or egg white and sugar mixtures which can bake into a solid meringue).

Typical measurements of gel textures are compression, stress relaxation, puncture force, texture profile analysis (TPA) using a texture analyzer; water activity using a water activity device; creep, oscillation using a rheometer. Texture Analyzers record the forces required to compress or stretch a substance and the force response of a material when it is deformed. Water activity is a measurement of the partial pressure of water in a substance relative to pure liquid water. A rheometer is a laboratory device used to measure the way in which a liquid, suspension or slurry flows in response to applied forces.

There are a variety of methods to induce gelation such as adding salt or other types of adjuvant, acidification, enzymatic reactions, or applying high pressure, but the most common method is heating or cooling. It is rare that only one type of protein is present in systems of interest and usually different proteins interact with each other in the system in one way or another. From a practical point of view the challenge is to find combinations of proteins that give desirable properties to the gels in terms of texture, nutrition, cost, etc. Most gel forming food proteins such as whey proteins, plant globulins and egg white proteins are globular proteins with a dense well-defined secondary and ternary structure. Aggregation and gelation of globular proteins is initiated by heating that renders the peptide chain more mobile allowing amino acids to interact with and bind to other proteins. (Erik van der Linden, 2009) (Nicolai, 2019)

C. Honey Bees

The sequences of honey proteins described in this disclosure may come from any species of bee. While about 20,000 species of bees exist, only eight species of honey bee are recognized, with a total of 43 subspecies. Recognized species of honey bees include *Apis andreniformis* (the black dwarf honey bee); *Apis cerana* (the eastern honey bee); *Apis dorsata* (the giant honey bee); *Apis florea* (the red dwarf honey bee); *Apis koschevnikovi* (Koschevnikov's honey bee); *Apis laboriosa* (the Himalayan giant honey bee); *Apis mellifera* (the western honey bee); and *Apis nigrocincta* (the Philippine honey bee). Only two species have been truly domesticated: *Apis mellifera* and *Apis cerana*.

D. Royal Jelly Major Proteins

Many honey proteins are also found in royal jelly at higher concentrations. Royal jelly is a nutrient-rich mixture bee secretion fed to larvae. It is secreted from the hypopharyngeal and mandibular glands of honeybees (*Apis mellifera*) and some other insect species including *Apis florea*, and *Apis dorsata*. Royal jelly is often taken as a supplement for various nutritional benefits. Royal jelly contains vitamins, sugars, fats, proteins, and enzymes. Royal jelly is 67% water, 12-15% protein, 11% simple sugars (monosaccharides), 6% fatty acids and free amino acids, together with several bioactive substances. Royal jelly may have up to about 50% protein content.

Royal jelly if consumed by humans is usually eaten only in small quantities of about 1 g per day or less. Consuming larger amounts may cause digestive distress, bloody stool and diarrhea, stomach pain, swelling of the throat and occasionally death. Thus, it is desirable to regulate the quantity of active royal jelly proteins consumed. One way of doing so without reducing protein content is to modify royal jelly proteins to decrease or eliminate their biological activity.

Major royal jelly proteins (RJMPs) are a family of proteins secreted by the honeybee. The family consists of nine proteins, of which RJMP1 (also called royalactin), RJMP2, RJMP3, RJMP4, and RJMPS are present in the royal jelly secreted by worker bees. The existence of a tenth RJMP (RJMP10) protein has also been proposed. (Helbing et al, *Comparative analyses of the major royal jelly protein gene cluster in three Apis species with long amplicon sequencing*, DNA Research 24 (3), 279-287 (217)). RJMPs have a common evolutionary origin with the Yellow protein family from insects and some bacteria. RJMP1 is the most abundant, and largest in volume. The five proteins constitute 82-90% of the total proteins in a royal jelly. Royal jelly is a nutrient-rich mixture of vitamins, sugars, fats, proteins, and enzymes. It is used for feeding the larvae. Royal jelly has been used in traditional medicine and the RJMPs are shown to be the main medicinal components. They are synthesized by a family of nine genes (RJMP genes), which are in turn members of the yellow family of genes common to most insects such as in the fruit fly (*Drosophila*) and found in some bacteria.

RJMP1 is the most abundant protein in royal jelly. It exists in two forms, as monomer (single structure) and as oligomer (combined structure) with another protein apimisin. The molecular size of the oligomer is 290-350 kDa. The oligomer is a combination of five monomers and can create a gel at concentrations or 5 mg/L, 6 mg/L, 7 mg/L, 8 mg/L, 9 mg/L, 10 mg/L or higher. RJMP1 isolated from royal jelly is tightly associated with apisimin, a serine-valine-rich 54-residue α-helical peptide that promotes the noncovalent assembly of RJMP1 into multimers. The monomer is 55 kDa in mass, while apimisin is 5 kDa. The monomer contains 432 amino acids and is divisible into three chains, such as jellein-1, jellein-2, and jellein-4. The monomers in the oligomer are held together by apimisin using noncovalent bonds. (Wenli Tian, 2018) Besides apisimin, two other key functional peptides are apalbumin and royalisin.

The recombinant proteins included in the food compositions of this disclosure may have sequences derived from a RJMP of *Apis mellifera* or other *Apis* species. The recombinant protein included in a food composition may be RJMP1, RJMP2, RJMP3, RJMP4, RJMP5, RJMP6, RJMP9, or RJMP10. The recombinant protein may be a portion of a RJMP such as apisimin, jellein-1, jellein-2, or jellein-4.

The control of the proportion of these protein constituents such as apisimin and RJMP1 can modulate the formation of gels and therefore the effect of protein additions into a food composition.

E. Immunostimulatory Properties

The recombinant protein may be a non-specific immunostimulant that contributes immunostimulatory properties to the food composition. Immunostimulants stimulate the immune system by inducing activation or increasing activity of any of its components. Non-specific immunostimulants act irrespective of antigenic specificity to stimulate components of the immune system without antigenic specificity.

Honey is known to have medicinal properties including immunostimulatory properties. (Won et al., 2009). For example, unfractionated honey is able to stimulate the release of TNF-α from monocytes/macrophages. The proteins contained in honey are one source of immunostimulatory components. RJMP1 exhibits a broad range of pharmacological activities in human health, such as promoting cell growth and wound healing, broad-spectrum antibacterial and antifungal activities, hypocholesterolemic effects, antitumor activity, vasodilative and anti-hypertension activity, and immune enhancement. The protein apisimin, which is present in honey and royal jelly, stimulates the release of TNF-α from blood monocytes. (Swapna Gannabathula, 2015). Apisimin has been reported to form a complex with the Royal Jelly protein RJMP1. (Tamura S., 2009) (Wenli Tian, 2018). The complex may include two RJMP1 proteins and two apisimin proteins in a 1:1 ratio. (Wenli Tian, 2018) This complex of apisimin and RJMP1 has immunostimulatory properties.

The ratio of apisimin to RJMP1 may be adjusted in order to control the immunostimulatory properties of a food composition. The greatest immunostimulatory properties are achieved when apisimin and RJMP1 are present at equal molar amounts in the food composition. As the ratio deviates from 1:1 the amount of one protein that is not complexed with the other increases and the immunostimulatory properties decrease. A food composition may contain recombinant apisimin and recombinant RJMP1 at any molar ratio such as, for example, between about 1:100 to 100:1. In an implementation, either apisimin, RCMP1, or both may be mutated or modified versions of the proteins that reduce immunostimulatory activity.

F. Recombinant Protein Expression

The term "recombinant" is an art known term. When referring to a nucleic acid (e.g., a gene), the term "recombinant" can be used, e.g., to describe a nucleic acid that has been removed from its naturally occurring environment, a nucleic acid that is not associated with all or a portion of a nucleic acid abutting or proximal to the nucleic acid when it is found in nature, a nucleic acid that is operatively linked to a nucleic acid which it is not linked to in nature, or a nucleic acid that does not occur in nature. The term "recombinant" can be used, e.g., to describe cloned DNA isolates, or a nucleic acid including an enzymatically or chemically-synthesized nucleotide analog. When "recombinant" is used to describe a protein, it can refer to, e.g., a protein that is produced in a cell of a different species or type, as compared to the species or type of cell that produces the protein in nature.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion, or a point mutation introduced artificially, e.g., by human intervention. A "recombinant nucleic acid" also includes a nucleic acid integrated into a host cell chromosome at a heterologous site and a nucleic acid construct present as an episome.

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell and are thereby replicated along with the host genome. Moreover, certain preferred vectors are capable of directing the expression of genes to which they are operatively linked. Such vectors are referred to herein as "recombinant expression vectors" (or simply "expression vectors").

The polypeptides can be produced by using an expression vector that contains an isolated nucleic acid encoding for the polypeptide. As used herein, the term "vector" refers to a nucleic acid molecule capable of transporting another nucleic acid to which it has been linked and can include a plasmid, cosmid, or viral vector. A vector is capable of autonomous replication and contains a nucleic acid in a form suitable for expression of the nucleic acid in a host cell. It includes one or more regulatory sequences operatively linked to the nucleic acid sequence to be expressed. The term "regulatory sequence" includes promoters, enhancers, and other expression control elements (e.g., polyadenylation signals). Regulatory sequences include those which direct constitutive expression of a nucleotide sequence, as well as tissue-specific regulatory or inducible sequences. A vector can be designed for expression of a polypeptide in prokaryotic or eukaryotic cells, e.g., bacterial cells (e.g., E. coli), insect cells (e.g., using baculovirus expression vectors), yeast cells (e.g., P. pastoris), or mammalian cells. Suitable host cells are discussed further in Goeddel, (1990) Gene Expression Technology: Methods in Enzymology 185, Academic Press, San Diego, Calif. Expression of a polypeptide can be carried out with vectors containing constitutive or inducible promoters directing the expression of either proteins or non-fusion proteins. A fusion protein may facilitate purification of soluble polypeptides. Fusion vectors add a number of amino acids to a polypeptide encoded therein, usually to the amino terminus of the polypeptide. Typical fusion expression vectors include pGEX (Pharmacia Biotech Inc; Smith and Johnson (1988) Gene 67:31-40), pMAL (New England Biolabs, Beverly, Mass.), and pRIT5 (Pharmacia, Piscataway, N.J.) which fuse glutathione S-transferase (GST), maltose E binding protein, or protein A, respectively, to the target polypeptide.

A vector can be introduced into host cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. A host cell of the invention can be used to express a polypeptide. The expressed polypeptide can be isolated from the host cell or a culture medium.

Promoters useful for expressing the recombinant genes described herein include both constitutive and inducible/repressible promoters. Examples of inducible/repressible promoters include galactose-inducible promoters (e.g., PLAC4-PBI). Where multiple recombinant genes are expressed in an engineered yeast, the different genes can be controlled by different promoters or by identical promoters in separate operons, or the expression of two or more genes may be controlled by a single promoter as part of an operon.

The term "operably linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences which are necessary to affect the expression of coding sequences to which they are operably linked. Expression control sequences are sequences which control the transcription, post-transcriptional events, and translation of nucleic acid sequences. Expression control sequences include appropriate transcription initiation, termination, promoter and enhancer sequences; efficient RNA processing signals, such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "transfect", "transfection", "transfecting," and the like refer to the introduction of a heterologous nucleic acid into eukaryote cells, both higher and lower eukaryote cells. Historically, the term "transformation" has been used to describe the introduction of a nucleic acid into a yeast or fungal cell; however, herein the term "transfection" is used to refer to the introduction of a nucleic acid into any eukaryote cell, including yeast and fungal cells.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. Host cells may be yeasts, fungi, or bacteria.

Nucleic Acids and Vectors

Also provided are nucleic acids (e.g., vectors) that include: a promoter (e.g., a yeast, bacterial, or a mammalian promoter); a sequence encoding a signal sequence; a sequence encoding a honey protein (e.g., any of the exemplary sequences described herein); and a termination sequence, where the promoter is operably linked to the signal sequence, the signal sequence is operably linked to the sequence encoding the honey protein, and the terminal sequence is operably linked to the sequence encoding the honey protein. In some examples of these nucleic acids, the promoter is a constitutive promoter or an inducible promoter. Non-limiting examples of promoters are described herein. For example, when cloning in bacterial systems, inducible promoters such as the hybrid lacZ promoter of the PBLUESCRIPT phagemid (Stratagene, La Jolla, Calif) or PSPORT1 plasmid (Gibco BRL, Gaithersburg, Md.) and the like may be used. In mammalian cell systems, promoters from mammalian genes or from mammalian viruses are generally preferred. Additional promoters that can be used in these nucleic acids are known in the art.

The signal sequence in any of the vectors described herein can be a signal sequence from the encoded polypeptide, a different polypeptide, or a signal sequence from a yeast mating factor (e.g., any alpha mating factor). Additional signal sequences that can be used in the present vectors are known in the art.

Any of the nucleic acids described herein can further include a bacterial origin of replication. Any of the nucleic acids described herein can further include a selection marker (e.g., an antibiotic resistance gene). The sequences of bacterial origin of replication are known in the art. Non-limiting examples of antibiotic resistance genes are described herein. Additional examples of resistance genes are known in the art.

Non-limiting examples of termination sequences are described herein. Additional examples of termination sequences are known in the art.

Some embodiments of the nucleic acids provided herein further include: an additional promoter sequence (e.g., any of the exemplary promoters described herein); an additional sequence encoding a signal sequence (e.g., any of the exemplary signal sequences described herein); a sequence encoding an additional protein; and an additional yeast termination sequence (e.g. any of the exemplary yeast termination sequences described herein), where the additional promoter sequence is operably linked to the additional sequence encoding a signal sequence, the sequence encoding the signal sequence is operably linked to the sequence encoding the additional protein, and the sequence encoding the additional protein is operably linked to the additional yeast terminal sequence. The promoter and the additional promoter can be the same or different. The termination sequence and the additional terminal sequence can be the same or different. The signal sequence and the additional signal sequence can be the same or different.

The present invention also encompasses a vector containing the isolated DNA sequence encoding a protein and host cells comprising the vector. The vector may further comprise an isolated DNA sequence comprising a nucleotide sequence encoding a protein, wherein the nucleotide sequence is operably linked to a promoter, a nucleotide sequence encoding an alpha mating factor, or a variant thereof, a nucleotide sequence encoding a bacterial resistance marker and a transcription terminator. One or more of suitable promoters are utilized for expression of the genes encoding honey proteins may be any promoter which is functional in the host cell and is able to elicit expression of the product encoded by the gene. Suitable promoters include, for example, PLAC4-PBI, T7, Ptac, Pgal, λPL, λPR, bla, spa, Adh, CYC, TDH3, ADH1 and CLB1.

In bacterial systems, a number of expression vectors may be selected depending upon the use intended for the expressed polypeptide. For example, when large quantities are needed, vectors which direct high-level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of D-galactosidase so that a hybrid protein is produced; pi N vectors (Van Heeke & Schuster, J. Biol. Chem. 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al., Methods Enzymol. 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, EMBO J. 6:307-311 (1987)). Alternatively, plant promoters such as the small subunit of RUBISCO or heat shock promoters may be used (Coruzzi et al., EMBO J. 3:1671-1680 (1984); Broglie et al., Science 224:838-843 (1984); and Winter et al., Results Probl. Cell Differ. 17:85-105 (1991)). These constructs can be introduced into plant cells by direct DNA transformation or pathogen-mediated transfection. Such techniques are described in a number of generally available reviews (see, e.g., Hobbs in McGraw Hill, Yearbook of Science and Technology, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard et al., Proc. Natl. Acad. Sci. U.S.A. 97:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, Proc. Natl. Acad. Sci. U.S.A. 87:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., Results Probl. Cell Differ. 20:125-162 (1994)).

Introducing Nucleic Acids into a Cell

Methods of introducing nucleic acids (e.g., any of the nucleic acids described herein) into a cell to generate a host cell are well-known in the art. Non-limiting examples of techniques that can be used to introduce a nucleic acid into a cell include: calcium phosphate transfection, dendrimer transfection, liposome transfection (e.g., cationic liposome transfection), cationic polymer transfection, electroporation, cell squeezing, sonoporation, optical transfection, protoplast fusion, impalefection, hydrodynamic delivery, gene gun, magnetofection, and viral transduction.

One skilled in the art would be able to select one or more suitable techniques for introducing the nucleic acids into a cell based on the knowledge in the art that certain techniques for introducing a nucleic acid into a cell work better for different types of host cells. Exemplary methods for introducing a nucleic acid into a yeast cell are described in Kawai et al., Bioeng. Bugs 1:395-403, 2010.

Host Cells

Also provided herein a host cells including any of the nucleic acid sequences (e.g., vectors) described herein. In some examples, the nucleic acid described herein is stably integrated within the genome (e.g., a chromosome) of the host cell. In other examples, the nucleic acid described herein is not stably integrated within the genome of the host cell. In some embodiments, the host cell is a yeast strain such as *Saccharomyces* sp., a bacterial strain, such as *E. coli*, or a protozoa such as a Tetrahymena thermophile. Additional strains suitable for use as host cells are known in the art.

A host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., Cell 77:223-232 (1977)) and adenine phosphoribosyltransferase (Lowy et al., Cell 22:817-823 (1990)) genes which can be employed in tkor aprtcells, respectively. Also, antimetabolite, antibiotic or herbicide resistance can be used as the basis for selection; for example, dhfr which confers resistance to methotrexate (Wigler et al., Proc. Natl. Acad. ScL U.S.A. 77:3567-70 (1980)); npt, which confers resistance to the aminoglycosides, neomycin and G-418 (Colbere-Garapin et al., J. MoI. Biol. 750:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, Proc. Natl. Acad. ScL U.S.A. 85:8047-51 (1988)). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., Methods MoI. Biol. 55:121-131 (1995)).

Methods of Producing a Recombinant Protein

Also provided are methods of producing a recombinant protein (e.g., one or more of any of the proteins described herein) that is unglycosylated or has a non-mammalian glycosylation pattern that include: culturing any of the host cells described herein in a culture medium under conditions sufficient to allow for secretion of the protein that is unglycosylated or has a non-mammalian glycosylation pattern; and harvesting the protein that is unglycosylated or has a non-mammalian glycosylation pattern from the culture medium. Suitable culture medium for use in these methods are known in the art. Culture conditions sufficient to allow for secretion of a recombinant protein are also known in the art. The host cells used in these methods can be any of the host cells described herein. The host cells can include any of the nucleic acids described herein including, but not limited to any of SEQ ID NOs. 34-41. Some of these methods further include isolating (e.g., purifying) the recombinant protein from the culture medium. Methods of isolating (e.g., purifying) a recombinant protein from a liquid are well-known in the art.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

Proteins can be separated on the basis of their molecular weight, for example, by size exclusion chromatography, ultrafiltration through membranes, or density centrifugation. In some embodiments, the proteins can be separated based on their surface charge, for example, by isoelectric precipitation, anion exchange chromatography, or cation exchange chromatography. Proteins also can be separated on the basis of their solubility, for example, by ammonium sulfate precipitation, isoelectric precipitation, surfactants, detergents, or solvent extraction. Proteins also can be separated by their affinity to another molecule, using, for example, hydrophobic interaction chromatography, reactive dyes, or hydroxyapatite. Affinity chromatography also can include using antibodies having specific binding affinity for the protein, nickel NTA for His-tagged recombinant proteins, lectins to bind to sugar moieties on a glycoprotein, or other molecules which specifically binds the protein.

Proteins may be purified by any technique known to those of ordinary skill in the art such as centrifugation and membrane filtration to remove any potential bacteria or contaminants, followed by lyophilization for protein isolation.

G. Polynucleotides and Polypeptides

Reference to a polynucleotide or polypeptide as described herein and/or reference to the nucleic acid or amino acid sequence of one or more SEQ ID NOs can include a polynucleotide or polypeptide with at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% nucleic acid or amino acid sequence similarity to the reference nucleic acid or amino acid sequence.

Reference to a conservatively substituted polypeptide as described herein and/or reference to the amino acid sequence of one or more SEQ ID NOs can include a polypeptide with at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence in which all differences from the listed sequences are conservative substitutions.

As used herein, the term "conserved amino acid substitutions" or "conservative substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. A conservative substitution for an amino acid in a polypeptide may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity. Specific, non-limiting examples of a conservative substitution include the following examples:

| Original Residue | Conservative Substitutions |
|---|---|
| Ala | Ser |
| Arg | Lys |
| Asn | Glu, His |
| Asp | Glu |
| Cys | Ser |
| Gln | Asn |
| Glu | Asp |
| His | Asn, Glu |
| Ile | Leu, Val |
| Leu | Ile, Val |
| Lys | Arg, Glu, Gln |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

In making conservative substitutions, the hydropathic index of amino acids may be considered. The importance of the hydropathic amino acid index in conferring interactive biologic function on a protein is generally understood in the art (Jack Kyte, Russell F. Doolittle, A simple method for displaying the hydropathic character of a protein, Journal of Molecular Biology, Volume 157, Issue 1, 1982, Pages 105-132,). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is also known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the conservative substitution of like amino acids can be made effectively on the basis of hydrophilicity.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, conservative amino acid substitutions are generally therefore based on the relative similarity of the amino acid side-chain substituents, for example, their hydrophobicity, hydrophilicity, charge, size, and the like.

Reference to a truncated polypeptide as described herein and/or reference to the amino acid sequence of one or more SEQ ID NOs can include a variant protein that is "truncated" with respect to a reference, full-length protein. Some truncated proteins retain the functional activity of the reference protein. A truncated protein may have 1-30 amino acids absent from either or both and the N-terminal and the C-terminal such as an N-terminal leader sequence or transmembrane domain.

A portion of a protein may be a signal peptide. A signal peptide is a short peptide (usually 16-30 amino acids long) present at the N-terminus of the majority of newly synthesized proteins that are destined toward the secretory pathway. Signal peptides function to prompt a cell to translocate the protein, usually to the cellular membrane or an organoid or intra-cellular compartment. The core of the signal peptide contains a long stretch of hydrophobic amino acids (about 5-16 amino acids long) that tends to form a single alpha-helix and is also referred to as the "h-region". In addition, many signal peptides begin with a short positively charged stretch of amino acids, which may help to enforce proper topology of the polypeptide during translocation by what is known as the positive-inside rule. Because of its close location to the N-terminus it is called the "n-region". At the end of the signal peptide there is typically a stretch of amino acids that is recognized and cleaved by signal peptidase and therefore named cleavage site.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species. A degenerate nucleic acid sequence includes all nucleic acid sequences encoding a specified polypeptide. Standard IUPAC notation is used to represent degenerate base symbols.

Reference to a nucleic acid sequence also includes the complementary sequence unless otherwise indicated. The choice between the two is dictated by the context. For instance, if the nucleic acid is used as a probe, the choice between the two is dictated by the requirement that the probe be complementary to the desired target.

The term "percent sequence identity" or "percent identity" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap, or Bestfit, which are programs in Wisconsin Package Version 10.0, Genetics Computer Group (GCG), Madison, Wis. FASTA provides alignments and percent sequence identity of the regions of the best overlap between the query and search sequences. See, e.g., Pearson, Methods Enzymol. 183:63-98, 1990 (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410, 1990; Gish and States, Nature Genet. 3:266-272, 1993; Madden et al., Meth. Enzymol. 266:131-141, 1996; Altschul et al., Nucleic Acids Res. 25:3389-3402, 1997; Zhang and Madden, Genome Res. 7:649-656, 1997, especially blastp or tblastn (Altschul et al., Nucleic Acids Res. 25:3389-3402, 1997.

The percent identity between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from the U.S. government's National Center for Biotechnology Information web site (ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity is determined by dividing the number of matches by the length of the full-length polypeptide amino acid sequence followed by multiplying the resulting value by 100. It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

The term "substantial homology" or "substantial identity," when referring to nucleic acid or amino acid sequences, indicates that, when optimally aligned with appropriate insertions or deletions with another nucleic acid (or its complementary strand) or amino acid, there is sequence identity in at least about 85%, preferably at least about 90%, and more preferably at least about 95%, 96%, 97%, 98% or 99% of the nucleotide bases or peptides, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y., page 9.51, 1989, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Examples of modified nucleotides are described in Malyshev et al., Nature 509:385-388, 2014; and Li et al., J. Am. Chem. Soc. 136:826-829, 2014. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted, or changed compared to a reference nucleic acid sequence. A single alteration may be made at a locus (a point mutation) or multiple nucleotides may be inserted, deleted, or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., Technique 1:11-15, 1989, and Caldwell and Joyce, PCR Methods Applic. 2:28-33, 1992); and "oligonucleotide-directed mutagenesis" (a process which enables the generation of site-specific mutations in any cloned DNA segment of interest; see, e.g., Reidhaar-Olson and Sauer, Science 241: 53-57, 1988).

EXAMPLES

H. Assessment of Food Compositions

Food products described herein can be assessed using trained human panelists. The evaluations can involve eyeing, feeling, chewing, and tasting of the product to judge product appearance, color, integrity, texture, flavor, and mouthfeel, etc. Mouthfeel of the food product may be determined by structure, dryness, wetness, density, adhesiveness, bounce, chewiness, coarseness, cohesiveness, fracturability, graininess, gumminess, hardness, heaviness, moisture adsorption, moisture release, mouthcoating, roughness, slipperiness, smoothness, springiness, uniformity, and viscosity.

Samples can be assigned random three-digit numbers and rotated in ballot position to prevent bias. Sensory judgments can be scaled for "acceptance" or "likeability" or use special terminology. For example, letter scales (A for excellent, B for good, C for poor) or number scales may be used (1=dislike, 2=fair, 3=good; 4=very good; 5=excellent). A scale can be used to rate the overall acceptability or quality of the food product or specific quality attributes such dryness, graininess, texture, and flavor. Panelists can be encouraged to rinse their mouths with water between samples and given opportunity to comment on each sample.

In some embodiments, a food composition described herein can be compared to the same food product without added protein. In some embodiments, a food composition with added honey protein can be compared to same food product supplemented with the same amount in weight of a plant-based protein.

These results will demonstrate that food compositions with added honey proteins are judged as preferable the same food compositions in which a plant-based protein is added. Additionally, these results can demonstrate that panelists cannot distinguish between unmodified food compositions and food compositions supplemented with recombinant proteins.

Tasting Panel 1

Five individuals will taste solutions of varying concentrations of RJMP1 in water (1, 10 and 100 mg/mL) extracted from honey to evaluate flavor and mouth feel. In preliminary tests, a faint taste of honey was detected, and mouth feel was not dry and flavorful reminding the tasters of honey. The RJMP1 was at least 90% pure as determined by SDS PAGE gel electrophoresis.

Tasting Panel 2

Panels will compare chocolate, cheese, yogurt, peanut butter, almond butter, cake, and bread supplemented with RJMP1—apisimin mixtures to the same food product supplemented with pea protein, soy protein, or no protein. The amount of protein added will be 5 g to a total weight of 42.5 g of chocolate bar. This provides a chocolate bar with 11.8 wt % protein and 6.7 g of protein per serving. The tasters can evaluate the chocolate for smoothness and moistness. Each serving will be rating on a scale of 1-10 for smoothness with 1 being very dry and 10 being very smooth. Each serving will also be rating on a scale of 1-10 for moistness with 1 being very dry and 10 being very moist. Sensory characteristics of food samples using the protein examining the Mouth feel, flavor and aroma can be evaluated. A sensory evaluation for aroma would include a qualitative review of the flavor/aroma at different stages of consumption: such as smell, when first put into mouth, while and after chewing. The texture of the food for its sponginess, smoothness, dryness, resistance to bite, melting can also be rated on the 1-10 scale described.

Illustrative Implementations

A food composition may be created that contains any of the features listed below combined in any order. All listed features may be optional or may not be present in every implementation of the food composition. Implementations may include one or more of the following features. The food composition where the food composition may include chocolate, jam, jelly, fruit juice, nut milks, doughs, cake, bread, milk, cheese, cream cheese, soft cheese, cheese sauce, peanut butters, nut butters, cereal, hard cheese, or yogurt. The food composition is hydrophobic. The food composition is hydrophilic. The food composition is a high-fat food composition. The food composition is a high-sugar food composition. The food composition contains no animal products. The recombinant honey protein is amphipathic. The recombinant honey protein is fat soluble. The recombinant honey protein is water soluble. The recombinant honey protein and the second recombinant honey protein are present in a predetermined molar ratio. The predetermined molar ratio is about 2:1. The recombinant honey protein and the second recombinant honey protein form a gel. The recombinant honey protein is rjmp1 and the second recombinant honey protein is apisimin. The recombinant honey protein may include a royal jelly major protein (rjmp). The rjmp is rjmp 1, rjmp 2, rjmp3, rjmp 4, or rjmp 5. A sequence of the rjmp is from *Apis mellifera*. The recombinant honey protein may include apisimin. The food composition may include a rjmp. The apisimin and the rjmp are present in a predetermined molar ratio. The rjmp is rjmp1. The predetermined molar ratio is between 1:100 and 100:1. The food composition has a cytostimulatory property. The cytostimulatory property may include stimulation of secretion of interleukins, transforming growth factor alpha or tumor necrosis factor alpha. The recombinant honey protein may include rjmp6, rjmp9, rjmp10, or, jelling-3, defensin-1. The recombinant honey protein may include a protein having an amino acid sequence with at least 90% identity to any of seq id nos: 1-41. The recombinant honey protein may include about 15% of the food composition by weight. The recombinant honey protein may include at least 90% of total protein in the food composition. The food composition has a smooth mouthfeel. The food composition has a uniform mouthfeel. The food composition has a low dryness mouthfeel. There is no detectable taste difference between the food composition with or without the recombinant honey protein. There is no detectable mouthfeel difference between the food composition with or without the recombinant honey protein.

One general aspect includes a method of producing a food composition supplemented with one or more recombinant honey proteins. The method of producing also includes recombinantly expressing one or more genes to produce the one or more recombinant honey proteins. The producing also includes isolating or purifying the recombinant honey proteins. The producing also includes combining the one or more recombinant honey proteins with the food composition.

Implementations may include one or more of the following features. The method where the food composition may include chocolate, jam, jelly, fruit juice, nut milks, doughs, cake, bread, milk, cheese, cream cheese, soft cheese, cheese sauce, peanut butters, nut butters, cereal, hard cheese, or yogurt. The one or more recombinant honey proteins may include at least one of a royal jelly major protein (rjmp) and apisimin. The one or more recombinant honey proteins may include a protein having an amino acid sequence with at least 90% identity to any of seq id nos. Recombinantly expressing one or more proteins may include introducing a nucleic acid sequence encoding the one or more recombinant honey proteins into a recombinant host cell. The recombinant host cell is a yeast cell or a bacterial cell. Combining the one or more recombinant honey proteins with the food composition may include adding a quantity of the one or more recombinant honey proteins to the food composition such that the food composition may include at least 15% recombinant honey protein by weight. The one or more recombinant honey proteins form a gel.

One general aspect includes a method of producing a food composition supplemented with one or more recombinant honey proteins. The method of producing also includes identifying a characteristic of the food composition. The producing also includes selecting a protein based on the characteristic of the food composition. The producing also includes recombinantly expressing one or more proteins to produce the one or more recombinant honey proteins. The producing also includes combining the one or more recombinant honey proteins with the food composition.

Implementations may include one or more of the following features. The method where the characteristic of the food composition is water content. The characteristic of the food composition is fat content. The characteristic of the food composition is sugar content.

Conclusion

Although the subject matter has been described in language specific to features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

Sequences

```
SEQ ID NO: 1 Major royal jelly protein 1 from Apis mellifera including signal peptide
MTRLFMLVCLGIVCQGTTGNILRGESLNKSLPILHEWKFFDYDFGSDERRQDAILSGEYDYKNNYPSDIDQWHDKIFVT
MLRYNGVPSSLNVISKKVGDGGPLLQPYPDWSFAKYDDCSGIVSASKLAIDKCDRLWVLDSGLVNNTQPMCSPKLLTF
DLTTSQLLKQVEIPHDVAVNATTKGRLSSLAVQSLDCNTNSDTMVYIADEKGEGLIVYHNSDDSFHRLTSNTFDYDPKF
TKMTIDGESYTAQDGISGMALSPMTNNLYYSPVASTSLYYVNTEQFRTSDYQQNDIHYEGVQNILDTQSSAKVVSKSG
VLFFGLVGDSALGCWNEHRTLERHNIRTVAQSDETLQMIASMKIKEALPHVPIFDRYINREYILVLSNKMQKMVNNDFN
FDDVNFRIMNANVNELILNTRCENPD NDRTPFKISIHL SEQ ID NO: 2 Major royal jelly protein 1 from Apis mellifera without signal peptide
NILRGESLNKSLPILHEWKFFDYDFGSDERRQDAILSGEYDYKNNYPSDIDQWHDKIFVTMLRYNGVPSSLNVISKKVG
DGGPLLQPYPDWSFAKYDDCSGIVSASKLAIDKCDRLWVLDSGLVNNTQPMCSPKLLTFDLTTSQLLKQVEIPHDVAV
NATTKGRLSSLAVQSLDCNTNSDTMVYIADEKGEGLIVYHNSDDSFHRLTSNTFDYDPKFTKMTIDGESYTAQDGISG
MALSPMTNNLYYSPVASTSLYYVNTEQFRTSDYQQNDIHYEGVQNILDTQSSAKWSKSGVLFFGLVGDSALGCWNE
HRTLERHNIRTVAQSDETLQMIASMKIKEALPHVPIFDRYINREYILVLSNKMQKMVNNDFNFDDVNFRIMNANVNELIL
NTRCENPDNDRTPFKISIHL SEQ ID NO: 3 Major royal jelly protein 1 from Apis cerana including signal peptide (SV = 1)
MTKWLFMVACLGIACQGAIIRQNSAKNLENSLNVIHEWKYIDYDFGSEERRQAAIQSGEYDHTKNYPFDVDQWHDKT
FVTILKYDGVPSTLNMISNKIGKGGRLLQPYPDWSWAENKDCSGIVSAFKIAIDKFDRLWVLDSGLINRTEPICAPKLHV
FDLKNTKHLKQIEIPHDIAVNATTGKGGLVSLWQAMDPMNTLVYIADHKGDALIVYQNSDDSFHRMTSNTFDYDPRY
AKMTINGESFTLKNGICGMALSPVTNNLYYSPLASHGLYYVNTEPFMKSQFGDNNNVQYEGSQDTLNTQSLAKAVSK
DGVLFVGLVGNSALGCLNEHQPLQRENLELVAQNEKTLQMIAGMKIKEELPHFVGSNKPVKDEYMLVLSNKMQKIVN
NDFNFNDVNFRILGANVKELMRNTHCANFNNKNNQKNNNQKNNNQNNNNQKNNNQKNNNQKNNNQKNNNQNTNN SEQ ID NO: 4 Major royal jelly protein 1 from Apis cerana without signal peptide (SV = 1)
AIIRQNSAKNLENSLNVIHEWKYIDYDFGSEERRQAAIQSGEYDHTKNYPFDVDQWHDKTFVTILKYDGVPSTLNMISN
KIGKGGRLLQPYPDWSWAENKDCSGIVSAFKIAIDKFDRLWVLDSGLINRTEPICAPKLHVFDLKNTKHLKQIEIPHDIA
VNATTGKGGLVSLWQAMDPMNTLVYIADHKGDALIVYQNSDDSFHRMTSNTFDYDPRYAKMTINGESFTLKNGICG
MALSPVTNNLYYSPLASHGLYYVNTEPFMKSQFGDNNNVQYEGSQDTLNTQSLAKAVSKDGVLFVGLVGNSALGCL
NEHQPLQRENLELVAQNEKTLQMIAGMKIKEELPHFVGSNKPVKDEYMLVLSNKMQKIVNNDFNFNDVNFRILGANVK
ELMRNTHCANFNNKNNQKNNNQKNNNQNNNNQKNNNQKNNNQKNNNQKNNNQNTNN SEQ ID NO: 5 Major royal jelly protein 1 from Apis cerana without signal peptide (SV = 2)
MTRWLFMWCLGIVCQGTTSSILRGESLNKSLSVLHEWKFFDYDFGSDERRQDAILSGEYDYRKNYPSDVDQWHGKI
FVTMLRYNGVPSSLNVISKKIGDGGPLLQPYPDWSFAKYDDCSGIVSATKLAIDKCDRLWVLDSGLVNNTQPMCSPKL
LTFDLTTSQLLKQVEIPHDVAVNATTGKGRLSSLAVQPLDCNINGDTMVYIADEKGEGLIVYHDSDNSFHRLTSKTFDY
DPKFTKMTINGESFTTQSGISGMALSPMTNNLYYSPVASTSLYYVNTEQFRTSNYEQNAVHYEGVQNILDTQSSAKWV
SKSGVLFFGLVGDSALGCWNEHRSLERHNIRTVAQSDETLQMIVGMKIKEALPHVPIFDRYINREYILVLSNRMQKMA
NNDYNFNDVNFRIMDANVNDLILNTRCENPNNDNTPFKISIHL SEQ ID NO: 6 Major royal jelly protein 1 from Apis dorsata without signal peptide
WKLVDYDFGSNERRENAILSGEYDYTKNYPSDVDEWHGKIFVSMLRYNGVPSSLNVISKKIGKGGPLLQPYPDWSFA
KYDDCSGIVSASQLAIDKCDRLWVLDSGLVDNTQPMCSPKLVTFDLTTSKLLKQVEIPHNVAVNTTTGNGRLSSLAVQ
PLDCNINGDTMVYIADEKGEGLIVY HNSDNSFQRLSS SEQ ID NO: 7 Major royal jelly protein 2 from Apis mellifera including signal peptide
MTRWLFMVACLGIACQGAIVRENSPRNLEKSLNVIHEWKYFDYDFGSEERRQAAIQSGEYDHTKNYPFDVDQWRDK
TFVTILRYDGVPSTLNVISGKTGKGGRLLKPYPDWSFAEFKDCSKIVSAFKIAIDKFDRLWVLDSGLVNRTVPVCAPKLH
VFDLKTSNHLKQIEIPHDIAVNATTGKGGLVSLAVQAIDLANTLVYMADHKGDALIVYQNADDSFHRLTSNTFDYDPRYA
KMTIDGESFTLKNGICGMALSPVTNNLYYSPLASHGLYYVNTAPFMKSQFGENNVQYQGSEDILNTQSLAKAVSKNGV
LFVGLVGNSAVGCWNEHQSLQRQNLEMVAQNDRTLQMIAGMKIKEELPHFVGSNKPVKDEYMLVLSNRMQKIVNDD
FNFDDVNFRILGANVKELIRNTHCVNNNQNDNIQNTNNQNDNNQKNNKKNANNQKNNNQNDN SEQ ID NO: 8 Major royal jelly protein 2 from Apis mellifera without signal peptide
AIVRENSPRNLEKSLNVIHEWKYFDYDFGSEERRQAAIQSGEYDHTKNYPFDVDQWRDKTFVTILRYDGVPSTLNVIS
GKTGKGGRLLKPYPDWSFAEFKDCSKIVSAFKIAIDKFDRLWVLDSGLVNRTVPVCAPKLHVFDLKTSNHLKQIEIPHDI
AVNATTGKGGLVSLAVQAIDLANTLVYMADHKGDALIVYQNADDSFHRLTSNTFDYDPRYAKMTIDGESFTLKNGICGM
ALSPVTNNLYYSPLASHGLYYVNTAPFMKSQFGENNVQYQGSEDILNTQSLAKAVSKNGVLFVGLVGNSAVGCWNEH
QSLQRQNLEMVAQNDRTLQMIAGMKIKEELPHFVGSNKPVKDEYMLVLSNRMQKIVNDDFNFDDVNFRILGANVKELI
RNTHCVNNNQNDNIQNTNNQNDNNQKNNKKNANNQKNNNQNDN SEQ ID NO: 9 Major royal jelly protein 2 from Apis cerana including signal peptide (SV = 1)
MTKWLLLMACLGIACQNIRGAVVRENSSRKKLTNTLNVIHEWKYVDYDFGSDEKRQAAIQSGEYDRTKNYPLDVDQW
HDKTFVTMLRYDGVPSSLNWSDKTGNGGPLLQPYPDWSFAKYEDCSGIVSANKIAIDEYERLWVLDSGLVNNIQPM
```

-continued

CSPKLLAFDLTTSKLLKQVEIPHDVAVNATTGKGGLASLAVQAMDSVNTMVYMADNKDDALIVYQNADDSFHRLSSHI
SNHNFRSDKMSQENLTLKEVDNRVFGMALSSVTHNLYYSPLSSQNLYYVNTTSLMNSQNQGNDVQYESVQDVFSS
QLSAKAVSKNGVLFFGFTNNTLGCWNEHQSLDRQNIDIVARNETLQMVGMKIQNLPQSGKVNNTQRNEHLLALTN
KKQDVLNNDLNLEHVNFQILDANVNDLIRNSRCANSDNQDNNQHNYNHNQVRHSSKSDNQNNNQHNNQAYHSSKS
DNWDNNNNQAHHSSKFDNQNNNQYNN

SEQ ID NO: 10 Major royal jelly protein 2 from Apis cerana including signal peptide (SV = 2)
MTRWLFMVACLGIACQGAIIRQNSAKNLENSLNVIHEWKYIDYDFGSEERRQAAIQSGEYDHTKNYPFDVDQWHDKT
FVTILKYDGVPSTLNMISNKIGKGGRLLQPYPDWSWAENKDCSGIVSAFKIAIDKFDRLWVLDSGLINRTEPICAPKLHV
FDLKNTKHLKQIEIPHDIAVNATTGKGGLVSLVVQAMDPMNTLVYIADHKGDALIVYQNSDDSFHRMTSNTFDYDPRYA
KMTINGESFTLKNGICGMALSPVTNNLYYSPLASHGLYYVNTEPPFMKSQFGDNNNVQYEGSQDTLNTQSLAKAVSKD
GVLFVGLVGNSALGCLNEHQPLQRENLELVAQNEKTLQMIAGMKIKEELPHFVGSNKPVKDEYMLVLSNKMQKIVNND
FNFNDVNFRILGANVKELMRNTHCANFNN KNNQKNNNQKNNNQNNNNQKNNNQKNNNQKNNNQKNNNQNTNN SEQ ID NO: 11 Major royal jelly protein 3 from Apis mellifera including signal peptide
MTKWLLLWCLGIACQDVTSAAVNHQRKSANNLAHSMKVIYEWKHIDFDFGSDERRDAAIKSGEFDHTKNYPFDVDR
WRDKTFVTIERNNGVPSSLNWTNKKGKGGPLLRPYPDWSFAKYEDCSGIVSAFKIAVDKFDRLWVLDSGLVNNNQP
MCSPKLLTFDLKTSKLVKQVEIPHNIAVNATTGMGELVSLAVQAIDRTNTMVYIADEKGEGLIMYQNSDDSFHRLTSNTF
DYDPRYTKLTVAGESFTVKNGIYGIALSPVTNNLYYSPLLSHGLYYVDTEQFSNPQYEENNVQYEGSQDILNTQSFGKV
VSKNGVLFLGLVGNSGIACVNEHQVLQRESFDWAQNEETLQMIVSMKIMENLPQSGRINDPEGNEYMLALSNRMQKI
INNDFNFNDVNFRILGANVDDLMRNTRCGRYHNQNAGNQNADNQNADNQNANNQNADNQNANKQNGNRQNDNR
QNDNKQNGNRQNDNKQNGNRQNDNKQNGNRQNGNKQNDNKQNGNRQNDNKRGNRQNDNQNNQNDNNRND
NQVHHSSKLH SEQ ID NO: 12 Major royal jelly protein 3 from Apis mellifera without signal peptide
AVNHQRKSANNLAHSMKVIYEWKHIDFDFGSDERRDAAIKSGEFDHTKNYPFDVDRWRDKTFVTIERNNGVPSSLNV
VTNKKGKGGPLLRPYPDWSFAKYEDCSGIVSAFKIAVDKFDRLWVLDSGLVNNNQPMCSPKLLTFDLKTSKLVKQVEI
PHNIAVNATTGMGELVSLAVQAIDRTNTMVYIADEKGEGLIMYQNSDDSFHRLTSNTFDYDPRYTKLTVAGESFTVKNG
IYGIALSPVTNNLYYSPLLSHGLYYVDTEQFSNPQYEENNVQYEGSQDILNTQSFGKVWSKNGVLFLGLVGNSGIACVN
EHQVLQRESFDWAQNEETLQMIVSMKIMENLPQSGRINDPEGNEYMLALSNRMQKIINNDFNFNDVNFRILGANVDD
LMRNTRCGRYHNQNAGNQNADNQNADNQNANNQNADNQNANKQNGNRQNDNRQNDNKQNGNRQNDNKQNGN
RQNDNKQNGNRQNGNKQNDNKQNGNRQNDNKRGNRQNDNQNNQNDNNRNDNQVHHSSKLH SEQ ID NO: 13 Major royal jelly protein 3 from Apis cerana including signal peptide
MTKWLLLLWCLGIACQDVTSAAVNHQRKSSKNLAHSMKVIYEWKHIDYDFGSVERRDAAIKSGEFDHTKNYPFDVDR
WRDKTFVTVERFDGVPSSLNWTNKKGKGGPLLHPYPDWSWAKYKDCSGIVSAFKIAVDKFDRLWVLDSGLVNNNQ
PMCSPKLVTFDLTTSKLLKQVEIPHNIAVNATTGMGELVSLAVQAIDPTNTMVYIADERGEALIIYQNSDDSFHRLTSNTF
DYDPRYTKLTVAGESFTVKNGICGIALSPVTNNLYYSPLASHSLYYVNTEQFRNPQYEENNVQYEGSQDILNTQSFAKA
VSKNGVVFLGLVSNSAVGCVNEHQVLQKENFDVVAQNEETLQMIVSMKIMQDLPQSGRINDPGNEYMLALSNKMQKII
NNDFNFNDVNFRILGANVNDLTRNTRCAKSNNQNANNQNANNQNANNQNANNQNANNQNDNNQNDNGNNRRNG
NNQNGNRQNDNKQNDNKQNANKQNANKQNDNKQNGNRQNDNRQNDNKQNDNRQNDNKQNGNRQNDN
RQNDNQRNGNRQNDNRQNDNKRGNRQNDNRQNDNKRGNRQNDNKQNDNRQNDNNQNNNQNDNN
RNNQAHHS SEQ ID NO: 14 Major royal jelly protein 3 from Apis cerana without signal peptide
AAVNHQRKSSKNLAHSMKVIYEWKHIDYDFGSVERRDAAIKSGEFDHTKNYPFDVDRWRDKTFVTVERFDGVPSSLN
WTNKKGKGGPLLHPYPDWSWAKYKDCSGIVSAFKIAVDKFDRLWVLDSGLVNNNQPMCSPKLVTFDLTTSKLLKQV
E1PHNIAVNATTGMGELVSLAVQAIDPTNTMVYIADERGEALIIYQNSDDSFHRLTSNTFDYDPRYTKLTVAGESFTVKN
GICGIALSPVTNNLYYSPLASHSLYYVNTEQFRNPQYEENNVQYEGSQDILNTQSFAKAVSKNGVVFLGLVSNSAVGC
VNEHQVLQKENFDVVAQNEETLQMIVSMKIMQDLPQSGRINDPGNEYMLALSNKMQKIINNDFNFNDVNFRILGANVN
DLTRNTRCAKSNNQNANNQNANNQNANNQNANNQNANNQNDNNQNDNGNNRRNGNNQNGNRQNDNKQNDNKQ
NANKQNANKQNDNKQNDNKQNGNRQNDNRQNDNKQNDNRQNDNKQNGNRQNDNRQNDNQRNGNRQNDNRQN
DNKRGNRQNDNRQNDNKRGNRQNDNKQNDNRQNDNNQNNNQNDNN RNNQAHHS SEQ ID NO: 15 Major royal jelly protein 3 from Apis florea without signal peptide
DVTSAAHQKKSSEDLAHSMKVIYEWKHIDYDFGSEEKRQAAIQSGEYDHTKNYPFDVDRWHDKTFVTVERFNGVPS
SLNVITNKKGKGGPLLQPYPDWSFAKYEDCSGIVNAFKIAIDKVDRLWVLDSGLVNNNNLMCSPKLLTFDLNTSKLLKQ
VEIPHNIAVNATTGMGELVSLAVQVIDPTNTMVYIADERGEGLIIYQNSDDSFHRLTSNTFDYDPRYTKLTVAGESFTVK
NGICGIALSPVTNNLYYSPLASHSLYYVNTEPPFMKSQFEENNVQYEGSQDILNTQSFAKAVSRNGVLFVGLVSNSGVG
CVNEHQVLQKENFDWAQNEETLQMWSMKIMQDRQQSRRINKSQRNEYMLALSNRMQKIINNNFNFDEVNFRILGA
NVNDLIRNTRCVNSNNQNANNQNANNQNANNQNANSQNANNQNGNKQSDNKQNGNMQNDNMQNGNKQNDNKQ
NGNRQNDNRQNGNRQNGNRQNDNKQNENRQNGKRQNDNRQNDDNQNNQNGNNQNDN SEQ ID NO: 16 Major royal jelly protein 3 from Apis dorsata without signal peptide
DVTSAAVNHQRKSLNNLANSMNVIYEWKHIDYDFGSEERQQAAIQSGEFDHTKNYPFDVDQWHDKIFVTIERLNGVP
SSLNWTNKKGKGGPLLQPYPNWSFAKYEDCSGIVSAFKIAIDKFDRLWVLDSGLVNNQPMCSPKLVTFDLNTSKLVK
QVEIPHNIAVNATTGMGELVSLAVQAIDPTNTMVYIADEKGQGLIIYQNSDDSFHRLTSNTFDYDPRYTKLTVAGESFTV
QNGICGIALSPVTNNLYYSPLASHALYYVNTEQFRKPQYDKDNQYDILDTQSFAKWSKDGVLFYGLVGNSGL
GCVNEHQVLQRESFDWAQNEETLQMIVSMKIIQNIPQFRIKDLRNEYMLALSNRMQKIITNDFNFNEVNFRILGANVN
DLIRNTRCEKSTNQNDNTQNVNNQNVNNQNANNQNANNQNAKNQNAKNQNANNQNANNQNDNKQNGHQQNDNQ
RNDNKQNVNKQNVRQNDNRKDNRQKDSRQNDNRQNDNRQNDNRQNDNRQNDNRQNDNRQNDNRQNDNRQ
NDNRQNDNRQNDNKQNGNKQNGNKQNGNRQNGNKQNENNRNDNNQNDN SEQ ID NO: 17 Major royal jelly protein 4 from Apis mellifera including signal peptide
MTKWLLLMVCLGIACQNIRGGWRENSSGKNLTNTLNVIHKWKYLDYDFDNDERRQAAIQSGEYDRTKNYPLDVDQ
WHNKTFLAVIRYNGVPSSLNWSDKTGNGGRLLQPYPDWSFAKYEDCSGIVSAHKIAIDEYERLWVLDSGLVNNTQP
MCSPKLFAFDLNTSQLLKQVEIPHDVATTGKGELVSLTVQAMDSTNTMVYMVDNKNTLIIYQNADDSFHRLSSHTLNH
NSDKMSDQQENLTLKEVDNKVYGMALSPVTHNLYYNSPSSENLYYVNTESLMKSENQGNDVQYERVQDVFDSQLTV
KAVSKNGVLLFGLANNTLSCWNEHQSLDRQNIDWARNEDTLQMWSMKIKQNVPQSGRVNNTQRNEYLLALSDRN
QNVLNNDLNLEHVNFQILGANVNDLIRNSRCANFDNQDNNHYNHNHNQARHSSKDNQNNNQHNDQAHHSSKSNN
RHNNND SEQ ID NO: 18 Major royal jelly protein 4 from Apis mellifera without signal peptide
GVVRENSSGKNLTNTLNVIHKWKYLDYDFDNDERRQAAIQSGEYDRTKNYPLDVDQWHNKTFLAVIRYNGVPSSLNV
VSDKTGNGGRLLQPYPDWSFAKYEDCSGIVSAHKIAIDEYERLWVLDSGLVNNTQPMCSPKLFAFDLNTSQLLKQVEI
PHDVATTGKGELVSLTVQAMDSTNTMVYMVDNKNTLIIYQNADDSPHRLSSHTLNHNSDKMSDQQENLTLKEVDNKV
YGMALSPVTHNLYYNSPSSENLYYVNTESLMKSENQGNDVQYERVQDVFDSQLTVKAVSKNGVLLFGLANNTLSCW
NEHQSLDRQNIDWARNEDTLQMWSMKIKQNVPQSGRVNNTQRNEYLLALSDRNQVLNNDLNLEHVNFQILGANV
NDLIRNSRCANFDNQDNNHYNHNHNQARHSSKSDNQNNNQHNDQAHHSSKSNNRHNNND SEQ ID NO: 19 Major royal jelly protein 4 from Apis cerena including signal peptide (SV = 1)
MTKWLLLMACLGIACQNIRGAWRENSSRKKLTNTLNVIHEWKYVDYDFGSDEKRQAAIQSGEYDRTKNYPLDVDQW
HDKTFVTMLRYDGVPSSLNWSDKTGNGGPLLQPYPDWSFAKYEDCSGIVSANKIAIDEYERLWVLDSGLVNNIQPM
CSPKLLAFDLTTSKLLKQVEIPHDVAVNATTGKGGLASLAVQAMDSVNTMVYMADNKDDALIVYQNADDSFHRLSSHIS
NHNFRSDKMSQENLTLKEVDNRVFGMALSSVTHNLYYSPLSSQNLYYVNTTSLMNSQNQGNDVQYESVQDVFSSQL
SAKAVSKNGVLFFGFTNNTLGCWNEHQSLDRQNIDIVARNETLQMWGMKIKQNLPQSGKVNNTQRNEHLLALTNKK
QDVLNNDLNLEHVNFQILDANVNDLIRNSRCANSDNQDNNQHNYNHNQVRHSSKSDNQNNNQHNNQAYHSSKSDN
WDNNNNQAHHSSKFDNQNNNQYNN SEQ ID NO: 20 Major royal jelly protein 4 from Apis cerena without signal peptide (SV = 1)
AWRENSSRKKLTNTLNVIHEWKYVDYDFGSDEKRQAAIQSGEYDRTKNYPLDVDQWHDKTFVTMLRYDGVPSSLN
WSDKTGNGGPLLQPYPDWSFAKYEDCSGIVSANKIAIDEYERLWVLDSGLVNNIQPMCSPKLLAFDLTTSKLLKQVEI
PHDVAVNATTGKGGLASLAVQAMDSVNTMVYMADNKDDALIVYQNADDSFHRLSSHISNHNFRSDKMSQENLTLKEV
DNRVFGMALSSVTHNLYYSPLSSQNLYYVNTTSLMNSQNQGNDVQYESVQDVFSSQLSAKAVSKNGVLFFGFTNNT
LGCWNEHQSLDRQNIDIVARNETLQMVVGMKIKQNLPQSGKVNNTQRNEHLLALTNKKQDVLNNDLNLEHVNFQILD
ANVNDLIRNSRCANSDNQDNNQHNYNHNQVRHSSKSDNQNNNQHNNQAYHSSKSDNWDNNNNQAHHSSKFDNQ
NN NQYNN SEQ ID NO: 21 Major royal jelly protein 4 from Apis cerena including signal peptide (SV = 2)
MTKWLLLMACLGIACQNIRGAWVRENSSRKKLTNTLNVIHEWKYVDYDFGSDEKRQAAIQSGEYDRTKNYPLDVDQW
QDKTFVTMLRYDGVPSSLNWSNKTGNGGPLLQPYPDWSFAKYEDCSGIVSANKIAIDEYERLWVLDSGLVNNIQPM
CSPKLLAFDLTTSKLLKQVEIPHDVAVNATTGKGGLASLAVQAMDSVNTMVYMADNKDDALIVYQNADDSFHRLSSHIS
NHNFRSDKMSQENLTLKEVDNRVFGMALSSVTHNLYYSPLSSQNLYYVNTTSLMNSQNQGNDVQYESVQDVFSSQL
SAKAVSKNGVLFFGFTNNTLGCWNEHQSLDRQNIDIVARNETLQMVVGMKIKQNLPQSGKVNNTQRNEHLLALTNKK
QDVLNNDLNLERVNFQILDANVNDLIRNSRCANSDNQDNNQHNYNHNQARHSSKSDNQNNNQHNNQAYHSSKSDN
WDNNNNQAHHSSKFDNQNNNQYNN SEQ ID NO: 22 Major royal jelly protein 4 from Apis cerena without signal peptide (SV = 2)
AWRENSSRKKLTNTLNVIHEWKYVDYDFGSDEKRQAAIQSGEYDRTKNYPLDVDQWQDKTFVTMLRYDGVPSSLN
WSNKTGNGGPLLQPYPDWSFAKYEDCSGIVSANKIAIDEYERLWVLDSGLVNNIQPMCSPKLLAFDLTTSKLLKQVEI
PHDVAVNATTGKGGLASLAVQAMDSVNTMVYMADNKDDALIVYQNADDSFHRLSSHISNHNFRSDKMSQENLTLKE
VDNRVFGMALSSVTHNLYYSPLSSQNLYYVNTTSLMNSQNQGNDVQYESVQDVFSSQLSAKAVSKNGVLFFGFTNN
TLGCWNEHQSLDRQNIDIVARNETLQMWGMKIKQNLPQSGKVNNTQRNEHLLALTNKKQDVLNNDLNLERVNFQIL
DANVNDLIRNSRCANSDNQDNNQHNYNHNQARHSSKSDNQNNNQHNNQAYHSSKSDNWDNNNNQAHHSSKFDN
QNNNQYNN SEQ ID NO: 23 Major royal jelly protein 5 from Apis mellifera including signal peptide
MTTWLLLWCLGIACQGITSVTVRENSPRKLANSMNVIHEWKYLDYDFGSDERRQAAMQSGEYDHTKNYPFDVDQW
RGMTFVTVPRYKGVPSSLNVISEKIGNGGRLLQPYPDWSWANYKDCSGIVSAYKIAIDKFDRLWILDSGIINNTQPMCS
PKLHVFDLNTSHQLKQVMPHDIAVNASTGNGGLVSLWQAMDPVNTIVYMADDKGDALIVYQNSDESFHRLTSNTFD
YDPKYIKMMDAGESFTAQDGIFGMALSPMTNNLYYSPLSSRSLYYVNTKPFMKSEYGANNVQYQGVQDIFNTESIAKI
MSKNGVLFFGLMNNSAIGCWNEHQPLQRENMDMVAQNEETLQTWAMKMMHLPQSNKMNRMHRMNRVNRVNRM
DRMDRIDRMDRMDRMDTMDTMDRIDRMDRMDRIDRIDRMHTMDTMDTMDRTDKMSSMDRMDRMDRVDRMDTM
DRTDKMSSMDRMDRMDRVDTMDTMDTMDRMDRMDRMDRMDRMDTMDRTDKMSRIDRMDKIDRMDRMDRT
NRMDRMNRMNRQMNEYMMALSMKLQKFINNDYNFNEVNFRILGANVNDLIMNTRCANSDNQNNNQNKHNN SEQ ID NO: 24 Major royal jelly protein 5 from Apis mellifera without signal peptide
ITSVTVRENSPRKLANSMNVIHEWKYLDYDFGSDERRQAAMQSGEYDHTKNYPFDVDQWRGMTFVTVPRYKGVPS
SLNVISEKIGNGGRLLQPYPDWSWANYKDCSGIVSAYKIAIDKFDRLWILDSGIINNTQPMCSPKLHVFDLNTSHQLKQ
WMPHDIAVNASTGNGGLVSLWQAMDPVNTIVYMADDKGDALIVYQNSDESFHRLTSNTFDYDPKYIKMMDAGESFT
AQDGIFGMALSPMTNNLYYSPLSSRSLYYVNTKPFMKSEYGANNVQYQGVQDIFNTESIAKIMSKNGVLFFGLMNNSA
IGCWNEHQPLQRENMDMVAQNEETLQTWAMKMMHLPQSNKMNRMHRMNRVNRVNRMDRMDRIDRMDRMDRM
DTMDTMDRIDRMDRMDRIDRIDRMHTMDTMDTMDRTDKMSSMDRMDRMDRVDRMDTMDRTDKMSSMDRMDRM
DRVDTMDTMDTMDRMDRMDRMDRMDRMDRMDRMDTMDRTDKMSRIDRMDKIDRMDRMDRTNRMDRMNRMNRQMN
EYMMALSMKLQKFINNDYNFNEVNFRILGANVNDLIMNTRCANSDNQNNNQNKHNN SEQ ID NO: 25 Major royal jelly protein 5 from Apis cerena including signal peptide
MTSWLLLWCLGIACQGITGATVRENSSRNLANSMNVIHEWKYLDYDFGSDEKRQAAIQSGEYDHTKNYPFDVDRWH
DMTFVTVLRYKGVPSSLNVISKKIGNGGPLLQPYPDWSWANYKDCSGIVSAYKIAIDKFDRLWVLDSGIINNTQPMCSP
KLHVFDLNTSQQIKQVMMPHDIAINATTGKGGLENLWQAMDPMNTLVYMADNKGDALIVYQNSDDSFHRLTSNTFDY
DPKYIKMMAAGESFTLQDGIFGMALSPMTNNLYYSPLASRSLYYVNTKPFMKSQYGTNNVQHEGVQDIFNTQSIAKIM
SKNGVLFFGLMNNSAIGCWNEHQPLQRQNMDMVAQNEETLQTWAMKMMHLPQSNRMNRMHRMNSMNRMDRM
DRMDRMDRMDRMDRMDRMDRMDRMDRMDRMDRMDIMDKMNKMDRMDSMI
RIDKMDRMDRMHRIDIMNRMDRMDRMDTRIDTRMDRMDRMDKMDKINKMHRMGRMDRMDRMNRMNRQMNEYM
MALSMKLQKFINNDYNFNEVNFRILAANVNDLIMNTRCANSNNQNDNQNKHNN SEQ ID NO: 26 Major royal jelly protein 5 from Apis cerena without signal peptide
ATVRENSSRNLANSMNVIHEWKYLDYDFGSDEKRQAAIQSGEYDHTKNYPFDVDRWHDMTFVTVLRYKGVPSSLNVI
SKKIGNGGPLLQPYPDWSWANYKDCSGIVSAYKIAIDKFDRLWVLDSGIINNTQPMCSPKLHVFDLNTSQQIKQVMMP
HDIAINATTGKGGLENLWQAMDPMNTLVYMADNKGDALIVYQNSDDSFHRLTSNTFDYDPKYIKMMAAGESFTLQDG
IFGMALSPMTNNLYYSPLASRSLYYVNTKPFMKSQYGTNNVQHEGVQDIFNTQSIAKIMSKNGVLFFGLMNNSAIGCW
NEHQPLQRQNMDMVAQNEETLQTWAMKMMHLPQSNRMNRMHRMNSMNRMDRMDRMDRMDRMDRMDRMDR -continued MDRMDRMDRMDRMDRMDRMDIMDRTNKMDRMDRMDIMDRMNKMDRMDSMIRIDKMDRMDRMHRIDIMNR
MDRMDRMDTRIDTRMDRMDRMDKMDKINKMHRMGRMDRMDRMNRMNRQMNEYMMALSMKLQKFINNDYNFNE
VNFRILAANVNDLIMNTRCANSNNQNDNQNKHNN SEQ ID NO: 27 Major royal jelly protein 5 from Apis florea without signal peptide
YDFGSDEKRQAAIQSGEYDHTKNYPFDVDHWHDMTFVTVLRYKGVPSSLNVISEKTGNGGQLLQPYPDWSWADYK
DCSGIVSAYKIAIDKFDRLWVMDSGIINNTQPMCSPKLHIFDLNTSQHLKQVTIPHDIAVNATTGKGGLEYLVVQAMDPIN
TMVYMADNKGDALIIYQNSDNSFQRMSS SEQ ID NO: 28 Major royal jelly protein 5 from Apis dorsata without signal peptide
WKLVDYDFGSDERRQAAIQSGEYDHTKNYPFDVDQWHDMTFVTVLRYKGVPSSLNIISEKTGNGGPLLQPYPDWSS
ANYEDCSGIVSAYKIAIDKFDRLWVLDSGIINNTQPMCSPKLHVFDLNTSQQVKQVTMPHDIAVNATTGKGGLEYLWQ
AIDPMNTMVYMADNKGDALIIYQNS DDSFHRMSS SEQ ID NO: 29 Major royal jelly protein 6 from Apis florea without signal peptide
YEWKLVDYDFGSDERRQAAIQSGEYDRMKNYPSDVDQWHDKTFVTMLRYDGVPSSLNWSEKTGNGGPLLQPYPD
WSFAKYEDCSGIVSAHKIAIDKFDRLWVLDSGLINNIQLICSPKLLAFDLNTSQLLKQVEIPHDIAVNASTGIGGLVSLWQ
DMDLINTMVYIADDRGNALIVYQ NSDDSFQRLSS SEQ ID NO: 30 Major royal jelly protein 9 from Apis florea without signal peptide
WKYFDYNFGSNERRQAAIQSGEYNYKNNFPIDVDRWHDKTFVTIIRDSGVPSSLNVISNKIGDGGPLLEPYPNWSWA
KNQNCSGITSVYRVAIDVWDRLWVLDNGISGQTSVCSSQIVVFDLKTSQLLKQVKIPHNIAINSTTGSRNLVTPIVQSFD
YNNTLVYIADVEGYALIIYNNAD DSFQR SEQ ID NO: 31 Major royal jelly protein 10 from Apis florea including signal peptide
MTSWLLLWLSVDIACHGITGANIIPENSSRNLVNSLNVIHEWKYIDYDFGSDERRQNAIQSGEYDHTKNYPFDIDQWH
DKIFITVIRYDGVPSSLNIISDKIGNGGRLLQPYPDWSWTNYKDCSGIVSVYRIAIDKFDRLWVLDSGLVNNTQHMCSPK
LLAFDLNTSHLLKQIHVPHDIAVNATTGKGGLVFLAVQAVDPINTMVYMSDNRGNALIIYQNSDDSFHRLTSNTFDYDPR
YIKMTIEGESLTLEDGIFGIAVSPVTNNLYYSPLSSHGLYYVNTEPFMKSQYGGNDVQYNGVEDIYNTQLSAKAVSKNG
VLFFGLVHNSAVGCLNEHQQIQRQNINMVAQNKETLQMIIAMKILEDLQQFGKINRTQRNEYMLVLSNRIQKIVNNDFNF
DEINFRILKANVNDLIRNTRCANNDIQNNNKNNN SEQ ID NO: 32 Major royal jelly protein 10 from Apis florea without signal peptide
NIIPENSSRNLVNSLNVIHEWKYIDYDFGSDERRQNAIQSGEYDHTKNYPFDIDQWHDKIFITVIRYDGVPSSLNIISDKI
GNGGRLLQPYPDWSWTNYKDCSGIVSVYRIAIDKFDRLWVLDSGLVNNTQHMCSPKLLAFDLNTSHLLKQIHVPHDIA
VNATTGKGGLVFLAVQAVDPINTMVYMSDNRGNALIIYQNSDDSFHRLTSNTFDYDPRYIKMTIEGESLTLEDGIFGIAV
SPVTNNLYYSPLSSHGLYYVNTEPFMKSQYGGNDVQYNGVEDIYNTQLSAKAVSKNGVLFFGLVHNSAVGCLNEHQQ
IQRQNINMVAQNKETLQMIIAMKILEDLQQFGKINRTQRNEYMLVLSNRIQKIVNNDFNFDEINFRILKANVNDLIRNTRC
ANNDIQNNNKNNN SEQ ID NO: 33 Major royal jelly protein 10 from Apis dorsata including signal peptide
MTRWLLLVCLGVASHGITGTITPENSSRNLANSLNVIHEWKYLDYDFGSEEKRQAAIQSGEYDFTKNYLFDVDQWHDK
TFATVIRYDGVPSSLNVISDKIGNGGRLLQPYPDWSWAKYKDCSGIVSVYKISIDKFDRLWVLDSGLINNTKLICSPKLLA
FDLNTSQLLKQVHIPHDIAVNATTGKGGLVFLAVQAVDPINTMAYMADNRGNALSVYQNSDNSLHRLTSNTFDYDPRY
TEFTIAGESFILQDGIFGIAVSPVTNNLYYSPLSSRSLYYVNTEPFMKSEYEGNNVQYKGVEDIYNTQLSAKAVSKNGW
FFGLVNNSALGCLNEHQPIQRQNIDMVAQNEETLQMIFSIKIKQDFPQSNRINKTERNEYMLALSNRLQKFMNHNYNF
NEVNFRVLSANVNDLIKNTRCANFN NQAHHSSKSH SEQ ID NO: 34 Major royal jelly protein 10 from Apis dorsata without signal peptide
TITPENSSRNLANSLNVIHEWKYLDYDFGSEEKRQAAIQSGEYDFTKNYLFDVDQWHDKTFATVIRYDGVPSSLNVIS
DKIGNGGRLLQPYPDWSWAKYKDCSGIVSVYKISIDKFDRLWVLDSGLINNTKLICSPKLLAFDLNTSQLLKQVHIPHDI
AVNATTGKGGLVFLAVQAVDPINTMAYMADNRGNALSVYQNSDNSLHRLTSNTFDYDPRYTEFTIAGESFILQDGIFGI
AVSPVTNNLYYSPLSSRSLYYVNTEPFMKSEYEGNNVQYKGVEDIYNTQLSAKAVSKNGWFFGLVNNSALGCLNEH
QPIQRQNIDMVAQNEETLQMIFSIKIKQDFPQSNRINKTERNEYMLALSNRLQKFMNHNYNFNEVNFRVLSANVNDLIK
NTRCANFN NQAHHSSKSH SEQ ID NO: 35 Jellein-3 from Apis mellifera
EPFKISIHL SEQ ID NO: 36 Defensin-1 protein from Apis mellifera carnica including signal peptide
MKIYFIVGLLFMAMVAIMAAPVEDEFEPLEHFENEERADRHRRVTCDLLSFKGQVNDSACAANCLSLGKAGGHCEKG
VCICRKTSFKDLWDKRFG SEQ ID NO: 37 Defensin-1 protein from Apis mellifera carnica without signal peptide
APVEDEFEPLEHFENEERADRHRRVTCDLLSFKGQVNDSACAANCLSLGKAGGHCEKGVCICRKTSFKDLWDKRFG SEQ ID NO: 38 Apisimin protein from Apismellifera including signal peptide
MSKIVAVWLAAFCVAMLVSDVSAKTSISVKGESNVDWSQINSLVSSIVSGANVSAVLLAQTLVNILQILIDANVFA SEQ ID NO: 39 Apisimin protein from Apis mellifera without signal peptide
KTSISVKGESNVDWSQINSLVSSIVSGANVSAVLLAQTLVNILQILIDANVFA SEQ ID NO: 40 Apisimin protein from Apis cerana cerana including signal peptide
MSKIIAVWLAAFCVAMLVSDVSAKTSISAKAESNVDWSQINSLVSSIVSGANVSAVLLAQTLVNILQILIDANVFA SEQ ID NO: 41 Apisimin protein from Apis cerana cerana without signal peptide
KTSISAKAESNVDWSQINSLVSSIVSGANVSAVLLAQTLVNILQILIDANVFA SEQ ID NO: 42 degenerate DNA sequence encoding for the RJMP1 polypeptideof SEQ ID NO: 1
atgacnmgnytnttyatgytngtntgyytngghathgtntgycarggnacnacnggnaayathytnmgnggngarwsnytnaayaarwsnyt
nccnathytncaygartggaarttyttygaytaygayttyggnwsngaygarmgnmgncargaygcnathytnwsnggngartaygaytaya -continued

```
araayaaytayccnwsngayathgaycartggcaygayaarathttygtnacnatgytnmgntayaayggngtnccnwsnwsnytnaaygtn
athwsnaaraargtnggngayggnggnccnytnytncarccntayccngaytggwsnttygcnaartaygaygaytgywsnggnathgtnws
ngcnwsnaarytngcnathgayaartgygaymgnytntgggtnytngaywsnggnytngtnaayaayacncarccnatgtgywsnccnaary
tnytnacnttygayytnacnacnwsncarytnytnaarcargtngarathccncaygaygtngcngtnaaygcnacnacnaarggnmgnytn
wsnwsnytngcngtncarwsnytngaytgyaayacnaaywsngayacnatggtntayathgcngaygaraarggngarggnytnathgtnta
ycayaaywsngaygaywsnttycaymgnytnacnwsnaayacnttygaytaygayccnaarttyacnaaratgacnathgayggngarwsnt
ayacngcncargayggnathwsnggnatggcnytnwsnccnatgacnaayaayytntaytaywsnccngtngcnwsnacnwsnytntaytay
gtnaayacngarcarttymgnacnwsngaytaycarcaraaygayathcaytaygarggngtncaraayathytngayacncarwsnwsngc
naargtngtnwsnaarwsnggngtnytnttyttyggnytngtnggngaywsngcnytnggntgytggaaygarcaymgnacnytngarmgnc
ayaayathmgnacngtngcncarwsngaygaracnytncaratgathgcnwsnatgaarathaargargcnytnccncaygtnccnathtty
gaymgntayathaaymgngartayathytngtnytnwsnaayaaratgcaraaratggtnaayaaygayttyaayttygaygaygtnaaytt
ymgnathatgaaygcnaaygtnaaygarytnathytnaayacnmgntgygaraayccngayaaygaymgnacnccnttyaarathwsnathc
ayytn
```

SEQ ID NO: 43 degenerate DNA sequence encoding for the RJMP2 polypeptide of SEQ ID NO: 6

```
atgacnmgntggytnttyatggtngcntgyytnggnathgcntgycarggngcnathgtnmgngaraaywsnccnmgnaayytngaraarws
nytnaaygtnathcaygartggaartayttygaytaygayttyggnwsngargarmgnmgncargcngcnathcarwsnggngartaygayc
ayacnaaraaytayccnttygaygtngaycartggmgngayaaracnttygtnacnathytnmgntaygayggngtnccnwsnacnytnaay
gtnathwsnggnaaracnggnaarggnggnmgnytnytnaarccntayccngaytggwsnttygcngarttyaargaytgywsnaarathgt
nwsngcnttyaarathgcnathgayaarttygaymgnytntgggtnytngaywsnggnytngtnaaymgnacngtnccngtntgygcnccna
arytncaygtnttygayytnaaracnwsnaaycayytnaarcarathgarathccncaygayathgcngtnaaygcnacnacnggnaarggn
ggnytngtnwsnytngcngtncargcnathgayytngcnaayacnytngtntayatggcngaycayaarggngaygcnytnathgtntayca
raaygcngaygaywsnttycaymgnytnacnwsnaayacnttygaytaygayccnmgntaygcnaaratgacnathgayggngarwsnttya
cnytnaaraayggnathtgyggnatggcnytnwsnccngtnacnaayaayytntaytaywsnccnytngcnwsncayggnytntaytaygtn
aayacngcnccnttyatgaarwsncarttyggngaraayaaygtncartaycarggnwsngargayathytnaayacncarwsnytngcnaa
rgcngtnwsnaaraayggngtnytnttygtnggnytngtnggnaaywsngcngtnggntgytggaaygarcaycarwsnytncarmgncara
ayytngaratggtngcncaraaygaymgnacnytncaratgathgcnggnatgaarathaargargarytnccncayttygtnggnwsnaay
aarccngtnaargaygartayatgytngtnytnwsnaaymgnatgcaraarathgtnaaygaygayttyaayttygaygaygtnaayttymg
nathytnggngcnaaygtnaargarytnathmgnaayacncaytgygtnaayaayaaycaraaygayaayathcaraayacnaayaaycara
aygayaayaaycaraaraayaayaaraaraaygcnaayaaycaraaraayaayaaycaraaygayaay
```

SEQ ID NO: 44 degenerate DNA sequence encoding for the RJMP3 polypeptide of SEQ ID NO: 10

```
atgacnaartggytnytnytngtngtntgyytnggnathgcntgycargaygtnacnwsngcngcngtnaaycaycarmgnaarwsngcnaa
yaayytngcncaywsnatgaargtnathtaygartggaarcayathgayttygayttyggnwsngaygarmgnmgngaygcngcnathaarw
snggngarttygaycayacnaaraaytayccnttygaygtngaymgntggmgngayaaracnttygtnacnathgarmgnaayaayggngtn
ccnwsnwsnytnaaygtngtnacnaayaaraarggnaarggnggnccnytnytnmgnccntayccngaytggwsnttygcnaartaygarga
ytgywsnggnathgtnwsngcnttyaarathgcngtngayaarttygaymgnytntgggtnytngaywsnggnytngtnaayaayaaycarc
cnatgtgywsnccnaarytnytnacnttygayytnaaracnwsnaarytngtnaarcargtngarathccncayaayathgcngtnaaygcn
acnacnggnatgggngarytngtnwsnytngcngtncargcnathgaymgnacnaayacnatggtntayathgcngaygaraarggngargg
nytnathatgtaycaraaywsngaygaywsnttycaymgnytnacnwsnaayacnttygaytaygayccnmgntayacnaarytnacngtng
cnggngarwsnttyacngtnaaraayggnathtayggnathgcnytnwsnccngtnacnaayaayytntaytaywsnccnytnytnwsncay
ggnytntaytaygtngayacngarcarttywsnaayccncartaygargaraayaaygtncartaygarggnwsncargayathytnaayac
ncarwsnttyggnaargtngtnwsnaaraayggngtnytnttyytnggnytngtnggnaaywsnggnathgcntgygtnaaygarcaycarg
tnytncarmgngarwsnttygaygtngtngcncaraaygargaracnytncaratgathgtnwsnatgaarathatggaraayytnccncar
wsnggnmgnathaaygayccngarggnaaygartayatgytngcnytnwsnaaymgnatgcaraarathathaayaaygayttyaayttyaa
ygaygtnaayttymgnathytnggngcnaaygtngaygayytnatgmgnaayacnmgntgyggnmgntaycayaaycaraaygcnggnaayc
araaygcngayaaycaraaygcngayaaycaraaygcnaayaaycaraaygcngayaaycaraaygcnaayaarcaraayggnaaymgncar
aaygayaaymgncaraaygayaayaarcaraayggnaaymgncaraaygayaayaarcaraayggnaaymgncaraaygayaayaarcaraa
yggnaaymgncaraayggnaayaarcaraaygayaayaarcaraayggnaaymgncaraaygayaayaarmgnaayggnaaymgncaraayg
ayaaycaraayaaycaraaygayaayaaymgnaaygayaaycargtncaycaywsnwsnaarytncay
```

SEQ ID NO: 45 degenerate DNA sequence encoding for the RJMP4 polypeptide of SEQ ID NO: 15

```
atgacnaartggytnytnytnatggtntgyytnggnathgcntgycaraayathmgnggnggngtngtnmgngaraaywsnwsnggnaaraa
yytnacnaayacnytnaaygtnathcayaartggaartayytngaytaygayttygayaaygaygarmgnmgncargcngcnathcarwsng
gngartaygaymgnacnaaraaytayccnytngaygtngaycartggcayaayaaracnttyytngcngtnathmgntayaayggngtnccn
wsnwsnytnaaygtngtnwsngayaaracnggnaayggnggnmgnytnytncarccntayccngaytggwsnttygcnaartaygargaytg
ywsnggnathgtnwsngcncayaarathgcnathgaygartaygarmgnytntgggtnytngaywsnggnytngtnaayaayacncarccna
tgtgywsnccnaarytnttygcnttygayytnaayacnwsncarytnytnaarcargtngarathccncaygaygtngcnacnacnggnaar
ggngarytngtnwsnytnacngtncargcnatggaywsnacnaayacnatggtntayatggtngayaayaaraayacnytnathathtayca
raaygcngaygaywsnttycaymgnytnwsnwsncayacnytnaaycayaaywsngayaaratgwsngaycarcargaraayytnacnytna
argargtngayaayaargtntayggnatggcnytnwsnccngtnacncayaayytntaytayaaywsnccnwsnwsngaraayytntaytay
gtnaayacngarwsnytnatgaarwsngaraaycarggnaaygaygtncartaygarmgngtncargaygtnttygaywsncarytnacngt
naargcngtnwsnaaraayggngtnytnytnttyggnytngcnaayaayacnytnwsntgytggaaygarcaycarwsnytngaymgncara
ayathgaygtngtngcnmgnaaygargayacnytncaratggtngtnwsnatgaarathaarcaraaygtnccncarwsnggnmgngtnaay
aayacncarmgnaaygartayytnytngcnytnwsngaymgnaaycaraaygtnytnaayaaygayytnaayytngarcaygtnaayttyca
rathytnggngcnaaygtnaaygayytnathmgnaaywsnmgntgygcnaayttygayaaycargayaayaaycaytayaaycayaaycaya
aycargcnmgncaywsnwsnaarwsngayaaycaraayaayaaycarcayaaygaycargcncaycaywsnwsnaarwsnaayaaymgncay
aayaayaaygay
```

SEQ ID NO: 46 degenerate DNA sequence encoding for the RJMP5 polypeptide of SEQ ID NO: 19

```
atgacnacntggytnytnytngtngtntgyytnggnathgcntgycarggnathacnwsngtnacngtnmgngaraaywsnccnmgnaaryt
ngcnaaywsnatgaaygtnathcaygartggaartayytngaytaygayttyggnwsngaygarmgnmgncargcngcnatgcarwsnggng
artaygaycayacnaaraaytayccnttygaygtngaycartggmgnggnatgacnttygtnacngtnccnmgntayaarggngtnccnwsn
wsnytnaaygtnathwsngaraarathggnaayggnggnmgnytnytncarccntayccngaytggwsntgggcnaaytayaargaytgyws
nggnathgtnwsngcntayaarathgcnathgayaarttygaymgnytntggathytngaywsnggnathathaayaayacncarccnatgt
gywsnccnaarytncaygtnttygayytnaayacnwsncaycarytnaarcargtngtnatgccncaygayathgcngtnaaygcnwsnacn
ggnaayggnggnytngtnwsnytngtngtncargcnatggayccngtnaayacnathgtntayatggcngaygayaarggngaygcnytnat
hgtntaycaraaywsngaygarwsnttycaymgnytnacnwsnaayacnttygaytaygayccnaartayathaaratgatggaygcnggng
arwsnttyacngcncargayggnathttyggnatggcnytnwsnccnatgacnaayaayytntaytaywsnccnytnwsnwsnmgnwsnytn
taytaygtnaayacnaarccnttyatgaarwsngartayggngcnaayaaygtncartaycarggngtncargayathttyaayacngarws
nathgcnaarathatgwsnaaraayggngtnytnttyttyggnytnatgaayaaywsngcnathggntgytggaaygarcaycarccnytnc
```

-continued armgngaraayatggayatggtngcncaraaygargaracnytncaracngtngtngcnatgaaratgatgcayytnccncarwsnaayaar
atgaaymgnatgcaymgnatgaaymgngtnaaymgngtnaaymgnatggaymgnatggaymgnathgaymgnatggaymgnatggaymgnat
ggayacnatggayacnatggaymgnathgaymgnatggaymgnatggaymgnathgaymgnathgaymgnatgcayacnatggayacnatgg
ayacnatggaymgnacngayaaratgwsnwsnatggaymgnatggaymgnatggaymgngtngaymgnatggayacnatggaymgnacngay
aaratgwsnwsnatggaymgnatggaymgnatggaymgngtngayacnatggayacnatggayacnatggaymgnatggaymgnatggaymg
natggaymgnatggaymgnatggaymgnatggayacnatggaymgnacngayaaratgwsnmgnathgaymgnatggayaarathgaymgna
tggaymgnatggaymgnacnaaymgnatggaymgnatgaaymgnatgaaymgncaratgaaygartayatgatggcnytnwsnatgaarytn
caraarttyathaayaaygaytayaayttyaaygargtnaayttymgnathytnggngcnaaygtnaaygayytnathatgaayacnmgntg
ygcnaaywsngayaaycaraayaayaaycaraayaarcayaayaay SEQ ID NO: 47 degenerate DNA sequence encoding for the jellin-3 polypeptide of SEQ ID NO: 35
garccnttyaarathwsnathcayytn SEQ ID NO: 48 degenerate DNA sequence encoding for the defensin-1 polypeptide of SEQ ID NO: 36
atgaarathtayttyathgtnggnytnytnttyatggcnatggtngcnathatggcngcnccngtngargaygarttygarccnytngarca
yttygaraaygargarmgngcngaymgncaymgnmgngtnacntgygayytnytnwsnttyaarggncargtnaaygaywsngcntgygcng
cnaaytgyytnwsnytnggnaargcnggnggncaytgygaraarggngtntgyathtgymgnaaracnwsnttyaargayytntgggayaar
mgnttyggn SEQ ID NO: 49 degenerate DNA sequence encoding for the apisimin polypeptide of SEQ ID NO: 40
atgwsnaarathgtngcngtngtngtnytngcngcnttytgygtngcnatgytngtnwsngaygtnwsngcnaaracnwsnathwsngtnaa
rggngarwsnaaygtngaygtngtnwsncarathaaywsnytngtnwsnwsnathgtnwsnggngcnaaygtnwsngcngtnytnytngcnc
aracnytngtnaayathytncarathytnathgaygcnaaygtnttygcn SEQ ID NO: 50 >tr|A0A2A3E6X8|A0A2A3E6X8_APICC Bee-milk protein OS = Apis cerana cerana
OX = 94128 GN = APICC_08462 PE = 3 SV = 1
MLICSINVGWNHTRESPTLIPYPSFEAHQYEAGSVPEIISPFRIRVDRCERLWVLDTGFTDILQNPEQEAPPALLVYDLK
NDRLLRKFVIPEDQKTHDSLFANIALEDYSCEDTFAYLGDLGGPGLWYSWKSRKSWLVKHRFFQPDPQSEEFNVSGI
SFHWTDGLFGMSIAPSNDGYSVMYFHPLSSTMEYSVSTKILRDPERANSPDNFKEFRALGSRGHNGQSSVSFLDPN
TGVLFYALTNLNAIACWKPRNTFTLHQQGFIYQNSITMVFPNDLKIDQNGNIWVLSDRLPTFMYARLDPEDYNFRILMG
SAKEAIRDTKGEKNDTMGKSESSIPGFENFPGREAKVKTGYAYLEGRRQVDGAEDLWRIGNSLYDLEGFAKFHPGGA
EWIRLTKGTDITELFQTHHLTDKATKLLPKYFIREAWPRKLPLTFEPNGFFSTFKRRALEALKDVNFHQPSTKTNLIADF
LFTSSLIFSILTAYTQSYLMIVFTGILLAWTAISGHNYLHMKDNFRMYYFDLSTMSSKDWRITHAMSHHMYPNTLWDYEI
YAFEPFIHWLPDPKKSLVMTFVSQLMSPIIWALVFYEQAIKRYYSVFFEYKTFEIRDAIPFFLPVLMSFFTPNFFTAVKLW
LLIIMATSFIFSIIGFNAAHHHPDIFHDGDIYRDDYDWGVLELDAVRERKVIDDSDFLVLTNFGLHGLHHLLPTVDHSYLPL
CVNAFEQTCKEFGIGIEKFTQWELIKGQFKQLAHRDFYSSPSGCRSKRGGNAEPSNWGLNAGR SEQ ID NO: 51 >tr|A0A2A3E8K1|A0A2A3E8K1_APICC Bee-milk protein OS = Apis cerana cerana
OX = 94128 GN = APICC_06912 PE = 3 SV = 1
MKKVLPEEMNFNINTYIHKDIVQVYKLSVKTRPLLNIEMFRKTFVLLVSLAYLGSVYGIQRWGTQFGQAPLLERFFWRT
LDFAYPDEASKTMAMMKGEYIPENALPVGIEIWRNKLFVTVPRWRNGIPATLTYISLDTNRGGTPKLTPYPNWTQNKA
GACGSAITTAYRIHADSCDRLWVLDTGTIGIGNTTIQACPYTLNIFDLTSDKLLRQYRLRAEDINMALIRIRVKKNTFIANIA
VDLGKGGCNDAFAYMSDELGYGLIVYSWEQNRSWRITHSYFMPDPLAGDYNIGGLNFQWGEEGIFGMSLSPISVNG
YRTLFFHPLSSRREFAVSTRILRDENLSQNSYHEFQILPERGELGHCTASVMDENGLQFFNLIDQNAVGCWNSLLPYS
PENQAWARHDEAMIFPSDVKINRGLLWIISDRMPVFLLSTLNYTDVNFRILTMPVRDAIAGTICENSAWGFVGNSLCFI
NTCGIQF SEQ ID NO: 52 >tr|V9I6T6|V9I6T6_APICE Bee-milk protein OS = Apis cerana OX = 7461 GN =
ACCB00004.3 PE = 2 SV = 1
MTKWLLLWCLGIACQDVTSAAVNHQRKSSKNLAHSMKVIYEWKHIDYDFGSVERRDAAIKSGEFDHTKNYPFDVDR
WRDKTFVTVERFDGVPSSLNWTNKKGKGGPLLHPYPDWSWANYKDCSGIVSAFKIAVDKFDRLWVLDSGLVNNNQ
PMCSPKLVTFDLTTSKLLKQVEIPHNIAVNATTGMGELVSLAVQAIDPTNTMVYIADERGEALIIYQNSDDSFHRLTSNTF
DYDPRYTKLTVAGESFTVKNGICGIALSPVTNNLYYSPLASHSLYYVNTEQFRNPQYEESNVQYEGSQDILNTQSFAKA
VSKNGVFLGLVSNSAVGCVNEHQVLQKENFDVVAQNEETLQMIVSMKIMQDLPQSGRINDPGNEYMLALSNKMQKII
NNDFNFNDVNFRILGANVNHLTRNTRCAKSNNQNANNQNANNQNANNQNANNQNANNQNDNNQNDNGNNRRNG
NNQNGNRQNDNKQNDNKQNANKQNDNKQNVTRQNDNRQNDNKQNDNRQNDNRQNDNQAEW SEQ ID NO: 53 >tr|V9I763|V9I763_APICE Bee-milk protein OS = Apis cerana OX = 7461 GN =
ACCB00004.6 PE = 2 SV = 1
MTKWLLLWCLGIACQDVTSAAVNHQRKSSKNLAHSMKVIYEWKHIDYDFGSVERRDAAIKSGEFDHTKNYPFDVDR
WRDKTFVTVERFDGVPSSLNVVTNKKGKGGPLLHPYPDWSWANYKDCSGIVSAFKIAVDKFDRLWVLDSGLVNNNQ
PMCSPKLVTFDLTTSKLLKQVEIPHNIAVNATTGMGELVSLAVQAIDPTNTMVYIADERGEALIIYQNSDDSFHRLTSNTF
DYDPRYTKLTVAGESFTVKNGICGIALSPVTNNLYYSPLASHSLYYVNTEQFRNPQYEESNVQYEGSQDILNTQSFAKA
VSKNGVVFLGLVSNSAVGCVNEHQVLQKENFDVVAQNEETLQMIVSMKIMQDLPQSGRINDPGNEYMLALSNKMQKII
NNDFNFNDVNFRILGANVNHLTRNTRCAKSNNQNANNQNANNQNANNQNANNQNANNQNDNNQNDNGNNRRNG
NNQNGNRQNDNKQNDNKQNANKQNANKQNDNKQNDNRQNDNRQNDNKKNDNRQNDNKQNDNRQNDNRQNDN
QAEW SEQ ID NO: 54 >tr|A0A2A3ELA5|A0A2A3ELA5_APICC Bee-milk protein OS = Apis cerana cerana
OX = 94128 GN = APICC_05636 PE = 3 SV = 1
MKNTQTNIYVEVNGKQISNGKEEIVENENDEVDAVQQAIGNLGRWQIYVCLAISLVKFPIAWHQLAIVFMAPHQDYNCT
SPTRTETADQCVTNVNGTLLECTEWEYDRRTFTETIISQWNLVCSRTHYANIQQSILMFGVLLGNIIFGNLADRYGRKM
PLMISWLQLASGIGCAWPWFPALLLMKLLSALATGGTMVTSYVICMEIVGTKWRAAITVLYQIPFSLGHMSLAGLAYY
FRHWQHLQIAITLPSVILLSYWWIVPESPRWLLAFGKQRAACKILQKAANINNIKNKDIPDMVKQHCLHQNSKRSDFDH
KASFLDLFRTPNMRIKSLSIFFNWWCGMGLFGMSQYIGQVGGNIFVNFTVSGAIQIPGNFVAWWAMNKLGRRITLICS
NSIAGISALLLVIVSNDIEWLRLILVCLGIVGMSVSFTTVYLFSGELFPTWRNIGVGTSSMCARIGSITAPFWSLDHIQT
WLPPACFGILPLLGAALCFLLPETVGCTLPETLQDDMWHFLWIVFLVLANGEEIKTIYSWNVIEYNFPNDNIRNTLISNG
DYIEENNMPNGIQIWNDKVFITIPRWKNGVPSNLNFFLKNDGSESPKLNPYPNWEMNNINKVDSIINIIRVRVDACDRL -continued WGVDTGVDDILGNNTVIHQPRIIIDLKTDKILRIYPLKSSDTSDSFFVDLVIDVDPNNCDNTYAYISDLGGYALVVYSWA
KNDSWRITHNFFYFDPRYGNYNINGFNFQWKDGLFGLSLSALQTDGYKILYFHAMSSIAEFSVSTEVLQDHTLEKSSD
YYAFHFEGEKGPNSQGPSSVIDTNTGVDYFTQINRNGIACWDTTTELNPNTFILVAEDNTTMVFCNDLSIDRSSNTMYV
LSDNFQQLLFSKYDVKKHNFFITVFDLDFLTNACKKKDDKPKRRLPHIL SEQ ID NO: 55 >tr|A0A2A3EG07|A0A2A3EG07_APICC Bee-milk protein OS = Apis cerana cerana
OX = 94128 GN = APICC_06207 PE = 3 SV = 1
MTKWLLLMACLGIACQNIRGAWRENSSRKKLTNTLNVIHEWKYVDYDFGSDEKRQAAIQSGEYDRTKNYPLDVDQW
HDKTFVTMLRYDGVPSSLNWSDKTGNGGPLLQPYPDWSFAKYEDCSGIVSANKIAIDEYERLWVLDSGLVNNIQPM
CSPKLLAFDLTTSKLLKQVEIPHDVAVNATTGKGGLASLAVQAMDSVNTMVYMADNKDDALIVYQNADDSFHRLSSHIS
NHNFRSDKMSQENLTLKEVDNRVFGMALSSVTHNLYYSPLSSQNLYYVNTTSLMNSQNQGNDVQYESVQDVFSSQL
SAKAVSKNGVLFFGFTNNTLGCWNEHQSLDRQNIDIVARNETLQMVVGMKIKQNLPQSGKVNNTQRNEHLLALTNKK
QDVLNNDLNLEHVNFQILDANVNDLIRNSRCANSDNQDNNQHNYNHNQVRHSSKSDNQNNNQHNNQAYHSSKSDN
WDNNNNQAHHSSKFDNQNNNQYNN SEQ ID NO: 56 >tr|Q5VK55|Q5VK55_APICC Bee-milk pro-
tein OS = Apis cerana cerana OX = 94128 PE = 2
SV = 1
MTKWLFMVACLGIACQGAIIRQNSAKNLENSLNVIHEWKYIDYDFGSEERRQAAIQSGEYDHTKNYPFDVDQWHDKT
FVTILKYDGVPSTLNMISNKIGKGGRLLQPYPDWSWAENKDCSGIVSAFKIAIDKFDRLWVLDSGLINRTEPICAPKLHV
FDLKNTKHLKQIEIPHDIAVNATTGKGGLVSLVVQAMDPMNTLVYIADHKGDALIVYQNSDDSFHRMTSNTFDYDPRYA
KMTINGESFTLKNGICGMALSPVTNNLYYSPLASHGLYYVNTEPPFMKSQFGDNNNVQYEGSQDTLNTQSLAKAVSKD
GVLFVGLVGNSALGCLNEHQPLQRENLELVAQNEKTLQMIAGMKIKEELPHFVGSNKPVKDEYMLVLSNKMQKIVNND
FNFNDVNFRILGANVKELMRNTHCANFNNKNNQKNNNQKNNNQNNNQKNNNQKNNNQKNNNQKNNNQ
NTNN SEQ ID NO: 57 >tr|Q5I223|Q5I223_APICE Bee-milk protein (Fragment) OS = Apis cerana OX = 7461
GN = MRJP7 PE = 3 SV = 1
CLGIACQGAIVRKKSARNLENSLNVLHEWKYIDYDFGSEERRQAAIQSGEYDHTKNYPFDVDQWRDKTFVTVLRYDG
VPSSLNVISDKTGNGGRLLQPYPDWLWTKYKDCSGIVNAYNIAVDKYDRLWVLDSGLINNIQPMCSPKLLVFDLNSSQL
LKQVDIPHDAVNTTTENGRLASLWQAMNPMNTLVYLSDNKGDALIVYQNSDDSFHRLSSNTL SEQ ID NO: 58 >tr|Q5I224|Q5I224_APICE Bee-milk protein (Fragment) OS = Apis cerana OX = 7461
GN = MRJP1 PE = 3 SV = 1
CLGIACQGTTSSILRGESLNKSLVLHEWKFFDYDFDSDERRQDAILSGEYDYRKNYPSDVDQWHGKIFVTMLRYNG
VPSSLNVISKKIGDGGPLLQPYPDWSFAKYDDCSGIVSATKLAIDKCDRLWVLDSGLVNNTQPMCSPKLLTFDLTTSQL
LKQVEIPHDVAVNATTGKGRLSSLAVQPLDCNINGDTMVYIADEKGEGLIVYHDSDNSFHRLSSNT SEQ ID NO: 59 >tr|Q5I222|Q5I222_APICE Bee-milk protein (Fragment) OS = Apis cerana OX = 7461
GN = MRJP5 PE = 3 SV = 1
CLGIACQGITGATVRENSSRNLANSMNVIHEWKYLDYDFGSDEKRQAAIQSGEYDHTKNYPFDVDRWHDMTFVTVLR
YKGVPSSLNVISKKIGNGGPLLQPYPDWSWANYKDCSGIVSAYKIAIDKFDRLWVLDSGIINNTQPMCSPKLHVFDLNT
SQQIKQVMMPHDIAINATTGKGGLENLWQAMDPMNTLVYMADSKGDALIVYQNSDDSFHRLTSNT SEQ ID NO: 60 >tr|Q3ZLX2|Q3ZLX2_APICE Bee-milk protein (Fragment) OS = Apis cerana OX = 7461
GN = MRJP6 PE = 3 SV = 1
GVLFLGLVNNSAIGCWNEHQPLQKQNMDMVAQNEETLQIITSVKIIQNLSYSGRMNRIHKNEYMLALSNRMQKIVNND
FNFNDINFRILGANEG SEQ ID NO: 61 >tr|D3GET7|D3GET7_APICE Bee-milk protein (Fragment) OS = Apis cerana OX = 7461
GN = mrjp9 PE = 3 SV = 1
WKYFDYNFGSNERRQAAIQSGKYNYKNNFPIDVDRWHDKTFVTILRNNGVPSSLNVISNKIGNGGPLLEPYPNWSWA
ENQNCSGITSVYRVAIDVWGRLWVLDNGISGQTSVCSSQIVVFDLKTSKLLKQVKIPHNIAVNSTTGNINWTPIVQSFD
YNNTLVYIADVEGYA SEQ ID NO: 62 >tr|V9I6G8|V9I6G8_APICE Bee-milk protein OS = Apis cerana OX = 7461 GN =
ACCB00004.9 PE = 2 SV = 1
MTKWLLLWCLGIACQDVTSAAVNHQRKSSKNLAHSMKVIYEWKHIDYDFGSVERRDAAIKSGEFDHTKNYPFDVDR
WRDKTFVTVERFDGVPSSLNWTNKKGKGGPLLHPYPDWSWANYKDCSGIVSAFKIAVDKFDRLWVLDSGLVNNNQ
PMCSPKLVTFDLTTSKLLKQVEIPHNIAVNATTGMGELVSLAVQAIDERGEALIIYQNSDDSFHRLTSNTF
DYDPRYTKLTVAGESFTVKNGICIALSPVTNNLYYSPLASHSLYYVNTEQFRNPQYEESNVQYEGSQDILNTQSFAKA
VSKNGWFLGLVSNSAVGCVNEHQVLQKENFDWAQNEETLQMIVSMKIMQDLPQSGRINDPGNEYMLALSNKMQKII
NNDFNFNDVNFRILGANVKELMRNTHCANFNNKNNQKNNNQKNNNQNNNQKNNNQKNNNQKNNNQKNNNQTNN
N SEQ ID NO: 63 >tr|A0A481UKK6|A0A481UKK6_APICE Bee-milk pro-
tein OS = Apis cerana OX = 7461 PE = 2
SV = 1
MTRWLFMVACLGIACQGAIIRQNSAKNLENSLNVIHEWKYIDYDFGSEERRQAAIQSGEYDHTKNYPFDVDQWHDKT
FVTILKYDGVPSTLNMISNKIGKGGRLLQPYPDWSWAENKDCSGIVSAFKIAIDKFDRLWVLDSGLINRTEPICAPKLHV
FDLKNTKHLKQIEIPHDIAVNATTGKGGLVSLWQAMDPMNTLVYIADHKGDALIVYQNSDDSFHRMTSNTFDYDPRYA
KMTINGESFTLKNGICGMALSPVTNNLYYSPLASHGLYYVNTEPPFMKSQFGDNNNVQYEGSQDTLNTQSLAKAVSKD
GVLFVGLVGNSALGCLNEHQPLQRENLELVAQNEKTLQMIAGMKIKEELPHFVGSNKPVKDEYMLVLSNKMQKIVNND
FNFNDVNFRILGANVKELMRNTHCANFNNKNNQKNNNQKNNNQNNNQKNNNQKNNNQKNNNQKNNNQ
NTNN SEQ ID NO: 64 >tr|A0A2A3EHI0|A0A2A3EHI0_APICC Bee-milk protein OS = Apis cerana cerana
OX = 94128 GN = APICC_10183 PE = 3 SV = 1
MTKWLLLVVCLGIACQDVTSAAVNHQRKSSKNLAHSMKVIYEWKHIDYDFGSVERRDAAIKSGEFDHTKNYPFDVDR
WRDKTFVTVERFDGVPSSLNVVTNKKGKGGPLLHPYPDWSWANYKDCSGIVSAFKIAVDKFDRLWVLDSGLVNNNQ -continued PMCSPKLVTFDLNTSKLLKQVEIPHNIAVNATTGMGELVSLAVQAVDPTNTMVYIADERGEALIIYQNSDDSFHRLTSNT
FDYDPRYTKLTVAGESFTVKNGICGIALSPVTNNLYYSPLLLTVCIMLTQNNSGIHNMKKVTSNMKDPKIF SEQ ID NO: 65 >tr|A0A2A3EFT9|A0A2A3EFT9_APICC Bee-milk protein OS = Apis cerana cerana
OX = 94128 GN = APICC_08933 PE = 3 SV = 1
MSFNIWWLILYFGIVCQTITKAHYYSRHFKANALKWYQWKYFDYNFGSNERRQAAIQSGKYNYKNNFPIDVDRWHG
KVYKVLIIIEYLCRINSTNQNKTFVTILRNNGVPSSLNVISNKIGNGGPLLEPYPNWSWAENQNCSGITSVYRVAIDVWD
RLWVLDNGISGQTSVCSSQIWFDLKTSKLLKQVKIPHNIAVNSTTGNRNWTPIVQSFDYNNTLVYIADVEGYALIIYNN
ADDSFQRLTSSTFVYDPRYTNYTINEESFTLQDGILGMALSRKTQNLYYSAMSSHNLNYVNTKQFTQGKYQANNIQYQ
GASDILWTQATAKAISKTGALFFGLVTDTALGCWNENRPLKRGNIEIVAKNNDTLQFISGLKISKEISSHIFGYQNNEYIW
ALSNKYQKIANGDLNFNEVNFRILTAPFLLVRDFITYAQT SEQ ID NO: 66 >tr|A0A2A3EG05|A0A2A3EG05_APICC Bee-milk protein OS = Apis cerana cerana
OX = 94128 GN = APICC_09307 PE = 3 SV = 1
MTSWLLLWCLGIACQGITGATVRENSSRNLANSMNVIHEWKYLDYDFGSDEKRQAAIQSGEYDHTKNYPFDVDRWH
GKISIDKFDRLWVLDSGIINNTQPMCSPKLHVFDLNTSQQIKQVMMPHDIAINATTGKGGLENLWQAMDPMNTLLSL SEQ ID NO: 67 >tr|A0A2A3EFW1|A0A2A3EFW1_APICC Bee-milk protein OS = Apis cerana cerana
OX = 94128 GN = APICC_06204 PE = 3 SV = 1
MLHLFLLAGLFCTLTECTEILETIVQWPLLDFALPYDREFLNQYRPENWPTGIEVGWDKIFISVPRLRVGIPATLNYISKN
LPLESSPQLNAYPSWDWHSAGKGDLNCSLLISVYRTKLDRCNRLWVIDSGVMTSIDDFRPVCQPKIMVFDVKTDQLVR
QYTFPRESLRPNTLLTNLILDDTSATTCDDMFLYISDTTGPDGATDRSWRILHASMYPHPDFSTYRIGSDMFELF
DGVIGLAFSARLGTLYYQPLATDRLFSVPTTALQAGPPAFGEQLPVTLVGKKSSQGLALAVDPREDTILFAPFTEMAIAS
WQPQTNQQRILAYTPEKLQFVAEIRWAERDNGNIWVMSTKFQKFFKQEEMRQFYFSVILFLLAIADSQTQEKLKNIYS
WKALEFAFPNEFAKLAAIKSGSYIPGVSLPIDVDVYNTDLHFFYNTKLNSLFQERQSTVFVAIPRIQDGVPLTLGYVTKE
VSVDGNPLIAPYPSWSYNDVKYCDGLTSVYRMQVDKCGRLWVLDTGILGEKQTCRPKIHVFSLHDNKLITMYRFPQN
QFKDSSLFVTIAVDVRDTEDKCKDTFAYIADVTGFALLVYDFRNSRSWKITNNLFYPYPPYGTFNIKGDTFDLMDGILGL
ALGPIRNNDRILYFHSLASRIESWVHTSVIRNYTLFNENSEAAARSFVPFSIERSSQSVAEVMDRNGVLFFGLLSDLAIG
CWNSEHFFEYGGNNIEIIVKDPETLQFPSGMKIISSKKGIQELWVFTISFQKYMTGTLNSNETNFRIQAGLVDELVRGTK
CDVSLLGRFIPSQ SEQ ID NO: 68 >tr|A0A2A3EGQ1|A0A2A3EGQ1_APICC Bee-milk protein OS = Apis cerana cerana
OX = 94128 GN = APICC_05409 PE = 3 SV = 1
MANWPWLLSICLFGLQEIAIQPGSNALSRNLETSGQRSVSSGFRSSLRNYKTLISSHDELPGHINCDSSKFDEDLMNK
LPTTPEYNNHLYGSTPDSRDYFSRPFEKRLHSRLPGRNFNLLRTDANSVNELESHGFNYDPGRGHIEDDYVGPAMEL
VYAWSTIDYTYDSIEARDSAIFDGDFIAENNLPLGLEVWRDKVFITLPKWKDGIPVTLSTVPKHSKTKSPKLRPYPNWE
WHTVGNCDGLTSVFRIQVDECDRLWVLDSGKVDIAKGGNLACPPAIFIFDLTTDTLIRKYIIPNEQVKEDSLYTNIWDIR
NEDCGSAIAYISDVFRYGLLVYDFFKDSSFRIQHHFFYPDPLASKYEIHGLKFQWTDGIFGMALSPVDIHDDRTLFFHP
MSSFREFAVSTSILGDKKTAEENTDYFMPIGRPRAKDYGHSSGSVIDRNGVMFFNMVTRDSVWCWDTRKEYIPQNLG
VIGTSNLSLVFPNDIKVDHEYDQNVWVLSNKLAMYLYGSIDSSKINYRIFKANVKEAVKDTVCDPNYWPGSEHGYDEI
C SEQ ID NO: 69 >tr|V9IC18|V9IC18_APICE Bee-milk protein OS = Apis cerana OX = 7461 GN =
ACCB00543.2 PE = 2 SV = 1
MTSWLLLWCLGIACQGITGATVRENSSRNLANSMNVIHEWKYLDYDFGSDEKRQAAIQSGEYDHTKNYPFDVDRWH
DMTFVTVLRYKGVPSSLNVISKKIGNGGPLLQPYPDWSWANYKDCSGIVSAYKIAIDKFDRLWVLDSGIINNTQPMCSP
KLHVFDLNTSQQIKQVMMPHDIAINATTGKGGLENLWQAMDPMNTLVYMADNKGDALIVYQNSDDSFHRLTSNTFDY
DPKYIKMMAAGESFTLQDGIFGMALSPMTNNLYYSPLASRSLYYINTKPFMKSQYGTNNVQHEGVQDIFNTQSIAKIMS
KNGVLFFGLMNNSAIGCWNEHQPLQRQNMDMVAQNEETLQTWAMKMMHLPQSNRMNRMHRMNSMNRMDRMD
RMDRMDRMDKMDRMDRMDRMDRMDRMDRMDRMDRMDRMDIMDRTNKMDRMDRMDIMDKTNKMDRMDS
MIRIDKMDRMDRMHRIDIMNRMDRMDRMDTRIDTRMDRMDRMDKMDKINKMHRGMRMDRMDRMNRMNRQMNEY
MMALSMKLQKFINNDYNFNEVNFRILAANVNDLIMNTRCANSNNQNDNQNKHNN SEQ ID NO: 70 >tr|V9IA99|V9IA99_APICE Bee-milk protein OS = Apis cerana OX = 7461 GN =
ACCB00210.1 PE = 2 SV = 1
MCSPKLLAFDLTTSKLLKQVEIPYDIAVNASTGMGGLVSLWQAMDPMNTMVYIADDRGDALIIYQNSDDSFHRLSSNT
FDNDPRYSELTVAGESFTVHDGIFGMALSPVTNNLYYSPLTSHLSLYYVNTEPPFMKSQYGENNIQYEGIQDIFNTQSSAK
VMSKNGVLFFGLVNNSAIGCWNEHQPLQKQNMDMVAQNEETLQTITSVKIIQNLQYSGRMNRIHKNEYMLALSNRMQ
KIVNNDFNFNDINFRILGANVKNLIKNTRCANSKNQNNNQKKHKNQAH SEQ ID NO: 71 >tr|A0A2A3EFY1|A0A2A3EFY1_APICC Bee-milk protein OS = Apis cerana cerana
OX = 94128 GN = APICC_09306 PE = 3 SV = 1
MNAVSRTVAQSDETLQMIVGMKIKEALPHVPIFDRYINREYILVLSNRMQKMANNDYNFNDVNFRIMDANVNDLILNTR
CENPNNDNTPFKISIHL SEQ ID NO: 72 >tr|A0A2A3EFT1|A0A2A3EFT1_APICC Bee-milk protein OS = Apis cerana cerana
OX = 94128 GN = APICC_02709 PE = 3 SV = 1
MRKMFKNYPHSHDITIIDNNESLIKLLPGNLFSRRSDRMKRLLCVILSLTSLTKIFQLSDGTPVLPQPLIFSGLSLDWPCQ
STKNIYETSGRYIARNVIATRAQIFEDKAILALPRYKPGVPFTLGIDLKSQNNCEPKVAPFPCWAIQEEGNCQALQSAV
DIVLDVQDILWVLDVGIVNTLEQPVRRCPPKWGVNAKTGKVNFVVKVIDLSSLADINSRLQYMAVDYAEDGQVYVYIS
DAGSGAIIVYNVTTDTGYRWLPAAVAGCTDKPDALYIALVRRESCGPVLYFTFLGSNRMFAIKAVNLRSGNANGSIVDI
GGKKNKIVLLGTDNAATIFFRIKGDSSIYMWNTDTSFVQDNFLLVQKAGDCRLPTEVIPGYNDLMWVIESNFQDYIDNN
VSCSGTSVAVHPLMNSS SEQ ID NO: 73 >tr|A0A2A3EHL3|A0A2A3EHL3_APICC Bee-milk protein OS = Apis cerana cerana
OX = 94128 GN = APICC_06609 PE = 3 SV = 1
MKAGGLEVAFQWKYLDWLWPTVHLTGKNQTLGNAFTQDVDIDKYGRVFVTSPQWLEGVPISLSLVTKVSGIGGPLLV
PYPDWTWHTSYNCDGIISVYRLAIDECNRLWWDTGRVQGNAVCPTKILIFDLATDHLLHKYWPDDQVLFGKAALVTP -continued
```
IVDVGKTCLDTYLYVADVDQNGLLIYDLYHDYSWRVNNTRGNAFGPDDDATNITIAGESFDLTDGTLGMSLSPYGYFN
ERYLYFNSLASYRQKFTDTYSLKQSKYKEPIVLESNYKRASQAGVQATSRRGVIFFQLVQLTAVACWNIEKPFIPENVWV
IAQDEKTLQYVSGIKVITNNQGEEELWFNTNRLQKTINMTLKPTETNFRIIRGKVDDIVRGTNCEPSGAKHGFPDTNFW
HRI
```

SEQ ID NO: 74 >tr|A0A2A3EAP0|A0A2A3EAP0_APICC Bee-milk protein OS = Apis cerana cerana
OX = 94128 GN = APICC_00498 PE = 3 SV = 1
```
MKIWLLVTLVAVAKCHEPFRWFQWNTIDVMWPSEENKEYAISHNDYVPANNFIAGIKFWKGKMYLTIPRWKDGVPVT
LGVTSAKPVNYITAPKLEAFPSWEMQKIGDCSAFQMVQSMEIDPIGRMWVLDSGKMSPLSLEVKTTCPPRLVILDLEK
NGEVLRIYEFPTNVAHHGTTHLNDIVLDHEDGGMAYITDSDRNDPGIIVYSLRNNTSWKVRHDSMKAKQEAVKFMISK
TPINIPVPVDGIALSPASSNDRQIYYSPLSSFHLYSIPTSVLKNNASNVDSYVKELGRKNSQTDGMMMSAKGVLYFGLL
ADDAVAMWDTKQSISFTTGQRVISRDHERMQWPDTFAFDEDGNFYCVTNSLQNILENRVNVSIPNYRWRSQTGVKS
YQYLEDGTAPEQPEIPTSAANRISLAVTTGLTILLAFWQ
```

SEQ ID NO: 75 >tr|V9I620|V9I620_APICE Bee-milk protein OS = Apis cerana OX = 7461 GN =
ACCB00004.1 PE = 2 SV = 1
```
MTKWLFMVACLGIACQGAIIRQNSAKNLENSLNVIHEWKYIDYDFGSEERRQAAIQSGEYDHTKNYPFDVDQWHDKT
FVTILKYDGVPSTLNMISNKIGKGGRLLQPYPDWSWAENKDCSGIVSAFKIAIDKFDRLWVLDSGLINRTEPICAPKLHV
FDLKNTKHLKQIEIPHDIAVNATTGKGGLVSLWQAMDPMNTLVYIADHKGDALIVYQNSDDSFHRMTSNTFDYDPRYA
KMTINGESFTLKNGICGMALSPVTNNLYYSPLASHGLYYVNTEPFMKSQFGDNNNVQYEGSQDTLNTQSLAKAVSKD
GVLFVGLVGNSALGCLNEHQPLQRENLELVAQNEKTLQMIAGMKIKEELPHFVGSNKPVKEMNICWL
```

SEQ ID NO: 76 >tr|Q5VK56|Q5VK56_APICC Bee-milk pro-
tein OS = Apis cerana cerana OX = 94128 PE = 2
SV = 1
```
MTSWLLLWVCLGIACQGITGATVRENSSRNLANSMNVIHEWKYLDYDFGSDEKRQAAIQSGEYDHTKNYPFDVDRWH
DMTFVTVLRYKGVPSSLNVISKKIGNGGPLLQPYPDWSWANYKDCSGIVSAYKIAIDKFDRLWVLDSGIINNTQPMCSP
KLHVFDLNTSQQIKQVMMPHDIAINATTGKGGLENLWVQAMDPMNTLVYMADNKGDALIVYQNSDDSFHRLTSNTFDY
DPKYIKMMAAGESFTLQDGIFGMALSPMTNNLYYSPLASRSLYYINTKPFMKSQYGTNNVQHEGVQDIFNTQSIAKIMS
KNGVLFFGLMNNSAIGCWNEHQPLQRQNMDMVAQNEETLQTWVAMKMMHLPQSNRMRMHKMNRVNSMNRMDR
MDRMDKMDRMDRMDRIDGMDRMDRMDRMHTMDTMYRMDRIDMDRTNKMDRMDRMDIMD
KMNKMDRMDSMIRIDKMDRMDRMDRIDIMNRMDRMDRMDTMDRIDTMDRMDRMDRMDKMDKINKMHRMGRMDR
MDRMNRMNQMNEYMMALSMKLQKFINNDYNFNEVNFRILAANVNDLIMNTRCANSNNQNDNQNKHNN
```

SEQ ID NO: 77 >tr|V9IFQ1|V9IFQ1_APICE Bee-milk protein OS = Apis cerana OX = 7461 GN =
ACCB02917 PE = 2 SV = 1
```
MKIWLLVTLVAVAKCHEPFRWFQWNTIDVMWPSEENKEYAISHNDYVPANNFIAGIKFWKGKMYLTIPRWKDGVPVT
LGVTSAKPVNYITAPKLEAFPSWEMQKIGDCSAFQMVQSMEIDPIGRMWVLDSGKMSPLSLEVKTTCPPRLVILDLEK
NGEVLRIYEFPTNVAHHGTTHLNDIVLDHEDGGMAYITDSDRNDPGIIVYSLRNNTSWKVRHDSMKAKQEAVKFMISK
TPINIPVPVDGIALSPASSNDRQIYYSPLSSFHLYSIPTSVLKNNASNVDSYVKELGRKNSQTDGMMMSAKGVLYFGLL
ADDAVAMWDTKQSISFTTGQRVISRDHERMQWPDTFAFDEDGNFYCVTNSLQNILENRVNVSIPNYRWRSQTGVKS
YQYLEDGTAPEQPEIPTSAANRISLAVTTGLTILLAFWQ
```

SEQ ID NO: 78 >tr|A0A2A3EI18|A0A2A3EI18_APICC Bee-milk protein OS = Apis cerana cerana OX =
94128 GN = APICC_06209 PE = 3 SV = 1
```
MMAAGESFTLQDGIFGMALSPMTNNLYYSPLASRSLYYINTKPFMKSQYGTNNVQHEGVQDIFNTQSIAKIMSKNGVL
FFGLMNNSAIGCWNEHQPLQRQNMDMVAQNEETLQTWAMKMMHLPQSNRMRMHRMNSMNRMDRMDRMDRM
DRMDRMDIMDRTNKMDRMDRMDIMDKTNKMDRMDSMIRIDKMDRMNRMHRIDIMNRMDRMDRMDTRIDTRMDRM
DRMDKMDKINKMHRMGRMDRMDRMNRMNRMNRQMNEYMMALSMKLQKFINNDYNFNEIDKFDRLWVLDSGLINNTKLI
CSPKLLAFDLNISQLLKQVHIPHDIAVNAITGKGGLVFLAVHAVDPINNMAYMADNRGNALSVYQNSDDSLHRLTSNTFD
YDSRYTELTIAGESFTLQDGIFRIAVSPVTNNLYYSPLSSRSLVEDIYNTQLSAKAVSKNGWFFGLVNNSVLGCLNEYQ
PIQRQNIVNKTFVTILKYDGVPSTLNMISNKIGKGGRLLQPYPDWSWAENKDCSGIVSAFKIAIDKFDRLWVLDSGLINR
TEPICAPKLHVFDLKNTKHLKQIEIPHDIAVNATTGKGGLVSLWQAMDPMNTLVSLNYN
```

SEQ ID NO: 79 >tr|V9IA93|V9IA93_APICE Bee-milk protein OS = Apis cerana OX = 7461 GN =
ACCB00543.1 PE = 2 SV = 1
```
MTSWLLLVVCLGIACQGITGATVRENSSRNLANSMNVIHEWKYLDYDFGSDEKRQAAIQSGEYDHTKNYPFDVDRWH
DMTFVTVLRYKGVPSSLNVISKKIGNGGPLLQPYPDWSWANYKDCSGIVSAYKIAIDKFDRLWVLDSGIINNTQPMCSP
KLHVFDLNTSQQIKQVMMPHDIAINATTGKGGLENLWVQAMDPMNTLVYMADNKGDALIVYQNSDDSFHRLTSNTFDY
DPKYIKMMAAGESFTLQDGIFGMALSPMTNNLYYSPLASRSLYYINTKPFMKSQYGTNNVQHEGVQDIFNTQSIAKIMS
KNGVLFFGLMNNSAIGCWNEHQPLQRQNMDMVAQNEETLQTVVAMKMMHLPQSNRMRMHRMNSMNRMDRMD
RMDRMDRMDRMDRMDRMDRMDIMDRTNKMDRMDSMIRIDKM
DRMDRMHRIDIMNRMDRMDRMDTRIDTRMDRMDRMDKMDKINKMHRMGRMDRMDRMNRMNRMNRQMNEYMMALSM
KLQKFINNDYNFNEVNFRILAANVNDLIMNTRCANSNNQNDNQNKHNN
```

SEQ ID NO: 80 >tr|A0A2A3EH93|A0A2A3EH93_APICC Bee-milk protein OS = Apis cerana cerana
OX = 94128 GN = APICC_06210 PE = 3 SV = 1
```
MKSQFGDNNNVQYEGSQDTLNTQSLAKAVSKDGVLFVGLVGNSALGCLNEHQPLQRENLELVAQNEKTLQMIAGMKI
KEELPHFVGSNKPVKDEYMLVLNKTFVTVLRYDGVPSSLNVISDKTGNGGRLLQPYPDWSWTKYKDCSGIVNAYNIAV
DKYDRLWVLDSGLINNIQPMCSPKLLFDLNSSQLLKQVDIPHDIAVNTTTENGRLASLVVQAMNPMNTLSLTNNLYYS
PLASRDLYYVNTKPFMKSEYGENNVQYKGVQNIFNTQSTAKAVSKNGVLFFGLVNNTAVGCWNEHQTLQRENTDMV
AQNEETLQMIVGMKIKELLPHIVIIDINNIINNEYMLVLSNRMQLNNDLNDINFRIDINFRILIGEKIFRKMIRWLLLMYLGIAC
QGVTDIHSKNLTNSLKVIYEWKYIDYDFGSDEKRQAAIQSGDYNYTMNYLFDTDQWGDKTFVIIMKFNGVPSSLNVITN
KTGNGGPLLAPYPDWTWAKNENCSGIMSVYKIEIDICDRLWVLDSGLINNVQSVCPPQLLVFDLNTSQLLKQVKIPHDI
AVNTTTGNGALVTLSVQPLSCEVNGSTLVYIGDNEGFALIIYNNSDNSFQRLTSTFASDPRYTTFTINGESFTLQSGIF
GMALSPVTQNLYYSALSSHNLNYVNTEQFLKSQYQANNVHYQGKENILWTQASAKGISDNGVLFFGLVGDTSLACWN
ENRLLDRKNIEWAKNKETLQAITGLKVKRKILLFVVHGFPVEYEYVLAANALKWYQWKYFDYNFGSNERRQAAIQSG
KYNYKNNFPIDVDRWHGKVYKVLIIIEYLCRINSTNQNKTFVTILRNNGVPSSLNVISNKIGNGGPLLEPYPNWSWAEN
```

```
QNCSGITSVYRVAIDVWDRLWVLDNGISGQTSVCSSQIWFDLKTSKLLKQVKIPHNIAVNSTTGNRNWVTPIVQSFDY
NNTLVYIADVEGYALIIYNNADDSFQRLTSSTFVYDPRYTNYTINEEESFTLQDGILGMALSRKTQNLYYSAMSSHNLNYV
NTKQFTQGKYQANNIQYQGASDILWTQATAKAISKTGALFFGLVTDTALGCWNENRPLKRGNIEIVAKNNDTLQFISGL
KISKEISSHIFGYQNNEYIWALSNKYQKIANGDLNFNEVNFRILTAPVNQLISHTRCENPNTNFFSIH

SEQ ID NO: 81 >tr|A0A2A3EHH1|A0A2A3EHH1_APICC Bee-milk protein OS = Apis cerana cerana
OX = 94128 GN = APICC_06208 PE = 3 SV = 1
MTNWLLLIVCLSIACQDVTSAIHRRKSSKNLEHSMNVIHEWKYLDYDFDSNEKKQAAIQFGEYDYTKNYPFDVDQWH
DKTFVAVIRYDGVPSSLNVISDKTGNGGRLLQPYPDWSWANYKDCSGIVSVYKIAIDKFDRLWVLDSGLINNIQLMCSP
KLLAFDLTTSKLLKQVEIPYDIAVNASTRMGGLVSLWQAMDPMNTMVYIADDRGDALIVYQNSDDSFHRLNSNTFDND
PRYSELTVAGESFTVHDGIFGMALSPVTNNLYYSPLTSHSLYYVNTEPFMKSQYGENNIQYEGIQDIFNTQSSAKVMSK
NGVLFFGLVNNSAIGCWNEHQPLQKQNMDMVAQNEETLQIITSVKIIQNLSYSGRMNRIHKNEYMLALSNRMQKIVNN
DFNFNDINFRILGANVKNLIKNTRCANSKNQNNNQKKHKNQAH SEQ ID NO: 82 >tr|A0A2A3EGP0|A0A2A3EGP0_APICC Bee-milk protein OS = Apis cerana cerana
OX = 94128 GN = APICC_10025 PE = 3 SV = 1
MYIKGHFAPAFTLTAILAWLELISCGNATLPETIKWTGGNFEWPSSTTKNMYKSNGKYIPKNVIATRVAMHNNEAIVALP
RFKAGIPATLAKLSKEAQNCEATLIPYPCWSLQEEGTCTALQNWDLYLDPQNILWILDTGWVDTLDEPVRKCPAKVLAI
DVTSEKLIKTVELTGLTSPTSRLQYVVSDYTQDGRVFIYVSDAASRAILVYDVTSGRGYRVVLPQAVSMGCTRRDVLYL
ALLRRSDGSTCLIFTYLSSSRMFSIRTEHLRNGSTRGRIHDLGMKPRKMWLGTDNGSALFFRYEGEADVYRWDAAS
NPFDPROFKKVYTSAECNLVTHIVADYARGSMRVLESNFPDYMQGTVGCGATQVLNVM SEQ ID NO: 83 >tr|Q5VLE2|Q5VLE2_APICC Bee-milk pro-
tein OS = Apis cerana cerana OX = 94128 PE = 2
SV = 1
MTRWLFMWCLGIVCQGTTSSILRGESLNKSLSVLHEWKFFDYDFDSDERRQDAILSGEYDYRKNYPSDVDQWHGKI
FVTMLRYNGVPSSLNVISKKIGDGGPLLQPYPDWSFAKYDDCSGIVSATKLAIDKCDRLWVLDSGLVNNTQPMCSPKL
LTFDLTTSQLLKQVEIPHDVAVNATTGKGRLSSLAVQPLDCNINGDTMVYIADEKGEGLIVYHDSDYSFHRLTSKTFDYD
PKFTKMTINGESFTTQNGISGMALSPMTNNLYYSPVASTSLYYVNTEQFRTSNYEQNAVHYEGVQNILDTQSSAKWS
KSGVLFFGLVGDSALGCWNEHRSLERHNIRTVAQSDETLQMIVGMKIKEALPHVPIFDRYINREYILVLSNRMQKMANN
DYNFNDVNFRIMDANVNDLILNTRCENPNNDNTPFKISIHL SEQ ID NO: 84 >tr|V9IHW6|V9IHW6_APICE Bee-milk pro-
tein OS = Apis cerana OX = 7461 GN = ACCB07077
PE = 2 SV = 1
MSFNIWWLILYFGIVCQTITKAHYYSRHFKANALKWYQWKYFDYNFGSNERRQAAIQSGKYNYKNNFPIDVDRWHD
KTFVTILRNNGVPSSLNVISNKIGNGGPLLEPYPNWSWAENQNCSGITSVYRVAIDVWDRLWVLDNGISGQTSVCSSQ
IVVFDLKTSKLLKQVKIPHNIAVNSTTGNRNWTPIVQSFDYNNTLVYIADVEGYALIIYNNADDSFQRLTSSTFVYDPRYT
NYTINEEESFTLQDGILGMALSRKTQNLYYSAMSSHNLNYVNTKQFTQGKYQANNIQYQGASDILWTQATAKAISKTGAL
FFGLVTDTALGCWNENRPLKRGNIEIVAKNNDTLQFISGLKISKEISSHIFGYQNNEYIWALSNKYQKIANGDLNFNEVN
FRILTAPVNQLISHTRCENPNTNFFSIH SEQ ID NO: 85 >tr|V9IJS1|V9IJS1_APICE Bee-milk pro-
tein OS = Apis cerana OX = 7461 GN = ACCB10451
PE = 2 SV = 1
MWHFLWIVFLVLANGEEIKTIYSWNVIEYNFPNDNIRNTLISNGDYIEENNMPNGMQIWNDKVFITIPRWKNGVPSNLNF
FLKNDGSESPKLNPYPNWEMNNINKVDSIINIIRVRVDACDRLWGVDTGVDDILGNNTVIHQPRIIIDLKTDKILRIYPLKS
SDQTSDSFFVDLVIDVDPNNCDNTYAYISDLGGYALWYSWAKNDSWRITHNFFYFDPRYGNYNINGFNFQWKDGLF
GLSLSLALQTDGYKILYFHAMSSIAEFSVSTEVLQDHTLEKSSDYYAFHFEGEKGPNSQGPSSVIDTNTGVDYFTQINRN
GIACWDTTTELNPNTFILVAEDNTTMVFCNDLSIDRSSNTMYVLSDNFQQLLFSKYDVKKHNFFITVFDLDFLTNACKKK
DDKPKRRLPHIL SEQ ID NO: 86 >tr|V9I606|V9I606_APICE Bee-milk protein OS = Apis cerana OX = 7461
GN = ACCB00004.10 PE = 2 SV = 1
MTIEGESFTTQNGISGMALSPLTNNLYYSPLASRDLYYVNTKPFMKSEYGENNVQYKGVQNIFNTQSTAKAVSKNGVL
FFGLVNNTAVGCWNEHQTLQRENTDMVAQNEETLQMIVGMKIKELLPHIVIIDINNIINNEYMLVLSNRMQKILNNDLNF
NDINFRILIGGVTDLLENTRCANSNIQNNNNQITILTVKITITI SEQ ID NO: 87 >tr|Q86M23|Q86M23_APIDO Bee-milk protein (Fragment) OS = Apis dorsata OX = 7462
PE = 3 SV = 1
VNNSALGCWNEHQSLQRQNMDMVAQNEETLQMIISVKIMQNLPYSGRMNRIHKNEYILALSNRMQKIVNNDFNFNKI
N
SEQ ID NO: 88 >tr|Q86M25|Q86M25_APIDO Major royal jelly protein 5-like protein (Fragment) OS =
Apis dorsata OX = 7462 GN = MRJP5 PE = 4 SV = 1
MKMMHLSQSNNMNRMHNMNRMDKMNGMDRINRMDSMDRMDSMDRVDRMDSMDRMDRMDRIDRMDRMNKMD
NMDRMDRQKNEY
```

REFERENCES

Arambepola, C. S. (2009). Defining low in fat' and 'high in fat' when applied to a food. *Public Health Nutrition,* 12(3), 341-350. doi:10.1017/S136898000800205X Bhattacharya, S. B. (2012). Food Gels: Gelling Process and New Applications, Critical Reviews in Food Science and Nutrition. 52(4), 334-346. doi:10.1080/10408398.2010.500234

Bocian, A., Buczkowicz, J., Jaromin, M., Hus, K., & Legáth, J. (2019). An Effective Method of Isolating Honey Proteins. *Molecules,* 24, 2399.

Brudzynski, K. S. (2015). MRJP1-containing glycoproteins isolated from honey, a novel antibacterial drug candidate with broad spectrum activity against multi-drug resistant clinical isolates. *Front. Microbiol.,* 6, 711.

Chua, L. S., Lee, J. Y., & Chan, F. F. (2015). Characterization of the Proteins in Honey. *Analytical Letters,* 48(4), 697-709. doi:10.1080/00032719.2014.952374

Erik van der Linden, &. F. (2009). Gelation. *Modern Biopolymer Science,* 29-91. doi:10.1016/b978-0-12-374195-0.00002-1

Formanski, K. (2019, May). Plant-based Proteins—*US. Mintel Reports.* Retrieved from https://reports.mintel.com/display/919520/#

Kossoff, E. a. (2008). The Modified Atkins Diet. *Epilepsia,* 49, 37-41. doi:10.1111/j.1528-1167.2008.01831.x Lemon, P. P. (1991). Protein Intake and Athletic Performance. *Sports Medicine,* 12, 313-325. doi:10.2165/00007256-199112050-00004

Lindeberg S, J. T. (2007, September). A Palaeolithic diet improves glucose tolerance more than a Mediterranean-like diet in individuals with ischaemic heart disease. *Diabetologia,* 50(9), 1795-1807. doi:10.1007/s00125-007-0716-y Majtan J, K. P. (2010, August). Effect of honey and its major royal jelly protein 1 on cytokine and MMP-9 mRNA transcripts in human keratinocytes. *Exp Dermatol.,* 19(8), e73-9. doi:10.1111/j 0.1600-0625.2009.00994.x Nicolai, T. (2019). Gelation of food protein-protein mixtures. *Advances in Colloid and Interface Science,* 270, 147-164. doi:10.1016/j.cis.2019.06.006

Swapna Gannabathula, G. W. (2015). Honeybee apisimin and plant arabinogalactans in honey costimulate. *Food Chemistry,* 168, 34-40. doi:10.1016/j.foodchem.2014.07.007

Tamura S., A. S. (2009). Molecular characteristics and physiological functions of major royal jelly protein 1 oligomer. *Proteomics,* 9, 5534-5543.

*The plant-based protein market is changing what it takes to succeed.* (2020, September 14). Retrieved from Food Navigator: https://www.foodnavigator.com/News/Promotional-Features/The-plant-based-protein-market-is-changing-what-it-takes-to-succeed Vezeteu, T. V. (2017). Food to some, poison to others—honeybee royal jelly and its growth inhibiting effect on European Foulbrood bacteria. *Microbiologyopen,* 6, e00397.

Wenli Tian, M. L. (2018). Architecture of the native major royal jelly protein 1 oligomer. *Nat Commun,* 9, 3373. doi:10.1038/s41467-018-05619-1

The invention claimed is:

1. A food composition supplemented with a mixture of isolated and purified recombinant honey proteins comprising of RJMP1 and apisimin in about a 1:1 molar ratio without other honey proteins wherein the recombinant honey proteins have immunostimulatory properties wherein the food composition comprises chocolate, jam, jelly, fruit juice, nuts, milks, doughs, cake, bread, milk, cheese, cream cheese, soft cheese, cheese sauce, peanut butters, nut butters, cereal, hard cheese, or yogurt.

2. The food composition of claim 1, wherein the food composition is hydrophobic.

3. The food composition of claim 1, wherein the food composition is hydrophilic.

4. The food composition of claim 1, wherein the food composition is a high-fat food composition, a high-sugar food composition, or contains no animal products.

5. The food composition of claim 1, wherein the recombinant honey protein is amphipathic.

6. The food composition of claim 1, wherein the recombinant honey protein is fat soluble.

7. The food composition of claim 1, wherein the recombinant honey protein is water soluble.

8. The food composition of claim 1, wherein the recombinant honey proteins form a gel.

9. The food composition of claim 1, wherein the food composition has a cytostimulatory property.

10. The food composition of claim 1, wherein the recombinant honey protein comprises a protein having an amino acid sequence with at least 90% identity to any of SEQ ID NOs: 1-6 and 38-41.

11. The food composition of claim 1, wherein the recombinant honey protein comprises about 15% of the food composition by weight.

12. The food composition of claim 1, wherein the recombinant honey protein comprises at least 90% of total protein in the food composition.

13. The food composition of claim 1, wherein the food composition has a smooth mouthfeel, a uniform mouthfeel, or a low dryness mouthfeel.

14. The food composition of claim 1, wherein there is no detectable taste difference between the food composition with or without the recombinant honey protein or no detectable mouthfeel difference between the food composition with or without the recombinant honey protein.

15. The food composition of claim 1, wherein the RJMP1 and apisimin form complex that include two RJMP1 proteins and two apisimin proteins.

16. A method of producing a food composition supplemented with one or more recombinant honey proteins, the method comprising:
recombinantly expressing one or more genes to produce the one or more recombinant honey proteins, wherein the honey proteins are RJMP1 and apisimin without other honey proteins;
isolating or purifying the recombinant honey proteins; and
combining the one or more recombinant honey proteins with the food composition, wherein the RJMP1 and apisimin are present in about a 1:1 molar ratio and wherein the recombinant honey proteins have immunostimulatory properties wherein the food composition comprises chocolate, jam, jelly, fruit juice, nut milks, doughs, cake, bread, milk, cheese, cream cheese, soft cheese, cheese sauce, peanut butters, nut butters, cereal, hard cheese, or yogurt.

17. The method of claim 16, wherein the one or more recombinant honey proteins comprise a protein having an amino acid sequence with at least 90% identity to any of SEQ ID NOs. 1-6 and 38-41.

18. The method of claim 16, wherein combining the one or more recombinant honey proteins with the food composition comprises adding a quantity of the one or more recombinant honey proteins to the food composition such that the food composition comprises at least 15% recombinant honey proteins by weight.

19. The method of claim 16, wherein the one or more recombinant honey proteins form a gel.

20. The method of claim 16, further comprising combining the RJMP1 and apisimin in the about 1:1 molar ratio such that the recombinant honey proteins form a complex that includes two RJMP1 proteins and two apisimin proteins.

* * * * *